United States Patent [19]

Pasteris

[11] Patent Number: 4,846,874

[45] Date of Patent: Jul. 11, 1989

[54] HERBICIDAL SULFONAMIDES

[75] Inventor: Robert J. Pasteris, Wilmington, Del.

[73] Assignee: E. I. Du Pont de Nemours and Company, Wilmington, Del.

[21] Appl. No.: 134,506

[22] Filed: Dec. 16, 1987

Related U.S. Application Data

[60] Division of Ser. No. 732,788, May 10, 1985, Pat. No. 4,737,184, which is a continuation-in-part of Ser. No. 660,233, Oct. 17, 1984, abandoned.

[51] Int. Cl.$^4$ ............... C07D 403/12; C07D 403/14; C07D 407/12; A01N 43/66

[52] U.S. Cl. ........................................ 71/91; 71/86; 71/87; 71/90; 71/93; 544/212; 544/207; 544/209; 544/198; 544/48; 544/2; 544/6; 544/10; 544/65; 544/66; 544/47; 544/90; 544/91; 544/92; 544/105; 544/195; 544/219; 544/70

[58] Field of Search ............... 71/93, 90, 91, 86; 544/212, 207, 209, 198, 48, 10, 47, 92, 219

[56] References Cited

U.S. PATENT DOCUMENTS

| | | | |
|---|---|---|---|
| 4,715,885 | 12/1987 | Wexler | 71/91 |
| 4,752,322 | 6/1988 | Dumas et al. | 71/90 |
| 4,772,313 | 9/1988 | Petersen | 71/93 |

*Primary Examiner*—John M. Ford

[57] ABSTRACT

Novel N-(heterocyclicaminocarbonyl) substituted thiophene-, furan- and pyrrolesulfonamides, such as N-[(4-methoxy-6-methylpyrimidin-2-yl)aminocarbonyl]-6,7-dihydro-5H-thieno-[3,2-b]thiopyran-3-sulfonamide, 4,4-dioxide and N-[(4,6-dimethoxypyrimidin-2-yl)aminocarbonyl]-6,7-dihydro-5H-thieno[3,2-b]thiopyran-3-sulfonamide, 4,4-dioxide and their method-of-use as herbicides are described.

81 Claims, No Drawings

HERBICIDAL SULFONAMIDES

RELATED APPLICATIONS

This application is a division of application Ser. No. 732,788, filed on May 10, 1985 now U.S. Pat. No. 4,737,184, is a continuation-in-part of my copending application U.S. Ser. No. 660,233, filed Oct. 17, 1984, now abandoned.

BACKGROUND OF THE INVENTION

The invention relates to novel N-(heterocyclicaminocarbonyl) substituted thiophenesulfonamides which are useful as herbicides, and their method-of-use as general pre-emergence or post-emergence herbicides or plant growth regulants.

In U.S. Pat. No. 4,127,405, issued Nov. 28, 1978 to Levitt, herbicidal benzene- and thiophenesulfonylureas are disclosed.

U.S. Pat. No. 4,398,939, issued Aug. 16, 1983 to Levitt discloses herbicidal thiophenesulfonylureas substituted by alkyl, OCH$_3$, NO$_2$, halogen, or sulfamoyl groups.

European Patent Application (EP-A)-No. 30,142, published June 10, 1981 teaches herbicidal thiophenesulfonylureas bearing ortho-carboxylic acid ester groups as well as other derivatives of carboxylic acids.

European Patent Application (EP-A)-No. 64,804, published Nov. 17, 1982, discloses herbicidal thiophenesulfonylureas bearing ortho-alkylsulfonyl groups.

U.S. Pat. No. 4,319,627, issued July 5, 1983 to Levitt discloses benzothiophenesulfonylureas.

European Patent Application (EP-A)-No. 79,683, published May 25, 1983, teaches herbicidal sulfonylureas including those of the general formulae:

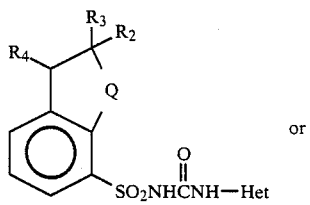

or

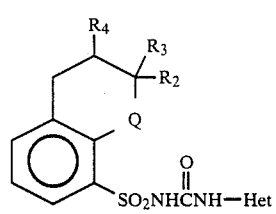

wherein
Q is O, S or SO$_2$;
R$_2$ is H or C$_1$-C$_3$ alkyl;
R$_3$ is H or CH$_3$; and
R$_4$ is H or CH$_3$.

EPA-No. 107,979, published May 9, 1984, teaches herbicidal sulfonylureas including those of the general formulae:

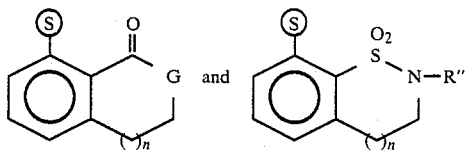

wherein
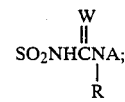
is $$SO_2NHCNA;\overset{W}{\underset{R}{\|}}$$

n is 0, 1 or 2;
G is O or NR''; and
R'' is alkyl.

South African Patent Application No. 83/5165 (Swiss priority 7/16/82, published 1/16/84) discloses herbicidal sulfonamides of formula

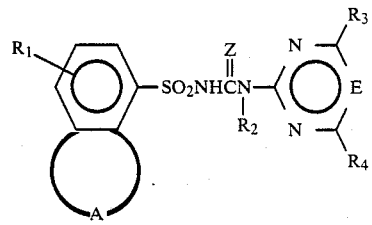

wherein A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or SO$_2$— group.

SUMMARY OF THE INVENTION

This invention relates to novel compounds of Formula I, suitable agricultural compositions containing them and their method-of-use as general preemergence and/or postemergence herbicides or plant growth regulants.

$$JSO_2NHCNA \overset{W}{\underset{R}{\|}} \qquad I$$

wherein
J is
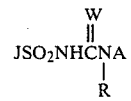

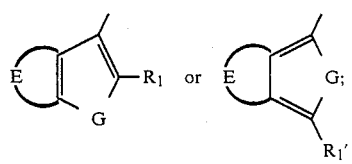

E is a bridge of 3 or 4 atoms, which may be substituted or unsubstituted, containing 0-2 heteroatoms selected from the group consisting of oxygen, sulfur and nitrogen and also containing 1–4 atoms of carbon, said bridge together with two carbon attachment sites forming a partially saturated 5 to 6 membered carbocyclic or heterocyclic ring; or E is a bridge of 3 or 4 atoms which may be substituted or unsubstituted containing at least 1 heteroatom selected from 0–1 oxygen or sulfur or 0–2 nitrogen and 1–3 atoms of carbon, said bridge together with two carbon attachment sites forming an unsaturated 5 to 6 membered heterocyclic ring, with the proviso that when E contains two atoms of oxygen or sulfur, then they must be separated by at least one atom of carbon and that oxygen and sulfur are only linked to each other if the sulfur is in the form of $SO$ or $SO_2$; in the bridging group E, nitrogen may take the form of N or N—O, sulfur may take the form of S, SO or $SO_2$, and one of the atoms of carbon may be a carbonyl, thiocarbonyl or the cyclic 5 and 6 membered ketals thereof; when one of the bridging atoms is a substituted carbon, the substituent on said carbon includes H, halogen, $C_1$–$C_4$ alkyl, $C_1$–$C_4$ haloalkyl, $C_3$–$C_4$ alkenyl, $C_3$–$C_4$ haloalkenyl, $C_3$–$C_4$ alkynyl, $C_3$–$C_4$ haloalkynyl, $C_1$–$C_3$ alkoxycarbonyl, CN, $NO_2$, OH, $C_1$–$C_3$ alkoxy, $C_1$–$C_3$ haloalkoxy, $C_1$–$C_3$ alkylthio, $C_1$–$C_3$ alkylsulfinyl, $C_1$–$C_3$ alkylsulfonyl, $C_1$–$C_3$ alkylcarbonyl, $C_1$–$C_3$ alkylsulfamoyl, di($C_1$–$C_3$ alkyl)sulfamoyl and $C_1$–$C_2$ alkyl substituted with $C_1$–$C_2$ alkoxy, $C_1$–$C_2$ alkylthio or CN; when the bridging atom is a nitrogen (other than nitrogen in the form of $R_6NSO_2$ in $J_7$, $J_8$, $J_{11}$ and $J_{12}$) substituents on said nitrogen include H, $C_1$–$C_4$ alkyl, $C_1$–$C_4$ haloalkyl, $C_3$–$C_4$ alkenyl, $C_3$–$C_4$ haloalkenyl, $C_3$–$C_4$ alkynyl, $C_3$–$C_4$ haloalkynyl, $C_1$–$C_3$ alkoxy, $C_1$–$C_4$ alkylcarbonyl, $C_1$–$C_3$ alkoxycarbonyl, $C_1$–$C_3$ alkylaminocarbonyl or $C_1$–$C_4$ alkylsulfonyl; when the bridging atom is a nitrogen, in the form of $R_6NSO_2$ as in $J_7$, $J_8$, $J_{11}$ and $J_{12}$, the nitrogen substituents are as defined for $R_6$.

G is O, S, NH or $NCH_3$;
W is O or S;
R is H or $CH_3$;
$R_1$ is H, F, Cl, Br, $NO_2$, $C_1$–$C_3$ alkyl, $C_1$–$C_3$ haloalkyl, $C_1$–$C_3$ alkoxy, $C_1$–$C_3$ haloalkoxy, $S(O)_p C_1$–$C_3$ alkyl, $S(O)_p C_1$–$C_3$ haloalkyl, $CO_2(C_1$–$C_3$ alkyl), $CO_2(C_1$–$C_3$ haloalkyl), $OCH_2CH$=$CHR_a$, $OCH_2C$≡$CR_a$, $CO_2(CH_2CH$=$CHR_a)$, $CO_2(CH_2C$≡$CR_a)$ or $SO_2NR_bR_c$;
$R_1'$ is H, $CH_3$, F or Cl;
p is 0, 1 or 2;
$R_a$ is H or $CH_3$;
$R_b$ is H, $C_1$–$C_3$ alkyl or $C_1$–$C_3$ haloalkyl;
$R_c$ is H, $C_1$–$C_3$ alkyl or $C_1$–$C_3$ haloalkyl;
A is

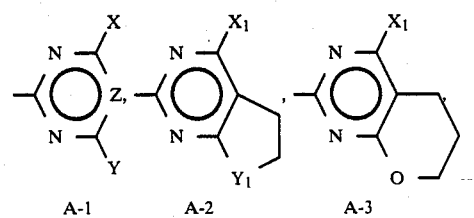

A-1   A-2   A-3

-continued

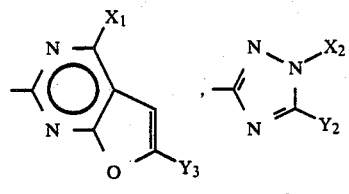

A-4   A-5

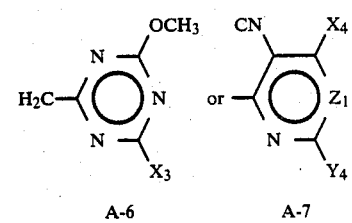

A-6   A-7

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino, di($C_1$–$C_3$-alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_3$–$C_5$ cycloalkyl, $C_2$–$C_4$ alkynyl,

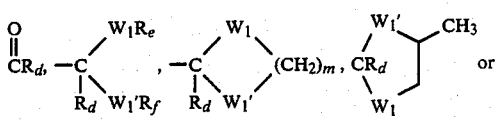

$N(OCH_3)CH_3$;

$W_1$ and $W'_1$ are independently O or S;
m is 2 or 3;
$R_d$ is H or $CH_3$;
$R_e$ is $C_1$–$C_2$ alkyl;
$R_f$ is $C_1$–$C_2$ alkyl;
Z is CH, N, $CCH_3$, $CC_2H_5$, CCl or CBr;
$Z_1$ is CH or N;
$Y_1$ is O or $CH_2$; $X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $OCF_2H$, $SCF_2H$, $CH_3$ or $CH_2CH_3$;
$X_3$ is $CH_3$ or $OCH_3$;
$Y_3$ is H or $CH_3$;
$X_4$ is $CH_3$, $OCH_3$, $OC_2H_5$, $CH_2OCH_3$ or Cl; and
$Y_4$ is $CH_3$, $OCH_3$ or $OC_2H_5$;
Exemplary values of J include

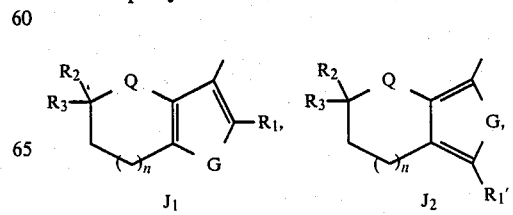

$J_1$   $J_2$

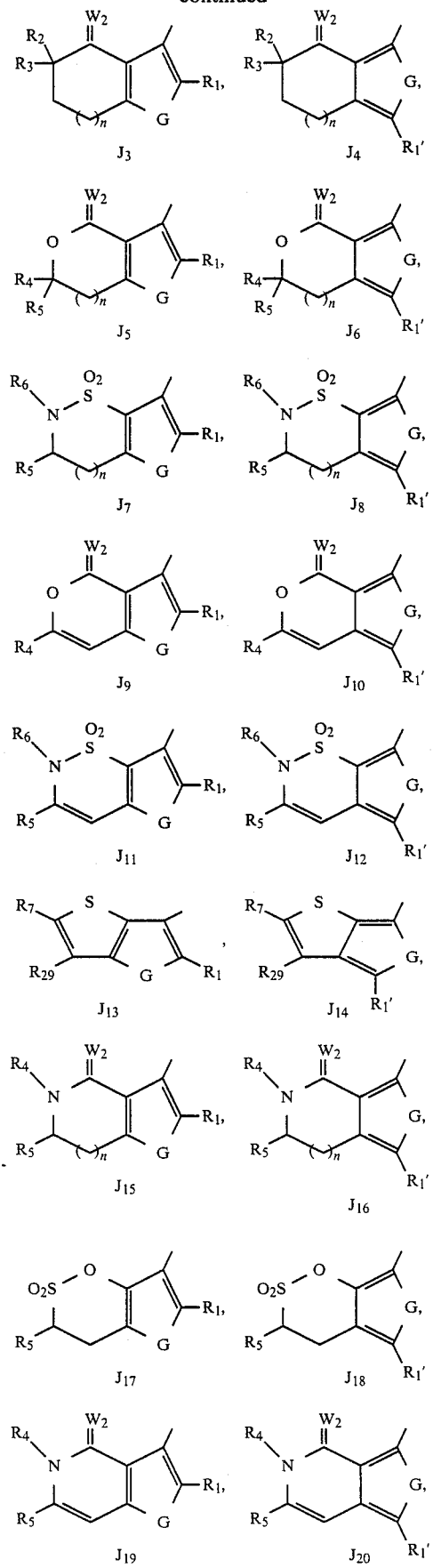
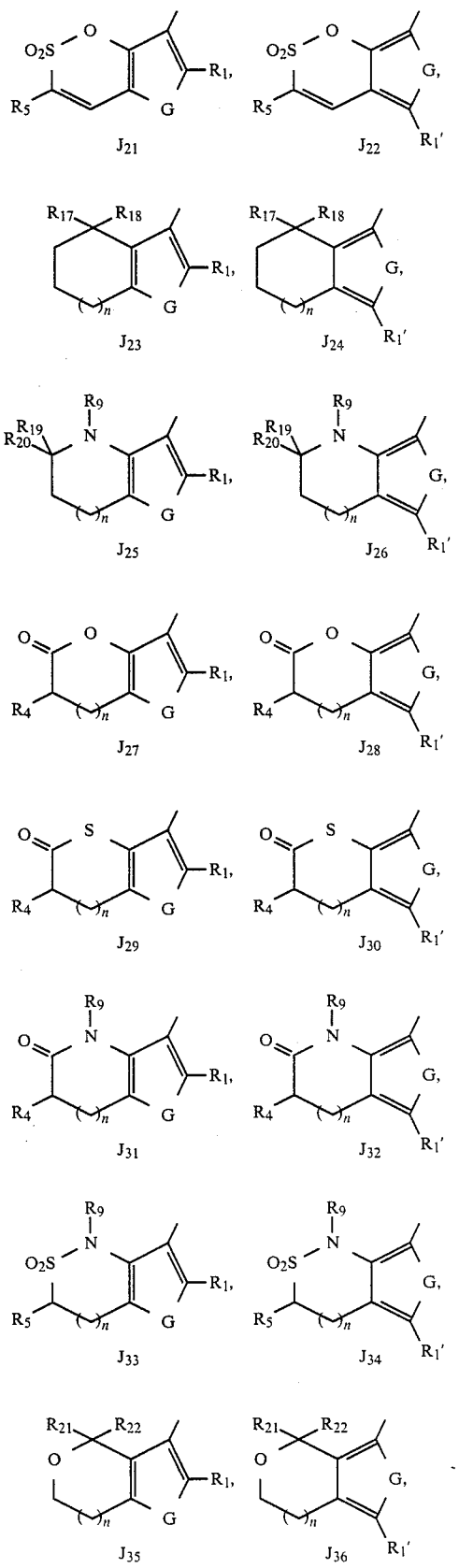

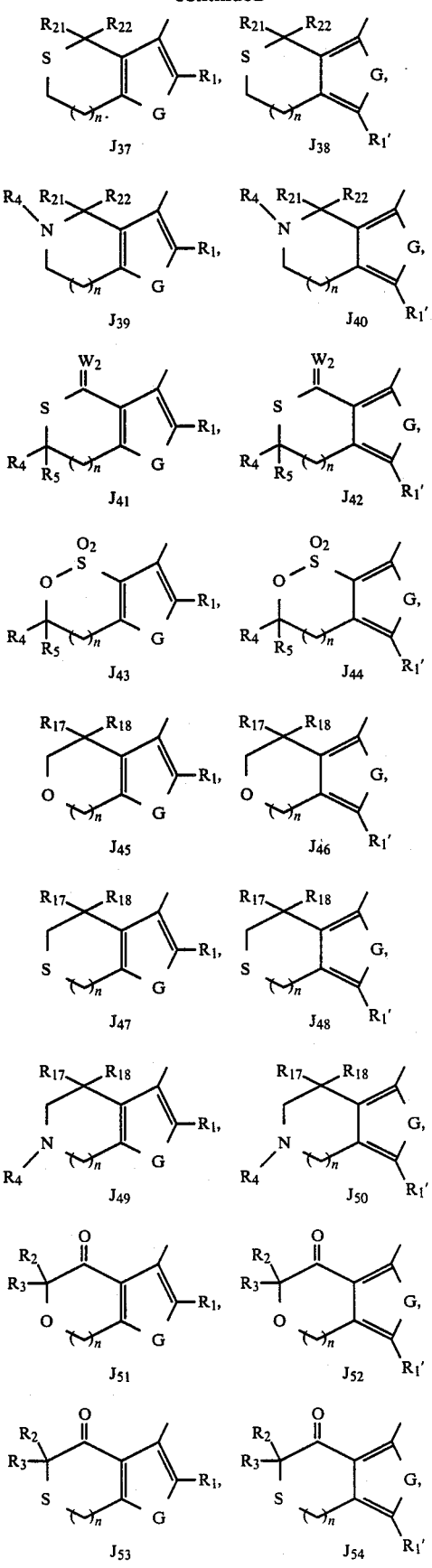
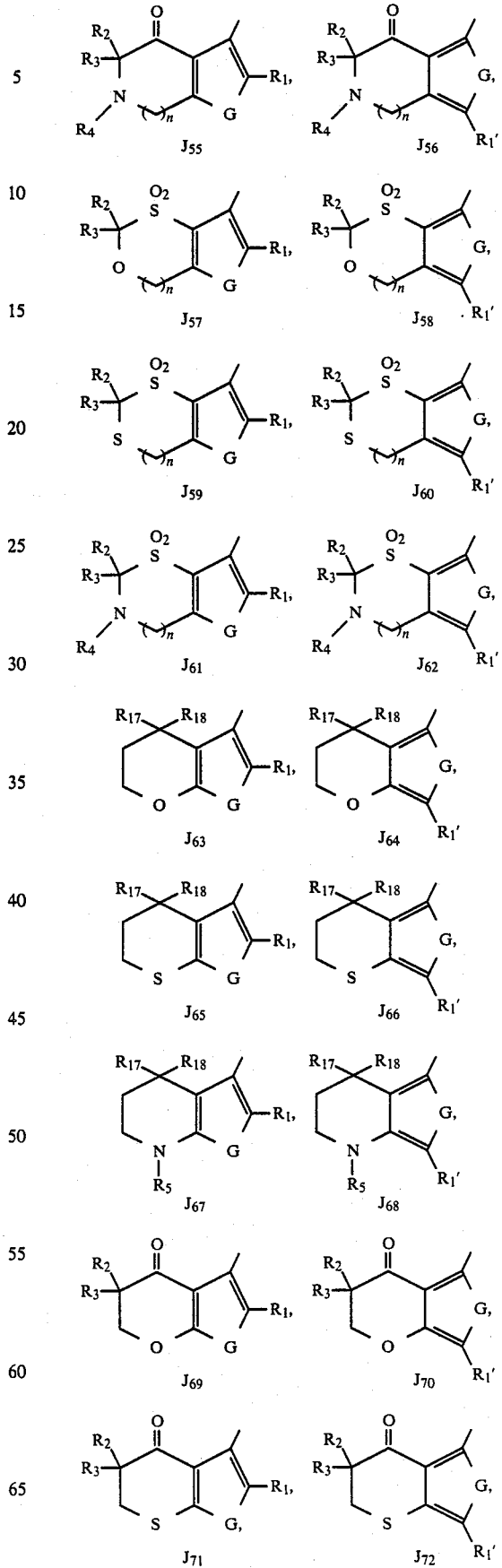

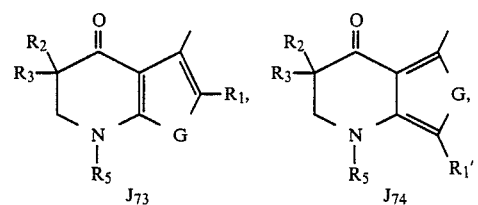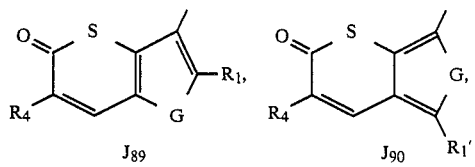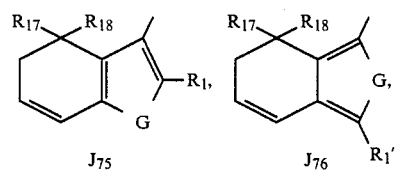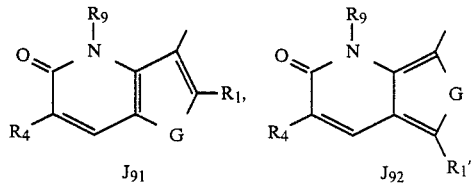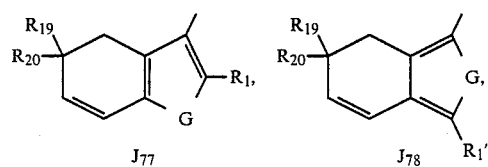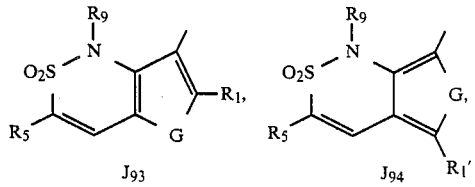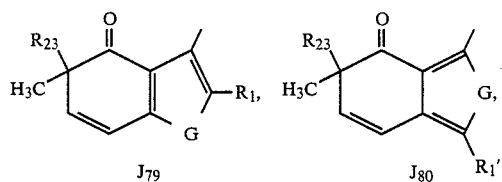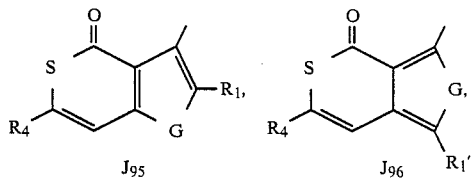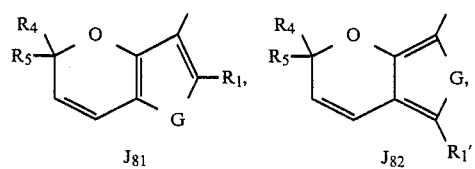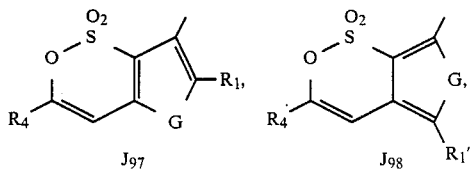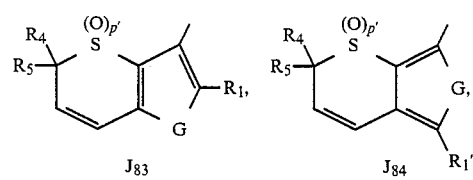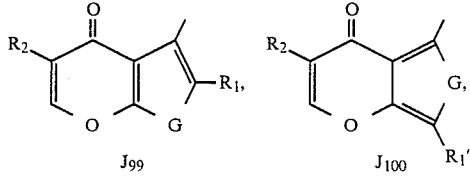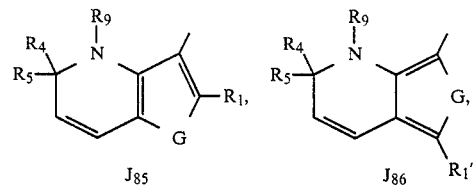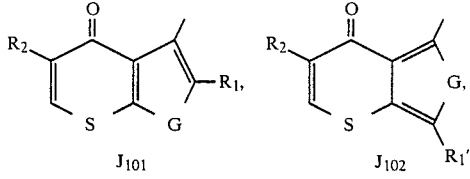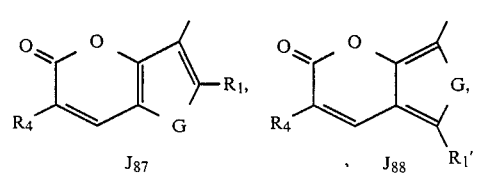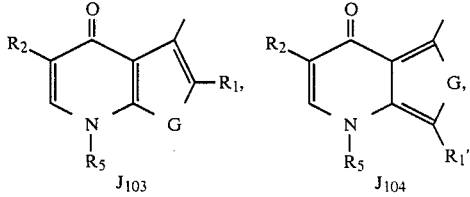

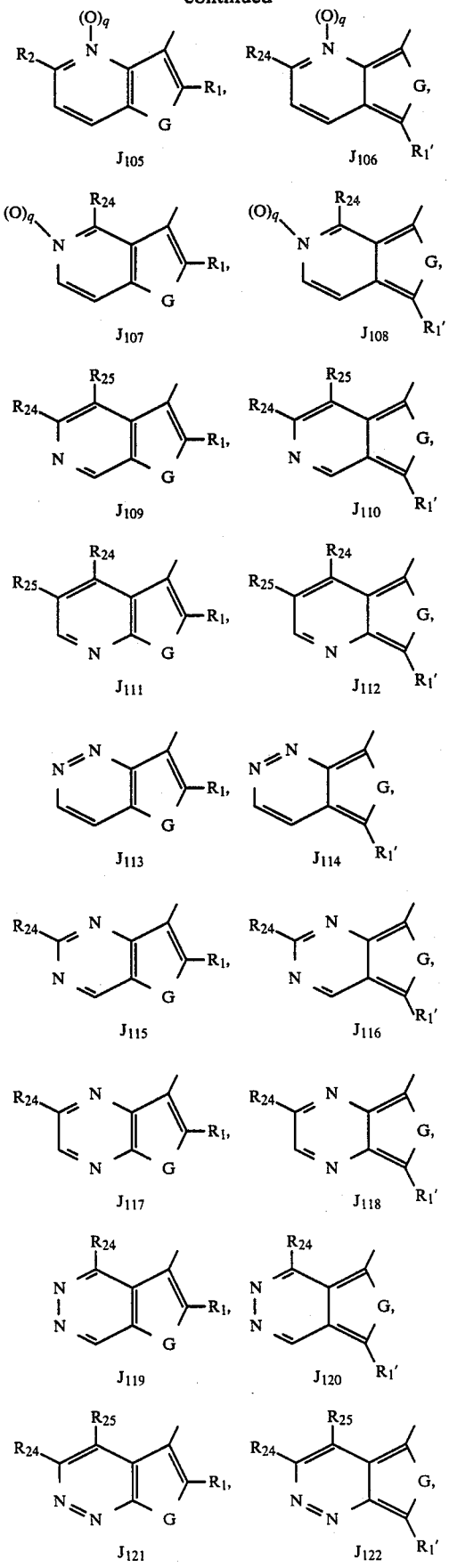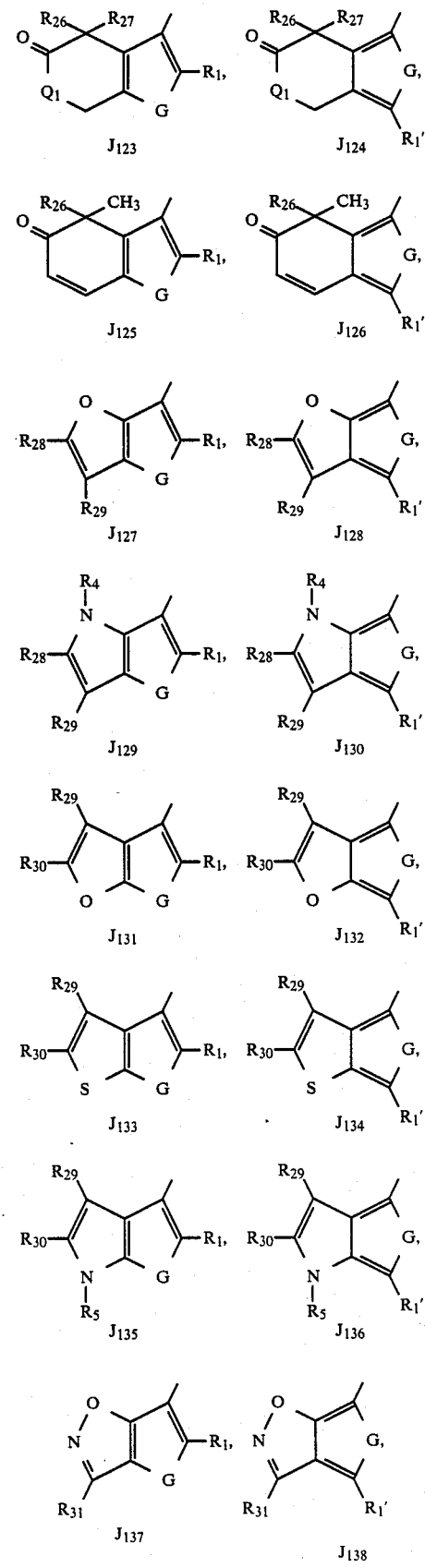

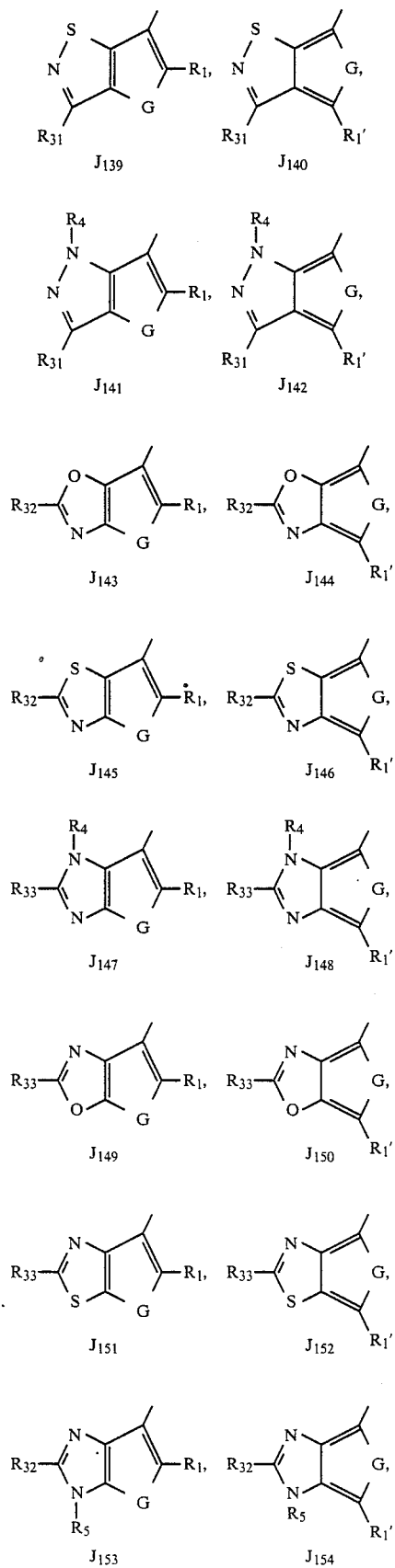
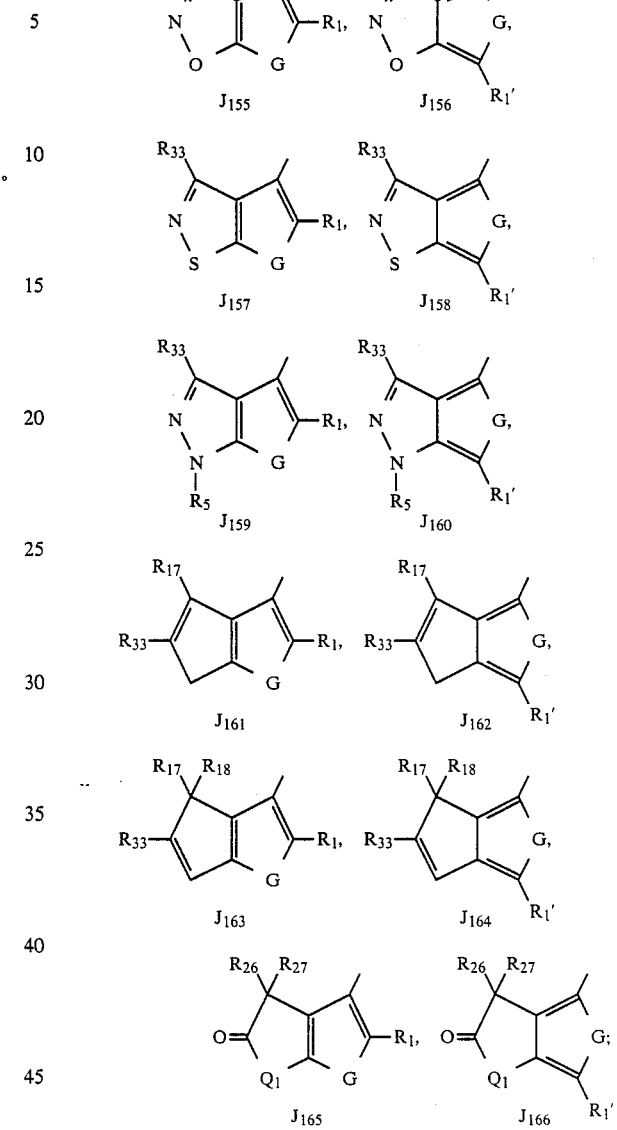

Q is O, S, SO, SO₂, CH₂ or CHCH₃;
$Q_1$ is O, S, CH₂ or NR₄;
$W_2$ is O or S;
$R_2$ is H, F, Cl or $C_1$-$C_4$ alkyl;
$R_3$ is H, F, Cl or CH₃;
$R_4$ is H or $C_1$-$C_4$ alkyl;
$R_5$ is H or CH₃;
$R_6$ is H, $R_8$, $SR_8$, $SO_2R_8$, $OR_8$, $C(O)R_8$, $C(O)L$, $(CO)_2OR_8$, $(CO)_2R_8$, $C(O)NR_9R_{10}$, C(O)NRA, $C(S)SR_8$, $NH_2$, $NR_9R_{10}$, OH, CN, $P(O)R_{11}R_{12}$, $P(S)R_{11}R_{12}$ or $Si(CH_3)_2R_{13}$;
$R_7$ is H, $C_1$-$C_6$ alkyl, Cl, Br, CN, $NO_2$, $SR_{13}$, $SO_2R_{13}$, $CO_2R_{13}$ or $C(O)R_{13}$;
$R_8$ is $C_1$-$C_{10}$ alkyl, $C_1$-$C_{10}$ alkoxyalkoxyalkyl, $C_2$-$C_{10}$ alkenyl, $C_2$-$C_{10}$ epoxyalkyl, $C_2$-$C_{10}$ alkynyl, $C_3$-$C_6$ cycloalkyl, $C_4$-$C_7$ cycloalkylalkyl or phenyl optionally substituted with $R_{14}$; when $R_8$ is $C_3$-$C_6$ cycloalkyl or $C_4$-$C_7$ cycloalkylalkyl, it may optionally be substituted by $C_1$-$C_4$ alkyl, 1 to 3 atoms of Cl or F or 1 Br; when $R_8$ is $C_1$-$C_{10}$ alkyl, $C_2$-$C_{10}$ alkenyl or $C_2$-$C_{10}$ alkynyl, it may optionally be substituted by one or more halogens and/or by $(R_{15})_r$ provided that when r is 2, the values of $R_{15}$ may be identical or different;

$R_9$ is H or $C_1$-$C_4$ alkyl;

$R_{10}$ is H, $C_1$-$C_{10}$ alkyl, $C_1$-$C_{10}$ haloalkyl, $C_2$-$C_{10}$ alkenyl, $C_2$-$C_{10}$ alkynyl, $C_3$-$C_6$ cycloalkyl or phenyl substituted with $R_{14}$;

$R_{11}$ and $R_{12}$ are independently $C_1$-$C_4$ alkyl, $C_1$-$C_4$ alkoxy or $C_1$-$C_4$ alkylthio;

$R_{13}$ is $C_1$-$C_{10}$ alkyl, benzyl or phenyl optionally substituted with $R_{14}$;

$R_{14}$ is H, F, Cl, Br, $CH_3$, $OCH_3$, $NO_2$, CN, $SCH_3$, $SO_2CH_3$ or $CF_3$;

$R_{15}$ is $OR_{10}$, $OC(O)R_{10}$, $OC(O)NR_9R_{10}$, $OSO_2R_{10}$, $OP(O)R_{11}R_{12}$, $OSi(CH_3)_2R_{13}$, $SR_{10}$, $SOR_{10}$, $SOR_2R_{10}$, SCN, CN, $SP(O)R_{11}R_{12}$, $SP(S)R_{11}R_{12}$, $P(O)R_{11}R_{12}$, $P(S)R_{11}R_{12}$, $NR_9R_{10}$, $N^+R_9R_{10}R_{13}$, $NR_9C(O)R_{10}$, $NR_9C(O)OR_{10}$, $NR_9C(O)NR_9R_{10}$, $NR_9SO_2R_{10}$, $NR_9P(O)R_{11}R_{12}$, $NR_9P(S)R_{11}R_{12}$, $NO_2$, $C(O)R_{10}$, $C(O)OR_{10}$, $C(O)NR_9R_{10}$, $C(R_{10})=NOR_{12}$, naphthyl, L, phenyl optionally substituted with $R_{14}$ and/or $R_{16}$,

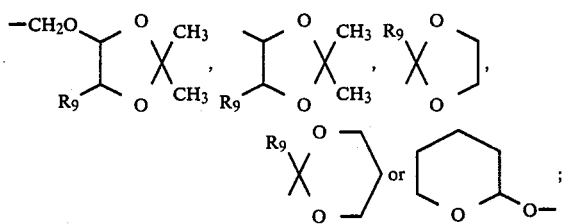

$R_{16}$ is H, F, Cl, Br, phenoxy optionally substituted with $R_{14}$, or phenyl optionally substituted with $R_{14}$;

$R_{17}$ is H, $C_1$-$C_3$ alkyl, $C_1$-$C_3$ alkoxy, $C_1$-$C_3$ alkoxycarbonyl, F, Cl or CN;

$R_{18}$ is H, $CH_3$, $C_1$-$C_3$ alkoxy, F, Cl or OH; or $R_{17}$ and $R_{18}$ may be taken together to form —$OCH_2CH_2O$— or —$OCH_2CH_2CH_2O$—;

$R_{19}$ is H or $C_1$-$C_4$ alkyl;

$R_{20}$ is H or $CH_3$;

$R_{21}$ and $R_{22}$ are independently H or $CH_3$;

$R_{23}$ is $C_1$-$C_4$ alkyl;

$R_{24}$ is H, F, Cl, $C_1$-$C_3$ alkyl or $C_1$-$C_3$ alkoxy;

$R_{25}$ is H, F, Cl or $C_1$-$C_3$ alkyl;

$R_{26}$ is H, F, Cl or $C_1$-$C_2$ alkyl;

$R_{27}$ is H, F, Cl or $CH_3$;

$R_{28}$ is H, $C_1$-$C_4$ alkyl, Cl, Br, CN, $NO_2$, $C_1$-$C_3$ alkylthio, $C_1$-$C_3$ alkylsulfonyl, $C_1$-$C_3$ alkoxycarbonyl or $C_1$-$C_3$ alkylcarbonyl;

$R_{29}$ is H, $CH_3$, Cl or Br;

$R_{30}$ is H, $CH_3$, Cl or Br;

$R_{31}$ is H or $CH_3$;

$R_{32}$ is H or $C_1$-$C_4$ alkyl;

$R_{33}$ is H, $C_1$-$C_4$ alkyl, $C_1$-$C_4$ alkoxy, $C_1$-$C_4$ alkylthio, F or Cl;

L is a 5- or 6-membered aromatic heterocycle, a 5- or 6-membered dihydroaromatic heterocycle or a 5- or 6-membered tetrahydroaromatic heterocycle which contains 1-4 heteroatoms selected from 0-1 oxygen atoms, 0-1 sulfur atoms and/or 0-4 nitrogen atoms, with the proviso that oxygen and sulfur are only linked to each other if the sulfur is in the form of SO or $SO_2$, and these heterocycles may optionally be substituted by 1-4 $CH_3$, 1-2 $OCH_3$, $SCH_3$, Cl, $N(CH_3)_2$ or CN groups or L is a 5- or 6-membered lactone, lactam or cycloalkanone which may optionally be substituted by 1-4 $CH_3$ groups;

n is 0 or 1;

p' is 0, 1 or 2;

q is 0 or 1; and r is 1 or 2;

provided that (a) when W is S, then R is H, A is A-1, Z is CH or N, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

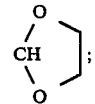

(b) the total number of carbon atoms in $R_2$ and $R_3$ is less than or equal to 4;

(c) when X is Cl, F, or Br, then Z is CH and Y is $OCH_3$, $OC_2H_5$, $NH_2$, $NHCH_3$, $N(CH_3)_2$ or $OCF_2H$;

(d) when J is $J_1$ or $J_2$, then $R_2$ and $R_3$ are other than F or Cl;

(e) the total number of carbons atoms in $R_4$ and $R_5$ is less than or equal to 4;

(f) the total number of carbon atoms in $R_6$ is less than or equal to 13;

(g) when J is $J_5$, $J_6$, $J_{27}$, $J_{28}$, $J_{29}$, $J_{30}$, $J_{31}$, $J_{32}$, $J_{33}$, $J_{34}$, $J_{41}$, $J_{42}$, $J_{43}$ or $J_{44}$ and n is O, then $R_4$ and/or $R_5$ is H;

(h) when J is $J_{61}$ or $J_{62}$ and n is 0, then $R_4$ is H or $CH_3$;

(i) when X or Y is $OCF_2H$, then Z is CH;

(j) when $R_{17}$ is $C_1$-$C_3$ alkoxy, then $R_{18}$ is H, $CH_3$ or $C_1$-$C_3$ alkoxy; and when $R_{18}$ is $C_1$-$C_3$ alkoxy, then $R_{17}$ is not F, or Cl;

(k) when $R_{18}$ is OH, then $R_{17}$ is H or $C_1$-$C_3$ alkyl; and (l) when the total number of carbon atoms of X and Y is greater than four, then the number of carbon atoms of $R_1$ is less than or equal to two, and the number of carbon atoms of $R_6$ is less than or equal to four;

and their agriculturally suitable salts.

In the above definitions, the term "alkyl", used either alone or in compound words such as "alkylthio" or "haloalkyl", denotes straight chain or branched alkyl, e.g. methyl, ethyl, n-propyl, isopropyl or the different butyl, pentyl, hexyl, heptyl, octyl, nonyl or decyl isomers.

Alkoxy denotes methoxy, ethoxy, n-propyloxy, isopropyloxy and the different butyl, pentyl, hexyl, heptyl, octyl or nonyl isomers.

Alkenyl denotes straight chain or branched alkenes, e.g. vinyl, 1-propenyl, 2-propenyl, 3-propenyl and the different butenyl, pentenyl, hexenyl, heptenyl, octenyl, nonenyl or decenyl isomers.

Alkynyl denotes straight chain or branch alkynes, e.g. ethynyl, 1-propynyl, 2-propynyl and the different butynyl, pentynyl, hexynyl, heptynyl, octynyl, nonynyl and decynyl isomers.

Alkylcarbonyl denotes e.g. acetyl, propionyl, and the different butyryl, pentanoyl, hexanoyl, heptanoyl, octanoyl and nonanoyl isomers.

Alkoxycarbonyl denotes e.g. methoxycarbonyl, ethoxycarbonyl, propoxycarbonyl isopropoxycarbonyl and the different butyloxy-, pentyloxy-, hexyloxy-, heptyloxy- and octyloxycarbonyl isomers.

Alkylsulfonyl denotes methylsulfonyl, ethylsulfonyl and the different propylsulfonyl, butylsulfonyl, pentylsulfonyl, hexylsulfonyl, heptylsulfonyl, octylsulfonyl and nonylsulfonyl isomers.

Alkylthio, alkylsulfinyl, alkylamino, alkylsulfamoyl, etc. are defined analogously to the above examples.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine.

The total number of carbon atoms in a substituent group is indicated by the $C_i$–$C_j$ prefix where i and j are numbers from 1 to 10. For example, $C_1$–$C_3$ alkylsulfonyl would designate methylsulfonyl through propylsulfonyl, $C_2$ alkoxyalkoxy would designate $OCH_2OCH_3$, $C_2$ cyanoalkyl would designate $CH_2CN$ and $C_3$ cyanoalkyl would designate $CH_2CH_2CN$ and $CH(CN)CH_3$.

PREFERRED COMPOUNDS

Preferred for reasons of greater ease of synthesis and/or greater herbicidal efficacy are:
1. Compounds of Formula I where J is $J_1$–$J_{166}$.
2. Compounds of Preferred 1 where
   R is H;
   W is O; and
   G is O or S.
3. Compounds of Preferred 2 where
   X is $CH_3$, $OCH_3$, $OCH_2CH_3$, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and
   Y is H, $CH_3$, $OCH_3$, $OC_2H_5$, $CH_2OCH_3$, $NHCH_3$, $N(OCH_3)CH_3$, $N(CH_3)_2$, $CH_2CH_3$, $CF_3$, $SCH_3$, $OCH_2CH=CH_2$, $OCH_2\equiv CH$, $CH_2OCH_2CH_3$, $OCH_2CH_2OCH_3$, $CH_2SCH_3$, $CH_2SCH_2CH_3$,

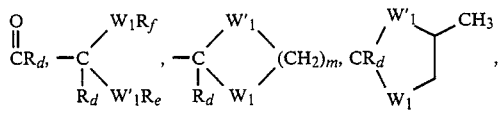

$OCF_2H$, $SCF_2H$, $C\equiv CH$ or $C\equiv CCH_3$;
4. Compounds of Preferred 3 wherein
   G is S;
   $R_1$ is H, Cl, Br or $CH_3$;
   $R_2$ and $R_4$ are H or $C_1$–$C_3$ alkyl;
   $R_3$ is H or $CH_3$;
   $R_6$ is H, $R_8$, $C(O)R_8$ or $CO_2R_8$;
   $R_7$ is H, $C_1$–$C_2$ alkyl, Cl, Br, $SC_1$–$C_2$ alkyl, $SO_2C_1$–$C_2$ alkyl, $CO_2C_1$–$C_2$ alkyl or $C(O)C_1$–$C_2$ alkyl;
   $R_8$ is $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_3$–$C_6$ epoxyalkyl or $C_1$–$C_4$ alkyl substituted with $C_1$–$C_2$ alkoxy, $C_1$–$C_2$ alkylthio, $C_1$–$C_2$ alkylsulfinyl, $C_1$–$C_2$ alkylsulfonyl, $CO_2(C_1$–$C_2$ alkyl), $C(O)C_1$–$C_2$ alkyl, CN or OH.
   $R_{17}$ is H, $C_1$–$C_3$ alkyl, $C_1$–$C_2$ alkoxy or $C_1$–$C_2$ alkoxycarbonyl;
   $R_{18}$ is H, $CH_3$, $C_1$–$C_2$ alkoxy or OH; or
   $R_{17}$ and $R_{18}$ may be taken together to form —$OCH_2CH_2O$— or —$OCH_2CH_2CH_2O$—;
   $R_{28}$ is H, $C_1$–$C_3$ alkyl, Cl, Br or $NO_2$; and
   $R_{33}$ is H or $CH_3$.
5. Compounds of Preferred 4 wherein $R_8$ is $C_1$–$C_6$ alkyl, $C_1$–$C_4$ haloalkyl, $C_3$–$C_4$ alkenyl, $C_3$–$C_4$ haloalkenyl, $C_3$–$C_4$ alkynyl, or $C_1$–$C_3$ alkyl substituted with $C_1$–$C_2$ alkoxy, $C_1$–$C_2$ alkylthio, $C_1$–$C_2$ alkylsulfonyl, CN, $C(O)C_1$–$C_2$ alkyl or $CO_2(C_1$–$C_2$ alkyl).
6. Compounds of Preferred 5 where
   A is A-1;
   Z is CH or N;
   X is $CH_3$, $OCH_3$, $OCH_2CH_3$, Cl, $OCF_2H$ or $OCH_2CF_3$; and
   Y is $CH_3$, $OCH_3$, $C_2H_5$, $CH_2OCH_3$, $NHCH_3$ or $CH(OCH_3)_2$;
7. Compounds of Preferred 6 where J is $J_1$ or $J_2$.
8. Compounds of Preferred 6 where J is $J_3$ or $J_4$.
9. Compounds of Preferred 6 where J is $J_5$ or $J_6$.
10. Compounds of Preferred 6 where J is $J_7$ or $J_8$.
11. Compounds of Preferred 6 where J is $J_9$ or $J_{10}$.
12. Compounds of Preferred 6 where J is $J_{11}$ or $J_{12}$.
13. Compounds of Preferred 6 where J is $J_{13}$ or $J_{14}$.
14. Compounds of Preferred 6 where J is $J_{15}$.
15. Compounds of Preferred 6 where J is $J_{23}$.
16. Compounds of Preferred 6 where J is $J_{25}$.
17. Compounds of Preferred 6 where J is $J_{27}$.
18. Compounds of Preferred 6 where J is $J_{35}$, $J_{37}$ or $J_{39}$.
19. Compounds of Preferred 6 where J is $J_{41}$.
20. Compounds of Preferred 6 where J is $J_{69}$ or $J_{71}$.
21. Compounds of Preferred 6 where J is $J_{79}$.
22. Compounds of Preferred 6 where J is $J_{87}$.
23. Compounds of Preferred 6 where J is $J_{95}$.
24. Compounds of Preferred 6 where J is $J_{105}$ or $J_{106}$.
25. Compounds of Preferred 6 where J is $J_{127}$ or $J_{129}$.
26. Compounds of Preferred 6 where J is $J_{131}$ or $J_{133}$.

Specifically Preferred for reasons of their highest herbicidal activity, greatest plant growth regulant activity and/or most favorable ease of synthesis are:

N-[(4-methoxy-6-methylpyrimidin-2-yl)aminocarbonyl]6,7-dihydro-5H-thieno[3,2-B]thiopyran-3-sulfonamide, 4,4-dioxide, m.p. 244°–225.5° C.

N-[(4,6-dimethoxypyrimidin-2-yl)aminocarbonyl]-6,7-dihydro-5H-thieno[3,2-B]thiopyran-3-sulfonamide, 4,4-dioxide, m.p. 228°–230° C.

N-[(4,6-dimethoxypyrimidin-2-yl)aminocarbonyl]-5,6-dihydro-5-methylthieno[3,2-B]-thiophene-3-sulfonamide-4,4-dioxide, m.p. 186°–187° C.

N-[(4-methoxy-6-methyltriazin-2-yl)aminocarbonyl]-5,6-dihydro-5-methylthieno[3,2-B]thiophene-3-sulfonamide-4,4-dioxide, m.p. 192°–193° C.

N-[(4-chloro-6-methoxypyrimidin-2-yl)aminocarbonyl]5,6-dihydro-5-methylthieno[3,2B-]thiophene-3-sulphonamide-4,4-dioxide, m.p. 203°–204° C.

DETAILED DESCRIPTION OF THE INVENTION

Synthesis

The following discussion represents a general outline for the preparation of the compounds of this invention. All of the syntheses described below are multistep with one or more methods being taught for each step. This allows for a wide variety of possible synthetic pathways to prepare a particular compound of Formula I. The proper choice of the synthetic pathway and the best ordering of the reaction sequences for each individual compound will be known to one skilled in the art.

The compounds of Formula I can be prepared by one or more of the methods described below in Equations 1 to 6.

As shown in Equation 1, many of the compounds of Formula I can be prepared by reacting a sulfonylisocyanate (W=O) or a sulfonylisothiocyanate (W=S) of Formula II with an appropriate heterocyclic amine of Formula III. R, A and W are as previously defined.

Equation 1

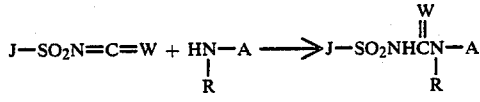

The reaction is carried out at 25° to 100° C. in an inert, aprotic solvent such as methylene chloride or xylene for 0.5 to 24 hours as taught in U.S. Pat. No. 4,127,405.

Many of the compounds of Formula I, where W is S and R is H, (Ia) can be prepared by reacting the appropriate sulfonamide of Formula IV with a heterocyclic isothiocyanate of Formula V, as shown in Equation 2.

Equation 2

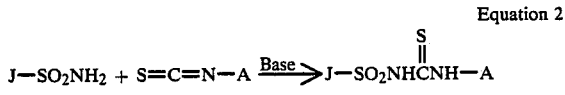

The reaction is carried out at 25° to 80° C. in an inert, aprotic solvent such as acetone or acetonitrile in the presence of a base such as potassium carbonate for 0.5 to 24 hours. The required heterocyclic isothiocyanates V are prepared from the corresponding amines III as taught in EPO Publication No. 35,893.

Many of the compounds of Formula I, where W is O (Ib) and J is other than $J_5$, $J_6$, $J_9$ and $J_{10}$, can be prepared by reacting the sulfonamides of Formula IV with an appropriate methylcarbamate of Formula VI in the presence of an equimolar amount of trimethylaluminum, as shown in Equation 3.

Equation 3

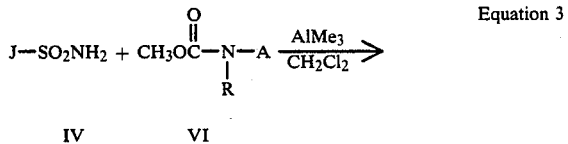

The reaction is carried out at 25° to 40° C. in a solvent such as methylene chloride for 10 to 96 hours under an inert atmosphere at taught in EPO Publication No. 82,681. The required carbamates VI are prepared by reacting the corresponding amines III with dimethylcarbonate or methyl chloroformate in the presence of a strong base.

Alternatively, many of the compounds of Formula Ib, can be prepared by reacting a sulfonylcarbamate of Formula VII with an appropriate amine of Formula III, as shown in Equation 4.

Equation 4

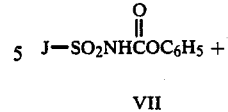

$J-SO_2NHCOC_6H_5$ +

VII

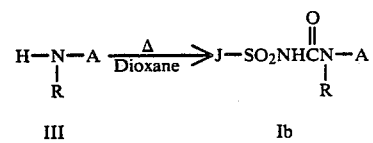

The reaction is carried out at 50° to 100° C. in a solvent such as dioxane for 0.5 to 24 hours at taught in EPO Publication No. 44,807. The required carbamates VII are prepared by reacting the corresponding sulfonamides IV with diphenylcarbonate in the presence of a strong base, such as sodium hydride.

Compounds of Formula Ib can also be prepared, as shown in Equation 5, by reacting a heterocyclic carbamate of Formula VIII with an appropriate sulfonamide of Formula IV.

Equation 5

$J-SO_2NH_2$ +

IV

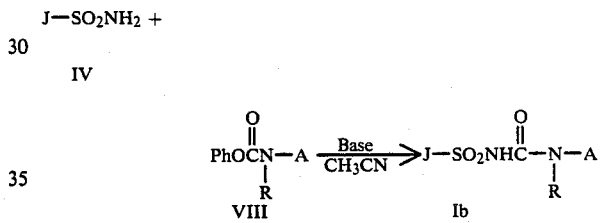

The reaction is carried out at 0° to 50° C. in a solvent such as acetonitrile or dioxane in the presence of a nonnucleophilic base such as DBU for 0.2 to 24 hours. The required phenylcarbamate VIII are prepared by reacting the corresponding heterocyic amines III with diphenylcarbonate or phenylchloroformate in the presence of a strong base, such as sodium hydride.

Many of the compounds of Formula Ib, particularly when G is NH or $NCH_3$ can be prepared by reacting the bicyclic heterocycles IX with a sulfamoyl chloride X as shown in Equation 6.

Equation 6

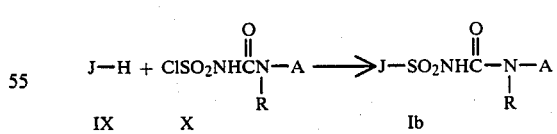

The reaction is carried out at −78° C. to 80° C. in a solvent such as tetrahydrofuran or nitroethane for 1 to 48 hours alone or in the presence of a Friedel-Crafts catalyst as taught in U.S. Pat. Nos. 4,368,067 and 4,473,394. The sulfamoyl chloride intermediates X are prepared by reacting the heterocyclic amines III with chlorosulfonylisocyanate by methods taught in U.S. Pat. No. 4,401,816.

The intermediate sulfonylisocyanates (W=O) and sulfonylisothiocyanates (W=S) of Formula II from Equation 1 can be prepared as shown in Equations 7, 8 and 9.

As shown in Equation 7, many of the sulfonylisocyanats of Formula IIa where J is other than J₃ and J₄ can be prepared by the reaction of sulfonamides of Formula IV with phosgene, in the presence of n-butylisocyanate and a tertiary amine catalyst, at reflux in a solvent such as xylene by the method of U.S. Pat. No. 4,238,621.

Equation 7

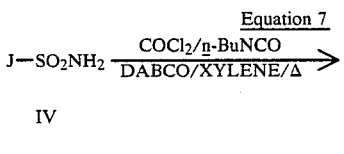

$$J-SO_2N=C=O$$

IIa

The sulfonylisocyanates can also be prepared from the sulfonamides by a two step procedure involving (a) reacting the sulfonamides with n-butylisocyanate in the presence of a base such as $K_2CO_3$ at reflux in an inert solvent such as 2-butanone forming a n-butylsulfonylurea; and (b) reacting this compound this phosgene and a tertiary amine catalyst at reflux in xylene solvent. The method is similar to a procedure taught by Ulrich and Sayigh, *Newer Methods of Preparative Organic Chemistry*, Vol. VI, p. 223-241, Academic Press, New York and London, W. Foerst Ed.

Alternatively, as shown in Equation 8, many of the sulfonylisocyanates of Formula IIa can be prepared by reacting the corresponding sulfonyl chlorides VIII with cyanic acid salts.

Equation 8

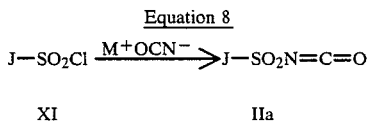

The reaction is carried out at 25° to 100° C. in an inert aprotic solvent such as acetonitrile for 0.5-24 hours in the presence of phosphorus pentoxide and an alkali metal salt such as lithium iodide according to the teachings of Japanese Patent No. 76/26,816 (*Chem. Abst.*, 85: 77892e (1976)).

Many of the sulfonylisothiocyanates of Formula IIb where J is other than J₃ and J₄ can be prepared, as shown in Equation 9, by contacting the sulfonamides of Formula IV with carbon disulfide in the presence of two equivalents of a strong base. The resulting salt is then reacted with phosgene according to the teachings of K. Hartke, *Arch. Pharm.*, 299, 174 (1966).

Equation 9

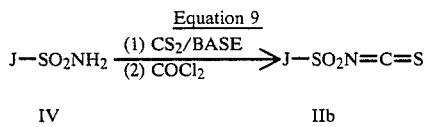

The sulfonamides of Formula IV of Equations 2, 3, 5, 7 and 9 are important intermediates for the preparation of the compounds of this invention. The syntheses of the required sulfonamide intermediates are described in Equations 10 to 15.

As shown in Equation 10, sulfonamides of Formula IV can be prepared from the corresponding sulfonyl chlorides of Formula XI by contacting with either anhydrous or aqueous ammonia.

Equation 10

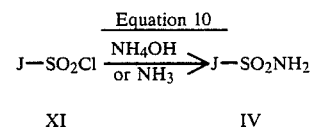

The preparation of sulfonamides from sulfonyl chlorides is widely reported in the literature, for reviews see: F. Hawking and J. S. Lawrence, "The Sulfonamides," H. K. Lewis and Co., London, 1950 and E. H. Northey, "The Sulfonamides and Allied Compounds," Reinhold Publishing Corp., New York, 1948.

Alternatively, many sulfonamides IV can be prepared by dealkylation of their corresponding N-t-butyl sulfonamides XII as shown in Equation 11.

Equation 11

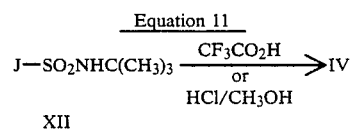

The reaction is carried out by contacting the N-t-butyl sulfonamide XII with a strong acid such as trifluoroacetic acid or methanolic HCl at 25° to 50° C. for 0.5 to 24 hours. The N-t-butyl sulfonamides XII are readily prepared by reacting sulfonylchlorides XI with t-butylamine and are useful either as an acid in purification, to enhance solubility for subsequent reactions such as Equations 12 below or to protect the sulfonamide function from competing with reactions at other parts of the molecule.

Many of the unsaturated sulfonamides of Formula IVa and IVb can be prepared from the corresponding saturated sulfonamides of Formula IVc and IVd by the two-step procedure shown in Equation 12. $G_1-G_2$ is e.g. CO—O, $SO_2$—$NR_6$, CO—$NR_4$ or O—$SO_2$ and R″ is H or $C(CH_3)_3$.

Equation 12

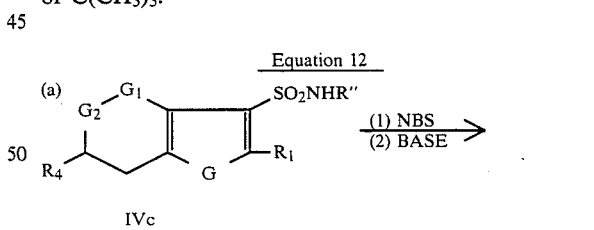

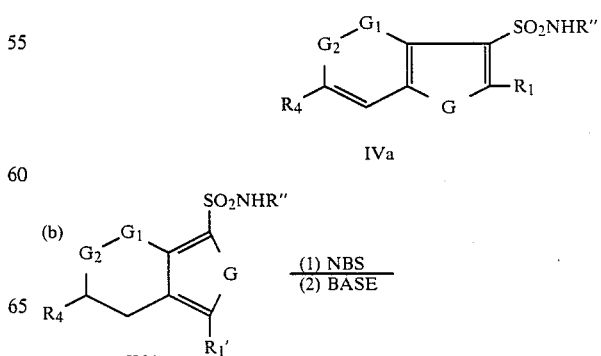

-continued
Equation 12

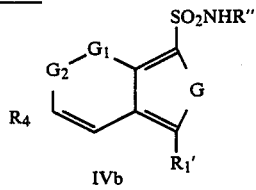

The first step involves α-bromination by N-bromosuccinimide to give a monobromide which is subsequently dehydrobrominated in a second step by reaction with a suitable base such as triethylamine or potassium-t-butoxide in an inert solvent such as THF. This method has been used to prepare isocoumarins from 3,4-dihydroisocoumarins, see R. Barry, *Chem. Rev.*, 64, 229 (1964). In case were $R_1$ or $R_1'$ is a methyl function, competitive bromination at this site may occur resulting in a mixture. The desired bromide may be separated at this stage, or after treatment with the base, by standard methods.

Many of the sulfonamides of Formula IVe and IVf can be prepared from sulfonamides of Formula IVg and IVh, respectively by dehalogenation as shown in Equation 13. $R_1$ and $R_1'$ are Cl or Br and R″ is H or $C(CH_3)_3$.

Equation 13

(a) 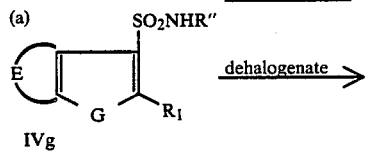

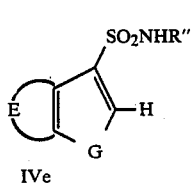

(b) 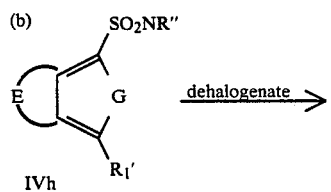

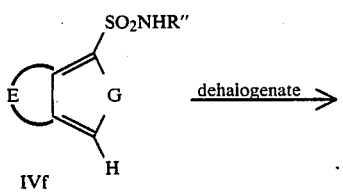

A typical dehalogenation method involves contacting the halo compound with zinc in aqueous acetic acid at 25° to 100° C. for 0.5 to 24 hours. A variety of dehalogenation methods are known, for example, see H. D. Hartough, *Thiophene and Derivatives*, Vol. III of *The Chemistry of Heterocyclic Compounds*, Interscience, New York, 1952.

Additionally, as shown in Equation 14, many of the sulfonamides of Formula IVi and IVj can be prepared by oxidation of sulfonamides of Formula IVk and IVl, respectively, m is 1 or 2. $R_1$ is not $SCH_3$ and R″ is H or $C(CH_3)_3$.

Equation 14

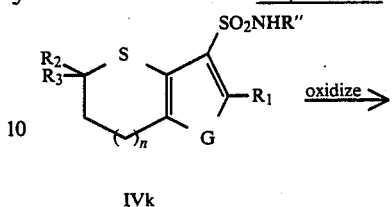

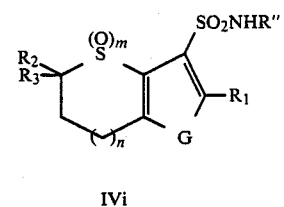

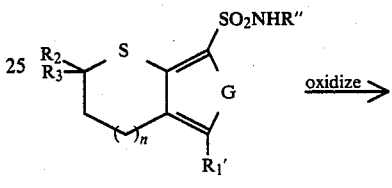

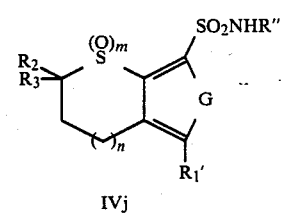

The oxidation of sulfides to sulfoxides and sulfones are widely reported in the literature, for an overview see: "Organic Chemistry of Sulfur", Plenum Press, New York, 1977, S. Oae Ed.

Many of the sulfonamides of Formula IVm and IVn can be prepared by functionalization of the corresponding N-unsubstituted sulfonamides of Formula IVo and IVp, respectively, as shown in Equation 15. $G_1-G_2$ is $(CH_2)_n-CHR_5$ or $CH=CR_5$, R″ is H or $C(CH_3)_3$ and X is Cl, Br, I or other readily displaceable groups.

Equation 15

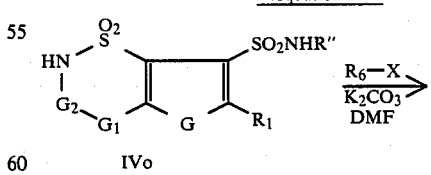

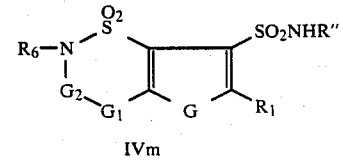

-continued
Equation 15

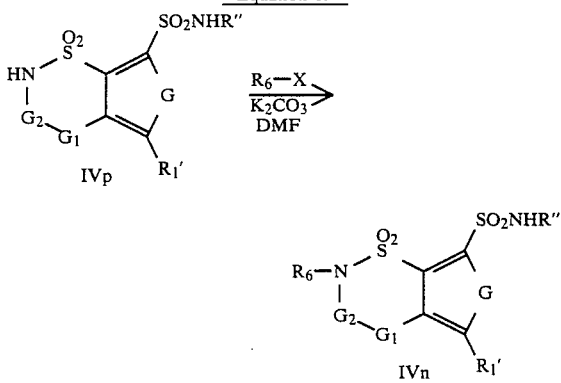

The reaction is carried out by contacting the sulfonamides IVo or IVp with the appropriate electrophile in the presence of a suitable base such as $K_2CO_3$ in an inert, polar solvent such as DMF at 0° to 100° C. for 0.5 to 24 hours. In some instances the $R_6$ function can also be introduced by Michael addition of IVo or IVp to the appropriate Michael acceptor as known to one skilled in the art.

While many of the $R_6$ groups can be introduced directly, as described above, some of the $R_6$ groups may best be prepared by standard functional group manipulations upon compounds of Formula IVm or IVn containing an appropriate $R_6$ group precursor as will be known to one skilled in the art. Some examples of these manipulations are the preparation of IVm or IVn where $R_6$ contains an epoxide by the epoxidation of IVm or IVn where $R_6$ contains a carbon-carbon double bond, the preparation of IVm or IVn where $R_6$ contains a sulfone by the oxidation of IVm or IVn where $R_6$ contains a thioether function, the preparation of IVm or IVn where $R_6$ contains $OC(O)CH_3$ by acetylation of IVm or IVn where $R_6$ contains OH, or the preparation of IVm or IVn where $R_6$ contains $NH_2$ by the reduction of IVm or IVn where $R_6$ contains $NO_2$.

The sulfonyl chlorides of Formula XI of Equations 8 and 10 can be prepared by methods outlined in Equations 16 to 19.

As shown in Equation 16, many of the sulfonyl chlorides of Formula XIa and XIb can be prepared from the bicyclic heterocycles of Formula XIIIa and XIIIb, respectively by direct chlorosulfonation. $R_1$ is not H.

Equation 16

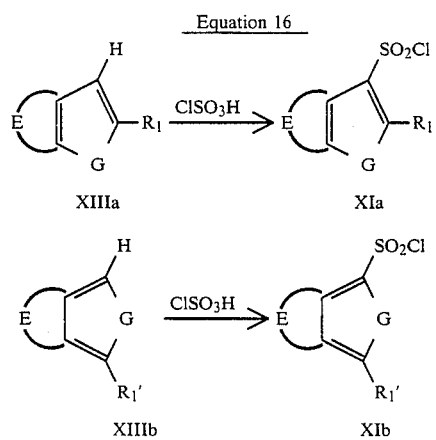

Direct chlorosulfonation can be carried out by standard methods such as those cited by Hartough (loc. cit.) for the preparation of thiophene sulfonylchlorides. For compounds of Formula XIIIa, $R_1$ cannot be hydrogen in order to avoid chlorosulfonation at the more reactive 2-position of the heterocyclic ring. For compounds of Formula IXb, mixtures may result when $R_1'$ is hydrogen due to competitive chlorosulfonation at the 5-position of the heterocyclic ring. These isomers can be separated by standard fractional crystallization, fractional distillation or chromatographic methods.

When G is NH or $NCH_3$, direct ring sulfonation with pyridine-sulfur trioxide complex may be preferable as known to one skilled in the art. The resulting sulfonic acid can be converted to the sulfonyl chlorides by standard methods.

Alternatively, many of the sulfonyl chlorides of Formula XIa and XIb can be prepared from compounds of Formula XIIIa and XIIIb by the four step sequence shown in Equation 17.

Equation 17

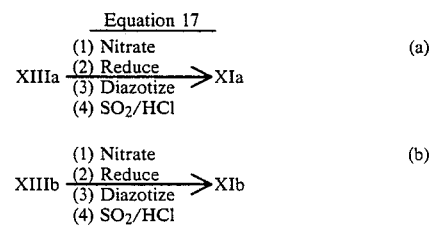

Nitration of compounds can be carried out by standard methods such as those cited by Hartough (loc. cit.) for the thiophene ring system. The same regioselectivity in nitration is observed as described for the chlorosulfonation of XIIa and XIIb (vide supra). The reduction of the intermediate nitro compounds to amines can be carried out by any of several methods as described in *Preparative Organic Chemistry*, 4th Edition, p. 557–563, John Wiley and Sons, New York and London, G. Hilgetag and A. Martini Ed. Diazotization of the amines with sodium nitrite in HCl, followed by reaction of the diazonium salt with sulfur dioxide and cupric chloride in acetic acid analogous to the teachings of Yale and Sowinski, *J. Org. Chem.*, 25, 1824 (1960) provides the desired sulfonyl chlorides.

Alternatively, many of the sulfonyl chlorides can be prepared by a modification of the above procedure whereby the diazotization reaction is carried out in dilute sulfuric acid and the resulting diazonium salt is reacted with sulfur dioxide, HCl and cupric chloride in a cosolvent mixture consisting of acetic acid-water (1:1) and an immiscible, inert solvent such as 1-chlorobutane or methylene chloride at 0°–40° C. for 1 to 24 hours.

Many of the sulfonyl chlorides of Formula XIc and XId can also be prepared from the bromoheterocycles XIIIc and XIIId by the three-step sequence shown in Equation 18. The E bridge must not contain functionality incompatible with the BuLi.

Equation 18

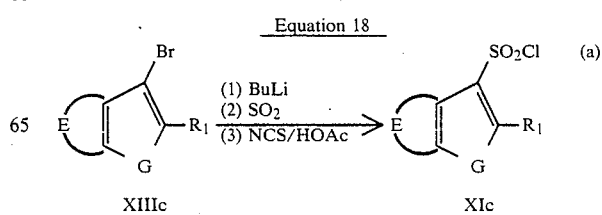

-continued
Equation 18

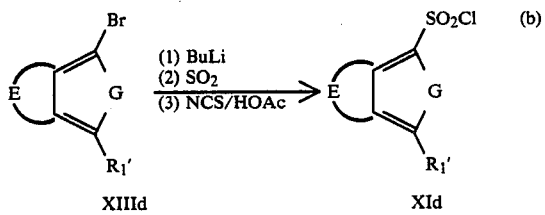

The compounds are contacted with 1.0 equivalents of n-BuLi at −78° C. in a solvent such as THF to give an organo-lithio species via metal-halogen exchange. The lithio species is reacted with sulfur dioxide to give an intermediate sufinate salt which precipitates and is isolated by filtration. The salt is dissolved in a solvent such as acetic acid and treated with a chlorine source such as N-chlorosuccinimide to give the desired sulfonyl chloride.

As shown in Equation 19, many of the sulfonyl chlorides of formula XI can be prepared aby a two step sequence from compounds of Formula XIIIe. X is Cl or Br, R″ is alkyl or benzyl. J must not contain functionality incompatible with a mercaptide anion or molecular chlorine.

Equation 19

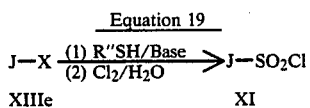

The halogenated heterocyclic XIIIe is contacted with an alkyl or benzyl mercaptan in the presence of a base such as $K_2CO_3$ or NaH, in a solvent such as DMF, at 0° to 150° C. for 1 to 24 hours to give an intermediate thioether. The thioether intermediate is oxidatively chlorinated by addition of molecular chlorine or a chlorine equivalent in the presence of water at −20° to 80° C. in an aliphatic carboxylic acid solvent such as propionic acid or an inert organic solvent such as dichloroethane for 1 to 24 hours.

The bicyclic heterocycles XIII in equations 16 to 19 are either known or can be prepared by one skilled in the art of thiophene, furan and pyrrole chemistry. For example, the bicyclic ring systems are accessible from suitably substituted thiophenes, furans or pyrroles by standard chemical manipulation including, but not limited to, alkylation, acylation, oxidation, reduction, addition, elimination, condensation, cyclization, halogenation and/or organometalic reactions. Examples of a variety of E-bridge forming reactions on a benzene nucleus can be found in EP-A-No. 107,979 and EP-A-No. 79,683. These methods can be adapted for use with a thiophene, a furan or a pyrrole nucleus as will be known to one skilled in the art. Alternatively, the bicyclic ring systems can be prepared from suitably substituted 1,4-dicarbonyl compounds by standard dehydrative cyclizations to form the thiophene, furan or pyrrole nucleus as known to one skilled in the art. The synthesis of 1,4-dicarbonyl compounds and their conversion to thiophenes, furans and pyrroles is widely reported. The literature on thiophenes, furans and pyrroles is extensive.

In some cases, formation of the E-bridge after the sulfonamide functionality is present may be preferable to alter the reactivity of the molecule as will be known to one skilled in the art. One example is shown in Equation 20 where behavior of the E-bridge forming reaction is affected by the presence of the sulfonamide substituent on the thiophene ring.

Equation 20

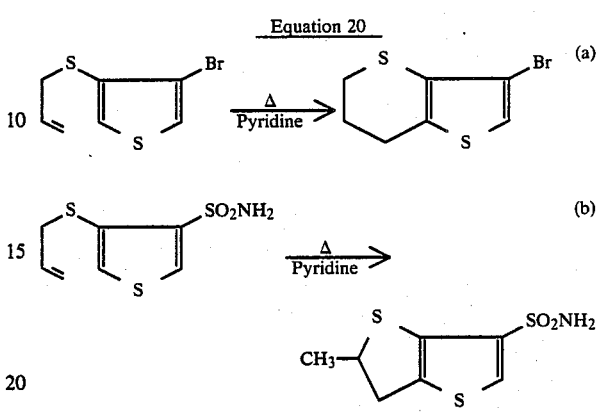

The thioclaisen reaction shown in equation 20a produces the six ring isomer as the major cyclization product while arrangement of the sulfonamide substituted system in Equation 20b gives predominantly the 5-ring isomer as product.

The amines of Formula III in Equations 1 and 4 are also important intermediates for the preparation of the compounds of this invention and are described below.

The pyrimidines and triazines of Formula (IIIa) to (IIId) below are either known or can be prepared by obvious methods known to one skilled in the art.

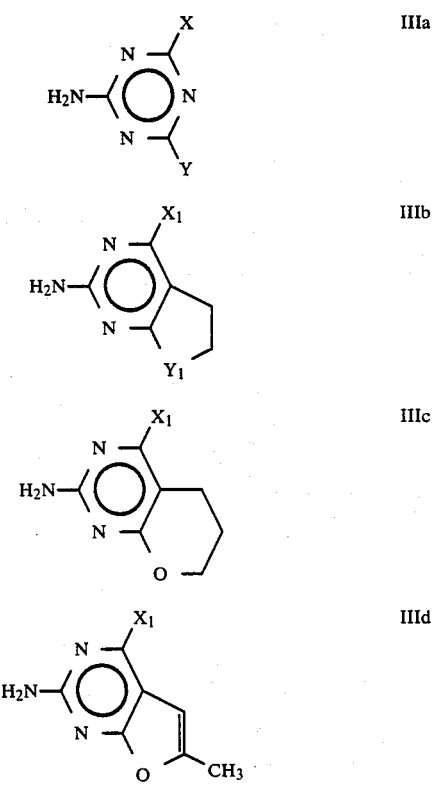

For a review of the synthesis the reactions of 2-aminopyrimidines (IIIa, Z=CR′) see *The Chemistry of Heterocyclic Compounds*, Vol. 16, John Wiley and Sons, New York (1962). For a review of the synthesis and reactions of 2-amino-s-triazines (IIIa, Z=N) see *The Chemistry of Heterocyclic Compounds*, Vol. 13, John Wiley, New York (1959), F. C. Schaefer, U.S. Pat. No. 3,154,547 and F. C. Schaefer and K. R. Huffman, *J. Org. Chem.*, 28, 1812 (1963). The synthesis of the bicyclic amines IIIb and IIIc is taught in European Patent Application No. 15,683. The synthesis of bicyclic amines IIId is taught in European Patent Application No. 46,677.

The amines of Formula III where X is $OCF_2H$ or $CF_3$; or $X_1$ is $OCF_2H$ and/or Y is $WCF_2T$ wherein W is O or S and T is H, CHClF, CHBrF or $CHFCF_3$ can be prepared by methods taught in South African Patent Application No. 82/5045, or by suitable modifications that would be obvious to one skilled in the art.

The pyrimidines of Formula IIIa (Z=CH) where Y is $-CR_5(OCH_3)_2$, $-CR_5(OCH_2CH_3)_2$,

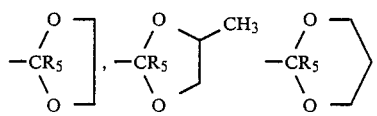

can be prepared according to the methods taught in European Patent Application No. 84,224 or suitable modifications thereof known to one skilled in the art.

The triazine amines of Formula IIIe where $X_3$ is $CH_3$ or $OCH_3$ and R is H or $CH_3$ can be prepared according to the methods of European Patent Application No. 94,260.

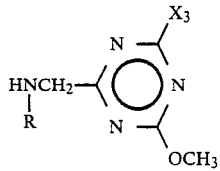

IIIe

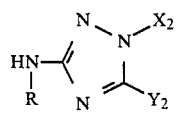

IIIf

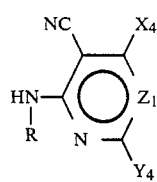

IIIg

Preparations of the 3-amino-1,2,4-triazoles of Formula IIIf and the cyanoheterocycles of Formula (IIIg) are described in European Patent Applications Nos. 73,562 and 126,864, respectively.

Many of the aminoheterocyclic intermediates of Formula (III) where R is methyl may be prepared by a two-step procedure as described for IIIh in Equation 21. X, Y and Z are as previously defined.

Equation 21

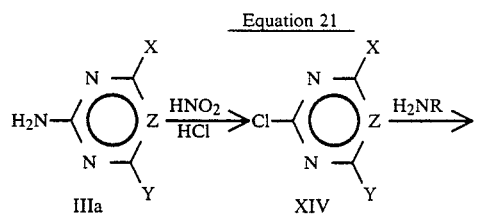

IIIh

A solution of the amine IIIa in concentrated hydrochloric acid is treated with sodium nitrite solution and the chloro compound X is isolated in the usual manner by filtration of the acidic solution. A representative procedure is described by Bee and Rose in *J. Chem. Soc. C.*, 2031 (1966), for the case in which Z=CH, and $X=Y=OCH_3$. Displacement of the chlorine of X may be accomplished by heating with an excess of methylamine in water to obtain the methylamino heterocycle (IIIh).

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydride). Quaternary amine salts can be made by similar techniques.

Salts of compounds of Formula I can als be prepared by exchange of one cation for another. Cationic exchange can be affected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid. e.g., p-toluenesulfonic acid, trichloroacetic acid or the like.

In the following examples, all parts are by weight and temperatures are in °C. unless otherwise indicated.

EXAMPLE 1

3-Allylthio-4-bromothiophene 48.4 g (0.20 mol) of 3,4-dibromothiophene was added to a −78° C. solution of 0.21 mol of n-butyllithium (130 mls of a 1.6M solution in hexanes, Aldrich) in 200 mls of anhydrous ether under a nitrogen atmosphere at such a rate that the temperature did not rise above −70° C. The mixture was stirred at −78° C. for 15 minutes and treated with 6.4 g (0.21 mol) of elemental sulfur causing the temperature to rise to −50° C. The suspension was recooled to −78° C., stirred for 1 hour, treated with 18.2 g (0.21 mol) of allyl bromide and allowed to warm to 20° C. The solution was washed with water and brine, dried over MgSO4 and concentrated to give 47.5 g of an orange oil. 38 g of this oil was chromatographed on 500 g of SiO2 eluting with hexane to give 30.2 g of the desired product as a colorless oil.

90 MHz NMR (CDCl3): δ 7.4–7.1 (AB, 2H, arom); 6.2–5.6 (m, 1H, vinyl); 5.2–4.9 (m, 2H, vinyl); 3.45 (d, 2H, CH2).

IR (neat) 3100, 1630, 1470, 1320, 980, 930 cm$^{-1}$.

EXAMPLE 2

3-Bromo-6,7-dihydro-5H-thieno[3,2-b]thiopyran

A solution of 30.2 g (0.13 mol) of 3-allylthio-4-bromothiophene and 10.3 mls (0.13 mol) of pyridine in 250 mls of toluene was refluxed for 68 hours, cooled, washed with 1N HCl solution, 1N NaOH solution, water and brine and dried over MgSO4 and concentrated to give 27.2 g of an amber oil. The oil was chromatographed on 500 g of SiO2 eluting with hexane to give 16.2 g of the desired product as a colorless oil (90% purity).

90 MHz NMR (CDCl3): δ 7.15 (s, 1H, arom); 3.1–2.7 (m, 4H, CH2's); 2.3–2.0 (m, 2H, CH2).

IR (neat) 3100, 2920, 1510, 1310, 1110, 960, 900 cm$^{-1}$.

EXAMPLE 3

6,7-Dihydro-5H-thieno[3,2-b]thiopyran-3-sulfonamide

A solution of 11.8 g (0.05 mol) of 3-bromo-6,7-dihydro-5H-thieno[3,2-b]thiopyran in 50 mls of anhydrous ether was added dropwise to a solution of 0.055 mol of n-butyllithium (1.6M in hexane) in 100 mls of anhydrous ether such that the temperature remained below −70° C. The solution was stirred for 15 minutes at −78° C., treated with 3.0 mls (0.07 mol) of liquified SO2 (exotherm to −50° C.), allowed to warm to 20° C. and stirred for 16 hours. The resulting precipitate was filtered, washed with ether and hexane and dried to give 12.5 g of the sulfinate salt as a cream colored powder, m.p. >300° C.

9.7 g (0.043 mol) of this salt was dissolved in 80 mls of glacial acetic acid and treated with 5.7 g of N-chlorosuccinimide. After 5 minutes, the solution was poured into ice-water and the resulting precipitate was filtered, washed with water and hexane and dried to give 8.15 g of the sulfonyl chloride as a yellow powder, m.p. 80°–87° C.

The sulfonyl chloride was dissolved in 100 mls of methylene chloride and treated with 2.5 mls of liquified ammonia at −78° C. The mixture was warmed to 20° C., 100 mls of 1N HCl was added and the methylene chloride phase was separated, washed with brine, dried over MgSO4 and concentrated to give 6.2 g of the desired sulfonamide as a white powder, m.p. 146°–149° C.

200 MHz NMR (CDCl3): δ 7.9 (s, 1H, arom); 4.95 (b, 2H, NH2); 3.10 (m, 2H, CH2); 2.90 (t, 2H, CH2); 2.30 (m, 2H, CH2).

IR (nujol) 3360, 3260, 3100, 1545, 1320, 1150, 960 cm$^{-1}$.

EXAMPLE 4

6,7-Dihydro-5H-thieno[3,2-b]thiopyran-3-sulfonamide, 4,4-dioxide

A suspension of 9.0 g (0.038 mol) of 6,7-dihydro-5H-thieno[3,2-b]thiopyran-3-sulfonamide in 200 mls of methylene chloride was treated with 2.0 equivalents of m-chloroperbenzoic acid at −5° C. to 0° C. The mixture was stirred for 30 minutes at 0° C., 200 mls of saturated sodium bicarbonate solution was added and the methylene chloride layer and suspended solids were separated. The methylene chloride layer was concentrated and the combined solids were washed with water and ether and dried to give 7.8 g of the desired sulfonamide as a white powder, m.p. 213°–215° C.

90 MHz NMR (CDCl3): δ 8.2 (s, 1H, arom); 7.2 (b, 2H, NH2); 3.7–2.2 (m, 6H, CH2's).

IR (nujol) 3390, 3270, 3100, 1345, 1280, 1150, 1115 cm$^{-1}$.

EXAMPLE 5

N-[(4,6-dimethoxypyrimidin-2-yl)aminocarbonyl]-6,7-dihydro-5H-thieno[3,2-b]thiopyran-3-sulfonamide, 4,4-dioxide A mixture of 10.5 g (0.039 mol) of 6,7-dihydro-5H-thieno[3,2-b]thiopyran-3-sulfonamide-4,4-dioxide, 6.9 g of potassium carbonate and 5.3 ml of n-butyl isocyanate were refluxed in 300 mls of dry acetonitrile for 16 hours, cooled and filtered. The solid was dissolved in water, acidified to pH 3 with concentrated HCl and the resulting precipitate was filtered, washed with water and ether and dried in vacuo at 70° C. to give 10.7 g of the n-butylurea as a cream colored solid, m.p. 193°–195° C.

A mixture of 10.2 g of the butylurea, 3.1 mls of butyl isocyanate and 0.1 g of DABCO were heated in 200 mls of dry xylenes and treated with 3.0 ml of liquified phosgene at such a rate that the temperature remained above 134° C. The mixture was refluxed for 1.5 hours, excess phosgene and HCl were purged with dry nitrogen and the mixture was cooled to 20° C. The resulting solid was filtered under nitrogen and washed with dry xylenes to give 7.0 g of the sulfonyl isocyanate as a light gray powder, m.p. 216°–230° C., IR 2240 cm$^{-1}$.

1.4 g of the sulfonyl isocyanate was dissolved in 20 mls of dry methylene chloride and filtered to remove some insolubles. The filtrate was treated with 0.31 g of 2-amino-4,6-dimethoxypyrimidine, heated to reflux for 1 minute and allowed to stir at 20° C. for 1.5 hours. The resulting precipitate was filtered, washed with dry methylene chloride and air dried to give 0.37 g of the desired sulfonylurea as a white powder, m.p. 228°–230° C.

200 MHz NMR (CDCl3): δ 12.57 (b, 1H, NH); 8.33 (s, 1H, arom); 7.20 (d, 1H, NH); 5.75 (s, 1H, CH); 3.97 (s, 6H, OCH3's); 3.40 (m, 2H, CH2); 3.05 (m, 2H, CH2); and 2.60 (m, 2H, CH2).

IR (nujol) 3380, 1720, 1700, 1600, 1445, 1375, 1195, 1155 cm$^{-1}$.

EXAMPLE 6

4-Bromo-3-thiophenecarboxylic Acid

To 400 ml of dry ether, under nitrogen, cooled to −70° C., was added a solution of 256 ml of n-butyllithium (1.6 m in hexane). A solution of 96.8 g of 3,4-dibromothiophene in 600 ml of ether was added, dropwise over a 20 minute period, maintaining the reaction temperature between −78° C. and −60° C. After stirring for an additional 5 minutes, the solution was transferred via a double-tipped needle, under nitrogen pressure, to an already prepared solution of 80 g of crushed dry ice in 400 ml of ether. The temperature was maintained at below −50° C. during this addition. The resulting white mixture was stirred for 5 minutes, quenched with 800 ml of water, and the layers separated. The etheral layer was washed with 500 ml of saturated sodium bicarbonate solution. The aqueous layers were combined and acidified with concentrated hydrochloric acid to yield a white solid which was filtered off and recrystallized from water/ethanol (5:2) to give 73 g of the title compound as needles; m.p. 157°–158° C.

EXAMPLE 7

4-Carboxy-3-thiopheneacetic ethyl ester

A solution of sodium ethoxide was prepared by portionwise addition of 16.8 g of sodium pellets, washed free of oil with hexane, to 960 ml of absolute ethanol. After all the sodium had reacted, the solution was cooled to 0° C. and 59 ml of ethyl acetoacetate was added dropwise over a 20 minute period. After stirring an additional 5 minutes at 0° C., 64 g of 4-bromo-3-thiophenecarboxylic acid and 3.2 g of copper powder were added in one portion. The copper colored mixture was refluxed for 7 hours, cooled, and poured into 3 l of water. Acidification with concentrated hydrochloric acid precipitated the product, which was filtered off and suction dried. Recrystallization from acetonitrile gave 45 g of the title compound as a white cottony solid; m.p. 159°–161° C.

EXAMPLE 8

6,7-Dihydro-4H-thieno[(3,4-C)]pyran-4-one

Sodium hydride (50% in oil), was washed free of oil with hexane, and suspended in 400 ml of dry tetrahydrofuran. To this suspension was added 28 g of the compound in the previous example, portionwise. A slight exotherm was noted with concommitant gas evolution. After the gas evolution had ceased, 7.0 g of lithium tetrahydridoborate was added in one portion and the resultant off white mixture was refluxed for 3 hours. After cooling, 1 l of water was added followed by careful acidification with concentrated hydrochloric acid to pH=1. The aqueous mixture was extracted with ether, washed with water and dried over magnesium sulfate. Evaporation of the solvent, followed by trituration of the crude residue with hexane, gave 20 g of the intermediate hydroxy-acid. To 19 g of this solid dissolved in 1 l of benzene was added 1.2 g of para-toluenesulfonic acid and the mixture refluxed, with a Dean Stark trap, for 2 hours. After cooling the benzene solution was washed with 200 ml of saturated sodium bicarbonate and dried over magnesium sulfate. Evaporation gave 16 g of the title compound as a white crystalline solid; m.p. 75°–77° C.

NMR (CDCl$_3$): ppm 8.25 (s, 1H, ArH); 7.2 (m, 1H, ArH); 4.5 (t, 2H, OCH$_2$); 3.0 (t, 2H, CH$_2$).

IR (Nujol) 1710 cm$^{-1}$ (C=O)

EXAMPLE 9

1-Chloro-6,7-dihydro-4H-thieno[(3,4-C)]-pyran-4-one

To a solution of 9.0 g of the lactone described in the previous example in 90 ml of benzene, containing 90 ml of acetic acid, was added 8.3 g of N-chlorosuccinimide in one portion. The mixture was stirred for 30 minutes at room temperature and then brought to reflux for 1 hour. After cooling, the reaction mixture was poured into 2 l of water and extracted with 3x-500 ml portions of ether. The combined ethereal layers were washed with saturated sodium bicarbonate, water, and dried over magnesium sulfate. Evaporation of the solvent gave an oil which crystallized on cooling to yield a yellow solid which was triturated with n-butylchloride to afford 8.0 g of the title compound as a white crystalline material; m.p. 116°–120° C.

NMR (CDCl$_3$); ppm 8.1 (s, 1H, ArH); 4.5 (t, 2H, OCH$_2$); 2.9 (t, 2H, CH$_2$).

EXAMPLE 10

1-Chloro-6,7-dihydro-4H-thieno[3,4-C]pyran-4-one-3-sulfonamide

To a solution of 10 ml of chloroform, containing 0.75 ml of chlorosulfonic acid, was added 1.0 g of the lactone described in the previous example. A slight exotherm was noted. The reaction solution was refluxed for 3 hours and cooled. To this mixture was added 0.8 ml of thionyl chloride and reflux was continued an additional 2 hours. The reaction was cooled, poured onto ice, and extracted with methylene chloride. The organic layer was washed with saturated sodium bicarbonate and dried over magnesium sulfate. Evaporation of the solvent afforded a yellow oil which slowly crystallized. The crude sulfonyl chloride was dissolved in 50 ml of tetrahydrofuran and treated with 0.5 ml of concentrated ammonium hydroxide. A slight exotherm was noted along with concomitant formation of a white solid. The reaction mixture was stirred overnight and the tetrahydrofuran evaporated. The residue was taken up in methylene chloride and water. The organic layer was dried over magnesium sulfate. Evaporation of the methylene chloride gave a tan residue, which after trituration with n-butylchloride, afforded 300 mg of the title compound, after filtration and drying, as a white solid; m.p. 205°–208° C.

EXAMPLE 11

1-Chloro-N-[(4,6-dimethoxypyrimidin-2-yl)aminocarbonyl]-6,7-dihydro-4-oxo-4H-thieno[3,4-c]pyran-3-sulfonamide To a cloudy solution of 0.27 g of the product of the previous example and 0.28 g of phenyl(4,6-dimethoxypyrimidin-2-yl)carbamate in 10 ml of p-dioxane was added 0.15 ml of 1,5-diazabicyclo[5.4.0]undec-5-ene (DBU). The reaction was stirred for 1 hour, diluted with 30 ml of water, and filtered. The filtrate was acidified with 5 drops of concentrated hydrochloric acid to afford a white precipitate which was filtered off and washed with a small portion of water. The precipitate was suction dried and further dried in vacuo at 60° C., to afford 200 mg of the title compound as a white solid; m.p. 110°–114° C.

NMR (CDCl$_3$) ppm 13.24 (bs, 1H, SO$_2$NH); 7.4 (bs, 1H, CONH); 5.79 (s, 1H, pyH); 4.53 (t, 2H, OCH$_2$); 4.02 (s, 6H, 2-OCH$_3$); 2.96 (s, 2H, CH$_2$).

IR (Nujol) 1720, 1705 cm$^{-1}$ (C=O's).

Following the procedures described in Equations 1–21 and Examples 1–11, one skilled in the art can readily prepare the following compounds.

GENERAL TABLE OF STRUCTURES
Structure Ia
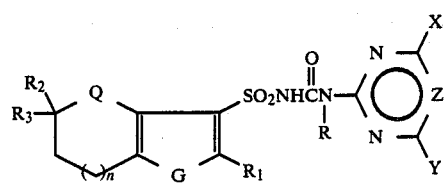
Structure Ib
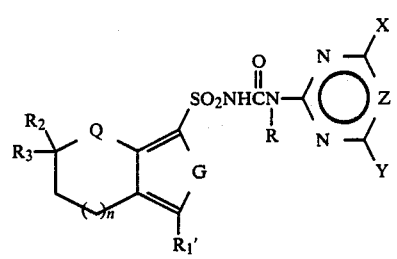
Structure Ic
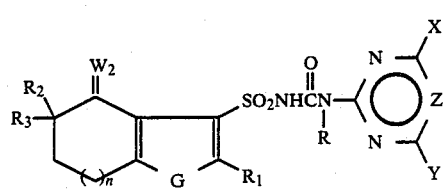
Structure Id
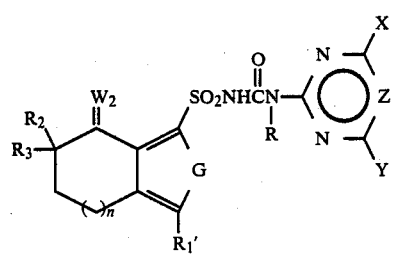
Structure Ie
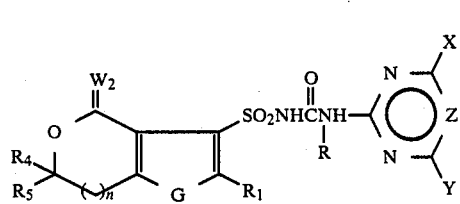
Structure If
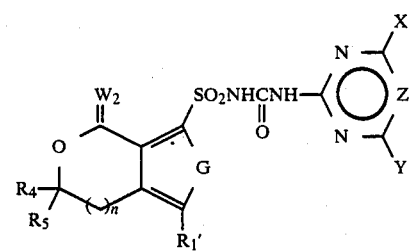
Structure Ig
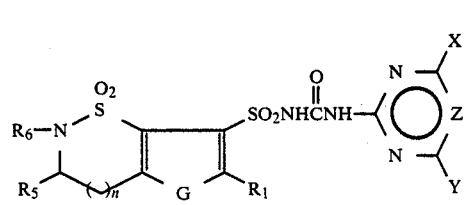
-continued
GENERAL TABLE OF STRUCTURES
Structure Ih
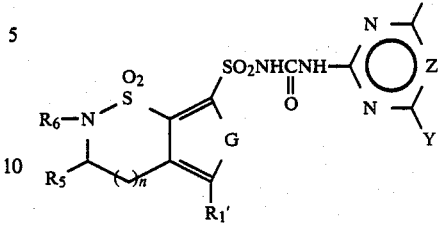
Structure Ii
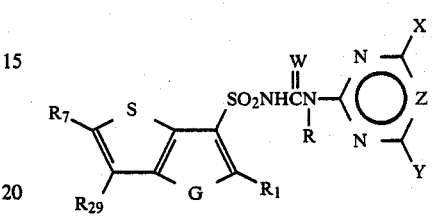
Structure Ij
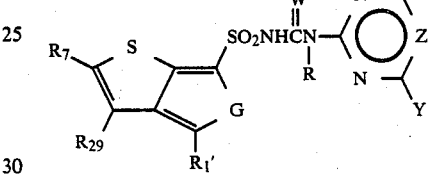
Structure Ik
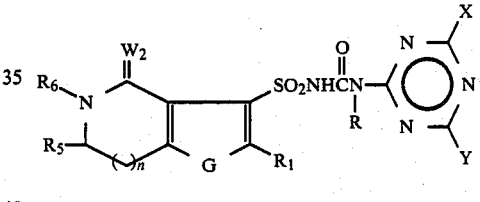
Structure Il
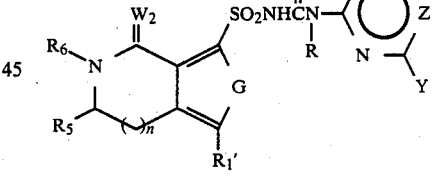
Structure Im
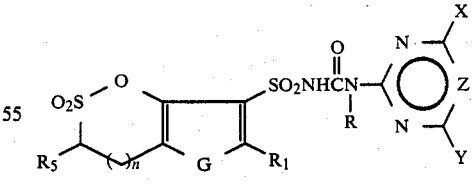
Structure In
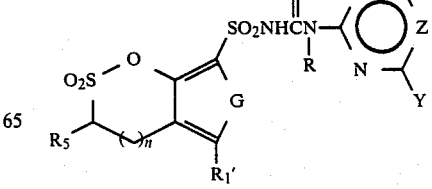

-continued
GENERAL TABLE OF STRUCTURES
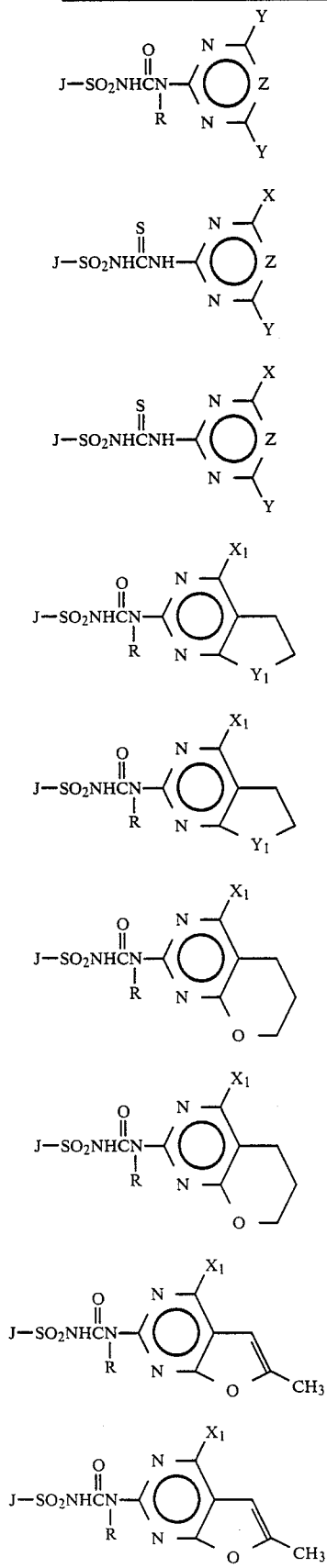
Structure Io
Structure Ip
Structure Iq
Structure IIa
Structure IIb
Structure IIIa
Structure IIIb
Structure IVa
Structure IVb
-continued
GENERAL TABLE OF STRUCTURES
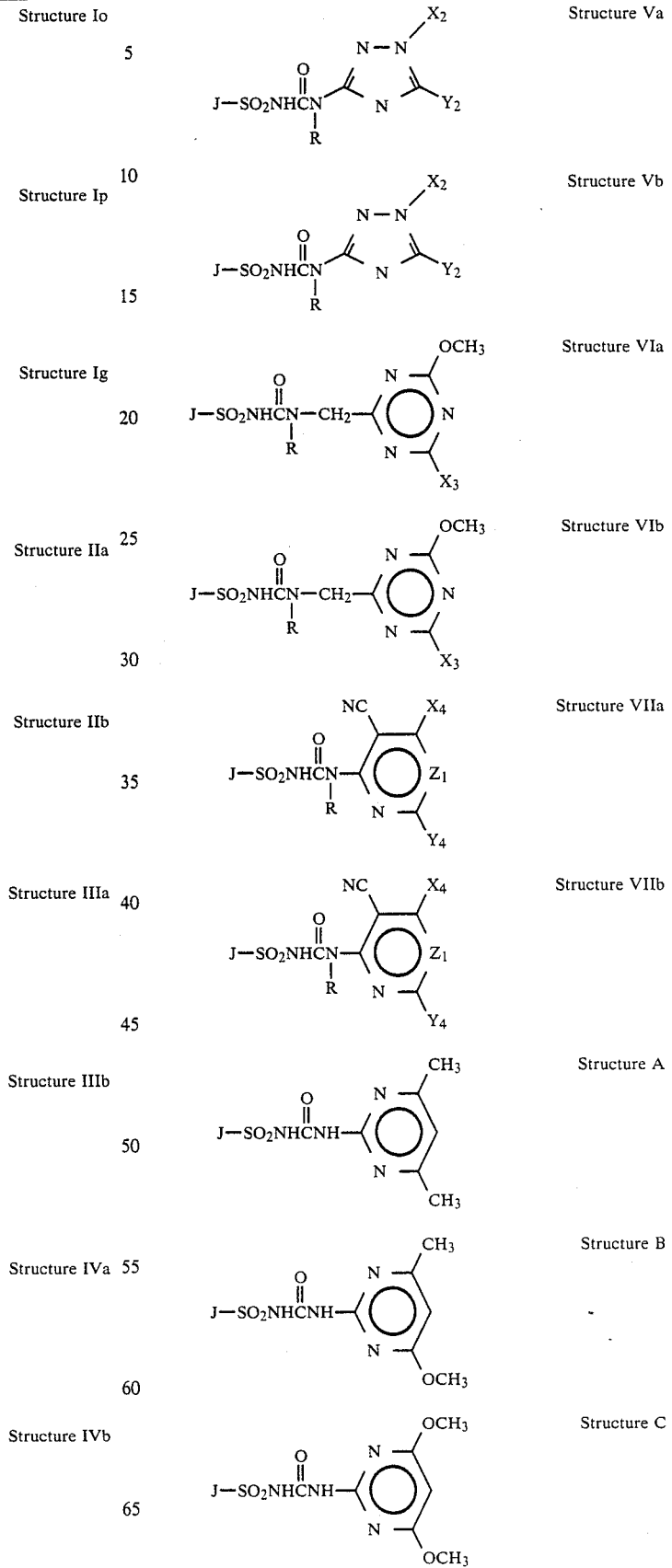
Structure Va
Structure Vb
Structure VIa
Structure VIb
Structure VIIa
Structure VIIb
Structure A
Structure B
Structure C -continued
GENERAL TABLE OF STRUCTURES

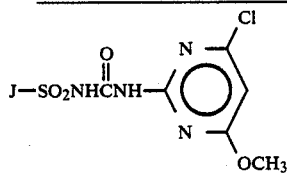
Structure D

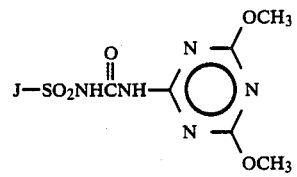
Structure F

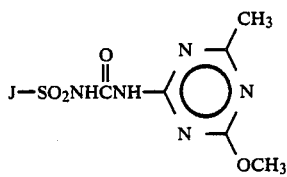
Structure E

TABLE Ia

| | | | | | Structure Ia | | | | | |
|---|---|---|---|---|---|---|---|---|---|---|
| n | Q | G | R | $R_1$ | $R_2$ | $R_3$ | X | Y | Z | m.p.(°C.) |
| 1 | $SO_2$ | S | H | H | H | H | $CH_3$ | $CH_3$ | CH | 214–220° |
| 1 | $SO_2$ | S | H | H | H | H | $CH_3$ | $OCH_3$ | CH | 224–226° |
| 1 | $SO_2$ | S | H | H | H | H | $OCH_3$ | $OCH_3$ | CH | 228–230° |
| 1 | $SO_2$ | S | H | H | H | H | Cl | $OCH_3$ | CH | 214–220° |
| 1 | $SO_2$ | S | H | H | H | H | $CH_3$ | $OCH_3$ | N | 195–197° |
| 1 | $SO_2$ | S | H | H | H | H | $OCH_3$ | $OCH_3$ | N | 190–194° |
| 0 | $SO_2$ | S | H | H | H | H | $CH_3$ | $CH_3$ | CH | |
| 0 | $SO_2$ | S | H | H | H | H | $CH_3$ | $OCH_3$ | CH | |
| 0 | $SO_2$ | S | H | H | H | H | $OCH_3$ | $OCH_3$ | CH | |
| 0 | $SO_2$ | S | H | H | H | H | Cl | $OCH_3$ | CH | |
| 0 | $SO_2$ | S | H | H | H | H | Br | $OCH_3$ | CH | |
| 0 | $SO_2$ | S | H | H | H | H | $CH_3$ | $OCH_3$ | N | |
| 0 | $SO_2$ | S | H | H | H | H | $OCH_3$ | $OCH_3$ | N | |
| 0 | $SO_2$ | S | H | H | $CH_3$ | H | $CH_3$ | $CH_3$ | CH | 218–219 |
| 0 | $SO_2$ | S | H | H | $CH_3$ | H | $CH_3$ | $OCH_3$ | CH | 208–209 |
| 0 | $SO_2$ | S | H | H | $CH_3$ | H | $OCH_3$ | $OCH_3$ | CH | 186–187 |
| 0 | $SO_2$ | S | H | H | $CH_3$ | H | Cl | $OCH_3$ | CH | 203–204 |
| 0 | $SO_2$ | S | H | H | $CH_3$ | H | Br | $OCH_3$ | CH | |
| 0 | $SO_2$ | S | H | H | $CH_3$ | H | $CH_3$ | $OCH_3$ | N | 192–193 |
| 0 | $SO_2$ | S | H | H | $CH_3$ | H | $OCH_3$ | $OCH_3$ | N | 176–178 |
| 0 | $SO_2$ | S | H | H | $CH_3$ | $CH_3$ | $CH_3$ | $CH_3$ | CH | 189–191 |
| 0 | $SO_2$ | S | H | H | $CH_3$ | $CH_3$ | $CH_3$ | $OCH_3$ | CH | 208–210 |
| 0 | $SO_2$ | S | H | H | $CH_3$ | $CH_3$ | $OCH_3$ | $OCH_3$ | CH | 237–238 |
| 0 | $SO_2$ | S | H | H | $CH_3$ | $CH_3$ | Cl | $OCH_3$ | CH | 231–232 |
| 0 | $SO_2$ | S | H | H | $CH_3$ | $CH_3$ | Br | $OCH_3$ | CH | |
| 0 | $SO_2$ | S | H | H | $CH_3$ | $CH_3$ | $CH_3$ | $OCH_3$ | N | 136–140 |
| 0 | $SO_2$ | S | H | H | $CH_3$ | $CH_3$ | $OCH_3$ | $OCH_3$ | N | 202–203 |
| 1 | $SO_2$ | S | H | H | $CH_3$ | H | $CH_3$ | $CH_3$ | CH | |
| 1 | $SO_2$ | S | H | H | $CH_3$ | H | $CH_3$ | $OCH_3$ | CH | |
| 1 | $SO_2$ | S | H | H | $CH_3$ | H | $OCH_3$ | $OCH_3$ | CH | |
| 1 | $SO_2$ | S | H | H | $CH_3$ | H | Cl | $OCH_3$ | CH | |
| 1 | $SO_2$ | S | H | H | $CH_3$ | H | Br | $OCH_3$ | CH | |
| 1 | $SO_2$ | S | H | H | $CH_3$ | H | $CH_3$ | $OCH_3$ | N | |
| 1 | $SO_2$ | S | H | H | $CH_3$ | H | $OCH_3$ | $OCH_3$ | N | |
| 1 | $SO_2$ | S | H | H | $CH_3$ | $CH_3$ | $CH_3$ | $OCH_3$ | CH | |
| 1 | $SO_2$ | S | H | H | $CH_3$ | $CH_3$ | $OCH_3$ | $OCH_3$ | CH | |
| 1 | S | S | H | H | H | H | $CH_3$ | $OCH_3$ | N | |
| 1 | S | S | H | H | H | H | $OCH_3$ | $OCH_3$ | CH | |
| 1 | S | S | H | H | $CH_3$ | H | $CH_3$ | $OCH_3$ | N | |
| 1 | S | S | H | H | $CH_3$ | H | $OCH_3$ | $OCH_3$ | CH | |
| 1 | S | S | H | H | $CH_3$ | $CH_3$ | $OCH_3$ | $OCH_3$ | CH | |
| 0 | S | S | H | H | H | H | $CH_3$ | $CH_3$ | CH | |
| 0 | S | S | H | H | H | H | $CH_3$ | $OCH_3$ | CH | |
| 0 | S | S | H | H | H | H | $OCH_3$ | $OCH_3$ | CH | |
| 0 | S | S | H | H | H | H | Cl | $OCH_3$ | CH | |
| 0 | S | S | H | H | H | H | Br | $OCH_3$ | CH | |
| 0 | S | S | H | H | H | H | $CH_3$ | $OCH_3$ | N | |
| 0 | S | S | H | H | H | H | $OCH_3$ | $OCH_3$ | N | |
| 0 | S | S | H | H | $CH_3$ | H | $CH_3$ | $CH_3$ | CH | 197–198 |
| 0 | S | S | H | H | $CH_3$ | H | $CH_3$ | $OCH_3$ | CH | 199–200 |
| 0 | S | S | H | H | $CH_3$ | H | $OCH_3$ | $OCH_3$ | CH | 190–191 |
| 0 | S | S | H | H | $CH_3$ | H | Cl | $OCH_3$ | CH | 185–186 |
| 0 | S | S | H | H | $CH_3$ | H | Br | $OCH_3$ | CH | |
| 0 | S | S | H | H | $CH_3$ | H | $CH_3$ | $OCH_3$ | N | 182–183 |
| 0 | S | S | H | H | $CH_3$ | H | $OCH_3$ | $OCH_3$ | N | 179–181 |
| 0 | S | S | H | H | $CH_3$ | $CH_3$ | $CH_3$ | $CH_3$ | CH | 190–191 |
| 0 | S | S | H | H | $CH_3$ | $CH_3$ | $CH_3$ | $OCH_3$ | CH | 163–164 |
| 0 | S | S | H | H | $CH_3$ | $CH_3$ | $OCH_3$ | $OCH_3$ | CH | 180–181 |

TABLE Ia-continued

Structure Ia

| n | Q | G | R | R₁ | R₂ | R₃ | X | Y | Z | m.p.(°C.) |
|---|---|---|---|----|----|----|---|---|---|-----------|
| 0 | S | S | H | H | CH₃ | CH₃ | Cl | OCH₃ | CH | 166–167 |
| 0 | S | S | H | H | CH₃ | CH₃ | Br | OCH₃ | CH | |
| 0 | S | S | H | H | CH₃ | CH₃ | CH₃ | OCH₃ | N | 187–188 |
| 0 | S | S | H | H | CH₃ | CH₃ | OCH₃ | OCH₃ | N | 173–174 |
| 0 | SO | S | H | H | CH₃ | H | CH₃ | CH₃ | CH | |
| 0 | SO | S | H | H | CH₃ | H | CH₃ | OCH₃ | CH | |
| 0 | SO | S | H | H | CH₃ | H | OCH₃ | OCH₃ | CH | |
| 0 | SO | S | H | H | CH₃ | H | Cl | OCH₃ | CH | |
| 0 | SO | S | H | H | CH₃ | H | Br | OCH₃ | CH | |
| 0 | SO | S | H | H | CH₃ | H | CH₃ | OCH₃ | N | |
| 0 | SO | S | H | H | CH₃ | H | OCH₃ | OCH₃ | N | |
| 0 | O | S | H | H | H | H | CH₃ | OCH₃ | N | |
| 0 | O | S | H | H | H | H | OCH₃ | OCH₃ | CH | |
| 0 | O | S | H | H | CH₃ | H | CH₃ | OCH₃ | N | |
| 0 | O | S | H | H | CH₃ | H | OCH₃ | OCH₃ | CH | |
| 0 | O | S | H | H | CH₃ | CH₃ | CH₃ | OCH₃ | N | |
| 0 | O | S | H | H | CH₃ | CH₃ | OCH₃ | OCH₃ | CH | |
| 1 | O | S | H | H | CH₃ | H | OCH₃ | OCH₃ | N | |
| 1 | O | S | H | H | CH₃ | H | OCH₃ | OCH₃ | CH | |
| 0 | CH₂ | S | H | H | H | H | CH₃ | OCH₃ | N | |
| 0 | CH₂ | S | H | H | H | H | OCH₃ | OCH₃ | CH | |
| 1 | CH₂ | S | H | H | H | H | CH₃ | OCH₃ | N | |
| 1 | CH₂ | S | H | H | H | H | OCH₃ | OCH₃ | CH | |
| 0 | CH₂ | O | H | H | H | H | CH₃ | OCH₃ | N | |
| 0 | CH₂ | O | H | H | H | H | OCH₃ | OCH₃ | CH | |
| 1 | CH₂ | O | H | H | H | H | CH₃ | OCH₃ | N | |
| 1 | CH₂ | O | H | H | H | H | OCH₃ | OCH₃ | CH | |
| 0 | CH₂ | NH | H | H | H | H | CH₃ | OCH₃ | N | |
| 0 | CH₂ | NH | H | H | H | H | OCH₃ | OCH₃ | CH | |
| 1 | CH₂ | NH | H | H | H | H | CH₃ | OCH₃ | N | |
| 1 | CH₂ | NH | H | H | H | H | OCH₃ | OCH₃ | CH | |
| 0 | CH₂ | NCH₃ | H | H | H | H | CH₃ | OCH₃ | N | |
| 0 | CH₂ | NCH₃ | H | H | H | H | OCH₃ | OCH₃ | CH | |
| 1 | CH₂ | NCH₃ | H | H | H | H | CH₃ | OCH₃ | N | |
| 1 | CH₂ | NCH₃ | H | H | H | H | OCH₃ | OCH₃ | CH | |
| 0 | CHCH₃ | S | H | H | H | H | CH₃ | OCH₃ | N | |
| 0 | CHCH₃ | S | H | H | H | H | OCH₃ | OCH₃ | CH | |
| 0 | SO₂ | O | H | CH₃ | H | H | CH₃ | CH₃ | CH | |
| 0 | SO₂ | O | H | CH₃ | H | H | CH₃ | OCH₃ | CH | |
| 0 | SO₂ | O | H | CH₃ | H | H | OCH₃ | OCH₃ | CH | |
| 0 | SO₂ | O | H | CH₃ | H | H | Cl | OCH₃ | CH | |
| 0 | SO₂ | O | H | CH₃ | H | H | Br | OCH₃ | CH | |
| 0 | SO₂ | O | H | CH₃ | H | H | CH₃ | OCH₃ | N | |
| 0 | SO₂ | O | H | CH₃ | H | H | OCH₃ | OCH₃ | N | |
| 0 | SO₂ | NH | H | CH₃ | H | H | CH₃ | CH₃ | CH | |
| 0 | SO₂ | NH | H | CH₃ | H | H | CH₃ | OCH₃ | CH | |
| 0 | SO₂ | NH | H | CH₃ | H | H | OCH₃ | OCH₃ | CH | |
| 0 | SO₂ | NH | H | CH₃ | H | H | Cl | OCH₃ | CH | |
| 0 | SO₂ | NH | H | CH₃ | H | H | Br | OCH₃ | CH | |
| 0 | SO₂ | NH | H | CH₃ | H | H | CH₃ | OCH₃ | N | |
| 0 | SO₂ | NH | H | CH₃ | H | H | OCH₃ | OCH₃ | N | |
| 0 | SO₂ | NCH₃ | H | CH₃ | H | H | CH₃ | CH₃ | CH | |
| 0 | SO₂ | NCH₃ | H | CH₃ | H | H | CH₃ | OCH₃ | CH | |
| 0 | SO₂ | NCH₃ | H | CH₃ | H | H | OCH₃ | OCH₃ | CH | |
| 0 | SO₂ | NCH₃ | H | CH₃ | H | H | Cl | OCH₃ | CH | |
| 0 | SO₂ | NCH₃ | H | CH₃ | H | H | Br | OCH₃ | CH | |
| 0 | SO₂ | NCH₃ | H | CH₃ | H | H | CH₃ | OCH₃ | N | |
| 0 | SO₂ | NCH₃ | H | CH₃ | H | H | OCH₃ | OCH₃ | N | |
| 0 | SO₂ | S | H | CH₃ | H | H | CH₃ | CH₃ | CH | |
| 0 | SO₂ | S | H | CH₃ | H | H | CH₃ | OCH₃ | CH | |
| 0 | SO₂ | S | H | CH₃ | H | H | OCH₃ | OCH₃ | CH | |
| 0 | SO₂ | S | H | CH₃ | H | H | Cl | OCH₃ | CH | |
| 0 | SO₂ | S | H | CH₃ | H | H | Br | OCH₃ | CH | |
| 0 | SO₂ | S | H | CH₃ | H | H | CH₃ | OCH₃ | N | |
| 0 | SO₂ | S | H | CH₃ | H | H | OCH₃ | OCH₃ | N | |
| 0 | SO₂ | S | H | CH₃ | CH₃ | H | CH₃ | CH₃ | CH | |
| 0 | SO₂ | S | H | CH₃ | CH₃ | H | CH₃ | OCH₃ | CH | |
| 0 | SO₂ | S | H | CH₃ | CH₃ | H | OCH₃ | OCH₃ | CH | |
| 0 | SO₂ | S | H | CH₃ | CH₃ | H | Cl | OCH₃ | CH | |
| 0 | SO₂ | S | H | CH₃ | CH₃ | H | Br | OCH₃ | CH | |
| 0 | SO₂ | S | H | CH₃ | CH₃ | H | CH₃ | OCH₃ | N | |
| 0 | SO₂ | S | H | CH₃ | CH₃ | H | OCH₃ | OCH₃ | N | |
| 0 | SO₂ | S | H | CH₃ | CH₃ | CH₃ | CH₃ | CH₃ | CH | |
| 0 | SO₂ | S | H | CH₃ | CH₃ | CH₃ | CH₃ | OCH₃ | CH | |
| 0 | SO₂ | S | H | CH₃ | CH₃ | CH₃ | Cl | OCH₃ | CH | |
| 0 | SO₂ | S | H | CH₃ | CH₃ | CH₃ | Br | OCH₃ | CH | |
| 0 | SO₂ | S | H | CH₃ | CH₃ | CH₃ | CH₃ | OCH₃ | N | |
| 0 | SO₂ | S | H | CH₃ | CH₃ | CH₃ | OCH₃ | OCH₃ | N | |
| 0 | SO₂ | S | H | Cl | H | H | CH₃ | CH₃ | CH | |

TABLE Ia-continued

Structure Ia

| n | Q | G | R | R₁ | R₂ | R₃ | X | Y | Z | m.p.(°C.) |
|---|---|---|---|---|---|---|---|---|---|---|
| 0 | SO₂ | S | H | Cl | H | H | CH₃ | OCH₃ | CH | |
| 0 | SO₂ | S | H | Cl | H | H | OCH₃ | OCH₃ | CH | |
| 0 | SO₂ | S | H | Cl | H | H | Cl | OCH₃ | CH | |
| 0 | SO₂ | S | H | Cl | H | H | Br | OCH₃ | CH | |
| 0 | SO₂ | S | H | Cl | H | H | CH₃ | OCH₃ | N | |
| 0 | SO₂ | S | H | Cl | H | H | OCH₃ | OCH₃ | N | |
| 0 | SO₂ | S | H | Cl | CH₃ | H | CH₃ | CH₃ | CH | |
| 0 | SO₂ | S | H | Cl | CH₃ | H | CH₃ | OCH₃ | CH | 214–215 |
| 0 | SO₂ | S | H | Cl | CH₃ | H | OCH₃ | OCH₃ | CH | 209–210 |
| 0 | SO₂ | S | H | Cl | CH₃ | H | Cl | OCH₃ | CH | 190–194 |
| 0 | SO₂ | S | H | Cl | CH₃ | H | Br | OCH₃ | CH | |
| 0 | SO₂ | S | H | Cl | CH₃ | H | CH₃ | OCH₃ | N | |
| 0 | SO₂ | S | H | Cl | CH₃ | H | OCH₃ | OCH₃ | N | |
| 0 | SO₂ | S | H | Cl | CH₃ | CH₃ | OCH₃ | OCH₃ | CH | |
| 0 | SO₂ | S | H | Br | H | H | CH₃ | OCH₃ | N | |
| 0 | SO₂ | S | H | Br | H | H | CH₃ | OCH₃ | CH | |
| 0 | SO₂ | S | H | Br | H | H | OCH₃ | OCH₃ | CH | |
| 0 | SO₂ | S | H | Br | CH₃ | H | CH₃ | OCH₃ | N | |
| 0 | SO₂ | S | H | Br | CH₃ | H | CH₃ | OCH₃ | CH | |
| 0 | SO₂ | S | H | Br | CH₃ | H | OCH₃ | OCH₃ | CH | |
| 0 | SO₂ | S | H | OCH₃ | H | H | CH₃ | OCH₃ | N | |
| 0 | SO₂ | S | H | OCH₃ | H | H | CH₃ | OCH₃ | CH | |
| 0 | SO₂ | S | H | OCH₃ | H | H | OCH₃ | OCH₃ | CH | |
| 0 | SO₂ | S | H | OCH₃ | CH₃ | H | CH₃ | OCH₃ | N | |
| 0 | SO₂ | S | H | OCH₃ | CH₃ | H | CH₃ | OCH₃ | CH | |
| 0 | SO₂ | S | H | OCH₃ | CH₃ | H | OCH₃ | OCH₃ | CH | |
| 0 | SO₂ | S | H | SCH₃ | H | H | CH₃ | OCH₃ | N | |
| 0 | SO₂ | S | H | SCH₃ | H | H | CH₃ | OCH₃ | CH | |
| 0 | SO₂ | S | H | SCH₃ | H | H | OCH₃ | OCH₃ | CH | |
| 0 | SO₂ | S | H | SCH₃ | CH₃ | H | CH₃ | OCH₃ | N | |
| 0 | SO₂ | S | H | SCH₃ | CH₃ | H | CH₃ | OCH₃ | CH | |
| 0 | SO₂ | S | H | SCH₃ | CH₃ | H | OCH₃ | OCH₃ | CH | |
| 0 | SO₂ | S | H | SO₂CH₃ | H | H | CH₃ | OCH₃ | N | |
| 0 | SO₂ | S | H | SO₂CH₃ | H | H | CH₃ | OCH₃ | CH | |
| 0 | SO₂ | S | H | SO₂CH₃ | H | H | OCH₃ | OCH₃ | CH | |
| 0 | SO₂ | S | H | SO₂CH₃ | CH₃ | H | CH₃ | OCH₃ | N | |
| 0 | SO₂ | S | H | SO₂CH₃ | CH₃ | H | CH₃ | OCH₃ | CH | |
| 0 | SO₂ | S | H | SO₂CH₃ | CH₃ | H | OCH₃ | OCH₃ | CH | |
| 0 | SO₂ | S | H | NO₂ | H | H | CH₃ | OCH₃ | N | |
| 0 | SO₂ | S | H | NO₂ | H | H | OCH₃ | OCH₃ | CH | |
| 0 | SO₂ | S | H | NO₂ | H | H | OCH₃ | OCH₃ | CH | |
| 0 | SO₂ | S | H | NO₂ | CH₃ | H | CH₃ | OCH₃ | N | |
| 0 | SO₂ | S | H | NO₂ | CH₃ | H | CH₃ | OCH₃ | CH | |
| 0 | SO₂ | S | H | NO₂ | CH₃ | H | OCH₃ | OCH₃ | CH | |
| 0 | S | S | H | CH₃ | CH₃ | H | CH₃ | OCH₃ | N | |
| 0 | S | S | H | CH₃ | CH₃ | H | CH₃ | OCH₃ | CH | |
| 0 | S | S | H | CH₃ | CH₃ | H | OCH₃ | OCH₃ | CH | |
| 0 | S | S | H | OCH₃ | CH₃ | H | CH₃ | OCH₃ | CH | |
| 0 | S | S | H | OCH₃ | CH₃ | H | OCH₃ | OCH₃ | CH | |
| 0 | S | S | H | Cl | CH₃ | H | CH₃ | CH₃ | CH | 200–202 |
| 0 | S | S | H | Cl | CH₃ | H | CH₃ | OCH₃ | CH | 180–182 |
| 0 | S | S | H | Cl | CH₃ | H | OCH₃ | OCH₃ | CH | 197–199 |
| 0 | S | S | H | Cl | CH₃ | H | CH₃ | OCH₃ | N | 157–159 |
| 0 | S | S | H | Cl | CH₃ | H | OCH₃ | OCH₃ | N | 163–164 |
| 0 | S | S | H | Cl | CH₃ | H | Cl | OCH₃ | CH | 168–170 |
| 0 | S | S | H | SCH₃ | CH₃ | H | CH₃ | OCH₃ | N | |
| 0 | S | S | H | SCH₃ | CH₃ | H | CH₃ | OCH₃ | CH | |
| 0 | S | S | H | SCH₃ | CH₃ | H | OCH₃ | OCH₃ | CH | |
| 0 | S | S | H | SO₂CH₃ | CH₃ | H | CH₃ | OCH₃ | N | |
| 0 | S | S | H | SO₂CH₃ | CH₃ | H | CH₃ | OCH₃ | CH | |
| 0 | S | S | H | SO₂CH₃ | CH₃ | H | OCH₃ | OCH₃ | CH | |
| 0 | S | S | H | NO₂ | CH₃ | H | CH₃ | OCH₃ | N | |
| 0 | S | S | H | NO₂ | CH₃ | H | CH₃ | OCH₃ | CH | |
| 0 | S | S | H | NO₂ | CH₃ | H | OCH₃ | OCH₃ | CH | |
| 0 | SO₂ | S | H | H | CH₂CH₃ | H | CH₃ | OCH₃ | N | |
| 0 | SO₂ | S | H | H | CH₂CH₃ | H | CH₃ | OCH₃ | CH | |
| 0 | SO₂ | S | H | H | CH₂CH₃ | H | OCH₃ | OCH₃ | CH | |
| 0 | SO₂ | S | H | H | CH₂CH₂CH₃ | H | OCH | OCH₃ | CH₃ | |
| 0 | SO₂ | S | H | H | H | CH(CH₃)₂ | OCH | OCH₃ | CH₃ | |
| 0 | SO₂ | S | H | H | H | C(CH₃)₃ | OCH₃ | OCH₃ | CH | |
| 0 | SO₂ | S | CH₃ | H | H | CH₃ | CH₃ | OCH₃ | CH | |
| 0 | SO₂ | S | CH₃ | H | H | CH₃ | CH₃ | OCH₃ | CH | |
| 0 | SO₂ | S | CH₃ | H | H | CH₃ | CH₃ | OCH₃ | N | |
| 0 | SO₂ | S | CH₃ | H | H | CH₃ | OCH₃ | OCH₃ | N | |
| 0 | SO₂ | S | H | H | CH₃ | H | OCH₂CH₃ | OCH₃ | CH | |
| 0 | SO₂ | S | H | H | CH₃ | H | OCH₂CH₂CH₃ | OCH₃ | CH | |
| 0 | SO₂ | S | H | H | CH₃ | H | OCH(CH₃)₂ | OCH₃ | CH | |
| 0 | SO₂ | S | H | H | CH₃ | H | F | OCH₃ | CH | |
| 0 | SO₂ | S | H | H | CH₃ | H | CH₂F | OCH₃ | CH | |

TABLE Ia-continued

Structure Ia

| n | Q | G | R | $R_1$ | $R_2$ | $R_3$ | X | Y | Z | m.p.(°C.) |
|---|---|---|---|---|---|---|---|---|---|---|
| 0 | $SO_2$ | S | H | H | $CH_3$ | H | $OCHF_2$ | $OCH_3$ | CH | |
| 0 | $SO_2$ | S | H | H | $CH_3$ | H | $OCH_2CF_3$ | CH | | |
| 0 | $SO_2$ | S | H | H | $CH_3$ | H | $CF_3$ | $OCH_3$ | CH | |
| 0 | $SO_2$ | S | H | H | $CH_3$ | H | $OCH_3$ | H | CH | |
| 0 | $SO_2$ | S | H | H | $CH_3$ | H | $OCH_3$ | $OCH_2CH_3$ | CH | |
| 0 | $SO_2$ | S | H | H | $CH_3$ | H | $OCH_3$ | $CH_2CH_3$ | CH | |
| 0 | $SO_2$ | S | H | H | $CH_3$ | H | $OCH_3$ | $CH_2CH_2CH_3$ | CH | |
| 0 | $SO_2$ | S | H | H | $CH_3$ | H | $OCH_3$ | cyclo-propyl | N | |
| 0 | $SO_2$ | S | H | H | $CH_3$ | H | $OCH_3$ | $C{\equiv}CH$ | CH | |
| 0 | $SO_2$ | S | H | H | $CH_3$ | H | $OCH_3$ | $C{\equiv}CCH_3$ | CH | |
| 0 | $SO_2$ | S | H | H | $CH_3$ | H | $OCH_3$ | $CH_2C{\equiv}CCH_3$ | CH | |
| 0 | $SO_2$ | S | H | H | $CH_3$ | H | $OCH_3$ | $CH_2OCH_3$ | CH | |
| 0 | $SO_2$ | S | H | H | $CH_3$ | H | $OCH_3$ | $NH_2$ | CH | |
| 0 | $SO_2$ | S | H | H | $CH_3$ | H | $OCH_2CH_3$ | $NHCH_3$ | N | |
| 0 | $SO_2$ | S | H | H | $CH_3$ | H | $OCH_3$ | $N(CH_3)_2$ | CH | |
| 0 | $SO_2$ | S | H | H | $CH_3$ | H | $OCH_3$ | $CF_3$ | CH | |
| 0 | $SO_2$ | S | H | H | $CH_3$ | H | $OCH_3$ | $SCH_3$ | CH | |
| 0 | $SO_2$ | S | H | H | $CH_3$ | H | $OCH_3$ | $OCH_2CH{=}CH_2$ | CH | |
| 0 | $SO_2$ | S | H | H | $CH_3$ | H | $OCH_3$ | $OCH_2C{\equiv}CH$ | CH | |
| 0 | $SO_2$ | S | H | H | $CH_3$ | H | $OCH_3$ | CH | CH | |
| 0 | $SO_2$ | S | H | H | $CH_3$ | H | $OCH_3$ | $N_3$ | CH | |
| 0 | $SO_2$ | S | H | H | $CH_3$ | H | $OCH_3$ | $OCH_2CH_2OCH_3$ | CH | |
| 0 | $SO_2$ | S | H | H | $CH_3$ | H | $OCH_3$ | $CH_2SCH_3$ | CH | |
| 0 | $SO_2$ | S | H | H | $CH_3$ | H | $OCH_3$ | $CH(OCH_3)_2$ | CH | |
| 0 | $SO_2$ | S | H | H | $CH_3$ | H | $OCH_3$ | $CH(SCH_3)_2$ | CH | |
| 0 | $SO_2$ | S | H | H | $CH_3$ | H | $OCH_3$ | $C(CH_3)(OCH_3)_2$ | CH | |
| 0 | $SO_2$ | S | H | H | $CH_3$ | H | $OCH_3$ | 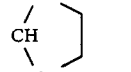 | CH | |
| 0 | $SO_2$ | S | H | H | $CH_3$ | H | $OCH_3$ | 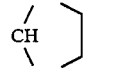 | CH | |
| 0 | $SO_2$ | S | H | H | $CH_3$ | H | $OCH_3$ | 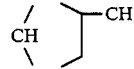 | CH | |
| 0 | $SO_2$ | S | H | H | $CH_3$ | H | $OCH_3$ | $CH(OCH_2CH_3)_2$ | CH | |
| 0 | $SO_2$ | S | H | H | $CH_3$ | H | $OCH_3$ | $OCF_2H$ | CH | |
| 0 | $SO_2$ | S | H | H | $CH_3$ | H | $OCH_3$ | $SCF_2H$ | CH | |
| 0 | $SO_2$ | S | H | H | $CH_3$ | H | $OCH_3$ | $OCF_2CHClF$ | CH | |
| 0 | $SO_2$ | S | H | H | $CH_3$ | H | $OCH_3$ | $OCF_2CHBrF$ | CH | |
| 0 | $SO_2$ | S | H | H | $CH_3$ | H | $OCH_3$ | $OCF_2CHFCF_3$ | CH | |
| 0 | $SO_2$ | S | H | H | $CH_3$ | H | $OCH_3$ | $OCH_3$ | $CCH_3$ | |
| 0 | $SO_2$ | S | H | H | $CH_3$ | H | $OCH_3$ | $OCH_3$ | $CC_2H_5$ | |
| 0 | $SO_2$ | S | H | H | $CH_3$ | H | $OCH_3$ | $OCH_3$ | CCl | |
| 0 | $SO_2$ | S | H | H | $CH_3$ | H | $OCH_3$ | $OCH_3$ | CBr | |
| 0 | $SO_2$ | S | H | H | $CH_3$ | H | $OCH_3$ | $(CH_2)_3CH_3$ | CH | |
| 0 | $SO_2$ | S | H | H | $CH_3$ | H | $OCH_3$ | $O(CH_2)_3CH_3$ | CH | |
| 0 | $SO_2$ | S | H | H | $CH_3$ | H | $OCH_3$ | $O(CH_2)_3CF_3$ | CH | |
| 0 | $SO_2$ | S | H | H | $CH_3$ | H | $OCH_3$ | $(CH_2)_3CF_3$ | CH | |
| 0 | $SO_2$ | S | H | H | $CH_3$ | H | $OCH_3$ | $S(CH_2)_3CF_3$ | CH | |
| 0 | $SO_2$ | S | H | H | $CH_3$ | H | $OCH_3$ | $S(CH_2)_2CH_3$ | CH | |
| 0 | $SO_2$ | S | H | H | $CH_3$ | H | $OCH_3$ | I | CH | |
| 0 | $SO_2$ | S | H | H | $CH_3$ | H | $OCH_3$ | $CH_2O(CH_2)_3CH_3$ | CH | |
| 0 | $SO_2$ | S | H | H | $CH_3$ | H | $OCH_3$ | $NH(CH_2)_3CH_3$ | CH | |
| 0 | $SO_2$ | S | H | H | $CH_3$ | H | $OCH_3$ | $N(CH_2CH_2CH_3)_2$ | CH | |
| 0 | $SO_2$ | S | H | H | $CH_3$ | H | $OCH_3$ | $OCH_2CH{=}CHCH_3$ | CH | |
| 0 | $SO_2$ | S | H | H | $CH_3$ | H | $OCH_3$ | $OCH_2C{\equiv}CCH_3$ | CH | |
| 0 | $SO_2$ | S | H | H | $CH_3$ | H | $OCH_3$ | $CH_2S(CH_2)_3CH_3$ | CH | |
| 0 | $SO_2$ | S | H | H | $CH_3$ | H | $OCH_3$ | $(CH_2)_4Cl$ | CH | |
| 0 | $SO_2$ | S | H | H | $CH_3$ | H | $OCH_3$ | cyclo-pentyl | CH | |
| 0 | $SO_2$ | S | H | H | $CH_3$ | H | $OCH_3$ | CHO | CH | |
| 0 | $SO_2$ | S | H | H | $CH_3$ | H | $OCH_3$ | $C(O)CH_3$ | CH | |
| 0 | $SO_2$ | S | H | H | $CH_3$ | H | $OCH_3$ | $CH(SCH_3)_2$ | CH | |
| 0 | $SO_2$ | S | H | H | $CH_3$ | H | $OCH_3$ | 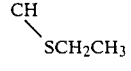 | CH | |

TABLE Ia-continued

Structure Ia

| n | Q | G | R | $R_1$ | $R_2$ | $R_3$ | X | Y | Z | m.p.(°C.) |
|---|---|---|---|---|---|---|---|---|---|---|
| 0 | $SO_2$ | S | H | H | $CH_3$ | H | $OCH_3$ | 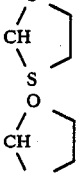 | CH | |
| 0 | $SO_2$ | S | H | H | $CH_3$ | H | $OCH_3$ | 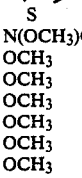 | CH | |
| 0 | $SO_2$ | S | H | H | $CH_3$ | H | $OCH_3$ | $N(OCH_3)CH_3$ | CH | |
| 0 | $SO_2$ | S | H | H | $CH_3$ | H | $CH_2CH_3$ | $OCH_3$ | CH | |
| 0 | $SO_2$ | S | H | H | $CH_3$ | H | $(CH_2)_3CH_3$ | $OCH_3$ | CH | |
| 0 | $SO_2$ | S | H | H | $CH_3$ | H | $O(CH_2)_3CH_3$ | $OCH_3$ | CH | |
| 0 | $SO_2$ | S | H | H | $CH_3$ | H | $O(CH_2)_3CCl_3$ | $OCH_3$ | CH | |
| 0 | $SO_2$ | S | H | H | $CH_3$ | H | $(CH_2)_4F$ | $OCH_3$ | CH | |
| 0 | $SO_2$ | S | H | H | $CH_3$ | H | $S(CH_2)_4Br$ | $OCH_3$ | CH | |
| 0 | $SO_2$ | S | H | H | $CH_3$ | H | $SC(CH_3)_3$ | $OCH_3$ | CH | |
| 0 | $SO_2$ | S | H | H | $CH_3$ | H | $(CH_2)_4OCH_3$ | $OCH_3$ | CH | |
| 0 | $SO_2$ | S | H | H | $CH_3$ | H | $O(CH_2)_4OCH_3$ | CH | | |
| 0 | $SO_2$ | S | H | H | $CH_3$ | H | $NH_2$ | $OCH_3$ | CH | |
| 0 | $SO_2$ | S | H | H | $CH_3$ | H | $NHCH(CH_3)_2$ | $OCH_3$ | CH | |
| 0 | $SO_2$ | S | H | H | $CH_3$ | H | $N[CH(CH_3)_2]_2$ | $OCH_3$ | CH | |
| 0 | $SO_2$ | S | H | H | H | H | $OCH_2CH_3$ | $NHCH_3$ | N | |
| 0 | $SO_2$ | S | H | $CH_3$ | $CH_3$ | H | $OCH_2CH_3$ | $NHCH_3$ | N | |
| 0 | $SO_2$ | S | H | Cl | $CH_3$ | H | $OCH_2CH_3$ | $NHCH_3$ | N | |

TABLE Ib

Structure Ib

| n | G | Q | R | $R_1'$ | $R_2$ | $R_3$ | X | Y | Z | m.p. (°C.) |
|---|---|---|---|---|---|---|---|---|---|---|
| 0 | S | $SO_2$ | H | H | $CH_3$ | H | $CH_3$ | $CH_3$ | CH | |
| 0 | S | $SO_2$ | H | H | $CH_3$ | H | $CH_3$ | $OCH_3$ | CH | |
| 0 | S | $SO_2$ | H | H | $CH_3$ | H | $OCH_3$ | $OCH_3$ | CH | |
| 0 | S | $SO_2$ | H | H | $CH_3$ | H | Cl | $OCH_3$ | CH | |
| 0 | S | $SO_2$ | H | H | $CH_3$ | H | Br | $OCH_3$ | CH | |
| 0 | S | $SO_2$ | H | H | $CH_3$ | H | $CH_3$ | $OCH_3$ | N | |
| 0 | S | $SO_2$ | H | H | $CH_3$ | H | $OCH_3$ | $OCH_3$ | N | |
| 0 | S | S | H | H | $CH_3$ | H | $CH_3$ | $CH_3$ | CH | |
| 0 | S | S | H | H | $CH_3$ | H | $CH_3$ | $OCH_3$ | CH | |
| 0 | S | S | H | H | $CH_3$ | H | $OCH_3$ | $OCH_3$ | CH | |
| 0 | S | S | H | H | $CH_3$ | H | Cl | $OCH_3$ | CH | |
| 0 | S | S | H | H | $CH_3$ | H | Br | $OCH_3$ | CH | |
| 0 | S | S | H | H | $CH_3$ | H | $CH_3$ | $OCH_3$ | N | |
| 0 | S | S | H | H | $CH_3$ | H | $OCH_3$ | $OCH_3$ | N | |
| 0 | S | $SO_2$ | H | H | H | H | $CH_3$ | $OCH_3$ | N | |
| 0 | S | $SO_2$ | H | H | H | H | $CH_3$ | $OCH_3$ | CH | |
| 0 | S | $SO_2$ | H | H | H | H | $OCH_3$ | $OCH_3$ | CH | |
| 0 | S | $SO_2$ | H | H | $CH_3$ | $CH_3$ | $CH_3$ | $OCH_3$ | N | |
| 0 | S | $SO_2$ | H | H | $CH_3$ | $CH_3$ | $CH_3$ | $OCH_3$ | CH | |
| 0 | S | $SO_2$ | H | H | $CH_3$ | $CH_3$ | $OCH_3$ | $OCH_3$ | CH | |
| 0 | S | S | H | H | H | H | $CH_3$ | $OCH_3$ | N | |
| 0 | S | S | H | H | H | H | $CH_3$ | $OCH_3$ | CH | |
| 0 | S | S | H | H | H | H | $OCH_3$ | $OCH_3$ | CH | |
| 0 | S | S | H | H | $CH_3$ | $CH_3$ | $CH_3$ | $OCH_3$ | N | |
| 0 | S | S | H | H | $CH_3$ | $CH_3$ | $CH_3$ | $OCH_3$ | CH | |
| 0 | S | S | H | H | $CH_3$ | $CH_3$ | $OCH_3$ | $OCH_3$ | CH | |
| 1 | S | $SO_2$ | H | H | $CH_3$ | H | $CH_3$ | $OCH_3$ | N | |
| 1 | S | $SO_2$ | H | H | $CH_3$ | H | $CH_3$ | $OCH_3$ | CH | |
| 1 | S | $SO_2$ | H | H | $CH_3$ | H | $OCH_3$ | $OCH_3$ | CH | |
| 0 | S | O | H | H | $CH_3$ | H | $CH_3$ | $OCH_3$ | N | |
| 0 | S | O | H | H | $CH_3$ | H | $CH_3$ | $OCH_3$ | CH | |
| 0 | S | O | H | H | $CH_3$ | H | $OCH_3$ | $OCH_3$ | CH | |
| 0 | S | $CH_2$ | H | H | H | H | $CH_3$ | $OCH_3$ | N | |
| 0 | S | $CH_2$ | H | H | H | H | $CH_3$ | $OCH_3$ | CH | |
| 0 | S | $CH_2$ | H | H | H | H | $OCH_3$ | $OCH_3$ | CH | |
| 1 | S | $CH_2$ | H | H | H | H | $CH_3$ | $OCH_3$ | N | |
| 1 | S | $CH_2$ | H | H | H | H | $CH_3$ | $OCH_3$ | CH | |
| 1 | S | $CH_2$ | H | H | H | H | $OCH_3$ | $OCH_3$ | CH | |
| 0 | S | $SO_2$ | H | Cl | $CH_3$ | H | $CH_3$ | $OCH_3$ | N | |
| 0 | S | $SO_2$ | H | Cl | $CH_3$ | H | $CH_3$ | $OCH_3$ | CH | |
| 0 | S | $SO_2$ | H | Cl | $CH_3$ | H | $OCH_3$ | $OCH_3$ | CH | |
| 0 | S | $SO_2$ | H | $CH_3$ | $CH_3$ | H | $CH_3$ | $OCH_3$ | N | |
| 0 | S | $SO_2$ | H | $CH_3$ | $CH_3$ | H | $CH_3$ | $OCH_3$ | CH | |
| 0 | S | $SO_2$ | H | $CH_3$ | $CH_3$ | H | $OCH_3$ | $OCH_3$ | CH | |

TABLE Ic

Structure Ic

| n | W₂ | G | R | R₁ | R₂ | R₃ | X | Y | Z | m.p. (°C.) |
|---|----|---|---|----|----|----|---|---|---|---|
| 1 | O | S | H | CH₃ | H | H | CH₃ | CH₃ | CH | |
| 1 | O | S | H | CH₃ | H | H | CH₃ | OCH₃ | CH | |
| 1 | O | S | H | CH₃ | H | H | OCH₃ | OCH₃ | CH | |
| 1 | O | S | H | CH₃ | H | H | Cl | OCH₃ | CH | |
| 1 | O | S | H | CH₃ | H | H | Br | OCH₃ | CH | |
| 1 | O | S | H | CH₃ | H | H | CH₃ | OCH₃ | N | |
| 1 | O | S | H | CH₃ | H | H | OCH₃ | OCH₃ | N | |
| 1 | O | O | H | CH₃ | H | H | CH₃ | CH₃ | CH | |
| 1 | O | O | H | CH₃ | H | H | CH₃ | OCH₃ | CH | |
| 1 | O | O | H | CH₃ | H | H | OCH₃ | OCH₃ | CH | |
| 1 | O | O | H | CH₃ | H | H | Cl | OCH₃ | CH | |
| 1 | O | O | H | CH₃ | H | H | Br | OCH₃ | CH | |
| 1 | O | O | H | CH₃ | H | H | CH₃ | OCH₃ | N | |
| 1 | O | O | H | CH₃ | H | H | OCH₃ | OCH₃ | N | |
| 1 | O | NH | H | CH₃ | H | H | CH₃ | CH₃ | CH | |
| 1 | O | NH | H | CH₃ | H | H | CH₃ | OCH₃ | CH | |
| 1 | O | NH | H | CH₃ | H | H | OCH₃ | OCH₃ | CH | |
| 1 | O | NH | H | CH₃ | H | H | Cl | OCH₃ | CH | |
| 1 | O | NH | H | CH₃ | H | H | Br | OCH₃ | CH | |
| 1 | O | NH | H | CH₃ | H | H | CH₃ | OCH₃ | N | |
| 1 | O | NH | H | CH₃ | H | H | OCH₃ | OCH₃ | N | |
| 1 | O | NCH₃ | H | CH₃ | H | H | CH₃ | CH₃ | CH | |
| 1 | O | NCH₃ | H | CH₃ | H | H | CH₃ | OCH₃ | CH | |
| 1 | O | NCH₃ | H | CH₃ | H | H | Cl | OCH₃ | CH | |
| 1 | O | NCH₃ | H | CH₃ | H | H | Br | OCH₃ | CH | |
| 1 | O | NCH₃ | H | CH₃ | H | H | CH₃ | OCH₃ | N | |
| 1 | O | NCH₃ | H | CH₃ | H | H | OCH₃ | OCH₃ | N | |
| 0 | O | S | H | CH₃ | H | H | CH₃ | CH₃ | CH | |
| 0 | O | S | H | CH₃ | H | H | CH₃ | OCH₃ | CH | |
| 0 | O | S | H | CH₃ | H | H | OCH₃ | OCH₃ | CH | |
| 0 | O | S | H | CH₃ | H | H | Cl | OCH₃ | CH | |
| 0 | O | S | H | CH₃ | H | H | Br | OCH₃ | CH | |
| 0 | O | S | H | CH₃ | H | H | CH₃ | OCH₃ | N | |
| 0 | O | S | H | CH₃ | H | H | OCH₃ | OCH₃ | N | |
| 1 | O | S | H | H | H | H | CH₃ | CH₃ | CH | |
| 1 | O | S | H | H | H | H | CH₃ | OCH₃ | CH | |
| 1 | O | S | H | H | H | H | OCH₃ | OCH₃ | CH | |
| 1 | O | S | H | H | H | H | Cl | OCH₃ | CH | |
| 1 | O | S | H | H | H | H | Br | OCH₃ | CH | |
| 1 | O | S | H | H | H | H | CH₃ | OCH₃ | N | |
| 1 | O | S | H | H | H | H | OCH | OCH₃ | N | |
| 1 | O | S | H | Cl | H | H | CH₃ | CH₃ | CH₃ | |
| 1 | O | S | H | Cl | H | H | CH₃ | OCH₃ | CH | |
| 1 | O | S | H | Cl | H | H | OCH₃ | OCH₃ | CH | |
| 1 | O | S | H | Cl | H | H | Cl | OCH₃ | CH | |
| 1 | O | S | H | Cl | H | H | Br | OCH₃ | CH | |
| 1 | O | S | H | Cl | H | H | CH₃ | OCH₃ | N | |
| 1 | O | S | H | Cl | H | H | OCH₃ | OCH₃ | N | |
| 1 | O | S | H | CH₃ | CH₃ | H | OCH₃ | OCH₃ | CH | |
| 1 | O | S | H | CH₃ | CH₃ | CH₃ | OCH₃ | OCH₃ | CH | |
| 1 | O | S | H | CH₃ | Cl | Cl | OCH₃ | OCH₃ | CH | |
| 1 | S | S | H | CH₃ | CH₃ | CH₃ | OCH₃ | OCH₃ | CH | |
| 1 | O | S | H | CH₃ | H | H | OCH₂CH₃ | NHCH₃ | N | |

TABLE Id

Structure Id

| n | W₂ | G | R | R₁' | R₂ | R₃ | X | Y | Z | m.p. (°C.) |
|---|----|---|---|-----|----|----|---|---|---|---|
| 1 | O | S | H | H | H | H | CH₃ | CH₃ | CH | |
| 1 | O | S | H | H | H | H | CH₃ | OCH₃ | CH | |
| 1 | O | S | H | H | H | H | OCH₃ | OCH₃ | CH | |
| 1 | O | S | H | H | H | H | Cl | OCH₃ | CH | |
| 1 | O | S | H | H | H | H | Br | OCH₃ | CH | |
| 1 | O | S | H | H | H | H | CH₃ | OCH₃ | N | |
| 1 | O | S | H | H | H | H | OCH₃ | OCH₃ | N | |
| 1 | O | S | H | H | CH₃ | H | OCH₃ | OCH₃ | CH | |
| 1 | O | S | H | H | CH₃ | CH₃ | OCH₃ | OCH₃ | CH | |
| 1 | O | S | H | H | Cl | Cl | OCH₃ | OCH₃ | CH | |
| 1 | O | S | H | CH₃ | H | H | OCH₃ | OCH₃ | CH | |
| 1 | O | S | H | Cl | H | H | OCH₃ | OCH₃ | CH | |
| 0 | O | S | H | H | H | H | CH₃ | CH₃ | CH | |
| 0 | O | S | H | H | H | H | CH₃ | OCH₃ | CH | |
| 0 | O | S | H | H | H | H | OCH₃ | OCH₃ | CH | |
| 0 | O | S | H | H | H | H | Cl | OCH₃ | CH | |
| 0 | O | S | H | H | H | H | Br | OCH₃ | CH | |
| 0 | O | S | H | H | H | H | CH₃ | OCH₃ | N | |
| 0 | O | S | H | H | H | H | OCH₃ | OCH₃ | N | |

TABLE Ie

Structure Ie

| n | W₂ | G | R | R₁ | R₄ | R₅ | X | Y | Z | m.p. (°C.) |
|---|----|---|---|----|----|----|---|---|---|---|
| 1 | O | S | H | CH₃ | H | H | CH₃ | CH₃ | CH | |
| 1 | O | S | H | CH₃ | H | H | CH₃ | OCH₃ | CH | |

TABLE Ie-continued

Structure Ie

| n | W₂ | G | R | R₁ | R₄ | R₅ | X | Y | Z | m.p. (°C.) |
|---|----|----|---|-----|-----|-----|-----|-----|----|-----|
| 1 | O | S | H | CH₃ | H | H | OCH₃ | OCH₃ | CH | |
| 1 | O | S | H | CH₃ | H | H | Cl | OCH₃ | CH | |
| 1 | O | S | H | CH₃ | H | H | Br | OCH₃ | CH | |
| 1 | O | S | H | CH₃ | H | H | CH₃ | OCH₃ | N | |
| 1 | O | S | H | CH₃ | H | H | OCH₃ | OCH₃ | N | |
| 1 | O | O | H | CH₃ | H | H | CH₃ | CH₃ | CH | |
| 1 | O | O | H | CH₃ | H | H | CH₃ | OCH₃ | CH | |
| 1 | O | O | H | CH₃ | H | H | OCH₃ | OCH₃ | CH | |
| 1 | O | O | H | CH₃ | H | H | Cl | OCH₃ | CH | |
| 1 | O | O | H | CH₃ | H | H | Br | OCH₃ | CH | |
| 1 | O | O | H | CH₃ | H | H | CH₃ | OCH₃ | N | |
| 1 | O | O | H | CH₃ | H | H | OCH₃ | OCH₃ | N | |
| 1 | O | NH | H | CH₃ | H | H | CH₃ | CH₃ | CH | |
| 1 | O | NH | H | CH₃ | H | H | CH₃ | OCH₃ | CH | |
| 1 | O | NH | H | CH₃ | H | H | OCH₃ | OCH₃ | CH | |
| 1 | O | NH | H | CH₃ | H | H | Cl | OCH₃ | CH | |
| 1 | O | NH | H | CH₃ | H | H | Br | OCH₃ | CH | |
| 1 | O | NH | H | CH₃ | H | H | CH₃ | OCH₃ | N | |
| 1 | O | NH | H | CH₃ | H | H | OCH₃ | OCH₃ | N | |
| 1 | O | NCH₃ | H | CH₃ | H | H | CH₃ | CH₃ | CH | |
| 1 | O | NCH₃ | H | CH₃ | H | H | CH₃ | OCH₃ | CH | |
| 1 | O | NCH₃ | H | CH₃ | H | H | OCH₃ | OCH₃ | CH | |
| 1 | O | NCH₃ | H | CH₃ | H | H | Cl | OCH₃ | CH | |
| 1 | O | NCH₃ | H | CH₃ | H | H | Br | OCH₃ | CH | |
| 1 | O | NCH₃ | H | CH₃ | H | H | CH₃ | OCH₃ | N | |
| 1 | O | NCH₃ | H | CH₃ | H | H | OCH₃ | OCH₃ | N | |
| 1 | O | S | H | H | H | H | OCH₃ | OCH₃ | CH | |
| 1 | O | S | H | Cl | H | H | OCH₃ | OCH₃ | CH | |
| 1 | O | S | H | H | CH₃ | H | OCH₃ | OCH₃ | CH | |
| 1 | O | S | H | H | CH | CH₃ | OCH₃ | OCH₃ | CH | |
| 1 | O | S | H | H | CH₂CH₃ | H | OCH₃ | OCH₃ | CH | |
| 1 | O | S | H | H | (CH₂)₃CH₃ | H | OCH₃ | OCH₃ | CH | |
| 0 | O | S | H | H | CH₃ | H | CH₃ | CH₃ | CH | |
| 0 | O | S | H | H | CH₃ | H | CH₃ | OCH₃ | CH | |
| 0 | O | S | H | H | CH₃ | H | OCH₃ | OCH₃ | CH | |
| 0 | O | S | H | H | CH₃ | H | Cl | OCH₃ | CH | |
| 0 | O | S | H | H | CH₃ | H | Br | OCH₃ | CH | |
| 0 | O | S | H | H | CH₃ | H | CH₃ | OCH₃ | N | |
| 0 | O | S | H | H | CH₃ | H | OCH₃ | OCH₃ | N | |
| 0 | S | S | H | H | H | H | OCH₃ | OCH₃ | CH | |
| 0 | O | S | H | H | H | H | OCH₂CH₃ | NCH₃ | N | |
| 1 | O | S | H | H | H | H | OCH₂CH₃ | NHCH₃ | N | |

TABLE If

Structure If

| W₂ | n | G | R | R₁' | R₄ | R₅ | X | Y | Z | m.p. (°C.) |
|----|---|---|---|-----|-----|-----|-----|-----|----|-----|
| O | 1 | S | H | H | H | H | CH₃ | CH₃ | CH | |
| O | 1 | S | H | H | H | H | CH₃ | OCH₃ | CH | |
| O | 1 | S | H | H | H | H | OCH₃ | OCH₃ | CH | |
| O | 1 | S | H | H | H | H | Cl | OCH₃ | CH | |
| O | 1 | S | H | H | H | H | Br | OCH₃ | CH | |
| O | 1 | S | H | H | H | H | CH₃ | OCH₃ | N | |
| O | 1 | S | H | H | H | H | OCH₃ | OCH₃ | N | |
| O | 0 | S | H | H | H | H | CH₃ | CH₃ | CH | |
| O | 0 | S | H | H | H | H | CH₃ | OCH₃ | CH | |
| O | 0 | S | H | H | H | H | OCH₃ | OCH₃ | CH | |
| O | 0 | S | H | H | H | H | Cl | OCH₃ | CH | |
| O | 0 | S | H | H | H | H | Br | OCH₃ | CH | |
| O | 0 | S | H | H | H | H | CH₃ | OCH₃ | N | |
| O | 0 | S | H | H | H | H | OCH₃ | OCH₃ | N | |
| O | 1 | S | H | CH₃ | H | H | OCH₃ | OCH₃ | CH | |
| O | 0 | S | H | CH₃ | H | H | OCH₃ | OCH₃ | CH | |
| O | 0 | S | H | Cl | H | H | OCH₃ | OCH₃ | CH | |
| O | 1 | S | H | Cl | H | H | CH₃ | CH₃ | CH | |
| O | 1 | S | H | Cl | H | H | CH₃ | OCH₃ | CH | |
| O | 1 | S | H | Cl | H | H | OCH₃ | OCH₃ | CH | |
| O | 1 | S | H | Cl | H | H | Cl | OCH₃ | CH | |
| O | 1 | S | H | Cl | H | H | Br | OCH₃ | CH | |
| O | 1 | S | H | Cl | H | H | CH₃ | OCH₃ | N | |
| O | 1 | S | H | Cl | H | H | OCH₃ | OCH₃ | N | |

TABLE Ig

Structure Ig

| n | G | R | R₁ | R₅ | R₆ | X | Y | Z | m.p. (°C.) |
|---|---|---|----|----|----|-----|-----|----|-----|
| 0 | S | H | H | H | H | CH₃ | CH₃ | CH | |
| 0 | S | H | H | H | H | CH₃ | OCH₃ | CH | |
| 0 | S | H | H | H | H | OCH₃ | OCH₃ | CH | |
| 0 | S | H | H | H | H | Cl | OCH₃ | CH | |
| 0 | S | H | H | H | H | Br | OCH₃ | CH | |
| 0 | S | H | H | H | H | CH₃ | OCH₃ | N | |
| 0 | S | H | H | H | H | OCH₃ | OCH₃ | N | |
| 0 | S | H | H | H | CH₃ | CH₃ | CH₃ | CH | |
| 0 | S | H | H | H | CH₃ | CH₃ | OCH₃ | CH | |
| 0 | S | H | H | H | CH₃ | OCH₃ | OCH₃ | CH | |

TABLE Ig-continued

Structure Ig

| n | G | R | $R_1$ | $R_5$ | $R_6$ | X | Y | Z | m.p. (° C.) |
|---|---|---|---|---|---|---|---|---|---|
| 0 | S | H | H | H | $CH_3$ | Cl | $OCH_3$ | CH | |
| 0 | S | H | H | H | $CH_3$ | Br | $OCH_3$ | CH | |
| 0 | S | H | H | H | $CH_3$ | $CH_3$ | $OCH_3$ | N | |
| 0 | S | H | H | H | $CH_3$ | $OCH_3$ | $OCH_3$ | N | |
| 0 | S | H | H | H | $CH_2CH_3$ | $CH_3$ | $CH_3$ | N | |
| 0 | S | H | H | H | $CH_2CH_3$ | $CH_3$ | $OCH_3$ | CH | |
| 0 | S | H | H | H | $CH_2CH_3$ | $OCH_3$ | $OCH_3$ | CH | |
| 0 | S | H | H | H | $CH_2CH_2CH_3$ | $CH_3$ | $OCH_3$ | N | |
| 0 | S | H | H | H | $CH_2CH_2CH_3$ | $CH_3$ | $OCH_3$ | CH | |
| 0 | S | H | H | H | $CH_2CH_2CH_3$ | $OCH_3$ | $OCH_3$ | CH | |
| 0 | S | H | H | H | $CH(CH_3)_2$ | $CH_3$ | $OCH_3$ | N | |
| 0 | S | H | H | H | $CH(CH_3)_2$ | $CH_3$ | $OCH_3$ | CH | |
| 0 | S | H | H | H | $CH(CH_3)_2$ | $OCH_3$ | $OCH_3$ | CH | |
| 0 | S | H | H | H | $CH_2CH_2CH_2CH_3$ | $CH_3$ | $CH_3$ | CH | |
| 0 | S | H | H | H | $CH_2CH_2CH_2CH_3$ | $CH_3$ | $OCH_3$ | CH | |
| 0 | S | H | H | H | $CH_2CH_2CH_2CH_3$ | $OCH_3$ | $OCH_3$ | CH | |
| 0 | S | H | H | H | $CH_2CH_2CH_2CH_3$ | Cl | $OCH_3$ | CH | |
| 0 | S | H | H | H | $CH_2CH_2CH_2CH_3$ | Br | $OCH_3$ | CH | |
| 0 | S | H | H | H | $CH_2CH_2CH_2CH_3$ | $CH_3$ | $OCH_3$ | N | |
| 0 | S | H | H | H | $CH_2CH_2CH_2CH_3$ | $OCH_3$ | $OCH_3$ | N | |
| 0 | S | H | H | H | $CH_2CH(CH_3)_2$ | $CH_3$ | $OCH_3$ | N | |
| 0 | S | H | H | H | $CH_2CH(CH_3)_2$ | $CH_3$ | $OCH_3$ | CH | |
| 0 | S | H | H | H | $CH_2CH(CH_3)_2$ | $OCH_3$ | $OCH_3$ | CH | |
| 0 | S | H | H | H | $CH(CH_3)CH_2CH_3$ | $CH_3$ | $OCH_3$ | N | |
| 0 | S | H | H | H | $CH(CH_3)CH_2CH_3$ | $CH_3$ | $OCH_3$ | CH | |
| 0 | S | H | H | H | $CH(CH_3)CH_2CH_3$ | $OCH_3$ | $OCH_3$ | CH | |
| 0 | S | H | H | H | $C(CH_3)_3$ | $CH_3$ | $OCH_3$ | N | |
| 0 | S | H | H | H | $C(CH_3)_3$ | $CH_3$ | $OCH_3$ | CH | |
| 0 | S | H | H | H | $C(CH_3)_3$ | $OCH_3$ | $OCH_3$ | CH | |
| 0 | S | H | H | H | $(CH_2)_5CH_3$ | $CH_3$ | $OCH_3$ | N | |
| 0 | S | H | H | H | $(CH_2)_5CH_3$ | $CH_3$ | $OCH_3$ | CH | |
| 0 | S | H | H | H | $(CH_2)_5CH_3$ | $OCH_3$ | $OCH_3$ | CH | |
| 0 | S | H | H | H | $CH_2CH=CH_2$ | $CH_3$ | $OCH_3$ | N | |
| 0 | S | H | H | H | $CH_2CH=CH_2$ | $CH_3$ | $OCH_3$ | CH | |
| 0 | S | H | H | H | $CH_2CH=CH_2$ | $OCH_3$ | $OCH_3$ | CH | |
| 0 | S | H | H | H | $CH_2CH=CH_2CH_3$ | $CH_3$ | $OCH_3$ | N | |
| 0 | S | H | H | H | $CH_2CH=CH_2CH_3$ | $CH_3$ | $OCH_3$ | CH | |
| 0 | S | H | H | H | $CH_2CH=CH_2CH_3$ | $OCH_3$ | $OCH_3$ | CH | |
| 0 | S | H | H | H | $CH_2C(CH_3)=C(CH_3)_2$ | $CH_3$ | $OCH_3$ | N | |
| 0 | S | H | H | H | $CH_2C(CH_3)=C(CH_3)_2$ | $CH_3$ | $OCH_3$ | CH | |
| 0 | S | H | H | H | $CH_2C(CH_3)=C(CH_3)_2$ | $OCH_3$ | $OCH_3$ | CH | |
| 0 | S | H | H | H | $CH_2CH\text{---}CH_2$ (epoxide, O bridge) | $OCH_3$ | $OCH_3$ | CH | |
| 0 | S | H | H | H | $CH_2C\equiv CH$ | $CH_3$ | $OCH_3$ | N | |
| 0 | S | H | H | H | $CH_2C\equiv CH$ | $CH_3$ | $OCH_3$ | CH | |
| 0 | S | H | H | H | $CH_2C\equiv CH$ | $OCH_3$ | $OCH_3$ | CH | |
| 0 | S | H | H | H | $CH_2C\equiv$ | $CH_3$ | $OCH_3$ | N | |
| 0 | S | H | H | H | $CH_2C\equiv$ | $CH_3$ | $OCH_3$ | CH | |
| 0 | S | H | H | H | $CH_2C\equiv$ | $OCH_3$ | $OCH_3$ | CH | |
| 0 | S | H | H | H | $(CH_2)_4C\equiv CH$ | $OCH_3$ | $OCH_3$ | CH | |
| 0 | S | H | H | H | cyclopropyl | $OCH_3$ | $OCH_3$ | CH | |
| 0 | S | H | H | H | cyclopentyl | $OCH_3$ | $OCH_3$ | CH | |
| 0 | S | H | H | H | cyclohexyl | $OCH_3$ | $OCH_3$ | CH | |
| 0 | S | H | H | H | $CH_2$—cyclopropyl | $OCH_3$ | $OCH_3$ | CH | |
| 0 | S | H | H | H | $CH_2$—cyclopentyl | $OCH_3$ | $OCH_3$ | CH | |
| 0 | S | H | H | H | phenyl | $OCH_3$ | $OCH_3$ | CH | |
| 0 | S | H | H | H | p-nitrophenyl | $OCH_3$ | $OCH_3$ | CH | |
| 0 | S | H | H | H | phenylthio | $OCH_3$ | $OCH_3$ | CH | |
| 0 | S | H | H | H | $SO_2CH_3$ | $OCH_3$ | $OCH_3$ | CH | |
| 0 | S | H | H | H | $OCH_3$ | $OCH_3$ | $OCH_3$ | CH | |
| 0 | S | H | H | H | $C(O)CH_3$ | $OCH_2CH_3$ | $NHCH_3$ | N | |
| 0 | S | H | H | H | $C(O)CH_2CH_3$ | $OCH_3$ | $OCH_3$ | CH | |
| 0 | S | H | H | H | $C(O)(CH_2)_5CH_3$ | $OCH_3$ | $OCH_3$ | CH | |
| 0 | S | H | H | H | $CO_2CH_3$ | $OCH_2CH_3$ | $NHCH_3$ | N | |
| 0 | S | H | H | H | $CO_2CH_2CH_3$ | $OCH_3$ | $OCH_3$ | CH | |
| 0 | S | H | H | H | $CO_2CH_2CH=CH_2$ | $OCH_3$ | $OCH_3$ | CH | |
| 0 | S | H | H | H | $N(CH_3)_2$ | $OCH_3$ | $OCH_3$ | CH | |
| 0 | S | H | H | H | CN | $OCH_3$ | $OCH_3$ | CH | |
| 0 | S | H | H | H | $Si(CH_3)_3$ | $OCH_3$ | $OCH_3$ | CH | |
| 0 | S | H | H | H | $Si(CH_3)_2C(CH_3)_3$ | $OCH_3$ | $OCH_3$ | CH | |
| 0 | S | H | H | H | $Si(CH_3)_2Ph$ | $OCH_3$ | $OCH_3$ | CH | |
| 0 | S | H | H | H | $Si(CH_3)_2CH_2Ph$ | $OCH_3$ | $OCH_3$ | CH | |
| 0 | S | H | H | H | $CH_2OCH_2CH_3$ | $OCH_3$ | $OCH_3$ | CH | |
| 0 | S | H | H | H | $CH_2CH_2Cl$ | $OCH_2CH_3$ | $NHCH_3$ | N | |
| 0 | S | H | H | H | $CH_2CH_2CH_2F$ | $OCH_2CH_3$ | $NHCH_3$ | N | |
| 0 | S | H | H | H | $CF_2H$ | $OCH_3$ | $OCH_3$ | CH | |

TABLE Ig-continued

Structure Ig

| n | G | R | R$_1$ | R$_5$ | R$_6$ | X | Y | Z | m.p. (° C.) |
|---|---|---|---|---|---|---|---|---|---|
| 0 | S | H | H | H | CH$_2$CH$_2$Br | OCH$_3$ | OCH$_3$ | CH | |
| 0 | S | H | H | H | CH$_2$CF$_3$ | OCH$_3$ | OCH$_3$ | CH | |
| 0 | S | H | H | H | CH$_2$C(Cl)=CH$_2$ | OCH$_3$ | OCH$_3$ | CH | |
| 0 | S | H | H | H | CH$_2$CH$_2$OH | OCH$_3$ | OCH$_3$ | CH | |
| 0 | S | H | H | H | CH$_2$CH$_2$OCH$_3$ | OCH$_2$CH$_3$ | NHCH$_3$ | N | |
| 0 | S | H | H | H | CH$_2$CH$_2$OCO$_2$(CH$_2$)$_5$CH$_3$ | OCH$_3$ | OCH$_3$ | CH | |
| 0 | S | H | H | H | CH$_2$CH$_2$OC(O)NHCN$_3$ | OCH$_3$ | OCH$_3$ | CH | |
| 0 | S | H | H | H | CH$_2$CH$_2$OSO$_2$Ph | OCH$_3$ | OCH$_3$ | CH | |
| 0 | S | H | H | H | CH$_2$CH$_2$OSi(CH$_3$)$_3$ | OCH$_3$ | OCH$_3$ | CH | |
| 0 | S | H | H | H | CH$_2$Si(CH$_3$)$_3$ | OCH$_3$ | OCH$_3$ | CH | |
| 0 | S | H | H | H | CH$_2$CH$_2$SCH$_3$ | OCH$_3$ | OCH$_3$ | CH | |
| 0 | S | H | H | H | CH$_2$CH$_2$SOCH$_3$ | OCH$_3$ | OCH$_3$ | CH | |
| 0 | S | H | H | H | CH$_2$CH$_2$SO$_2$CH$_3$ | OCH$_3$ | OCH$_3$ | CH | |
| 0 | S | H | H | H | CH$_2$SCN | OCH$_3$ | OCH$_3$ | CH | |
| 0 | S | H | H | H | CH$_2$CN | OCH$_3$ | OCH$_3$ | CH | |
| 0 | S | H | H | H | CH$_2$CH$_2$CN | OCH$_3$ | OCH$_3$ | CH | |
| 0 | S | H | H | H | CH$_2$NO$_2$ | OCH$_3$ | OCH$_3$ | CH | |
| 0 | S | H | H | H | CH$_2$C(O)CH$_3$ | OCH$_3$ | OCH$_3$ | CH | |
| 0 | S | H | H | H | CH$_2$CH$_2$C(O)CH$_3$ | OCH$_3$ | OCH$_3$ | CH | |
| 0 | S | H | H | H | CH$_2$CO$_2$CH$_3$ | OCH$_3$ | OCH$_3$ | CH | |
| 0 | S | H | H | H | CH$_2$CO$_2$C(CH$_3$)$_3$ | OCH$_3$ | OCH$_3$ | CH | |
| 0 | S | H | H | H | CH$_2$C(O)N(CH$_3$)$_2$ | OCH$_3$ | OCH$_3$ | CH | |
| 0 | S | H | H | H | benzyl | OCH$_3$ | OCH$_3$ | CH | |
| 0 | S | H | H | H | p-chlorobenzyl | OCH$_3$ | OCH$_3$ | CH | |
| 0 | S | H | H | H | m-fluorobenzyl | OCH$_3$ | OCH$_3$ | CH | |
| 0 | S | H | H | H | o-bromobenzyl | OCH$_3$ | OCH$_3$ | CH | |
| 0 | S | H | H | H | p-methylbenzyl | OCH$_3$ | OCH$_3$ | CH | |
| 0 | S | H | H | H | p-methoxybenzyl | OCH$_3$ | OCH$_3$ | CH | |
| 0 | S | H | H | H | p-cyanobenzyl | OCH$_3$ | OCH$_3$ | CH | |
| 0 | S | H | H | H | p-nitrobenzyl | OCH$_3$ | OCH$_3$ | CH | |
| 0 | S | H | H | H | p-methylthiobenzyl | OCH$_3$ | OCH$_3$ | CH | |
| 0 | S | H | H | H | p-methylsulfonylbenzyl | OCH$_3$ | OCH$_3$ | CH | |
| 0 | S | H | H | H | m-trifluromethylbenzyl | OCH$_3$ | OCH$_3$ | CH | |
| 0 | S | H | H | H | CH$_2$CO$_2$phenyl | OCH$_3$ | OCH$_3$ | CH | |
| 0 | S | H | H | H | CH$_2$CO—cyclopentyl | OCH$_3$ | OCH$_3$ | CH | |
| 0 | S | H | H | H | CH$_2$CO$_2$CH$_2$CH$_2$Cl | OCH$_3$ | OCH$_3$ | CH | |
| 0 | S | H | H | H | CH$_2$CO$_2$CH$_2$C≡CH | OCH$_3$ | OCH$_3$ | CH | |
| 0 | S | H | H | H | CH$_2$CH(OCH$_3$)$_2$ | OCH$_3$ | OCH$_3$ | CH | |
| 0 | S | H | H | H | CH$_2$CH(CN)SO$_2$CH$_3$ | OCH$_3$ | OCH$_3$ | CH | |
| 0 | S | H | H | H | 2-pyridylmethyl | OCH$_3$ | OCH$_3$ | CH | |
| 0 | S | H | H | H | 3-pyridylmethyl | OCH$_3$ | OCH$_3$ | CH | |
| 0 | S | H | H | H | 4-pyridylmethyl | OCH$_3$ | OCH$_3$ | CH | |
| 0 | S | H | H | H | 2-thienomethyl | OCH$_3$ | OCH$_3$ | CH | |
| 0 | S | H | H | H | 3-thienomethyl | OCH$_3$ | OCH$_3$ | CH | |
| 0 | S | H | H | H | 2-furanylmethyl | OCH$_3$ | OCH$_3$ | CH | |
| 0 | S | H | H | CH$_3$ | CH$_3$ | OCH$_3$ | OCH$_3$ | CH | |
| 0 | S | CH$_3$ | H | H | CH$_3$ | OCH$_3$ | OCH$_3$ | CH | |
| 0 | S | H | CH$_3$ | H | CH$_3$ | CH$_3$ | CH$_3$ | CH | |
| 0 | S | H | CH$_3$ | H | CH$_3$ | CH$_3$ | OCH$_3$ | CH | |
| 0 | S | H | CH$_3$ | H | CH$_3$ | OCH$_3$ | OCH$_3$ | CH | |
| 0 | S | H | CH$_3$ | H | CH$_3$ | Cl | OCH$_3$ | CH | |
| 0 | S | H | CH$_3$ | H | CH$_3$ | Br | OCH$_3$ | CH | |
| 0 | S | H | CH$_3$ | H | CH$_3$ | CH$_3$ | OCH$_3$ | N | |
| 0 | S | H | CH$_3$ | H | CH$_3$ | OCH$_3$ | OCH$_3$ | N | |
| 0 | S | H | Cl | H | CH$_3$ | CH$_3$ | CH$_3$ | CH | |
| 0 | S | H | Cl | H | CH$_3$ | CH$_3$ | OCH$_3$ | CH | |
| 0 | S | H | Cl | H | CH$_3$ | OCH$_3$ | OCH$_3$ | CH | |
| 0 | S | H | Cl | H | CH$_3$ | Cl | OCH$_3$ | CH | |
| 0 | S | H | Cl | H | CH$_3$ | Br | OCH$_3$ | CH | |
| 0 | S | H | Cl | H | CH$_3$ | CH$_3$ | OCH$_3$ | N | |
| 0 | S | H | Cl | H | CH$_3$ | OCH$_3$ | OCH$_3$ | N | |
| 0 | S | H | CH$_3$ | H | CH$_2$CH$_2$CH$_2$CH$_3$ | CH$_3$ | OCH$_3$ | CH | |
| 0 | S | H | CH$_3$ | H | CH$_2$CH$_2$CH$_2$CH$_3$ | OCH$_3$ | OCH$_3$ | CH | |
| 0 | S | H | Cl | H | CH$_2$CH$_2$CH$_2$CH$_3$ | CH$_3$ | OCH$_3$ | CH | |
| 0 | S | H | Cl | H | CH$_2$CH$_2$CH$_2$CH$_3$ | OCH$_3$ | OCH$_3$ | CH | |
| 1 | S | H | H | H | CH$_3$ | CH$_3$ | OCH$_3$ | N | |
| 1 | S | H | H | H | CH$_3$ | OCH$_3$ | OCH$_3$ | CH | |
| 1 | S | H | H | H | H | CH$_3$ | OCH$_3$ | N | |
| 1 | S | H | H | H | H | CH$_3$ | OCH$_3$ | CH | |
| 1 | S | H | H | H | H | OCH$_3$ | OCH$_3$ | CH | |
| 0 | O | H | CH$_3$ | H | CH$_3$ | CH$_3$ | OCH$_3$ | N | |
| 0 | O | H | CH$_3$ | H | CH$_3$ | CH$_3$ | OCH$_3$ | CH | |
| 0 | O | H | CH$_3$ | H | CH$_3$ | OCH$_3$ | OCH$_3$ | CH | |
| 0 | NH | H | CH$_3$ | H | CH$_3$ | CH$_3$ | OCH$_3$ | N | |
| 0 | NH | H | CH$_3$ | H | CH$_3$ | CH$_3$ | OCH$_3$ | CH | |
| 0 | NH | H | CH$_3$ | H | CH$_3$ | OCH$_3$ | OCH$_3$ | CH | |
| 0 | NCH$_3$ | H | CH$_3$ | H | CH$_3$ | CH$_3$ | OCH$_3$ | N | |
| 0 | NCH$_3$ | H | CH$_3$ | H | CH$_3$ | CH$_3$ | OCH$_3$ | CH | |
| 0 | NCH$_3$ | H | CH$_3$ | H | CH$_3$ | OCH$_3$ | OCH$_3$ | CH | |

4,846,874

TABLE Ig-continued

Structure Ig

| n | G | R | $R_1$ | $R_5$ | $R_6$ | X | Y | Z | m.p. (° C.) |
|---|---|---|---|---|---|---|---|---|---|
| 0 | O | H | $CH_3$ | H | $CH_2CH_2CH_2CH_3$ | $CH_3$ | $OCH_3$ | CH | |
| 0 | O | H | $CH_3$ | H | $CH_2CH_2CH_2CH_3$ | $OCH_3$ | $OCH_3$ | CH | |
| 0 | NH | H | $CH_3$ | H | $CH_2CH_2CH_2CH_3$ | $CH_3$ | $OCH_3$ | CH | |
| 0 | NH | H | $CH_3$ | H | $CH_2CH_2CH_2CH_3$ | $OCH_3$ | $OCH_3$ | CH | |
| 0 | $NCH_3$ | H | $CH_3$ | H | $CH_2CH_2CH_2CH_3$ | $CH_3$ | $OCH_3$ | CH | |
| 0 | $NCH_3$ | H | $CH_3$ | H | $CH_2CH_2CH_2CH_3$ | $OCH_3$ | $OCH_3$ | CH | |
| 0 | O | H | H | H | $CH_2CH_2CH_2CH_3$ | $CH_3$ | $OCH_3$ | CH | |
| 0 | O | H | H | H | $CH_2CH_2CH_2CH_3$ | $OCH_3$ | $OCH_3$ | CH | |
| 0 | NH | H | H | H | $CH_2CH_2CH_2CH_3$ | $CH_3$ | $OCH_3$ | CH | |
| 0 | NH | H | H | H | $CH_2CH_2CH_2CH_3$ | $OCH_3$ | $OCH_3$ | CH | |
| 0 | $NCH_3$ | H | H | H | $CH_2CH_2CH_2CH_3$ | $CH_3$ | $OCH_3$ | CH | |
| 0 | $NCH_3$ | H | H | H | $CH_2CH_2CH_2CH_3$ | $OCH_3$ | $OCH_3$ | CH | |
| 0 | S | H | H | H | 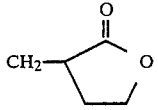 | $OCH_3$ | $OCH_3$ | CH | |
| 0 | S | H | H | H | 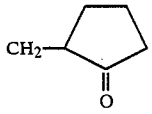 | $OCH_3$ | $OCH_3$ | CH | |
| 0 | S | H | H | H | $(CO)_2CH_3$ | $CH_3$ | $OCH_3$ | CH | |
| 0 | S | H | H | H | $(CO)_2CH_3$ | $OCH_3$ | $OCH_3$ | CH | |
| 0 | S | H | H | H | $(CO)_2CH_3$ | $CH_3$ | $OCH_3$ | N | |
| 0 | S | H | H | H | $(CO)_2CH_3$ | $OCH_3$ | $OCH_3$ | N | |
| 0 | S | H | H | H | $C(O)N(CH_3)_2$ | $CH_3$ | $OCH_3$ | CH | |
| 0 | S | H | H | H | $C(O)N(CH_3)_2$ | $OCH_3$ | $OCH_3$ | CH | |
| 0 | S | H | H | H | $C(O)N(CH_3)_2$ | $CH_3$ | $OCH_3$ | N | |
| 0 | S | H | H | H | $C(O)N(CH_3)_2$ | $OCH_3$ | $OCH_3$ | N | |
| 0 | S | H | H | H | $C(O)NH_2$ | $CH_3$ | $OCH_3$ | CH | |
| 0 | S | H | H | H | $C(O)NH_2$ | $OCH_3$ | $OCH_3$ | CH | |
| 0 | S | H | H | H | $C(O)NH_2$ | $CH_3$ | $OCH_3$ | N | |
| 0 | S | H | H | H | $C(O)NH_2$ | $OCH_3$ | $OCH_3$ | N | |
| 0 | S | H | H | H | $C(S)SCH_3$ | $CH_3$ | $OCH_3$ | CH | |
| 0 | S | H | H | H | $C(S)SCH_3$ | $OCH_3$ | $OCH_3$ | CH | |
| 0 | S | H | H | H | $C(S)SCH_3$ | $CH_3$ | $OCH_3$ | N | |
| 0 | S | H | H | H | $C(S)SCH_3$ | $OCH_3$ | $OCH_3$ | N | |
| 0 | S | H | H | H | $C(S)SCH_2CH=CH_2$ | $CH_3$ | $OCH_3$ | CH | |
| 0 | S | H | H | H | $C(S)SCH_2CH=CH_2$ | $OCH_3$ | $OCH_3$ | CH | |
| 0 | S | H | H | H | $C(S)SCH_2CH=CH_2$ | $CH_3$ | $OCH_3$ | N | |
| 0 | S | H | H | H | $C(S)SCH_2CH=CH_2$ | $OCH_3$ | $OCH_3$ | N | |
| 0 | S | H | H | H | C(O)—2-thiophene | $CH_3$ | $OCH_3$ | CH | |
| 0 | S | H | H | H | C(O)—2-thiophene | $OCH_3$ | $OCH_3$ | CH | |
| 0 | S | H | H | H | C(O)—2-thiophene | $CH_3$ | $OCH_3$ | N | |
| 0 | S | H | H | H | C(O)—2-thiophene | $OCH_3$ | $OCH_3$ | N | |
| 0 | S | H | H | H | C(O)—2-pyridine | $CH_3$ | $OCH_3$ | CH | |
| 0 | S | H | H | H | C(O)—2-pyridine | $OCH_3$ | $OCH_3$ | CH | |
| 0 | S | H | H | H | C(O)—2-pyridine | $CH_3$ | $OCH_3$ | N | |
| 0 | S | H | H | H | C(O)—2-pyridine | $OCH_3$ | $OCH_3$ | N | |
| 0 | S | H | H | H | C(O)—2-furan | $CH_3$ | $OCH_3$ | CH | |
| 0 | S | H | H | H | C(O)—2-furan | $OCH_3$ | $OCH_3$ | CH | |
| 0 | S | H | H | H | C(O)—2-furan | $CH_3$ | $OCH_3$ | N | |
| 0 | S | H | H | H | C(O)—2-furan | $OCH_3$ | $OCH_3$ | N | |
| 0 | S | H | H | H | C(O)—2-thiazole | $CH_3$ | $OCH_3$ | CH | |
| 0 | S | H | H | H | C(O)—2-thiazole | $OCH_3$ | $OCH_3$ | CH | |
| 0 | S | H | H | H | C(O)—2-thiazole | $CH_3$ | $OCH_3$ | N | |
| 0 | S | H | H | H | C(O)—2-thiazole | $OCH_3$ | $OCH_3$ | N | |
| 0 | S | H | H | H | C(O)—2-oxazole | $CH_3$ | $OCH_3$ | CH | |
| 0 | S | H | H | H | C(O)—2-oxazole | $OCH_3$ | $OCH_3$ | CH | |
| 0 | S | H | H | H | C(O)—2-oxazole | $CH_3$ | $OCH_3$ | N | |
| 0 | S | H | H | H | C(O)—2-oxazole | $OCH_3$ | $OCH_3$ | N | |
| 0 | S | H | H | H | C(O)—2-cyclopentanone | $CH_3$ | $OCH_3$ | CH | |
| 0 | S | H | H | H | C(O)—2-cyclopentanone | $OCH_3$ | $OCH_3$ | CH | |
| 0 | S | H | H | H | C(O)—2-cyclopentanone | $CH_3$ | $OCH_3$ | N | |
| 0 | S | H | H | H | C(O)—2-cyclopentanone | $OCH_3$ | $OCH_3$ | N | |
| 0 | S | H | H | H | C(O)—2-butyrolactone | $CH_3$ | $OCH_3$ | CH | |
| 0 | S | H | H | H | C(O)—2-butyrolactone | $OCH_3$ | $OCH_3$ | CH | |
| 0 | S | H | H | H | C(O)—2-butyrolactone | $CH_3$ | $OCH_3$ | N | |
| 0 | S | H | H | H | C(O)—2-butyrolactone | $OCH_3$ | $OCH_3$ | N | |
| 0 | S | H | H | H | C(O)—2-(5-Cl)thiophene | $CH_3$ | $OCH_3$ | CH | |
| 0 | S | H | H | H | C(O)—2-(5-Cl)thiophene | $OCH_3$ | $OCH_3$ | CH | |
| 0 | S | H | H | H | C(O)—2-(5-Cl)thiophene | $CH_3$ | $OCH_3$ | N | |
| 0 | S | H | H | H | C(O)—2-(5-Cl)thiophene | $OCH_3$ | $OCH_3$ | N | |
| 0 | S | H | H | H | $CH_2OP(O)(CH_3)_2$ | $CH_3$ | $OCH_3$ | CH | |
| 0 | S | H | H | H | $CH_2OP(O)(CH_3)_2$ | $OCH_3$ | $OCH_3$ | CH | |

TABLE Ig-continued

Structure Ig

| n | G | R | $R_1$ | $R_5$ | $R_6$ | X | Y | Z | m.p. (°C.) |
|---|---|---|---|---|---|---|---|---|---|
| 0 | S | H | H | H | $CH_2OP(O)(CH_3)_2$ | $CH_3$ | $OCH_3$ | N | |
| 0 | S | H | H | H | $CH_2OP(O)(CH_3)_2$ | $OCH_3$ | $OCH_3$ | N | |
| 0 | S | H | H | H | $CH_2CH_2OP(O)OCH_3)_2$ | $CH_3$ | $OCH_3$ | CH | |
| 0 | S | H | H | H | $CH_2CH_2OP(O)OCH_3)_2$ | $OCH_3$ | $OCH_3$ | CH | |
| 0 | S | H | H | H | $CH_2CH_2OP(O)OCH_3)_2$ | $CH_3$ | $OCH_3$ | N | |
| 0 | S | H | H | H | $CH_2CH_2OP(O)OCH_3)_2$ | $OCH_3$ | $OCH_3$ | N | |
| 0 | S | H | H | H | $CH_2SP(O)(CH_3)_2$ | $CH_3$ | $OCH_3$ | CH | |
| 0 | S | H | H | H | $CH_2SP(O)(CH_3)_2$ | $OCH_3$ | $OCH_3$ | CH | |
| 0 | S | H | H | H | $CH_2SP(O)(CH_3)_2$ | $CH_3$ | $OCH_3$ | N | |
| 0 | S | H | H | H | $CH_2SP(O)(CH_3)_2$ | $OCH_3$ | $OCH_3$ | N | |
| 0 | S | H | H | H | $CH_2SP(O)(SCH_3)_2$ | $CH_3$ | $OCH_3$ | CH | |
| 0 | S | H | H | H | $CH_2SP(O)(SCH_3)_2$ | $OCH_3$ | $OCH_3$ | CH | |
| 0 | S | H | H | H | $CH_2SP(O)(SCH_3)_2$ | $CH_3$ | $OCH_3$ | N | |
| 0 | S | H | H | H | $CH_2SP(O)(SCH_3)_2$ | $OCH_3$ | $OCH_3$ | N | |
| 0 | S | H | H | H | $CH_2SP(S)(CH_2CH_3)_2$ | $CH_3$ | $OCH_3$ | CH | |
| 0 | S | H | H | H | $CH_2SP(S)(CH_2CH_3)_2$ | $OCH_3$ | $OCH_3$ | CH | |
| 0 | S | H | H | H | $CH_2SP(S)(CH_2CH_3)_2$ | $CH_3$ | $OCH_3$ | N | |
| 0 | S | H | H | H | $CH_2SP(S)(CH_2CH_3)_2$ | $OCH_3$ | $OCH_3$ | N | |
| 0 | S | H | H | H | $CH_2CH_2P(O)(OCH_3)_2$ | $CH_3$ | $OCH_3$ | CH | |
| 0 | S | H | H | H | $CH_2CH_2P(O)(OCH_3)_2$ | $OCH_3$ | $OCH_3$ | CH | |
| 0 | S | H | H | H | $CH_2CH_2P(O)(OCH_3)_2$ | $CH_3$ | $OCH_3$ | N | |
| 0 | S | H | H | H | $CH_2CH_2P(O)(OCH_3)_2$ | $OCH_3$ | $OCH_3$ | N | |
| 0 | S | H | H | H | $CH_2P(O)(OCH_2CH_3)_2$ | $CH_3$ | $OCH_3$ | CH | |
| 0 | S | H | H | H | $CH_2P(O)(OCH_2CH_3)_2$ | $OCH_3$ | $OCH_3$ | CH | |
| 0 | S | H | H | H | $CH_2P(O)(OCH_2CH_3)_2$ | $CH_3$ | $OCH_3$ | N | |
| 0 | S | H | H | H | $CH_2P(O)(OCH_2CH_3)_2$ | $OCH_3$ | $OCH_3$ | N | |
| 0 | S | H | H | H | $CH_2NHC(O)Ph$ | $CH_3$ | $OCH_3$ | CH | |
| 0 | S | H | H | H | $CH_2NHC(O)Ph$ | $OCH_3$ | $OCH_3$ | CH | |
| 0 | S | H | H | H | $CH_2NHC(O)Ph$ | $CH_3$ | $OCH_3$ | N | |
| 0 | S | H | H | H | $CH_2NHC(O)Ph$ | $OCH_3$ | $OCH_3$ | N | |
| 0 | S | H | H | H | $CH_2NHC(O)CH_2Cl$ | $CH_3$ | $OCH_3$ | CH | |
| 0 | S | H | H | H | $CH_2NHC(O)CH_2Cl$ | $OCH_3$ | $OCH_3$ | CH | |
| 0 | S | H | H | H | $CH_2NHC(O)CH_2Cl$ | $CH_3$ | $OCH_3$ | N | |
| 0 | S | H | H | H | $CH_2NHC(O)CH_2Cl$ | $OCH_3$ | $OCH_3$ | N | |
| 0 | S | H | H | H | $CH_2NHC(O)OCH_3$ | $CH_3$ | $OCH_3$ | CH | |
| 0 | S | H | H | H | $CH_2NHC(O)OCH_3$ | $OCH_3$ | $OCH_3$ | CH | |
| 0 | S | H | H | H | $CH_2NHC(O)OCH_3$ | $CH_3$ | $OCH_3$ | N | |
| 0 | S | H | H | H | $CH_2NHC(O)OCH_3$ | $OCH_3$ | $OCH_3$ | N | |
| 0 | S | H | H | H | $CH_2NHC(O)NHCH_3$ | $CH_3$ | $OCH_3$ | CH | |
| 0 | S | H | H | H | $CH_2NHC(O)NHCH_3$ | $OCH_3$ | $OCH_3$ | CH | |
| 0 | S | H | H | H | $CH_2NHC(O)NHCH_3$ | $CH_3$ | $OCH_3$ | N | |
| 0 | S | H | H | H | $CH_2NHC(O)NHCH_3$ | $OCH_3$ | $OCH_3$ | N | |
| 0 | S | H | H | H | $CH_2NHSO_2CH_3$ | $CH_3$ | $OCH_3$ | CH | |
| 0 | S | H | H | H | $CH_2NHSO_2CH_3$ | $OCH_3$ | $OCH_3$ | CH | |
| 0 | S | H | H | H | $CH_2NHSO_2CH_3$ | $CH_3$ | $OCH_3$ | N | |
| 0 | S | H | H | H | $CH_2NHSO_2CH_3$ | $OCH_3$ | $OCH_3$ | N | |
| 0 | S | H | H | H | $CH_2CH_2NHSO_2CH_3$ | $CH_3$ | $OCH_3$ | CH | |
| 0 | S | H | H | H | $CH_2CH_2NHSO_2CH_3$ | $OCH_3$ | $OCH_3$ | CH | |
| 0 | S | H | H | H | $CH_2CH_2NHSO_2CH_3$ | $CH_3$ | $OCH_3$ | N | |
| 0 | S | H | H | H | $CH_2CH_2NHSO_2CH_3$ | $OCH_3$ | $OCH_3$ | N | |
| 0 | S | H | H | H | $CH_2NHP(O)(CH_3)_2$ | $CH_3$ | $OCH_3$ | CH | |
| 0 | S | H | H | H | $CH_2NHP(O)(CH_3)_2$ | $OCH_3$ | $OCH_3$ | CH | |
| 0 | S | H | H | H | $CH_2NHP(O)(CH_3)_2$ | $CH_3$ | $OCH_3$ | N | |
| 0 | S | H | H | H | $CH_2NHP(O)(CH_3)_2$ | $OCH_3$ | $OCH_3$ | N | |
| 0 | S | H | H | H | OH | $CH_3$ | $OCH_3$ | CH | |
| 0 | S | H | H | H | OH | $OCH_3$ | $OCH_3$ | CH | |
| 0 | S | H | H | H | OH | $CH_3$ | $OCH_3$ | N | |
| 0 | S | H | H | H | OH | $OCH_3$ | $OCH_3$ | N | |
| 0 | S | H | H | H | $NH_2$ | $CH_3$ | $OCH_3$ | CH | |
| 0 | S | H | H | H | $NH_2$ | $OCH_3$ | $OCH_3$ | CH | |
| 0 | S | H | H | H | $NH_2$ | $CH_3$ | $OCH_3$ | N | |
| 0 | S | H | H | H | $NH_2$ | $OCH_3$ | $OCH_3$ | N | |
| 0 | S | H | H | H | $P(O)(CH_3)_2$ | $CH_3$ | $OCH_3$ | CH | |
| 0 | S | H | H | H | $P(O)(CH_3)_2$ | $OCH_3$ | $OCH_3$ | CH | |
| 0 | S | H | H | H | $P(O)(CH_3)_2$ | $CH_3$ | $OCH_3$ | N | |
| 0 | S | H | H | H | $P(O)(CH_3)_2$ | $OCH_3$ | $OCH_3$ | N | |
| 0 | S | H | H | H | $P(O)(OCH_2CH_3)_2$ | $CH_3$ | $OCH_3$ | CH | |
| 0 | S | H | H | H | $P(O)(OCH_2CH_3)_2$ | $OCH_3$ | $OCH_3$ | CH | |
| 0 | S | H | H | H | $P(O)(OCH_2CH_3)_2$ | $CH_3$ | $OCH_3$ | N | |
| 0 | S | H | H | H | $P(O)OCH_2CH_3)_2$ | $OCH_3$ | $OCH_3$ | N | |
| 0 | S | H | H | H | $P(O)(SCH_2CH_3)_2$ | $CH_3$ | $OCH_3$ | CH | |
| 0 | S | H | H | H | $P(O)(SCH_2CH_3)_2$ | $OCH_3$ | $OCH_3$ | CH | |
| 0 | S | H | H | H | $P(O)(SCH_2CH_3)_2$ | $CH_3$ | $OCH_3$ | N | |
| 0 | S | H | H | H | $P(O)(SCH_2CH_3)_2$ | $OCH_3$ | $OCH_3$ | N | |
| 0 | S | H | H | H | $P(S)(SCH_3)_2$ | $OCH_3$ | $OCH_3$ | CH | |
| 0 | S | H | H | H | $P(S)(SCH_3)_2$ | $OCH_3$ | $OCH_3$ | N | |
| 0 | S | H | H | H | $(CO)_2OCH_2CH_3$ | $CH_3$ | $OCH_3$ | CH | |
| 0 | S | H | H | H | $(CO)_2OCH_2CH_3$ | $OCH_3$ | $OCH_3$ | CH | |
| 0 | S | H | H | H | $(CO)_2OCH_2CH_3$ | $CH_3$ | $OCH_3$ | N | |
| 0 | S | H | H | H | $CH_2NHP(O)(OCH_3)_2$ | $CH_3$ | $OCH_3$ | CH | |

TABLE Ig-continued

Structure Ig

| n | G | R | R$_1$ | R$_5$ | R$_6$ | X | Y | Z | m.p. (° C.) |
|---|---|---|---|---|---|---|---|---|---|
| 0 | S | H | H | H | CH$_2$NHP(O)(OCH$_3$)$_2$ | OCH$_3$ | OCH$_3$ | CH | |
| 0 | S | H | H | H | CH$_2$NHP(O)(OCH$_3$)$_2$ | CH$_3$ | OCH$_3$ | N | |
| 0 | S | H | H | H | CH$_2$NHP(O)(OCH$_3$)$_2$ | OCH$_3$ | OCH$_3$ | N | |
| 0 | S | H | H | H | CH$_2$NHP(S)(CH$_3$)$_2$ | CH$_3$ | OCH$_3$ | CH | |
| 0 | S | H | H | H | CH$_2$NHP(S)(CH$_3$)$_2$ | OCH$_3$ | OCH$_3$ | CH | |
| 0 | S | H | H | H | CH$_2$NHP(S)(CH$_3$)$_2$ | CH$_3$ | OCH$_3$ | N | |
| 0 | S | H | H | H | CH$_2$NHP(S)(CH$_3$)$_2$ | OCH$_3$ | OCH$_3$ | N | |
| 0 | S | H | H | H | CH$_2$NHP(S)(SCH$_3$)$_2$ | CH$_3$ | OCH$_3$ | CH | |
| 0 | S | H | H | H | CH$_2$NHP(S)(SCH$_3$)$_2$ | OCH$_3$ | OCH$_3$ | CH | |
| 0 | S | H | H | H | CH$_2$NHP(S)(SCH$_3$)$_2$ | CH$_3$ | OCH$_3$ | N | |
| 0 | S | H | H | H | CH$_2$NHP(S)(SCH$_3$)$_2$ | OCH$_3$ | OCH$_3$ | N | |
| 0 | S | H | H | H | CH$_2$—1-Naphthyl | CH$_3$ | OCH$_3$ | CH | |
| 0 | S | H | H | H | CH$_2$—1-Naphthyl | OCH$_3$ | OCH$_3$ | CH | |
| 0 | S | H | H | H | CH$_2$—1-Naphthyl | CH$_3$ | OCH$_3$ | N | |
| 0 | S | H | H | H | CH$_2$—1-Naphthyl | OCH$_3$ | OCH$_3$ | N | |
| 0 | S | H | H | H | CH$_2$—2-Naphthyl | CH$_3$ | OCH$_3$ | CH | |
| 0 | S | H | H | H | CH$_2$—2-Naphthyl | OCH$_3$ | OCH$_3$ | CH | |
| 0 | S | H | H | H | CH$_2$—2-Naphthyl | CH$_3$ | OCH$_3$ | N | |
| 0 | S | H | H | H | CH$_2$—2-Naphthyl | OCH$_3$ | OCH$_3$ | N | |
| 0 | S | H | H | H | CH(SCH$_3$)$_2$ | CH$_3$ | OCH$_3$ | CH | |
| 0 | S | H | H | H | CH(SCH$_3$)$_2$ | OCH$_3$ | OCH$_3$ | CH | |
| 0 | S | H | H | H | CH(SCH$_3$)$_2$ | CH$_3$ | OCH$_3$ | N | |
| 0 | S | H | H | H | CH(SCH$_3$)$_2$ | OCH$_3$ | OCH$_3$ | N | |
| 0 | S | H | H | H | CH(OCH$_3$)$_2$ | CH$_3$ | OCH$_3$ | CH | |
| 0 | S | H | H | H | CH(OCH$_3$)$_2$ | OCH$_3$ | OCH$_3$ | CH | |
| 0 | S | H | H | H | CH(OCH$_3$)$_2$ | CH$_3$ | OCH$_3$ | N | |
| 0 | S | H | H | H | CH(OCH$_3$)$_2$ | OCH$_3$ | OCH$_3$ | N | |
| 0 | S | H | H | H | CH(Cl)SO$_2$CH$_3$ | CH$_3$ | OCH$_3$ | CH | |
| 0 | S | H | H | H | CH(Cl)SO$_2$CH$_3$ | OCH$_3$ | OCH$_3$ | CH | |
| 0 | S | H | H | H | CH(Cl)SO$_2$CH$_3$ | CH$_3$ | OCH$_3$ | N | |
| 0 | S | H | H | H | CH(Cl)SO$_2$CH$_3$ | OCH$_3$ | OCH$_3$ | N | |
| 0 | S | H | H | H | CH(CN)OCH$_3$ | CH$_3$ | OCH$_3$ | CH | |
| 0 | S | H | H | H | CH(CN)OCH$_3$ | OCH$_3$ | OCH$_3$ | CH | |
| 0 | S | H | H | H | CH(CN)OCH$_3$ | CH$_3$ | OCH$_3$ | N | |
| 0 | S | H | H | H | CH(CN)OCH$_3$ | OCH$_3$ | OCH$_3$ | N | |
| 0 | S | H | H | H | CH$_2$CH(Cl)CH$_2$Cl | CH$_3$ | OCH$_3$ | CH | |
| 0 | S | H | H | H | CH$_2$CH(Cl)CH$_2$Cl | OCH$_3$ | OCH$_3$ | CH | |
| 0 | S | H | H | H | CH$_2$CH(Cl)CH$_2$Cl | CH$_3$ | OCH$_3$ | N | |
| 0 | S | H | H | H | CH$_2$CH(Cl)CH$_2$Cl | OCH$_3$ | OCH$_3$ | N | |
| 0 | S | H | H | H | CH$_2$C(CH$_3$)=NOCH$_3$ | CH$_3$ | OCH$_3$ | CH | |
| 0 | S | H | H | H | CH$_2$C(CH$_3$)=NOCH$_3$ | OCH$_3$ | OCH$_3$ | CH | |
| 0 | S | H | H | H | CH$_2$C(CH$_3$)=NOCH$_3$ | CH$_3$ | OCH$_3$ | N | |
| 0 | S | H | H | H | CH$_2$C(CH$_3$)=NOCH$_3$ | OCH$_3$ | OCH$_3$ | N | |
| 0 | S | H | H | H | CH$_2$C(CH$_3$)=NOCH$_2$CH$_3$ | CH$_3$ | OCH$_3$ | CH | |
| 0 | S | H | H | H | CH$_2$C(CH$_3$)=NOCH$_2$CH$_3$ | OCH$_3$ | OCH$_3$ | CH | |
| 0 | S | H | H | H | CH$_2$C(CH$_3$)=NOCH$_2$CH$_3$ | CH$_3$ | OCH$_3$ | N | |
| 0 | S | H | H | H | CH$_2$C(CH$_3$)=NOCH$_2$CH$_3$ | OCH$_3$ | OCH$_3$ | N | |
| 0 | S | H | H | H | CH=CHC(O)CH$_3$ | CH$_3$ | OCH$_3$ | CH | |
| 0 | S | H | H | H | CH=CHC(O)CH$_3$ | OCH$_3$ | OCH$_3$ | CH | |
| 0 | S | H | H | H | CH=CHC(O)CH$_3$ | CH$_3$ | OCH$_3$ | N | |
| 0 | S | H | H | H | CH=CHC(O)CH$_3$ | OCH$_3$ | OCH$_3$ | N | |
| 0 | S | H | H | H | CH=CHC(O)OCH$_3$ | CH$_3$ | OCH$_3$ | CH | |
| 0 | S | H | H | H | CH=CHC(O)OCH$_3$ | OCH$_3$ | OCH$_3$ | CH | |
| 0 | S | H | H | H | CH=CHC(O)OCH$_3$ | CH$_3$ | OCH$_3$ | N | |
| 0 | S | H | H | H | CH=CHC(O)OCH$_3$ | OCH$_3$ | OCH$_3$ | N | |
| 0 | S | H | H | H | CH$_2$CH=CHN(CH$_3$)$_2$ | CH$_3$ | OCH$_3$ | CH | |
| 0 | S | H | H | H | CH$_2$CH=CHN(CH$_3$)$_2$ | OCH$_3$ | OCH$_3$ | CH | |
| 0 | S | H | H | H | CH$_2$CH=CHN(CH$_3$)$_2$ | CH$_3$ | OCH$_3$ | N | |
| 0 | S | H | H | H | CH$_2$CH=CHN(CH$_3$)$_2$ | OCH$_3$ | OCH$_3$ | N | |
| 0 | S | H | H | H | CH=CHC(O)NH$_2$ | CH$_3$ | OCH$_3$ | CH | |
| 0 | S | H | H | H | CH=CHC(O)NH$_2$ | OCH$_3$ | OCH$_3$ | CH | |
| 0 | S | H | H | H | CH=CHC(O)NH$_2$ | CH$_3$ | OCH$_3$ | N | |
| 0 | S | H | H | H | CH=CHC(O)NH$_2$ | OCH$_3$ | OCH$_3$ | N | |
| 0 | S | H | H | H | CH=C(CH$_3$)C(O)N(CH$_3$)$_2$ | CH$_3$ | OCH$_3$ | CH | |
| 0 | S | H | H | H | CH=C(CH$_3$)C(O)N(CH$_3$)$_2$ | OCH$_3$ | OCH$_3$ | CH | |
| 0 | S | H | H | H | CH=C(CH$_3$)C(O)N(CH$_3$)$_2$ | CH$_3$ | OCH$_3$ | N | |
| 0 | S | H | H | H | CH=C(CH$_3$)C(O)N(CH$_3$)$_2$ | OCH$_3$ | OCH$_3$ | N | |
| 0 | S | H | H | H | CH=CHP(O)(OCH$_3$)$_2$ | CH$_3$ | OCH$_3$ | CH | |
| 0 | S | H | H | H | CH=CHP(O)(OCH$_3$)$_2$ | OCH$_3$ | OCH$_3$ | CH | |
| 0 | S | H | H | H | CH=CHP(O)(OCH$_3$)$_2$ | CH$_3$ | OCH$_3$ | N | |
| 0 | S | H | H | H | CH=CHP(O)(OCH$_3$)$_2$ | OCH$_3$ | OCH$_3$ | N | |
| 0 | S | H | H | H | CH$_2$CH=CH(NO$_2$) | CH$_3$ | OCH$_3$ | CH | |
| 0 | S | H | H | H | CH$_2$CH=CH(NO$_2$) | OCH$_3$ | OCH$_3$ | CH | |
| 0 | S | H | H | H | CH$_2$CH=CH(NO$_2$) | CH$_3$ | OCH$_3$ | N | |
| 0 | S | H | H | H | CH$_2$CH=CH(NO$_2$) | OCH$_3$ | OCH$_3$ | N | |
| 0 | S | H | H | H | CH=CHCN | CH$_3$ | OCH$_3$ | CH | |
| 0 | S | H | H | H | CH=CHCN | OCH$_3$ | OCH$_3$ | CH | |
| 0 | S | H | H | H | CH=CHCN | CH$_3$ | OCH$_3$ | N | |
| 0 | S | H | H | H | CH=CHCN | OCH$_3$ | OCH$_3$ | N | |
| 0 | S | H | H | H | CH$_2$OCH$_2$CH$_2$OCH$_3$ | CH$_3$ | OCH$_3$ | CH | |

TABLE Ig-continued

Structure Ig

| n | G | R | $R_1$ | $R_5$ | $R_6$ | X | Y | Z | m.p. (°C.) |
|---|---|---|---|---|---|---|---|---|---|
| 0 | S | H | H | H | $CH_2OCH_2CH_2OCH_3$ | $OCH_3$ | $OCH_3$ | CH | |
| 0 | S | H | H | H | $CH_2OCH_2CH_2OCH_3$ | $CH_3$ | $OCH_3$ | N | |
| 0 | S | H | H | H | $CH_2OCH_2CH_2OCH_3$ | $OCH_3$ | $OCH_3$ | N | |
| 0 | S | H | H | H | $CH_2C\equiv CC(O)CH_3$ | $CH_3$ | $OCH_3$ | CH | |
| 0 | S | H | H | H | $CH_2C\equiv CC(O)CH_3$ | $OCH_3$ | $OCH_3$ | CH | |
| 0 | S | H | H | H | $CH_2C\equiv CC(O)CH_3$ | $CH_3$ | $OCH_3$ | N | |
| 0 | S | H | H | H | $CH_2C\equiv CC(O)CH_3$ | $OCH_3$ | $OCH_3$ | N | |
| 0 | S | H | H | H | $CH_2C\equiv CC(O)OCH_3$ | $CH_3$ | $OCH_3$ | CH | |
| 0 | S | H | H | H | $CH_2C\equiv CC(O)OCH_3$ | $OCH_3$ | $OCH_3$ | CH | |
| 0 | S | H | H | H | $CH_2C\equiv CC(O)OCH_3$ | $CH_3$ | $OCH_3$ | N | |
| 0 | S | H | H | H | $CH_2C\equiv CC(O)OCH_3$ | $OCH_3$ | $OCH_3$ | N | |
| 0 | S | H | H | H | $CH_2C\equiv CC(O)NHPh$ | $CH_3$ | $OCH_3$ | CH | |
| 0 | S | H | H | H | $CH_2C\equiv CC(O)NHPh$ | $OCH_3$ | $OCH_3$ | CH | |
| 0 | S | H | H | H | $CH_2C\equiv CC(O)NHPh$ | $CH_3$ | $OCH_3$ | N | |
| 0 | S | H | H | H | $CH_2C\equiv CC(O)NHPh$ | $OCH_3$ | $OCH_3$ | N | |
| 0 | S | H | H | H | $CH=CH-2$-Thienyl | $CH_3$ | $OCH_3$ | CH | |
| 0 | S | H | H | H | $CH=CH-2$-Thienyl | $OCH_3$ | $OCH_3$ | CH | |
| 0 | S | H | H | H | $CH=CH-2$-Thienyl | $CH_3$ | $OCH_3$ | N | |
| 0 | S | H | H | H | $CH=CH-2$-Thienyl | $OCH_3$ | $OCH_3$ | N | |
| 0 | S | H | H | H | $CH=CH-2$-Pyridyl | $CH_3$ | $OCH_3$ | CH | |
| 0 | S | H | H | H | $CH=CH-2$-Pyridyl | $OCH_3$ | $OCH_3$ | CH | |
| 0 | S | H | H | H | $CH=CH-2$-Pyridyl | $CH_3$ | $OCH_3$ | N | |
| 0 | S | H | H | H | $CH=CH-2$-Pyridyl | $OCH_3$ | $OCH_3$ | N | |
| 0 | S | H | H | H | $CH=CH-2$-Cyclopentanone | $CH_3$ | $OCH_3$ | CH | |
| 0 | S | H | H | H | $CH=CH-2$-Cyclopentanone | $OCH_3$ | $OCH_3$ | CH | |
| 0 | S | H | H | H | $CH=CH-2$-Cyclopentanone | $CH_3$ | $OCH_3$ | N | |
| 0 | S | H | H | H | $CH=CH-2$-Cyclopentanone | $OCH_3$ | $OCH_3$ | N | |
| 0 | S | H | H | H | $C\equiv C-2$-thienyl | $CH_3$ | $OCH_3$ | CH | |
| 0 | S | H | H | H | $C\equiv C-2$-thienyl | $OCH_3$ | $OCH_3$ | CH | |
| 0 | S | H | H | H | $C\equiv C-2$-thienyl | $CH_3$ | $OCH_3$ | N | |
| 0 | S | H | H | H | $C\equiv C-2$-thienyl | $OCH_3$ | $OCH_3$ | N | |
| 0 | S | H | H | $CH_3$ | H | $CH_3$ | $OCH_3$ | CH | |
| 0 | S | H | H | $CH_3$ | H | $OCH_3$ | $OCH_3$ | CH | |
| 0 | S | H | H | $CH_3$ | H | $CH_3$ | $OCH_3$ | N | |
| 0 | S | H | H | $CH_3$ | H | $OCH_3$ | $OCH_3$ | N | |
| 0 | S | H | H | $CH_3$ | $CH_3$ | $CH_3$ | $OCH_3$ | CH | |
| 0 | S | H | H | $CH_3$ | $CH_3$ | $OCH_3$ | $OCH_3$ | CH | |
| 0 | S | H | H | $CH_3$ | $CH_3$ | $CH_3$ | $OCH_3$ | N | |
| 0 | S | H | H | $CH_3$ | $CH_3$ | $OCH_3$ | $OCH_3$ | N | |
| 0 | S | H | H | $CH_3$ | $CH_2CH_3$ | $CH_3$ | $OCH_3$ | CH | |
| 0 | S | H | H | $CH_3$ | $CH_2CH_3$ | $OCH_3$ | $OCH_3$ | CH | |
| 0 | S | H | H | $CH_3$ | $CH_2CH_3$ | $CH_3$ | $OCH_3$ | N | |
| 0 | S | H | H | $CH_3$ | $CH_2CH_3$ | $OCH_3$ | $OCH_3$ | N | |
| 0 | S | H | H | $CH_3$ | $CH_2CN$ | $CH_3$ | $OCH_3$ | CH | |
| 0 | S | H | H | $CH_3$ | $CH_2CN$ | $OCH_3$ | $OCH_3$ | CH | |
| 0 | S | H | H | $CH_3$ | $CH_2CN$ | $CH_3$ | $OCH_3$ | N | |
| 0 | S | H | H | $CH_3$ | $CH_2CN$ | $OCH_3$ | $OCH_3$ | N | |
| 0 | S | H | H | $CH_3$ | $CH_2CH_2CH_3$ | $CH_3$ | $OCH_3$ | CH | |
| 0 | S | H | H | $CH_3$ | $CH_2CH_2CH_3$ | $OCH_3$ | $OCH_3$ | CH | |
| 0 | S | H | H | $CH_3$ | $CH_2CH_2CH_3$ | $CH_3$ | $OCH_3$ | N | |
| 0 | S | H | H | $CH_3$ | $CH_2CH_2CH_3$ | $OCH_3$ | $OCH_3$ | N | |
| 0 | S | H | H | $CH_3$ | $C(O)CH_3$ | $CH_3$ | $OCH_3$ | CH | |
| 0 | S | H | H | $CH_3$ | $C(O)CH_3$ | $OCH_3$ | $OCH_3$ | CH | |
| 0 | S | H | H | $CH_3$ | $C(O)CH_3$ | $CH_3$ | $OCH_3$ | N | |
| 0 | S | H | H | $CH_3$ | $C(O)CH_3$ | $OCH_3$ | $OCH_3$ | N | |
| 0 | S | H | H | $CH_3$ | $C(O)OCH_3$ | $CH_3$ | $OCH_3$ | CH | |
| 0 | S | H | H | $CH_3$ | $C(O)OCH_3$ | $OCH_3$ | $OCH_3$ | CH | |
| 0 | S | H | H | $CH_3$ | $C(O)OCH_3$ | $CH_3$ | $OCH_3$ | N | |
| 0 | S | H | H | $CH_3$ | $C(O)OCH_3$ | $OCH_3$ | $OCH_3$ | N | |
| 0 | S | H | H | H | H | H | $OCH_3$ | CH | |
| 0 | S | H | H | H | H | $NHCH_3$ | $OCH_3$ | N | |
| 0 | S | H | H | H | H | $NHCH_3$ | $OCH_2CH_3$ | N | |
| 0 | S | H | H | H | H | $OCH_3$ | $C\equiv CH$ | CH | |
| 0 | S | H | H | H | H | $OCH_3$ | $OCF_2H$ | CH | |
| 0 | S | H | H | H | H | $OCH_3$ | cyclopropyl | CH | |
| 0 | S | H | H | H | H | $OCH_3$ | $OCH_2CF_3$ | CH | |
| 0 | S | H | H | H | $CH_3$ | H | $OCH_3$ | CH | |
| 0 | S | H | H | H | $CH_3$ | $NHCH_3$ | $OCH_3$ | N | |
| 0 | S | H | H | H | $CH_3$ | $NHCH_3$ | $OCH_2CH_3$ | N | |
| 0 | S | H | H | H | $CH_3$ | $OCH_3$ | $C\equiv CH$ | CH | |
| 0 | S | H | H | H | $CH_3$ | $OCH_3$ | $OCF_2H$ | CH | |
| 0 | S | H | H | H | $CH_3$ | $OCH_3$ | cyclopropyl | CH | |
| 0 | S | H | H | H | $CH_3$ | $OCH_3$ | $OCH_2CF_3$ | CH | |
| 0 | S | H | H | H | $CH_2(CH_2)_2CH_3$ | H | $OCH_3$ | CH | |
| 0 | S | H | H | H | $CH_2(CH_2)_2CH_3$ | $NHCH_3$ | $OCH_3$ | N | |
| 0 | S | H | H | H | $CH_2(CH_2)_2CH_3$ | $NHCH_3$ | $OCH_2CH_3$ | N | |
| 0 | S | H | H | H | $CH_2(CH_2)_2CH_3$ | $OCH_3$ | $C\equiv CH$ | CH | |
| 0 | S | H | H | H | $CH_2(CH_2)_2CH_3$ | $OCH_3$ | $OCF_2H$ | CH | |
| 0 | S | H | H | H | $CH_2(CH_2)_2CH_3$ | $OCH_3$ | cyclopropyl | CH | |
| 0 | S | H | H | H | $CH_2(CH_2)_2CH_3$ | $OCH_3$ | $OCH_2CF_3$ | CH | |

TABLE Ig-continued

Structure Ig

| n | G | R | $R_1$ | $R_5$ | $R_6$ | X | Y | Z | m.p. (°C.) |
|---|---|---|---|---|---|---|---|---|---|
| 0 | S | H | H | H | $CH_2CH_3$ | H | $OCH_3$ | CH | |
| 0 | S | H | H | H | $CH_2CH_3$ | $NHCH_3$ | $OCH_3$ | N | |
| 0 | S | H | H | H | $CH_2CH_3$ | $NHCH_3$ | $OCH_2CH_3$ | N | |
| 0 | S | H | H | H | $CH_2CH_3$ | $OCH_3$ | $C\equiv CH$ | CH | |
| 0 | S | H | H | H | $CH_2CH_3$ | $OCH_3$ | $OCF_2H$ | CH | |
| 0 | S | H | H | H | $CH_2CH_3$ | $OCH_3$ | cyclopentyl | CH | |
| 0 | S | H | H | H | $CH_2CH_3$ | $OCH_3$ | $OCH_2CF_3$ | CH | |
| 0 | S | H | H | H | $CH_2CH_2F$ | $CH_3$ | $CH_3$ | CH | |
| 0 | S | H | H | H | $CH_2CH_2F$ | $CH_3$ | $OCH_3$ | CH | |
| 0 | S | H | H | H | $CH_2CH_2F$ | $OCH_3$ | $OCH_3$ | CH | |
| 0 | S | H | H | H | $CH_2CH_2F$ | Cl | $OCH_3$ | CH | |
| 0 | S | H | H | H | $CH_2CH_2F$ | $CH_3$ | $OCH_3$ | N | |
| 0 | S | H | H | H | $CH_2CH_2F$ | $OCH_3$ | $OCH_3$ | N | |
| 0 | S | H | $CH_3$ | H | $CH_2CH_2F$ | $CH_3$ | $CH_3$ | CH | |
| 0 | S | H | $CH_3$ | H | $CH_2CH_2F$ | $CH_3$ | $OCH_3$ | CH | |
| 0 | S | H | $CH_3$ | H | $CH_2CH_2F$ | $OCH_3$ | $OCH_3$ | CH | |
| 0 | S | H | $CH_3$ | H | $CH_2CH_2F$ | Cl | $OCH_3$ | CH | |
| 0 | S | H | $CH_3$ | H | $CH_2CH_2F$ | $CH_3$ | $OCH_3$ | N | |
| 0 | S | H | $CH_3$ | H | $CH_2CH_2F$ | $OCH_3$ | $OCH_3$ | N | |
| 0 | S | H | Cl | H | $CH_2CH_2F$ | $CH_3$ | $CH_3$ | CH | |
| 0 | S | H | Cl | H | $CH_2CH_2F$ | $CH_3$ | $OCH_3$ | CH | |
| 0 | S | H | Cl | H | $CH_2CH_2F$ | $OCH_3$ | $OCH_3$ | CH | |
| 0 | S | H | Cl | H | $CH_2CH_2F$ | Cl | $OCH_3$ | CH | |
| 0 | S | H | Cl | H | $CH_2CH_2F$ | $CH_3$ | $OCH_3$ | N | |
| 0 | S | H | Cl | H | $CH_2CH_2F$ | $OCH_3$ | $OCH_3$ | N | |
| 0 | S | H | H | H | $CH_2CH_2Cl$ | $CH_3$ | $CH_3$ | CH | |
| 0 | S | H | H | H | $CH_2CH_2Cl$ | $CH_3$ | $OCH_3$ | CH | |
| 0 | S | H | H | H | $CH_2CH_2Cl$ | $OCH_3$ | $OCH_3$ | CH | |
| 0 | S | H | H | H | $CH_2CH_2Cl$ | Cl | $OCH_3$ | CH | |
| 0 | S | H | H | H | $CH_2CH_2Cl$ | $CH_3$ | $OCH_3$ | N | |
| 0 | S | H | H | H | $CH_2CH_2Cl$ | $OCH_3$ | $OCH_3$ | N | |
| 0 | S | H | $CH_3$ | H | $CH_2CH_2Cl$ | $CH_3$ | $CH_3$ | CH | |
| 0 | S | H | $CH_3$ | H | $CH_2CH_2Cl$ | $CH_3$ | $OCH_3$ | CH | |
| 0 | S | H | $CH_3$ | H | $CH_2CH_2Cl$ | $OCH_3$ | $OCH_3$ | CH | |
| 0 | S | H | $CH_3$ | H | $CH_2CH_2Cl$ | Cl | $OCH_3$ | CH | |
| 0 | S | H | $CH_3$ | H | $CH_2CH_2Cl$ | $CH_3$ | $OCH_3$ | N | |
| 0 | S | H | $CH_3$ | H | $CH_2CH_2Cl$ | $OCH_3$ | $OCH_3$ | N | |
| 0 | S | H | Cl | H | $CH_2CH_2Cl$ | $CH_3$ | $CH_3$ | CH | |
| 0 | S | H | Cl | H | $CH_2CH_2Cl$ | $CH_3$ | $OCH_3$ | CH | |
| 0 | S | H | Cl | H | $CH_2CH_2Cl$ | $OCH_3$ | $OCH_3$ | CH | |
| 0 | S | H | Cl | H | $CH_2CH_2Cl$ | Cl | $OCH_3$ | CH | |
| 0 | S | H | Cl | H | $CH_2CH_2Cl$ | $CH_3$ | $OCH_3$ | N | |
| 0 | S | H | Cl | H | $CH_2CH_2Cl$ | $OCH_3$ | $OCH_3$ | N | |
| 0 | S | H | H | H | $CH_2CH_2CH_2F$ | $CH_3$ | $CH_3$ | CH | |
| 0 | S | H | H | H | $CH_2CH_2CH_2F$ | $CH_3$ | $OCH_3$ | CH | |
| 0 | S | H | H | H | $CH_2CH_2CH_2F$ | $OCH_3$ | $OCH_3$ | CH | |
| 0 | S | H | H | H | $CH_2CH_2CH_2F$ | Cl | $OCH_3$ | CH | |
| 0 | S | H | H | H | $CH_2CH_2CH_2F$ | $CH_3$ | $OCH_3$ | N | |
| 0 | S | H | H | H | $CH_2CH_2CH_2F$ | $OCH_3$ | $OCH_3$ | N | |
| 0 | S | H | $CH_3$ | H | $CH_2CH_2CH_2F$ | $CH_3$ | $CH_3$ | CH | |
| 0 | S | H | $CH_3$ | H | $CH_2CH_2CH_2F$ | $CH_3$ | $OCH_3$ | CH | |
| 0 | S | H | $CH_3$ | H | $CH_2CH_2CH_2F$ | $OCH_3$ | $OCH_3$ | CH | |
| 0 | S | H | $CH_3$ | H | $CH_2CH_2CH_2F$ | Cl | $OCH_3$ | CH | |
| 0 | S | H | $CH_3$ | H | $CH_2CH_2CH_2F$ | $CH_3$ | $OCH_3$ | N | |
| 0 | S | H | $CH_3$ | H | $CH_2CH_2CH_2F$ | $OCH_3$ | $OCH_3$ | N | |
| 0 | S | H | Cl | H | $CH_2CH_2CH_2F$ | $CH_3$ | $CH_3$ | CH | |
| 0 | S | H | Cl | H | $CH_2CH_2CH_2F$ | $CH_3$ | $OCH_3$ | CH | |
| 0 | S | H | Cl | H | $CH_2CH_2CH_2F$ | $OCH_3$ | $OCH_3$ | CH | |
| 0 | S | H | Cl | H | $CH_2CH_2CH_2F$ | Cl | $OCH_3$ | CH | |
| 0 | S | H | Cl | H | $CH_2CH_2CH_2F$ | $CH_3$ | $OCH_3$ | N | |
| 0 | S | H | Cl | H | $CH_2CH_2CH_2F$ | $OCH_3$ | $OCH_3$ | N | |
| 0 | S | H | H | H | $CH_2OCH_3$ | $CH_3$ | $CH_3$ | CH | |
| 0 | S | H | H | H | $CH_2OCH_3$ | $CH_3$ | $OCH_3$ | CH | |
| 0 | S | H | H | H | $CH_2OCH_3$ | $OCH_3$ | $OCH_3$ | CH | |
| 0 | S | H | H | H | $CH_2OCH_3$ | Cl | $OCH_3$ | CH | |
| 0 | S | H | H | H | $CH_2OCH_3$ | $CH_3$ | $OCH_3$ | N | |
| 0 | S | H | H | H | $CH_2OCH_3$ | $OCH_3$ | $OCH_3$ | N | |
| 0 | S | H | $CH_3$ | H | $CH_2OCH_3$ | $CH_3$ | $CH_3$ | CH | |
| 0 | S | H | $CH_3$ | H | $CH_2OCH_3$ | $CH_3$ | $OCH_3$ | CH | |
| 0 | S | H | $CH_3$ | H | $CH_2OCH_3$ | $OCH_3$ | $OCH_3$ | CH | |
| 0 | S | H | $CH_3$ | H | $CH_2OCH_3$ | Cl | $OCH_3$ | CH | |
| 0 | S | H | $CH_3$ | H | $CH_2OCH_3$ | $CH_3$ | $OCH_3$ | N | |
| 0 | S | H | $CH_3$ | H | $CH_2OCH_3$ | $OCH_3$ | $OCH_3$ | N | |
| 0 | S | H | Cl | H | $CH_2OCH_3$ | $CH_3$ | $CH_3$ | CH | |
| 0 | S | H | Cl | H | $CH_2OCH_3$ | $CH_3$ | $OCH_3$ | CH | |
| 0 | S | H | Cl | H | $CH_2OCH_3$ | $OCH_3$ | $OCH_3$ | CH | |
| 0 | S | H | Cl | H | $CH_2OCH_3$ | Cl | $OCH_3$ | CH | |
| 0 | S | H | Cl | H | $CH_2OCH_3$ | $CH_3$ | $OCH_3$ | N | |
| 0 | S | H | Cl | H | $CH_2OCH_3$ | $OCH_3$ | $OCH_3$ | N | |
| 0 | S | H | H | H | $CH_2CH_2OCH_3$ | $CH_3$ | $CH_3$ | CH | |

TABLE Ig-continued

Structure Ig

| n | G | R | $R_1$ | $R_5$ | $R_6$ | X | Y | Z | m.p. (° C.) |
|---|---|---|-------|-------|-------|---|---|---|-------------|
| 0 | S | H | H | H | $CH_2CH_2OCH_3$ | $CH_3$ | $OCH_3$ | CH | |
| 0 | S | H | H | H | $CH_2CH_2OCH_3$ | $OCH_3$ | $OCH_3$ | CH | |
| 0 | S | H | H | H | $CH_2CH_2OCH_3$ | Cl | $OCH_3$ | CH | |
| 0 | S | H | H | H | $CH_2CH_2OCH_3$ | $CH_3$ | $OCH_3$ | N | |
| 0 | S | H | H | H | $CH_2CH_2OCH_3$ | $OCH_3$ | $OCH_3$ | N | |
| 0 | S | H | $CH_3$ | H | $CH_2CH_2OCH_3$ | $CH_3$ | $CH_3$ | CH | |
| 0 | S | H | $CH_3$ | H | $CH_2CH_2OCH_3$ | $CH_3$ | $OCH_3$ | CH | |
| 0 | S | H | $CH_3$ | H | $CH_2CH_2OCH_3$ | $OCH_3$ | $OCH_3$ | CH | |
| 0 | S | H | $CH_3$ | H | $CH_2CH_2OCH_3$ | Cl | $OCH_3$ | CH | |
| 0 | S | H | $CH_3$ | H | $CH_2CH_2OCH_3$ | $CH_3$ | $OCH_3$ | N | |
| 0 | S | H | $CH_3$ | H | $CH_2CH_2OCH_3$ | $OCH_3$ | $OCH_3$ | N | |
| 0 | S | H | Cl | H | $CH_2CH_2OCH_3$ | $CH_3$ | $CH_3$ | CH | |
| 0 | S | H | Cl | H | $CH_2CH_2OCH_3$ | $CH_3$ | $OCH_3$ | CH | |
| 0 | S | H | Cl | H | $CH_2CH_2OCH_3$ | $OCH_3$ | $OCH_3$ | CH | |
| 0 | S | H | Cl | H | $CH_2CH_2OCH_3$ | Cl | $OCH_3$ | CH | |
| 0 | S | H | Cl | H | $CH_2CH_2OCH_3$ | $CH_3$ | $OCH_3$ | N | |
| 0 | S | H | Cl | H | $CH_2CH_2OCH_3$ | $OCH_3$ | $OCH_3$ | N | |
| H | S | H | H | H | $C(O)CH_3$ | $CH_3$ | $CH_3$ | CH | |
| H | S | H | H | H | $C(O)CH_3$ | $CH_3$ | $OCH_3$ | CH | |
| H | S | H | H | H | $C(O)CH_3$ | $OCH_3$ | $OCH_3$ | CH | |
| H | S | H | H | H | $C(O)CH_3$ | Cl | $OCH_3$ | CH | |
| H | S | H | H | H | $C(O)CH_3$ | $CH_3$ | $OCH_3$ | N | |
| H | S | H | H | H | $C(O)CH_3$ | $OCH_3$ | $OCH_3$ | N | |
| H | S | H | $CH_3$ | H | $C(O)CH_3$ | $CH_3$ | $CH_3$ | CH | |
| H | S | H | $CH_3$ | H | $C(O)CH_3$ | $CH_3$ | $OCH_3$ | CH | |
| H | S | H | $CH_3$ | H | $C(O)CH_3$ | $OCH_3$ | $OCH_3$ | CH | |
| H | S | H | $CH_3$ | H | $C(O)CH_3$ | Cl | $OCH_3$ | CH | |
| H | S | H | $CH_3$ | H | $C(O)CH_3$ | $CH_3$ | $OCH_3$ | N | |
| H | S | H | $CH_3$ | H | $C(O)CH_3$ | $OCH_3$ | $OCH_3$ | N | |
| H | S | H | Cl | H | $C(O)CH_3$ | $CH_3$ | $CH_3$ | CH | |
| H | S | H | Cl | H | $C(O)CH_3$ | $CH_3$ | $OCH_3$ | CH | |
| H | S | H | Cl | H | $C(O)CH_3$ | $OCH_3$ | $OCH_3$ | CH | |
| H | S | H | Cl | H | $C(O)CH_3$ | Cl | $OCH_3$ | CH | |
| H | S | H | Cl | H | $C(O)CH_3$ | $CH_3$ | $OCH_3$ | N | |
| H | S | H | Cl | H | $C(O)CH_3$ | $OCH_3$ | $OCH_3$ | N | |
| H | S | H | H | H | $CH_2C(O)CH_3$ | $CH_3$ | $CH_3$ | CH | |
| H | S | H | H | H | $CH_2C(O)CH_3$ | $CH_3$ | $OCH_3$ | CH | |
| H | S | H | H | H | $CH_2C(O)CH_3$ | $OCH_3$ | $OCH_3$ | CH | |
| H | S | H | H | H | $CH_2C(O)CH_3$ | Cl | $OCH_3$ | CH | |
| H | S | H | H | H | $CH_2C(O)CH_3$ | $CH_3$ | $OCH_3$ | N | |
| H | S | H | H | H | $CH_2C(O)CH_3$ | $OCH_3$ | $OCH_3$ | N | |
| H | S | H | $CH_3$ | H | $CH_2C(O)CH_3$ | $CH_3$ | $CH_3$ | CH | |
| H | S | H | $CH_3$ | H | $CH_2C(O)CH_3$ | $CH_3$ | $OCH_3$ | CH | |
| H | S | H | $CH_3$ | H | $CH_2C(O)CH_3$ | $OCH_3$ | $OCH_3$ | CH | |
| H | S | H | $CH_3$ | H | $CH_2C(O)CH_3$ | Cl | $OCH_3$ | CH | |
| H | S | H | $CH_3$ | H | $CH_2C(O)CH_3$ | $CH_3$ | $OCH_3$ | N | |
| H | S | H | $CH_3$ | H | $CH_2C(O)CH_3$ | $OCH_3$ | $OCH_3$ | N | |
| 0 | S | H | Cl | H | $CH_2C(O)CH_3$ | $CH_3$ | $CH_3$ | CH | |
| 0 | S | H | Cl | H | $CH_2C(O)CH_3$ | $CH_3$ | $OCH_3$ | CH | |
| 0 | S | H | Cl | H | $CH_2C(O)CH_3$ | $OCH_3$ | $OCH_3$ | CH | |
| 0 | S | H | Cl | H | $CH_2C(O)CH_3$ | Cl | $OCH_3$ | CH | |
| 0 | S | H | Cl | H | $CH_2C(O)CH_3$ | $CH_3$ | $OCH_3$ | N | |
| 0 | S | H | Cl | H | $CH_2C(O)CH_3$ | $OCH_3$ | $OCH_3$ | N | |
| 0 | S | H | H | H | $CO_2CH_3$ | $CH_3$ | $CH_3$ | CH | |
| 0 | S | H | H | H | $CO_2CH_3$ | $CH_3$ | $OCH_3$ | CH | |
| 0 | S | H | H | H | $CO_2CH_3$ | $OCH_3$ | $OCH_3$ | CH | |
| 0 | S | H | H | H | $CO_2CH_3$ | Cl | $OCH_3$ | CH | |
| 0 | S | H | H | H | $CO_2CH_3$ | $CH_3$ | $OCH_3$ | N | |
| 0 | S | H | H | H | $CO_2CH_3$ | $OCH_3$ | $OCH_3$ | N | |
| 0 | S | H | $CH_3$ | H | $CO_2CH_3$ | $CH_3$ | $CH_3$ | CH | |
| 0 | S | H | $CH_3$ | H | $CO_2CH_3$ | $CH_3$ | $OCH_3$ | CH | |
| 0 | S | H | $CH_3$ | H | $CO_2CH_3$ | $OCH_3$ | $OCH_3$ | CH | |
| 0 | S | H | $CH_3$ | H | $CO_2CH_3$ | Cl | $OCH_3$ | CH | |
| 0 | S | H | $CH_3$ | H | $CO_2CH_3$ | $CH_3$ | $OCH_3$ | N | |
| 0 | S | H | $CH_3$ | H | $CO_2CH_3$ | $OCH_3$ | $OCH_3$ | N | |
| 0 | S | H | Cl | H | $CO_2CH_3$ | $CH_3$ | $CH_3$ | CH | |
| 0 | S | H | Cl | H | $CO_2CH_3$ | $CH_3$ | $OCH_3$ | CH | |
| 0 | S | H | Cl | H | $CO_2CH_3$ | $OCH_3$ | $OCH_3$ | CH | |
| 0 | S | H | Cl | H | $CO_2CH_3$ | Cl | $OCH_3$ | CH | |
| 0 | S | H | Cl | H | $CO_2CH_3$ | $CH_3$ | $OCH_3$ | N | |
| 0 | S | H | Cl | H | $CO_2CH_3$ | $OCH_3$ | $OCH_3$ | N | |

TABLE Ih

Structure Ih

| n | G | R | $R_1'$ | $R_5$ | $R_6$ | X | Y | Z | m.p. (°C.) |
|---|---|---|--------|-------|-------|---|---|---|------------|
| 0 | S | H | H | H | H | $CH_3$ | $CH_3$ | CH | |

TABLE Ih-continued

Structure Ih

| n | G | R | R₁' | R₅ | R₆ | X | Y | Z | m.p. (°C.) |
|---|---|---|---|---|---|---|---|---|---|
| 0 | S | H | H | H | H | CH₃ | OCH₃ | CH | |
| 0 | S | H | H | H | H | OCH₃ | OCH₃ | CH | |
| 0 | S | H | H | H | H | Cl | OCH₃ | CH | |
| 0 | S | H | H | H | H | Br | OCH₃ | CH | |
| 0 | S | H | H | H | H | CH₃ | OCH₃ | N | |
| 0 | S | H | H | H | H | OCH₃ | OCH₃ | N | |
| 0 | S | H | H | H | CH₃ | CH₃ | CH₃ | CH | |
| 0 | S | H | H | H | CH₃ | CH₃ | OCH₃ | CH | |
| 0 | S | H | H | H | CH₃ | OCH₃ | OCH₃ | CH | |
| 0 | S | H | H | H₃ | CH | Cl₃ | OCH | CH | |
| 0 | S | H | H | H | CH₃ | Br | OCH₃ | CH | |
| 0 | S | H | H | H | CH₃ | CH₃ | OCH₃ | N | |
| 0 | S | H | H · | H | CH₃ | OCH₃ | OCH₃ | N | |
| 0 | S | H | H | H | CH₂CH₂CH₂CH₃ | CH₃ | CH₃ | CH | |
| 0 | S | H | H | H | CH₂CH₂CH₂CH₃ | CH₃ | OCH₃ | CH | |
| 0 | S | H | H | H | CH₂CH₂CH₂CH₃ | OCH₃ | OCH₃ | CH | |
| 0 | S | H | H | H | CH₂CH₂CH₂CH₃ | Cl | OCH₃ | CH | |
| 0 | S | H | H | H | CH₂CH₂CH₂CH₃ | Br | OCH₃ | CH | |
| 0 | S | H | H | H | CH₂CH₂CH₂CH₃ | CH₃ | OCH₃ | N | |
| 0 | S | H | H | H | CH₂CH₂CH₂CH₃ | OCH₃ | OCH₃ | N | |
| 0 | S | H | Cl | H | H | CH₃ | CH₃ | CH | |
| 0 | S | H | Cl | H | H | CH₃ | OCH₃ | CH | |
| 0 | S | H | Cl | H | H | OCH₃ | OCH₃ | CH | |
| 0 | S | H | Cl | H | H | Cl | OCH₃ | CH | |
| 0 | S | H | Cl | H | H | Br | OCH₃ | CH | |
| 0 | S | H | Cl | H | H | CH₃ | OCH₃ | N | |
| 0 | S | H | Cl | H | H | OCH₃ | OCH₃ | N | |
| 0 | S | H | Cl | H | CH₃ | CH₃ | CH₃ | CH | |
| 0 | S | H | Cl | H | CH₃ | CH₃ | OCH₃ | CH | |
| 0 | S | H | Cl | H | CH₃ | OCH₃ | OCH₃ | CH | |
| 0 | S | H | Cl | H | CH₃ | Cl | OCH₃ | CH | |
| 0 | S | H | Cl | H | CH₃ | Br | OCH₃ | CH | |
| 0 | S | H | Cl | H | CH₃ | CH₃ | OCH₃ | N | |
| 0 | S | H | Cl | H | CH₃ | OCH₃ | OCH₃ | N | |
| 0 | S | H | Cl | H | CH₂CH₂CH₂CH₃ | CH₃ | CH₃ | CH | |
| 0 | S | H | Cl | H | CH₂CH₂CH₂CH₃ | CH₃ | OCH₃ | CH | |
| 0 | S | H | Cl | H | CH₂CH₂CH₂CH₃ | OCH₃ | OCH₃ | CH | |
| 0 | S | H | Cl | H | CH₂CH₂CH₂CH₃ | Cl | OCH₃ | CH | |
| 0 | S | H | Cl | H | CH₂CH₂CH₂CH₃ | Br | OCH₃ | CH | |
| 0 | S | H | Cl | H | CH₂CH₂CH₂CH₃ | CH₃ | OCH₃ | N | |
| 0 | S | H | Cl | H | CH₂CH₂CH₂CH₃ | OCH₃ | OCH₃ | N | |
| 1 | S | H | H | H | CH₃ | OCH₃ | OCH₃ | CH | |
| 0 | S | H | H | H | C(O)CH₃ | OCH₂CH₃ | NHCH₃ | N | |
| 0 | S | H | H | H | CO₂CH₃ | OCH₂CH₃ | NHCH₃ | N | |
| 0 | S | H | H | H | CO₂Ph | OCH₃ | OCH₃ | CH | |
| 0 | S | H | H | H | CH₂CH=CH₂ | OCH₃ | OCH₃ | CH | |
| 0 | S | H | H | H | CH₂CH=CHCH₃ | OCH₃ | OCH₃ | CH | |
| 0 | S | H | H | H | CH₂C≡CH | OCH₃ | OCH₃ | CH | |
| 0 | S | H | H | H | CH₂C≡CCH₃ | OCH₃ | OCH₃ | CH | |
| 0 | S | H | H | H | (CO)₂CH₃ | CH₃ | OCH₃ | CH | |
| 0 | S | H | H | H | (CO)₂CH₃ | OCH₃ | OCH₃ | CH | |
| 0 | S | H | H | H | (CO)₂CH₃ | CH₃ | OCH₃ | N | |
| 0 | S | H | H | H | (CO)₂CH₃ | OCH₃ | OCH₃ | N | |
| 0 | S | H | H | H | C(O)N(CH₃)₂ | CH₃ | OCH₃ | CH | |
| 0 | S | H | H | H | C(O)N(CH₃)₂ | OCH₃ | OCH₃ | CH | |
| 0 | S | H | H | H | C(O)N(CH₃)₂ | CH₃ | OCH₃ | N | |
| 0 | S | H | H | H | C(O)N(CH₃)₂ | OCH₃ | OCH₃ | N | |
| 0 | S | H | H | H | C(O)NH₂ | CH₃ | OCH₃ | CH | |
| 0 | S | H | H | H | C(O)NH₂ | OCH₃ | OCH₃ | CH | |
| 0 | S | H | H | H | C(O)NH₂ | CH₃ | OCH₃ | N | |
| 0 | S | H | H | H | C(O)NH₂ | OCH₃ | OCH₃ | N | |
| 0 | S | H | H | H | C(S)SCH₃ | CH₃ | OCH₃ | CH | |
| 0 | S | H | H | H | C(S)SCH₃ | OCH₃ | OCH₃ | CH | |
| 0 | S | H | H | H | C(S)SCH₃ | CH₃ | OCH₃ | N | |
| 0 | S | H | H | H | C(S)SCH₃ | OCH₃ | OCH₃ | N | |
| 0 | S | H | H | H | C(S)SCH₂CH=CH₂ | CH₃ | OCH₃ | CH | |
| 0 | S | H | H | H | C(S)SCH₂CH=CH₂ | OCH₃ | OCH₃ | CH | |
| 0 | S | H | H | H | C(S)SCH₂CH=CH₂ | CH₃ | OCH₃ | N | |
| 0 | S | H | H | H | C(S)SCH₂CH=CH₂ | OCH₃ | OCH₃ | N | |
| 0 | S | H | H | H | C(O)—2-thiophene | CH₃ | OCH₃ | CH | |
| 0 | S | H | H | H | C(O)—2-thiophene | OCH₃ | OCH₃ | CH | |
| 0 | S | H | H | H | C(O)—2-thiophene | CH₃ | OCH₃ | N | |
| 0 | S | H | H | H | C(O)—2-thiophene | OCH₃ | OCH₃ | N | |
| 0 | S | H | H | H | C(O)—2-pyridine | CH₃ | OCH₃ | CH | |
| 0 | S | H | H | H | C(O)—2-pyridine | OCH₃ | OCH₃ | CH | |
| 0 | S | H | H | H | C(O)—2-pyridine | CH₃ | OCH₃ | N | |
| 0 | S | H | H | H | C(O)—2-pyridine | OCH₃ | OCH₃ | N | |
| 0 | S | H | H | H | C(O)—2-furan | CH₃ | OCH₃ | CH | |
| 0 | S | H | H | H | C(O)—2-furan | OCH₃ | OCH₃ | CH | |

TABLE Ih-continued

Structure Ih

| n | G | R | R₁' | R₅ | R₆ | X | Y | Z | m.p. (°C.) |
|---|---|---|-----|----|----|---|---|---|------------|
| 0 | S | H | H | H | C(O)—2-furan | CH₃ | OCH₃ | N | |
| 0 | S | H | H | H | C(O)—2-furan | OCH₃ | OCH₃ | N | |
| 0 | S | H | H | H | C(O)—2-thiazole | CH₃ | OCH₃ | CH | |
| 0 | S | H | H | H | C(O)—2-thiazole | OCH₃ | OCH₃ | CH | |
| 0 | S | H | H | H | C(O)—2-thiazole | CH₃ | OCH₃ | N | |
| 0 | S | H | H | H | C(O)—2-thiazole | OCH₃ | OCH₃ | N | |
| 0 | S | H | H | H | C(O)—2-oxazole | CH₃ | OCH₃ | CH | |
| 0 | S | H | H | H | C(O)—2-oxazole | OCH₃ | OCH₃ | CH | |
| 0 | S | H | H | H | C(O)—2-oxazole | CH₃ | OCH₃ | N | |
| 0 | S | H | H | H | C(O)—2-oxazole | OCH₃ | OCH₃ | N | |
| 0 | S | H | H | H | C(O)—2-cyclopentanone | CH₃ | OCH₃ | CH | |
| 0 | S | H | H | H | C(O)—2-cyclopentanone | OCH₃ | OCH₃ | CH | |
| 0 | S | H | H | H | C(O)—2-cyclopentanone | CH₃ | OCH₃ | N | |
| 0 | S | H | H | H | C(O)—2-cyclopentanone | OCH₃ | OCH₃ | N | |
| 0 | S | H | H | H | C(O)—2-butyrolactone | CH₃ | OCH₃ | CH | |
| 0 | S | H | H | H | C(O)—2-butyrolactone | OCH₃ | OCH₃ | CH | |
| 0 | S | H | H | H | C(O)—2-butyrolactone | CH₃ | OCH₃ | N | |
| 0 | S | H | H | H | C(O)—2-butyrolactone | OCH₃ | OCH₃ | N | |
| 0 | S | H | H | H | C(O)—2-(5-Cl)thiophene | CH₃ | OCH₃ | CH | |
| 0 | S | H | H | H | C(O)—2-(5-Cl)thiophene | OCH₃ | OCH₃ | CH | |
| 0 | S | H | H | H | C(O)—2-(5-Cl)thiophene | CH₃ | OCH₃ | N | |
| 0 | S | H | H | H | C(O)—2-(5-Cl)thiophene | OCH₃ | OCH₃ | N | |
| 0 | S | H | H | H | CH₂OP(O)(CH₃)₂ | CH₃ | OCH₃ | CH | |
| 0 | S | H | H | H | CH₂OP(O)(CH₃)₂ | OCH₃ | OCH₃ | CH | |
| 0 | S | H | H | H | CH₂OP(O)(CH₃)₂ | CH₃ | OCH₃ | N | |
| 0 | S | H | H | H | CH₂OP(O)(CH₃)₂ | OCH₃ | OCH₃ | N | |
| 0 | S | H | H | H | CH₂CH₂OP(O)OCH₃)₂ | CH₃ | OCH₃ | CH | |
| 0 | S | H | H | H | CH₂CH₂OP(O)OCH₃)₂ | OCH₃ | OCH₃ | CH | |
| 0 | S | H | H | H | CH₂CH₂OP(O)OCH₃)₂ | CH₃ | OCH₃ | N | |
| 0 | S | H | H | H | CH₂CH₂OP(O)OCH₃)₂ | OCH₃ | OCH₃ | N | |
| 0 | S | H | H | H | CH₂SP(O)(CH₃)₂ | CH₃ | OCH₃ | CH | |
| 0 | S | H | H | H | CH₂SP(O)(CH₃)₂ | OCH₃ | OCH₃ | CH | |
| 0 | S | H | H | H | CH₂SP(O)(CH₃)₂ | CH₃ | OCH₃ | N | |
| 0 | S | H | H | H | CH₂SP(O)(CH₃)₂ | OCH₃ | OCH₃ | N | |
| 0 | S | H | H | H | CH₂SP(O)(SCH₃)₂ | CH₃ | OCH₃ | CH | |
| 0 | S | H | H | H | CH₂SP(O)(SCH₃)₂ | OCH₃ | OCH₃ | CH | |
| 0 | S | H | H | H | CH₂SP(O)(SCH₃)₂ | CH₃ | OCH₃ | N | |
| 0 | S | H | H | H | CH₂SP(O)(SCH₃)₂ | OCH₃ | OCH₃ | N | |
| 0 | S | H | H | H | CH₂SP(S)(CH₂CH₃)₂ | CH₃ | OCH₃ | CH | |
| 0 | S | H | H | H | CH₂SP(S)(CH₂CH₃)₂ | OCH₃ | OCH₃ | CH | |
| 0 | S | H | H | H | CH₂SP(S)(CH₂CH₃)₂ | CH₃ | OCH₃ | N | |
| 0 | S | H | H | H | CH₂SP(S)(CH₂CH₃)₂ | OCH₃ | OCH₃ | N | |
| 0 | S | H | H | H | CH₂CH₂P(O)(OCH₃)₂ | CH₃ | OCH₃ | CH | |
| 0 | S | H | H | H | CH₂CH₂P(O)(OCH₃)₂ | OCH₃ | OCH₃ | CH | |
| 0 | S | H | H | H | CH₂CH₂P(O)(OCH₃)₂ | CH₃ | OCH₃ | N | |
| 0 | S | H | H | H | CH₂CH₂P(O)(OCH₃)₂ | OCH₃ | OCH₃ | N | |
| 0 | S | H | H | H | CH₂P(O)(OCH₂CH₃)₂ | CH₃ | OCH₃ | CH | |
| 0 | S | H | H | H | CH₂P(O)(OCH₂CH₃)₂ | OCH₃ | OCH₃ | CH | |
| 0 | S | H | H | H | CH₂P(O)(OCH₂CH₃)₂ | CH₃ | OCH₃ | N | |
| 0 | S | H | H | H | CH₂P(O)(OCH₂CH₃)₂ | OCH₃ | OCH₃ | N | |
| 0 | S | H | H | H | CH₂NHC(O)Ph | CH₃ | OCH₃ | CH | |
| 0 | S | H | H | H | CH₂NHC(O)Ph | OCH₃ | OCH₃ | CH | |
| 0 | S | H | H | H | CH₂NHC(O)Ph | CH₃ | OCH₃ | N | |
| 0 | S | H | H | H | CH₂NHC(O)Ph | OCH₃ | OCH₃ | N | |
| 0 | S | H | H | H | CH₂NHC(O)CH₂Cl | CH₃ | OCH₃ | CH | |
| 0 | S | H | H | H | CH₂NHC(O)CH₂Cl | OCH₃ | OCH₃ | CH | |
| 0 | S | H | H | H | CH₂NHC(O)CH₂Cl | CH₃ | OCH₃ | N | |
| 0 | S | H | H | H | CH₂NHC(O)CH₂Cl | OCH₃ | OCH₃ | N | |
| 0 | S | H | H | H | CH₂NHC(O)OCH₃ | CH₃ | OCH₃ | CH | |
| 0 | S | H | H | H | CH₂NHC(O)OCH₃ | OCH₃ | OCH₃ | CH | |
| 0 | S | H | H | H | CH₂NHC(O)OCH₃ | CH₃ | OCH₃ | N | |
| 0 | S | H | H | H | CH₂NHC(O)OCH₃ | OCH₃ | OCH₃ | N | |
| 0 | S | H | H | H | CH₂NHC(O)NHCH₃ | CH₃ | OCH₃ | CH | |
| 0 | S | H | H | H | CH₂NHC(O)NHCH₃ | OCH₃ | OCH₃ | CH | |
| 0 | S | H | H | H | CH₂NHC(O)NHCH₃ | CH₃ | OCH₃ | N | |
| 0 | S | H | H | H | CH₂NHC(O)NHCH₃ | OCH₃ | OCH₃ | N | |
| 0 | S | H | H | H | CH₂NHSO₂CH₃ | CH₃ | OCH₃ | CH | |
| 0 | S | H | H | H | CH₂NHSO₂CH₃ | OCH₃ | OCH₃ | CH | |
| 0 | S | H | H | H | CH₂NHSO₂CH₃ | CH₃ | OCH₃ | N | |
| 0 | S | H | H | H | CH₂NHSO₂CH₃ | OCH₃ | OCH₃ | N | |
| 0 | S | H | H | H | CH₂CH₂NHSO₂CH₃ | CH₃ | OCH₃ | CH | |
| 0 | S | H | H | H | CH₂CH₂NHSO₂CH₃ | OCH₃ | OCH₃ | CH | |
| 0 | S | H | H | H | CH₂CH₂NHSO₂CH₃ | CH₃ | OCH₃ | N | |
| 0 | S | H | H | H | CH₂CH₂NHSO₂CH₃ | OCH₃ | OCH₃ | N | |
| 0 | S | H | H | H | CH₂NHP(O)(CH₃)₂ | CH₃ | OCH₃ | CH | |
| 0 | S | H | H | H | CH₂NHP(O)(CH₃)₂ | OCH₃ | OCH₃ | CH | |
| 0 | S | H | H | H | CH₂NHP(O)(CH₃)₂ | CH₃ | OCH₃ | N | |
| 0 | S | H | H | H | CH₂NHP(O)(CH₃)₂ | OCH₃ | OCH₃ | N | |
| 0 | S | H | H | H | OH | CH₃ | OCH₃ | CH | |

TABLE Ih-continued

Structure Ih

| n | G | R | R₁' | R₅ | R₆ | X | Y | Z | m.p. (°C.) |
|---|---|---|---|---|---|---|---|---|---|
| 0 | S | H | H | H | OH | OCH₃ | OCH₃ | CH | |
| 0 | S | H | H | H | OH | CH₃ | OCH₃ | N | |
| 0 | S | H | H | H | OH | OCH₃ | OCH₃ | N | |
| 0 | S | H | H | H | NH₂ | CH₃ | OCH₃ | CH | |
| 0 | S | H | H | H | NH₂ | OCH₃ | OCH₃ | CH | |
| 0 | S | H | H | H | NH₂ | CH₃ | OCH₃ | N | |
| 0 | S | H | H | H | NH₂ | OCH₃ | OCH₃ | N | |
| 0 | S | H | H | H | P(O)(CH₃)₂ | CH₃ | OCH₃ | CH | |
| 0 | S | H | H | H | P(O)(CH₃)₂ | OCH₃ | OCH₃ | CH | |
| 0 | S | H | H | H | P(O)(CH₃)₂ | CH₃ | OCH₃ | N | |
| 0 | S | H | H | H | P(O)(CH₃)₂ | OCH₃ | OCH₃ | N | |
| 0 | S | H | H | H | P(O)(OCH₂CH₃)₂ | CH₃ | OCH₃ | H | |
| 0 | S | H | H | H | P(O)(OCH₂CH₃)₂ | OCH₃ | OCH₃ | CH | |
| 0 | S | H | H | H | P(O)(OCH₂CH₃)₂ | CH₃ | OCH₃ | N | |
| 0 | S | H | H | H | P(O)(OCH₂CH₃)₂ | OCH₃ | OCH₃ | N | |
| 0 | S | H | H | H | P(O)(SCH₂CH₃)₂ | CH₃ | OCH₃ | CH | |
| 0 | S | H | H | H | P(O)(SCH₂CH₃)₂ | OCH₃ | OCH₃ | CH | |
| 0 | S | H | H | H | P(O)(SCH₂CH₃)₂ | CH₃ | OCH₃ | N | |
| 0 | S | H | H | H | P(O)(SCH₂CH₃)₂ | OCH₃ | OCH₃ | N | |
| 0 | S | H | H | H | P(S)(SCH₃)₂ | CH₃ | OCH₃ | CH | |
| 0 | S | H | H | H | P(S)(SCH₃)₂ | OCH₃ | OCH₃ | CH | |
| 0 | S | H | H | H | P(S)(SCH₃)₂ | CH₃ | OCH₃ | N | |
| 0 | S | H | H | H | P(S)(SCH₃)₂ | OCH₃ | OCH₃ | N | |
| 0 | S | H | H | H | (CO)₂OCH₂CH₃ | CH₃ | OCH₃ | CH | |
| 0 | S | H | H | H | (CO)₂OCH₂CH₃ | OCH₃ | OCH₃ | CH | |
| 0 | S | H | H | H | (CO)₂OCH₂CH₃ | CH₃ | OCH₃ | N | |
| 0 | S | H | H | H | (CO)₂OCH₂CH₃ | OCH₃ | OCH₃ | N | |
| 0 | S | H | H | H | CH₂NHP(O)(OCH₃)₂ | CH₃ | OCH₃ | CH | |
| 0 | S | H | H | H | CH₂NHP(O)(OCH₃)₂ | OCH₃ | OCH₃ | CH | |
| 0 | S | H | H | H | CH₂NHP(O)(OCH₃)₂ | CH₃ | OCH₃ | N | |
| 0 | S | H | H | H | CH₂NHP(O)(OCH₃)₂ | OCH₃ | OCH₃ | N | |
| 0 | S | H | H | H | CH₂NHP(S)(CH₃)₂ | CH₃ | OCH₃ | CH | |
| 0 | S | H | H | H | CH₂NHP(S)(CH₃)₂ | OCH₃ | OCH₃ | CH | |
| 0 | S | H | H | H | CH₂NHP(S)(CH₃)₂ | CH₃ | OCH₃ | N | |
| 0 | S | H | H | H | CH₂NHP(S)(CH₃)₂ | OCH₃ | OCH₃ | N | |
| 0 | S | H | H | H | CH₂NHP(S)(SCH₃)₂ | CH₃ | OCH₃ | CH | |
| 0 | S | H | H | H | CH₂NHP(S)(SCH₃)₂ | OCH₃ | OCH₃ | CH | |
| 0 | S | H | H | H | CH₂NHP(S)(SCH₃)₂ | CH₃ | OCH₃ | N | |
| 0 | S | H | H | H | CH₂NHP(S)(SCH₃)₂ | OCH₃ | OCH₃ | N | |
| 0 | S | H | H | H | CH₂—1-Naphthyl | CH₃ | OCH₃ | CH | |
| 0 | S | H | H | H | CH₂—1-Naphthyl | OCH₃ | OCH₃ | CH | |
| 0 | S | H | H | H | CH₂—1-Naphthyl | CH₃ | OCH₃ | N | |
| 0 | S | H | H | H | CH₂—1-Naphthyl | OCH₃ | OCH₃ | N | |
| 0 | S | H | H | H | CH₂—2-Naphthyl | CH₃ | OCH₃ | CH | |
| 0 | S | H | H | H | CH₂—2-Naphthyl | OCH₃ | OCH₃ | CH | |
| 0 | S | H | H | H | CH₂—2-Naphthyl | CH₃ | OCH₃ | N | |
| 0 | S | H | H | H | CH₂—2-Naphthyl | OCH₃ | OCH₃ | N | |
| 0 | S | H | H | H | CH(SCH₃)₂ | CH₃ | OCH₃ | CH | |
| 0 | S | H | H | H | CH(SCH₃)₂ | OCH₃ | OCH₃ | CH | |
| 0 | S | H | H | H | CH(SCH₃)₂ | CH₃ | OCH₃ | N | |
| 0 | S | H | H | H | CH(SCH₃)₂ | OCH₃ | OCH₃ | N | |
| 0 | S | H | H | H | CH(OCH₃)₂ | CH₃ | OCH₃ | CH | |
| 0 | S | H | H | H | CH(OCH₃)₂ | OCH₃ | OCH₃ | CH | |
| 0 | S | H | H | H | CH(OCH₃)₂ | CH₃ | OCH₃ | N | |
| 0 | S | H | H | H | CH(OCH₃)₂ | OCH₃ | OCH₃ | N | |
| 0 | S | H | H | H | CH(Cl)SO₂CH₃ | CH₃ | OCH₃ | CH | |
| 0 | S | H | H | H | CH(Cl)SO₂CH₃ | OCH₃ | OCH₃ | CH | |
| 0 | S | H | H | H | CH(Cl)SO₂CH₃ | CH₃ | OCH₃ | N | |
| 0 | S | H | H | H | CH(Cl)SO₂CH₃ | OCH₃ | OCH₃ | N | |
| 0 | S | H | H | H | CH(CN)OCH₃ | CH₃ | OCH₃ | CH | |
| 0 | S | H | H | H | CH(CN)OCH₃ | OCH₃ | OCH₃ | CH | |
| 0 | S | H | H | H | CH(CN)OCH₃ | CH₃ | OCH₃ | N | |
| 0 | S | H | H | H | CH(CN)OCH₃ | OCH₃ | OCH₃ | N | |
| 0 | S | H | H | H | CH₂CH(Cl)CH₂Cl | CH₃ | OCH₃ | CH | |
| 0 | S | H | H | H | CH₂CH(Cl)CH₂Cl | OCH₃ | OCH₃ | CH | |
| 0 | S | H | H | H | CH₂CH(Cl)CH₂Cl | CH₃ | OCH₃ | N | |
| 0 | S | H | H | H | CH₂CH(Cl)CH₂Cl | OCH₃ | OCH₃ | N | |
| 0 | S | H | H | H | CH₂C(CH₃)=NOCH₃ | CH₃ | OCH₃ | CH | |
| 0 | S | H | H | H | CH₂C(CH₃)=NOCH₃ | OCH₃ | OCH₃ | CH | |
| 0 | S | H | H | H | CH₂C(CH₃)=NOCH₃ | CH₃ | OCH₃ | N | |
| 0 | S | H | H | H | CH₂C(CH₃)=NOCH₃ | OCH₃ | OCH₃ | N | |
| 0 | S | H | H | H | CH₂C(CH₃)=NOCH₂CH₃ | CH₃ | OCH₃ | CH | |
| 0 | S | H | H | H | CH₂C(CH₃)=NOCH₂CH₃ | OCH₃ | OCH₃ | CH | |
| 0 | S | H | H | H | CH₂C(CH₃)=NOCH₂CH₃ | CH₃ | OCH₃ | N | |
| 0 | S | H | H | H | CH₂C(CH₃)=NOCH₂CH₃ | OCH₃ | OCH₃ | N | |
| 0 | S | H | H | H | CH=CHC(O)CH₃ | CH₃ | OCH₃ | CH | |
| 0 | S | H | H | H | CH=CHC(O)CH₃ | OCH₃ | OCH₃ | CH | |
| 0 | S | H | H | H | CH=CHC(O)CH₃ | CH₃ | OCH₃ | N | |
| 0 | S | H | H | H | CH=CHC(O)CH₃ | OCH₃ | OCH₃ | N | |

TABLE Ih-continued

Structure Ih

| n | G | R | R₁' | R₅ | R₆ | X | Y | Z | m.p. (°C.) |
|---|---|---|---|---|---|---|---|---|---|
| 0 | S | H | H | H | CH=CHC(O)OCH₃ | CH₃ | OCH₃ | CH | |
| 0 | S | H | H | H | CH=CHC(O)OCH₃ | OCH₃ | OCH₃ | CH | |
| 0 | S | H | H | H | CH=CHC(O)OCH₃ | CH₃ | OCH₃ | N | |
| 0 | S | H | H | H | CH=CHC(O)OCH₃ | OCH₃ | OCH₃ | N | |
| 0 | S | H | H | H | CH₂CH=CHN(CH₃)₂ | CH₃ | OCH₃ | CH | |
| 0 | S | H | H | H | CH₂CH=CHN(CH₃)₂ | OCH₃ | OCH₃ | CH | |
| 0 | S | H | H | H | CH₂CH=CHN(CH₃)₂ | CH₃ | OCH₃ | N | |
| 0 | S | H | H | H | CH₂CH=CHN(CH₃)₂ | OCH₃ | OCH₃ | N | |
| 0 | S | H | H | H | CH=CHC(O)NH₂ | CH₃ | OCH₃ | CH | |
| 0 | S | H | H | H | CH=CHC(O)NH₂ | OCH₃ | OCH₃ | CH | |
| 0 | S | H | H | H | CH=CHC(O)NH₂ | CH₃ | OCH₃ | N | |
| 0 | S | H | H | H | CH=CHC(O)NH₂ | OCH₃ | OCH₃ | N | |
| 0 | S | H | H | H | CH=C(CH₃)C(O)N(CH₃)₂ | CH₃ | OCH₃ | CH | |
| 0 | S | H | H | H | CH=C(CH₃)C(O)N(CH₃)₂ | OCH₃ | OCH₃ | CH | |
| 0 | S | H | H | H | CH=C(CH₃)C(O)N(CH₃)₂ | CH₃ | OCH₃ | N | |
| 0 | S | H | H | H | CH=C(CH₃)C(O)N(CH₃)₂ | OCH₃ | OCH₃ | N | |
| 0 | S | H | H | H | CH=CHP(O)(OCH₃)₂ | CH₃ | OCH₃ | CH | |
| 0 | S | H | H | H | CH=CHP(O)(OCH₃)₂ | OCH₃ | OCH₃ | CH | |
| 0 | S | H | H | H | CH=CHP(O)(OCH₃)₂ | CH₃ | OCH₃ | N | |
| 0 | S | H | H | H | CH=CHP(O)(OCH₃)₂ | OCH₃ | OCH₃ | N | |
| 0 | S | H | H | H | CH₂CH=CH(NO₂) | CH₃ | OCH₃ | CH | |
| 0 | S | H | H | H | CH₂CH=CH(NO₂) | OCH₃ | OCH₃ | CH | |
| 0 | S | H | H | H | CH₂CH=CH(NO₂) | CH₃ | OCH₃ | N | |
| 0 | S | H | H | H | CH₂CH=CH(NO₂) | OCH₃ | OCH₃ | N | |
| 0 | S | H | H | H | CH=CHCN | CH₃ | OCH₃ | CH | |
| 0 | S | H | H | H | CH=CHCN | OCH₃ | OCH₃ | CH | |
| 0 | S | H | H | H | CH=CHCN | CH₃ | OCH₃ | N | |
| 0 | S | H | H | H | CH=CHCN | OCH₃ | OCH₃ | N | |
| 0 | S | H | H | H | CH₂OCH₂CH₂OCH₃ | CH₃ | OCH₃ | CH | |
| 0 | S | H | H | H | CH₂OCH₂CH₂OCH₃ | OCH₃ | OCH₃ | CH | |
| 0 | S | H | H | H | CH₂OCH₂CH₂OCH₃ | CH₃ | OCH₃ | N | |
| 0 | S | H | H | H | CH₂OCH₂CH₂OCH₃ | OCH₃ | OCH₃ | N | |
| 0 | S | H | H | H | CH₂C≡CC(O)CH₃ | CH₃ | OCH₃ | CH | |
| 0 | S | H | H | H | CH₂C≡CC(O)CH₃ | OCH₃ | OCH₃ | CH | |
| 0 | S | H | H | H | CH₂C≡CC(O)CH₃ | CH₃ | OCH₃ | N | |
| 0 | S | H | H | H | CH₂C≡CC(O)CH₃ | OCH₃ | OCH₃ | N | |
| 0 | S | H | H | H | CH₂C≡CC(O)OCH₃ | CH₃ | OCH₃ | CH | |
| 0 | S | H | H | H | CH₂C≡CC(O)OCH₃ | OCH₃ | OCH₃ | CH | |
| 0 | S | H | H | H | CH₂C≡CC(O)OCH₃ | CH₃ | OCH₃ | N | |
| 0 | S | H | H | H | CH₂C≡CC(O)OCH₃ | OCH₃ | OCH₃ | N | |
| 0 | S | H | H | H | CH₂C≡CC(O)NHPh | CH₃ | OCH₃ | CH | |
| 0 | S | H | H | H | CH₂C≡CC(O)NHPh | OCH₃ | OCH₃ | CH | |
| 0 | S | H | H | H | CH₂C≡CC(O)NHPh | CH₃ | OCH₃ | N | |
| 0 | S | H | H | H | CH₂C≡CC(O)NHPh | OCH₃ | OCH₃ | N | |
| 0 | S | H | H | H | CH=CH—2-Thienyl | CH₃ | OCH₃ | CH | |
| 0 | S | H | H | H | CH=CH—2-Thienyl | OCH₃ | OCH₃ | CH | |
| 0 | S | H | H | H | CH=CH—2-Thienyl | CH₃ | OCH₃ | N | |
| 0 | S | H | H | H | CH=CH—2-Thienyl | OCH₃ | OCH₃ | N | |
| 0 | S | H | H | H | CH=CH—2-Pyridyl | CH₃ | OCH₃ | CH | |
| 0 | S | H | H | H | CH=CH—2-Pyridyl | OCH₃ | OCH₃ | CH | |
| 0 | S | H | H | H | CH=CH—2-Pyridyl | CH₃ | OCH₃ | N | |
| 0 | S | H | H | H | CH=CH—2-Pyridyl | OCH₃ | OCH₃ | N | |
| 0 | S | H | H | H | CH=CH—2-Cyclopentanone | CH₃ | OCH₃ | CH | |
| 0 | S | H | H | H | CH=CH—2-Cyclopentanone | OCH₃ | OCH₃ | CH | |
| 0 | S | H | H | H | CH=CH—2-Cyclopentanone | CH₃ | OCH₃ | N | |
| 0 | S | H | H | H | CH=CH—2-Cyclopentanone | OCH₃ | OCH₃ | N | |
| 0 | S | H | H | H | C≡C—2-thienyl | CH₃ | OCH₃ | CH | |
| 0 | S | H | H | H | C≡C—2-thienyl | OCH₃ | OCH₃ | CH | |
| 0 | S | H | H | H | C≡C—2-thienyl | CH₃ | OCH₃ | N | |
| 0 | S | H | H | H | C≡C—2-thienyl | OCH₃ | OCH₃ | N | |
| 0 | S | H | H | CH₃ | H | CH₃ | OCH₃ | CH | |
| 0 | S | H | H | CH₃ | H | OCH₃ | OCH₃ | CH | |
| 0 | S | H | H | CH₃ | H | CH₃ | OCH₃ | N | |
| 0 | S | H | H | CH₃ | H | OCH₃ | OCH₃ | N | |
| 0 | S | H | H | CH₃ | CH₃ | CH₃ | OCH₃ | CH | |
| 0 | S | H | H | CH₃ | CH₃ | OCH₃ | OCH₃ | CH | |
| 0 | S | H | H | CH₃ | CH₃ | CH₃ | OCH₃ | N | |
| 0 | S | H | H | CH₃ | CH₃ | OCH₃ | OCH₃ | N | |
| 0 | S | H | H | CH₃ | CH₃ | CH₃ | OCH₃ | CH | |
| 0 | S | H | H | CH₃ | CH₃ | OCH₃ | OCH₃ | CH | |
| 0 | S | H | H | CH₃ | CH₃ | CH₃ | OCH₃ | N | |
| 0 | S | H | H | CH₃ | CH₃ | OCH₃ | OCH₃ | N | |
| 0 | S | H | H | CH₃ | CH₂CN | CH₃ | OCH₃ | CH | |
| 0 | S | H | H | CH₃ | CH₂CN | OCH₃ | OCH₃ | CH | |
| 0 | S | H | H | CH₃ | CH₂CN | CH₃ | OCH₃ | N | |
| 0 | S | H | H | CH₃ | CH₂CN | OCH₃ | OCH₃ | N | |
| 0 | S | H | H | CH₃ | CH₂CH₂CH₃ | CH₃ | OCH₃ | CH | |
| 0 | S | H | H | CH₃ | CH₂CH₂CH₃ | OCH₃ | OCH₃ | CH | |
| 0 | S | H | H | CH₃ | CH₂CH₂CH₃ | CH₃ | OCH₃ | N | |

TABLE Ih-continued

Structure Ih

| n | G | R | R₁' | R₅ | R₆ | X | Y | Z | m.p. (°C.) |
|---|---|---|---|---|---|---|---|---|---|
| 0 | S | H | H | CH₃ | CH₂CH₂CH₃ | OCH₃ | OCH₃ | N | |
| 0 | S | H | H | CH₃ | C(O)CH₃ | CH₃ | OCH₃ | CH | |
| 0 | S | H | H | CH₃ | C(O)CH₃ | OCH₃ | OCH₃ | CH | |
| 0 | S | H | H | CH₃ | C(O)CH₃ | CH₃ | OCH₃ | N | |
| 0 | S | H | H | CH₃ | C(O)CH₃ | OCH₃ | OCH₃ | N | |
| 0 | S | H | H | CH₃ | C(O)OCH₃ | CH₃ | OCH₃ | CH | |
| 0 | S | H | H | CH₃ | C(O)OCH₃ | OCH₃ | OCH₃ | CH | |
| 0 | S | H | H | CH₃ | C(O)OCH₃ | CH₃ | OCH₃ | N | |
| 0 | S | H | H | CH₃ | C(O)OCH₃ | OCH₃ | OCH₃ | N | |
| 0 | S | H | H | H | H | H | OCH₃ | CH | |
| 0 | S | H | H | H | H | NHCH₃ | OCH₃ | N | |
| 0 | S | H | H | H | H | HCH₃ | OCH₂CH₃ | N | |
| 0 | S | H | H | H | H | OCH₃ | C≡CH | CH | |
| 0 | S | H | H | H | H | OCH₃ | OCF₂H | CH | |
| 0 | S | H | H | H | H | OCH₃ | cyclopropyl | CH | |
| 0 | S | H | H | H | H | OCH₃ | OCH₂CF₃ | CH | |
| 0 | S | H | H | H | CH₃ | H | OCH₃ | CH | |
| 0 | S | H | H | H | CH₃ | NHCH₃ | OCH₃ | N | |
| 0 | S | H | H | H | CH₃ | HCH₃ | OCH₂CH₃ | N | |
| 0 | S | H | H | H | CH₃ | OCH₃ | C≡CH | CH | |
| 0 | S | H | H | H | CH₃ | OCH₃ | OCF₂H | CH | |
| 0 | S | H | H | H | CH₃ | OCH₃ | cyclopropyl | CH | |
| 0 | S | H | H | H | CH₃ | OCH₃ | OCH₃ | CH | |
| 0 | S | H | H | H | CH₂(CH₂)₂CH₃ | H | OCH₃ | CH | |
| 0 | S | H | H | H | CH₂(CH₂)₂CH₃ | NHCH₃ | OCH₃ | N | |
| 0 | S | H | H | H | CH₂(CH₂)₂CH₃ | NHCH₃ | OCH₂CH₃ | N | |
| 0 | S | H | H | H | CH₂(CH₂)₂CH₃ | OCH₃ | C≡CH | CH | |
| 0 | S | H | H | H | CH₂(CH₂)₂CH₃ | OCH₃ | OCF₂H | CH | |
| 0 | S | H | H | H | CH₂(CH₂)₂CH₃ | OCH₃ | cyclopropyl | CH | |
| 0 | S | H | H | H | CH₂(CH₂)₂CH₃ | OCH₃ | OCH₂CF₃ | CH | |
| 0 | S | H | H | H | CH₂CH₃ | H | OCH₃ | CH | |
| 0 | S | H | H | H | CH₂CH₃ | NHCH₃ | OCH₃ | N | |
| 0 | S | H | H | H | CH₂CH₃ | NHCH₃ | OCH₂CH₃ | N | |
| 0 | S | H | H | H | CH₂CH₃ | OCH₃ | C≡CH | CH | |
| 0 | S | H | H | H | CH₂CH₃ | OCH₃ | OCF₂H | CH | |
| 0 | S | H | H | H | CH₂CH₃ | OCH₃ | cyclopropyl | CH | |
| 0 | S | H | H | H | CH₂CH₃ | OCH₃ | OCH₃ | CH | |
| 0 | S | H | H | H | CH₂CH₂F | CH₃ | CH₃ | CH | |
| 0 | S | H | H | H | CH₂CH₂F | CH₃ | OCH₃ | CH | |
| 0 | S | H | H | H | CH₂CH₂F | OCH₃ | OCH₃ | CH | |
| 0 | S | H | H | H | CH₂CH₂F | Cl | OCH₃ | CH | |
| 0 | S | H | H | H | CH₂CH₂F | CH₃ | OCH₃ | N | |
| 0 | S | H | H | H | CH₂CH₂F | OCH₃ | OCH₃ | N | |
| 0 | S | H | CH₃ | H | CH₂CH₂F | CH₃ | CH₃ | CH | |
| 0 | S | H | CH₃ | H | CH₂CH₂F | CH₃ | OCH₃ | CH | |
| 0 | S | H | CH₃ | H | CH₂CH₂F | OCH₃ | OCH₃ | CH | |
| 0 | S | H | CH₃ | H | CH₂CH₂F | Cl | OCH₃ | CH | |
| 0 | S | H | CH₃ | H | CH₂CH₂F | CH₃ | OCH₃ | N | |
| 0 | S | H | CH₃ | H | CH₂CH₂F | OCH₃ | OCH₃ | N | |
| 0 | S | H | Cl | H | CH₂CH₂F | CH₃ | CH₃ | CH | |
| 0 | S | H | Cl | H | CH₂CH₂F | CH₃ | OCH₃ | CH | |
| 0 | S | H | Cl | H | CH₂CH₂F | OCH₃ | OCH₃ | CH | |
| 0 | S | H | Cl | H | CH₂CH₂F | Cl | OCH₃ | CH | |
| 0 | S | H | Cl | H | CH₂CH₂F | CH₃ | OCH₃ | N | |
| 0 | S | H | Cl | H | CH₂CH₂F | OCH₃ | OCH₃ | N | |
| 0 | S | H | H | H | CH₂CH₂Cl | CH₃ | CH₃ | CH | |
| 0 | S | H | H | H | CH₂CH₂Cl | CH₃ | OCH₃ | CH | |
| 0 | S | H | H | H | CH₂CH₂Cl | OCH₃ | OCH₃ | CH | |
| 0 | S | H | H | H | CH₂CH₂Cl | Cl | OCH₃ | CH₃ | |
| 0 | S | H | H | H | CH₂CH₂Cl | CH₃ | OCH₃ | N | |
| 0 | S | H | H | H | CH₂CH₂Cl | OCH₃ | OCH₃ | N | |
| 0 | S | H | CH₃ | H | CH₂CH₂Cl | CH₃ | CH₃ | CH | |
| 0 | S | H | CH₃ | H | CH₂CH₂Cl | CH₃ | OCH₃ | CH | |
| 0 | S | H | CH₃ | H | CH₂CH₂Cl | OCH₃ | OCH₃ | CH | |
| 0 | S | H | CH₃ | H | CH₂CH₂Cl | Cl | OCH₃ | CH | |
| 0 | S | H | CH₃ | H | CH₂CH₂Cl | CH₃ | OCH₃ | N | |
| 0 | S | H | CH₃ | H | CH₂CH₂Cl | OCH₃ | OCH₃ | N | |
| 0 | S | H | Cl | H | CH₂CH₂Cl | CH₃ | CH₃ | CH | |
| 0 | S | H | Cl | H | CH₂CH₂Cl | CH₃ | OCH₃ | CH₃ | |
| 0 | S | H | Cl | H | CH₂CH₂Cl | OCH₃ | OCH₃ | CH | |
| 0 | S | H | Cl | H | CH₂CH₂Cl | Cl | OCH₃ | CH | |
| 0 | S | H | Cl | H | CH₂CH₂Cl | CH₃ | OCH₃ | N | |
| 0 | S | H | Cl | H | CH₂CH₂Cl | OCH₃ | OCH₃ | N | |
| 0 | S | H | H | H | CH₂CH₂CH₂F | CH₃ | CH₃ | CH | |
| 0 | S | H | H | H | CH₂CH₂CH₂F | CH₃ | OCH₃ | CH | |
| 0 | S | H | H | H | CH₂CH₂CH₂F | OCH₃ | OCH₃ | CH | |
| 0 | S | H | H | H | CH₂CH₂CH₂F | Cl | OCH₃ | CH | |
| 0 | S | H | H | H | CH₂CH₂CH₂F | CH₃ | OCH₃ | N | |
| 0 | S | H | H | H | CH₂CH₂CH₂F | OCH₃ | OCH₃ | N | |

TABLE Ih-continued

Structure Ih

| n | G | R | $R_1'$ | $R_5$ | $R_6$ | X | Y | Z | m.p. (°C.) |
|---|---|---|---|---|---|---|---|---|---|
| 0 | S | H | $CH_3$ | H | $CH_2CH_2CH_2F$ | $CH_3$ | $CH_3$ | CH | |
| 0 | S | H | $CH_3$ | H | $CH_2CH_2CH_2F$ | $CH_3$ | $OCH_3$ | CH | |
| 0 | S | H | $CH_3$ | H | $CH_2CH_2CH_2F$ | $OCH_3$ | $OCH_3$ | CH | |
| 0 | S | H | $CH_3$ | H | $CH_2CH_2CH_2F$ | Cl | $OCH_3$ | CH | |
| 0 | S | H | $CH_3$ | H | $CH_2CH_2CH_2F$ | $CH_3$ | $OCH_3$ | N | |
| 0 | S | H | $CH_3$ | H | $CH_2CH_2CH_2F$ | $OCH_3$ | $OCH_3$ | N | |
| 0 | S | H | Cl | H | $CH_2CH_2CH_2F$ | $CH_3$ | $CH_3$ | CH | |
| 0 | S | H | Cl | H | $CH_2CH_2CH_2F$ | $CH_3$ | $OCH_3$ | CH | |
| 0 | S | H | Cl | H | $CH_2CH_2CH_2F$ | $OCH_3$ | $OCH_3$ | CH | |
| 0 | S | H | Cl | H | $CH_2CH_2CH_2F$ | Cl | $OCH_3$ | CH | |
| 0 | S | H | Cl | H | $CH_2CH_2CH_2F$ | $CH_3$ | $OCH_3$ | N | |
| 0 | S | H | Cl | H | $CH_2CH_2CH_2F$ | $OCH_3$ | $OCH_3$ | N | |
| 0 | S | H | H | H | $CH_2OCH_3$ | $CH_3$ | $CH_3$ | CH | |
| 0 | S | H | H | H | $CH_2OCH_3$ | $CH_3$ | $OCH_3$ | CH | |
| 0 | S | H | H | H | $CH_2OCH_3$ | $OCH_3$ | $OCH_3$ | CH | |
| 0 | S | H | H | H | $CH_2OCH_3$ | Cl | $OCH_3$ | CH | |
| 0 | S | H | H | H | $CH_2OCH_3$ | $CH_3$ | $OCH_3$ | N | |
| 0 | S | H | H | H | $CH_2OCH_3$ | $OCH_3$ | $OCH_3$ | N | |
| 0 | S | H | $CH_3$ | H | $CH_2OCH_3$ | $CH_3$ | $CH_3$ | CH | |
| 0 | S | H | $CH_3$ | H | $CH_2OCH_3$ | $CH_3$ | $OCH_3$ | CH | |
| 0 | S | H | $CH_3$ | H | $CH_2OCH_3$ | $OCH_3$ | $OCH_3$ | CH | |
| 0 | S | H | $CH_3$ | H | $CH_2OCH_3$ | Cl | $OCH_3$ | CH | |
| 0 | S | H | $CH_3$ | H | $CH_2OCH_3$ | $CH_3$ | $OCH_3$ | N | |
| 0 | S | H | $CH_3$ | H | $CH_2OCH_3$ | $OCH_3$ | $OCH_3$ | N | |
| 0 | S | H | Cl | H | $CH_2OCH_3$ | $CH_3$ | $CH_3$ | CH | |
| 0 | S | H | Cl | H | $CH_2OCH_3$ | $CH_3$ | $OCH_3$ | CH | |
| 0 | S | H | Cl | H | $CH_2OCH_3$ | $OCH_3$ | $OCH_3$ | CH | |
| 0 | S | H | Cl | H | $CH_2OCH_3$ | Cl | $OCH_3$ | CH | |
| 0 | S | H | Cl | H | $CH_2OCH_3$ | $CH_3$ | $OCH_3$ | N | |
| 0 | S | H | Cl | H | $CH_2OCH_3$ | $OCH_3$ | $OCH_3$ | N | |
| 0 | S | H | H | H | $CH_2CH_2OCH_3$ | $CH_3$ | $CH_3$ | CH | |
| 0 | S | H | H | H | $CH_2CH_2OCH_3$ | $CH_3$ | $OCH_3$ | CH | |
| 0 | S | H | H | H | $CH_2CH_2OCH_3$ | $OCH_3$ | $OCH_3$ | CH | |
| 0 | S | H | H | H | $CH_2CH_2OCH_3$ | Cl | $OCH_3$ | CH | |
| 0 | S | H | H | H | $CH_2CH_2OCH_3$ | $CH_3$ | $OCH_3$ | N | |
| 0 | S | H | H | H | $CH_2CH_2OCH_3$ | $OCH_3$ | $OCH_3$ | N | |
| 0 | S | H | $CH_3$ | H | $CH_2CH_2OCH_3$ | $CH_3$ | $CH_3$ | CH | |
| 0 | S | H | $CH_3$ | H | $CH_2CH_2OCH_3$ | $CH_3$ | $OCH_3$ | CH | |
| 0 | S | H | $CH_3$ | H | $CH_2CH_2OCH_3$ | $OCH_3$ | $OCH_3$ | CH | |
| 0 | S | H | $CH_3$ | H | $CH_2CH_2OCH_3$ | Cl | $OCH_3$ | CH | |
| 0 | S | H | $CH_3$ | H | $CH_2CH_2OCH_3$ | $CH_3$ | $OCH_3$ | N | |
| 0 | S | H | $CH_3$ | H | $CH_2CH_2OCH_3$ | $OCH_3$ | $OCH_3$ | N | |
| 0 | S | H | Cl | H | $CH_2CH_2OCH_3$ | $CH_3$ | $CH_3$ | CH | |
| 0 | S | H | Cl | H | $CH_2CH_2OCH_3$ | $CH_3$ | $OCH_3$ | CH | |
| 0 | S | H | Cl | H | $CH_2CH_2OCH_3$ | $OCH_3$ | $OCH_3$ | CH | |
| 0 | S | H | Cl | H | $CH_2CH_2OCH_3$ | Cl | $OCH_3$ | CH | |
| 0 | S | H | Cl | H | $CH_2CH_2OCH_3$ | $CH_3$ | $OCH_3$ | N | |
| 0 | S | H | Cl | H | $CH_2CH_2OCH_3$ | $OCH_3$ | $OCH_3$ | N | |
| 0 | S | H | H | H | $C(O)OCH_3$ | $CH_3$ | $CH_3$ | CH | |
| 0 | S | H | H | H | $C(O)OCH_3$ | $CH_3$ | $OCH_3$ | CH | |
| 0 | S | H | H | H | $C(O)OCH_3$ | $CH_3$ | $OCH_3$ | CH | |
| 0 | S | H | H | H | $C(O)OCH_3$ | Cl | $OCH_3$ | CH | |
| 0 | S | H | H | H | $C(O)OCH_3$ | $CH_3$ | $OCH_3$ | N | |
| 0 | S | H | H | H | $C(O)OCH_3$ | $OCH_3$ | $OCH_3$ | N | |
| 0 | S | H | $CH_3$ | H | $C(O)OCH_3$ | $CH_3$ | $CH_3$ | CH | |
| 0 | S | H | $CH_3$ | H | $C(O)OCH_3$ | $CH_3$ | $OCH_3$ | CH | |
| 0 | S | H | $CH_3$ | H | $C(O)OCH_3$ | $OCH_3$ | $OCH_3$ | CH | |
| 0 | S | H | $CH_3$ | H | $C(O)OCH_3$ | Cl | $OCH_3$ | CH | |
| 0 | S | H | $CH_3$ | H | $C(O)OCH_3$ | $CH_3$ | $OCH_3$ | N | |
| 0 | S | H | $CH_3$ | H | $C(O)OCH_3$ | $OCH_3$ | $OCH_3$ | N | |
| 0 | S | H | Cl | H | $C(O)OCH_3$ | $CH_3$ | $CH_3$ | CH | |
| 0 | S | H | Cl | H | $C(O)OCH_3$ | $CH_3$ | $OCH_3$ | CH | |
| 0 | S | H | Cl | H | $C(O)OCH_3$ | $OCH_3$ | $OCH_3$ | CH | |
| 0 | S | H | Cl | H | $C(O)OCH_3$ | Cl | $OCH_3$ | CH | |
| 0 | S | H | Cl | H | $C(O)OCH_3$ | $CH_3$ | $OCH_3$ | N | |
| 0 | S | H | Cl | H | $C(O)OCH_3$ | $OCH_3$ | $OCH_3$ | N | |
| 0 | S | H | H | H | $CH_2C(O)CH_3$ | $CH_3$ | $CH_3$ | CH | |
| 0 | S | H | H | H | $CH_2C(O)CH_3$ | $CH_3$ | $OCH_3$ | CH | |
| 0 | S | H | H | H | $CH_2C(O)CH_3$ | $OCH_3$ | $OCH_3$ | CH | |
| 0 | S | H | H | H | $CH_2C(O)CH_3$ | Cl | $OCH_3$ | CH | |
| 0 | S | H | H | H | $CH_2C(O)CH_3$ | $CH_3$ | $OCH_3$ | N | |
| 0 | S | H | H | H | $CH_2C(O)CH_3$ | $OCH_3$ | $OCH_3$ | N | |
| 0 | S | H | $CH_3$ | H | $CH_2C(O)CH_3$ | $CH_3$ | $CH_3$ | CH | |
| 0 | S | H | $CH_3$ | H | $CH_2C(O)CH_3$ | $CH_3$ | $OCH_3$ | CH | |
| 0 | S | H | $CH_3$ | H | $CH_2C(O)CH_3$ | $OCH_3$ | $OCH_3$ | CH | |
| 0 | S | H | $CH_3$ | H | $CH_2C(O)CH_3$ | Cl | $OCH_3$ | CH | |
| 0 | S | H | $CH_3$ | H | $CH_2C(O)CH_3$ | $CH_3$ | $OCH_3$ | N | |
| 0 | S | H | $CH_3$ | H | $CH_2C(O)CH_3$ | $OCH_3$ | $OCH_3$ | N | |
| 0 | S | H | Cl | H | $CH_2C(O)CH_3$ | $CH_3$ | $CH_3$ | CH | |

TABLE Ih-continued

Structure Ih

| n | G | R | R$_1'$ | R$_5$ | R$_6$ | X | Y | Z | m.p. (°C.) |
|---|---|---|---|---|---|---|---|---|---|
| 0 | S | H | Cl | H | CH$_2$C(O)CH$_3$ | CH$_3$ | OCH$_3$ | CH | |
| 0 | S | H | Cl | H | CH$_2$C(O)CH$_3$ | OCH$_3$ | OCH$_3$ | CH | |
| 0 | S | H | Cl | H | CH$_2$C(O)CH$_3$ | Cl | OCH$_3$ | CH | |
| 0 | S | H | Cl | H | CH$_2$C(O)CH$_3$ | CH$_3$ | OCH$_3$ | N | |
| 0 | S | H | Cl | H | CH$_2$C(O)CH$_3$ | OCH$_3$ | OCH$ | N | |
| 0 | S | H | H | H | CO$_2$CH$_3$ | CH$_3$ | CH$_3$ | CH | |
| 0 | S | H | H | H | CO$_2$CH$_3$ | CH$_3$ | OCH$_3$ | CH | |
| 0 | S | H | H | H | CO$_2$CH$_3$ | OCH$_3$ | OCH$_3$ | CH | |
| 0 | S | H | H | H | CO$_2$CH$_3$ | Cl | OCH$_3$ | CH | |
| 0 | S | H | H | H | CO$_2$CH$_3$ | CH$_3$ | OCH$_3$ | N | |
| 0 | S | H | H | H | CO$_2$CH$_3$ | OCH$_3$ | OCH$_3$ | N | |
| 0 | S | H | CH$_3$ | H | CO$_2$CH$_3$ | CH$_3$ | CH$_3$ | CH | |
| 0 | S | H | CH$_3$ | H | CO$_2$CH$_3$ | CH$_3$ | OCH$_3$ | CH | |
| 0 | S | H | CH$_3$ | H | CO$_2$CH$_3$ | OCH$_3$ | OCH$_3$ | CH | |
| 0 | S | H | CH$_3$ | H | CO$_2$CH$_3$ | Cl | OCH$_3$ | CH | |
| 0 | S | H | CH$_3$ | H | CO$_2$CH$_3$ | CH$_3$ | OCH$_3$ | N | |
| 0 | S | H | CH$_3$ | H | CO$_2$CH$_3$ | OCH$_3$ | OCH$_3$ | N | |
| 0 | S | H | Cl | H | CO$_2$CH$_3$ | CH$_3$ | CH$_3$ | CH | |
| 0 | S | H | Cl | H | CO$_2$CH$_3$ | CH$_3$ | OCH$_3$ | CH | |
| 0 | S | H | Cl | H | CO$_2$CH$_3$ | OCH$_3$ | CH$_3$ | N | |
| 0 | S | H | Cl | H | CO$_2$CH$_3$ | Cl | OCH$_3$ | CH | |
| 0 | S | H | Cl | H | CO$_2$CH$_3$ | CH$_3$ | OCH$_3$ | N | |
| 0 | S | H | Cl | H | CO$_2$CH$_3$ | OCH$_3$ | OCH$_3$ | N | |

TABLE Ii

Structure Ii

| w | G | R | R$_1$ | R$_7$ | R$_{29}$ | X | Y | Z | m.p. (°C.) |
|---|---|---|---|---|---|---|---|---|---|
| O | S | H | H | H | H | CH$_3$ | CH$_3$ | CH | |
| O | S | H | H | H | H | CH$_3$ | OCH$_3$ | CH | |
| O | S | H | H | H | H | OCH$_3$ | OCH$_3$ | CH | |
| O | S | H | H | H | H | Cl | OCH$_3$ | CH | |
| O | S | H | H | H | H | Br | OCH$_3$ | CH | |
| O | S | H | H | H | H | CH$_3$ | OCH$_3$ | N | |
| O | S | H | H | H | H | OCH$_3$ | OCH$_3$ | N | |
| O | S | H | H | CH$_3$ | H | CH$_3$ | CH$_3$ | CH | 191–192 |
| O | S | H | H | CH$_3$ | H | CH$_3$ | OCH$_3$ | CH | 175–176 |
| O | S | H | H | CH$_3$ | H | OCH$_3$ | OCH$_3$ | CH | 200–201 |
| O | S | H | H | CH$_3$ | H | Cl | OCH$_3$ | CH | 189–190 |
| O | S | H | H | CH$_3$ | H | Br | OCH$_3$ | CH | |
| O | S | H | H | CH$_3$ | H | CH$_3$ | OCH$_3$ | N | 176–177 |
| O | S | H | H | CH$_3$ | H | OCH$_3$ | OCH$_3$ | N | 193–194 |
| O | S | H | CH$_3$ | CH$_3$ | H | CH$_3$ | CH$_3$ | CH | |
| O | S | H | CH$_3$ | CH$_3$ | H | CH$_3$ | OCH$_3$ | CH | |
| O | S | H | CH$_3$ | CH$_3$ | H | OCH$_3$ | OCH$_3$ | CH | |
| O | S | H | CH$_3$ | CH$_3$ | H | Cl | OCH$_3$ | CH | |
| O | S | H | CH$_3$ | CH$_3$ | H | Br | OCH$_3$ | CH | |
| O | S | H | CH$_3$ | CH$_3$ | H | CH$_3$ | OCH$_3$ | N | |
| O | S | H | CH$_3$ | CH$_3$ | H | OCH$_3$ | OCH$_3$ | N | |
| O | S | H | H | CH$_2$CH$_3$ | H | CH$_3$ | OCH$_3$ | N | |
| O | S | H | H | CH$_2$CH$_3$ | H | CH$_3$ | OCH$_3$ | CH | |
| O | S | H | H | CH$_2$CH$_3$ | H | OCH$_3$ | OCH$_3$ | CH | |
| O | S | H | H | (CH$_2$)$_5$CH$_3$ | H | OCH$_3$ | OCH$_3$ | CH | |
| O | S | H | Cl | Cl | H | CH$_3$ | CH$_3$ | CH | |
| O | S | H | Cl | Cl | H | CH$_3$ | OCH$_3$ | CH | |
| O | S | H | Cl | Cl | H | OCH$_3$ | OCH$_3$ | CH | |
| O | S | H | Cl | Cl | H | Cl | OCH$_3$ | CH | |
| O | S | H | Cl | Cl | H | Br | OCH$_3$ | CH | |
| O | S | H | Cl | Cl | H | CH$_3$ | OCH$_3$ | N | |
| O | S | H | Cl | Cl | H | OCH$_3$ | OCH$_3$ | N | |
| O | S | H | H | Br | H | CH$_3$ | OCH$_3$ | N | |
| O | S | H | H | Br | H | CH$_3$ | OCH$_3$ | CH | |
| O | S | H | H | Br | H | OCH$_3$ | OCH$_3$ | CH | |
| O | S | H | H | CN | H | CH$_3$ | OCH$_3$ | N | |
| O | S | H | H | CN | H | CH$_3$ | OCH$_3$ | CH | |
| O | S | H | H | CN | H | OCH$_3$ | OCH$_3$ | CH | |
| O | S | H | H | NO$_2$ | H | CH$_3$ | OCH$_3$ | N | |
| O | S | H | H | NO$_2$ | H | CH$_3$ | OCH$_3$ | CH | |
| O | S | H | H | NO$_2$ | H | OCH$_3$ | OCH$_3$ | CH | |
| O | S | H | H | SCH$_3$ | H | CH$_3$ | OCH$_3$ | N | |
| O | S | H | H | SCH$_3$ | H | CH$_3$ | OCH$_3$ | CH | |
| O | S | H | H | SCH$_3$ | H | OCH$_3$ | OCH$_3$ | CH | |
| O | S | H | H | SO$_2$CH$_3$ | H | CH$_3$ | OCH$_3$ | N | |
| O | S | H | H | SO$_2$CH$_3$ | H | CH$_3$ | OCH$_3$ | CH | |
| O | S | H | H | SO$_2$CH$_3$ | H | OCH$_3$ | OCH$_3$ | CH | |
| O | S | H | H | CO$_2$CH$_3$ | H | CH$_3$ | OCH$_3$ | N | |
| O | S | H | H | CO$_2$CH$_3$ | H | CH$_3$ | OCH$_3$ | CH | |

TABLE Ii-continued

Structure Ii

| w | G | R | R₁ | R₇ | R₂₉ | X | Y | Z | m.p. (°C.) |
|---|---|---|---|---|---|---|---|---|---|
| O | S | H | H | CO₂CH₃ | H | OCH₃ | OCH₃ | CH | |
| O | S | H | H | C(O)CH₃ | H | CH₃ | OCH₃ | N | |
| O | S | H | H | C(O)CH₃ | H | CH₃ | OCH₃ | CH | |
| O | S | H | H | C(O)CH₃ | H | OCH₃ | OCH₃ | CH | |
| O | S | H | H | C(O)(CH₂)₃CH₃ | H | OCH₃ | OCH₃ | CH | |
| O | S | H | H | CO₂CH₂Ph | H | OCH₃ | OCH₃ | CH | |
| O | S | H | H | SO₂Ph | H | OCH₃ | OCH₃ | CH | |
| S | S | H | H | CH₃ | H | OCH₃ | OCH₃ | CH | |
| O | S | H | H | CH₃ | CH₃ | OCH₃ | OCH₃ | CH | |
| O | S | H | H | CH₃ | Br | OCH₃ | OCH₃ | CH | |
| O | S | H | H | Cl | Cl | OCH₃ | OCH₃ | CH | |

TABLE Ij

Structure Ij

| w | G | R | R₁' | R₇ | R₂₉ | X | Y | Z | m.p. (°C.) |
|---|---|---|---|---|---|---|---|---|---|
| O | S | H | H | H | H | CH₃ | CH₃ | CH | |
| O | S | H | H | H | H | CH₃ | OCH₃ | CH | |
| O | S | H | H | H | H | OCH₃ | OCH₃ | CH | |
| O | S | H | H | H | H | Cl | OCH₃ | CH | |
| O | S | H | H | H | H | Br | OCH₃ | CH | |
| O | S | H | H | H | H | CH₃ | OCH₃ | N | |
| O | S | H | H | H | H | OCH₃ | OCH₃ | N | |
| O | S | H | H | CH₃ | H | CH₃ | CH₃ | CH | |
| O | S | H | H | CH₃ | H | CH₃ | OCH₃ | CH | |
| O | S | H | H | CH₃ | H | OCH₃ | OCH₃ | CH | |
| O | S | H | H | CH₃ | H | Cl | OCH₃ | CH | |
| O | S | H | H | CH₃ | H | Br | OCH₃ | CH | |
| O | S | H | H | CH₃ | H | CH₃ | OCH3 | N | |
| O | S | H | H | CH₃ | H | OCH₃ | OCH₃ | N | |
| O | S | H | H | CO₂CH₃ | H | CH₃ | OCH₃ | N | |
| O | S | H | H | CO₂CH₃ | H | CH₃ | OCH₃ | CH | |
| O | S | H | H | CO₂CH₃ | H | OCH₃ | OCH₃ | CH | |
| S | S | H | H | CH₃ | H | OCH₃ | OCH₃ | CH | |

TABLE Im

Structure Im

| n | G | R | R₁ | R₅ | X | Y | Z | m.p. (°C.) |
|---|---|---|---|---|---|---|---|---|
| 1 | S | H | H | H | CH₃ | OCH₃ | N | |
| 1 | S | H | H | H | CH₃ | OCH₃ | CH | |
| 1 | S | H | H | H | OCH₃ | OCH₃ | CH | |
| 1 | S | H | CH₃ | H | CH₃ | OCH₃ | N | |
| 1 | S | H | CH₃ | H | CH₃ | OCH₃ | CH | |
| 1 | S | H | CH₃ | H | OCH₃ | OCH₃ | CH | |
| 1 | O | H | CH₃ | H | CH₃ | OCH₃ | N | |
| 1 | O | H | CH₃ | H | CH₃ | OCH₃ | CH | |
| 1 | O | H | CH₃ | H | OCH₃ | OCH₃ | CH | |
| 1 | NH | H | CH₃ | H | CH₃ | OCH₃ | N | |
| 1 | NH | H | CH₃ | H | CH₃ | OCH₃ | CH | |
| 1 | NH | H | CH₃ | H | OCH₃ | OCH₃ | CH | |
| 1 | NCH₃ | H | CH₃ | H | CH₃ | OCH₃ | N | |
| 1 | NCH₃ | H | CH₃ | H | CH₃ | OCH₃ | CH | |
| 1 | NCH₃ | H | CH₃ | H | OCH₃ | OCH₃ | CH | |
| 1 | S | H | H | CH₃ | OCH₃ | OCH₃ | CH | |
| 0 | S | H | H | H | OCH₃ | OCH₃ | CH | |

TABLE Ik

Structure Ik

| n | W₂ | G | R | R₁ | R₄ | R₅ | X | Y | Z | m.p. (°C.) |
|---|---|---|---|---|---|---|---|---|---|---|
| 0 | O | S | H | H | H | H | CH₃ | OCH₃ | N | |
| 0 | O | S | H | H | H | H | CH₃ | OCH₃ | CH | |
| 0 | O | S | H | H | H | H | OCH₃ | OCH₃ | CH | |
| 0 | O | S | H | H | CH₃ | H | CH₃ | OCH₃ | N | |
| 0 | O | S | H | H | CH₃ | H | CH₃ | OCH₃ | CH | |
| 0 | O | S | H | H | CH₃ | H | OCH₃ | OCH₃ | CH | |
| 0 | O | S | H | H | (CH₂)₃CH₃ | H | OCH₃ | OCH₃ | CH | |
| 1 | O | S | H | H | CH₃ | H | OCH₃ | OCH₃ | CH | |
| 1 | O | S | H | H | CH₃ | CH₃ | OCH₃ | OCH₃ | CH | |
| 0 | O | S | H | CH₃ | CH₃ | H | OCH₃ | OCH₃ | CH | |
| 0 | O | O | H | CH₃ | CH₃ | H | OCH₃ | OCH₃ | CH | |
| 0 | O | NH | H | CH₃ | CH₃ | H | OCH₃ | OCH₃ | CH | |
| 0 | O | NCH₃ | H | CH₃ | CH₃ | H | OCH₃ | OCH₃ | CH | |
| 0 | S | S | H | H | CH₃ | H | OCH₃ | OCH₃ | CH | |

TABLE Il

Structure Il

| n | W₂ | G | R | R₁ | R₄ | R₅ | X | Y | Z | m.p. (°C.) |
|---|---|---|---|---|---|---|---|---|---|---|
| 0 | O | S | H | H | H | H | CH₃ | OCH₃ | N | |
| 0 | O | S | H | H | H | H | CH₃ | OCH₃ | CH | |
| 0 | O | S | H | H | H | H | OCH₃ | OCH₃ | CH | |
| 0 | O | S | H | H | CH₃ | H | CH₃ | OCH₃ | N | |
| 0 | O | S | H | H | CH₃ | H | CH₃ | OCH₃ | CH | |
| 0 | O | S | H | H | CH₃ | H | OCH₃ | OCH₃ | CH | |
| 0 | O | S | H | H | CH₃ | CH₃ | OCH₃ | OCH₃ | CH | |
| 1 | O | S | H | H | CH₃ | H | OCH₃ | OCH₃ | CH | |

TABLE In

Stucture In

| n | G | R | R₁' | R₅ | X | Y | Z | m.p. (°C.) |
|---|---|---|---|---|---|---|---|---|
| 0 | S | H | H | H | CH₃ | OCH₃ | N | |
| 0 | S | H | H | H | CH₃ | OCH₃ | CH | |
| 0 | S | H | H | H | OCH₃ | OCH₃ | CH | |
| 1 | S | H | H | H | CH₃ | OCH₃ | N | |
| 1 | S | H | H | H | CH₃ | OCH₃ | CH | |
| 1 | S | H | H | H | OCH₃ | OCH₃ | CH | |
| 1 | S | H | H | CH₃ | OCH₃ | OCH₃ | CH | |

Table Io

Structure A, B, C, D, E, and F

| J | G | R | R₁ | R₁' | R₄ | R₅ | R₆ | W₂ |
|---|---|---|---|---|---|---|---|---|
| J-9 | S | H | H | — | H | — | — | O |

Table Io-continued

Structure A, B, C, D, E, and F

| J | G | R | R₁ | R₁' | R₄ | R₅ | R₆ | W₂ |
|---|---|---|----|----|----|----|----|----|
| J-9 | S | H | CH₃ | — | H | — | — | O |
| J-9 | O | H | CH₃ | — | H | — | — | O |
| J-9 | NH | H | CH₃ | — | H | — | — | O |
| J-9 | NCH₃ | H | CH₃ | — | H | — | — | O |
| J-10 | S | H | — | H | H | — | — | O |
| J-11 | S | H | H | — | — | H | CH₃ | — |
| J-11 | S | H | CH₃ | — | — | H | CH₃ | — |
| J-11 | O | H | CH₃ | — | — | H | CH₃ | — |
| J-11 | NH | H | CH₃ | — | — | H | CH₃ | — |
| J-11 | NCH₃ | H | CH₃ | — | — | H | CH₃ | — |
| J-12 | S | H | — | H | — | H | CH₃ | — |
| J-19 | S | H | H | — | CH₃ | H | — | O |
| J-19 | S | H | CH₃ | — | CH₃ | H | — | O |
| J-19 | O | H | CH₃ | — | CH₃ | H | — | O |
| J-19 | NH | H | CH₃ | — | CH₃ | H | — | O |
| J-19 | NCH₃ | H | CH₃ | — | CH₃ | H | — | O |
| J-20 | S | H | — | H | CH₃ | H | — | O |
| J-21 | S | H | H | — | — | H | — | — |
| J-21 | S | H | CH₃ | — | — | H | — | — |
| J-21 | O | H | CH₃ | — | — | H | — | — |
| J-21 | NH | H | CH₃ | — | — | H | — | — |
| J-21 | NCH₃ | H | CH₃ | — | — | H | — | — |
| J-22 | S | H | — | H | — | H | — | — |

TABLE Ip

Structure Ip

| J | W₂ | G | n | Q | R₁(R₁') | R₂ | R₃ | X | Y | Z | m.p. (°C.) |
|---|----|---|---|---|--------|----|----|----|----|----|------|
| J-1 | — | S | 1 | S | H | H | H | OCH₃ | OCH₃ | CH | |
| J-1 | — | S | 0 | S | H | CH₃ | H | OCH₃ | OCH₃ | CH | |
| J-1 | — | S | 0 | SO₂ | H | CH₃ | H | OCH₃ | OCH₃ | CH | |
| J-1 | — | O | 0 | SO₂ | CH₃ | H | H | OCH₃ | OCH₃ | CH | |
| J-1 | — | NH | 0 | SO₂ | CH₃ | H | H | OCH₃ | OCH₃ | CH | |
| J-1 | — | NCH₃ | 0 | SO₂ | CH₃ | H | H | OCH₃ | OCH₃ | CH | |
| J-1 | — | S | 0 | SO₂ | H | CH₃ | H | CH₃ | OCH₃ | N | |
| J-2 | — | S | 0 | SO₂ | H | CH₃ | H | OCH₃ | OCH₃ | CH | |
| J-3 | O | S | 1 | — | H | H | H | OCH₃ | OCH₃ | CH | |
| J-3 | O | S | 1 | — | CH₃ | H | H | OCH₃ | OCH₃ | CH | |
| J-3 | O | O | 1 | — | CH₃ | H | H | OCH₃ | OCH₃ | CH | |
| J-3 | O | NH | 1 | — | CH₃ | H | H | OCH₃ | OCH₃ | CH | |
| J-3 | O | NCH₃ | 1 | — | CH₃ | H | H | OCH₃ | OCH₃ | CH | |
| J-4 | O | S | 1 | — | H | H | H | OCH₃ | OCH₃ | CH | |
| J-4 | O | S | 0 | — | H | H | H | OCH₃ | OCH₃ | CH | |

TABLE Iq

Structure Iq

| J | W₂ | G | n | R₁(R₁') | R₄ | R₅ | R₆ | X | Y | Z | m.p. (°C.) |
|---|----|---|---|--------|----|----|----|----|----|----|------|
| J-5 | O | S | 1 | H | H | H | — | OCH₃ | OCH₃ | CH | |
| J-5 | O | S | 1 | CH₃ | H | H | — | OCH₃ | OCH₃ | CH | |
| J-5 | O | O | 1 | CH₃ | H | H | — | OCH₃ | OCH₃ | CH | |
| J-5 | O | NH | 1 | CH₃ | H | H | — | OCH₃ | OCH₃ | CH | |
| J-5 | O | NCH₃ | 1 | CH₃ | H | H | — | OCH₃ | OCH₃ | CH | |
| J-5 | O | S | 0 | H | H | H | — | CH₃ | OCH₃ | N | |
| J-6 | O | S | 1 | H | H | H | — | OCH₃ | OCH₃ | CH | |
| J-6 | O | S | 1 | Cl | H | H | — | OCH₃ | OCH₃ | CH | |
| J-7 | — | S | 0 | H | — | H | CH₃ | OCH₃ | OCH₃ | CH | |
| J-7 | — | O | 0 | H | — | H | CH₃ | OCH₃ | OCH₃ | CH | |
| J-7 | — | S | 1 | H | — | H | CH₃ | OCH₃ | OCH₃ | CH | |
| J-8 | — | S | 0 | H | — | H | CH₃ | OCH₃ | OCH₃ | CH | |
| J-9 | O | S | — | CH₃ | H | — | — | OCH₃ | OCH₃ | CH | |
| J-9 | O | O | — | CH₃ | H | — | — | OCH₃ | OCH₃ | CH | |
| J-9 | O | NH | — | CH₃ | H | — | — | OCH₃ | OCH₃ | CH | |
| J-9 | O | NCH₃ | — | CH₃ | H | — | — | OCH₃ | OCH₃ | CH | |
| J-9 | O | S | — | H | H | — | — | CH₃ | OCH₃ | N | |
| J-10 | O | S | — | H | H | — | — | OCH₃ | OCH₃ | CH | |
| J-11 | — | S | — | H | — | H | CH₃ | OCH₃ | OCH₃ | CH | |
| J-12 | — | S | — | H | — | H | CH₃ | OCH₃ | OCH₃ | CH | |
| J-15 | O | S | 1 | H | CH₃ | H | — | OCH₃ | OCH₃ | CH | |
| J-15 | O | S | 0 | H | CH₃ | H | — | OCH₃ | OCH₃ | CH | |
| J-16 | O | S | 0 | H | CH₃ | H | — | OCH₃ | OCH₃ | CH | |
| J-17 | — | S | — | H | — | H | — | OCH₃ | OCH₃ | CH | |
| J-18 | — | S | — | H | — | H | — | OCH₃ | OCH₃ | CH | |
| J-19 | O | S | — | H | CH₃ | H | — | OCH₃ | OCH₃ | CH | |
| J-20 | O | S | — | H | CH₃ | H | — | OCH₃ | OCH₃ | CH | |
| J-21 | — | S | — | H | — | H | — | OCH₃ | OCH₃ | CH | |
| J-22 | — | S | — | H | — | H | — | OCH₃ | OCH₃ | CH | |

TABLE IIa

Structure IIa

| J | W₂ | G | Q | n | R | R₁(R₁') | R₂ | R₃ | X₁ | Y₁ | m.p. (°C.) |
|---|----|---|---|---|---|--------|----|----|----|----|------|
| J₁ | — | S | O | 0 | H | H | H | H | CH₃ | O | |

TABLE IIa-continued

Structure IIa

| J | $W_2$ | G | Q | n | R | $R_1(R_1')$ | $R_2$ | $R_3$ | $X_1$ | $Y_1$ | m.p. (°C.) |
|---|---|---|---|---|---|---|---|---|---|---|---|
| $J_1$ | — | S | O | 0 | H | H | H | $CH_3$ | $OCH_3$ | $CH_2$ | |
| $J_1$ | — | S | O | 0 | H | H | $CH_3$ | $CH_3$ | $OCH_2CH_3$ | O | |
| $J_1$ | — | S | O | 1 | H | H | H | H | $OCF_2H$ | $CH_2$ | |
| $J_1$ | — | S | O | 1 | H | H | H | $CH_3$ | $CH_3$ | $CH_2$ | |
| $J_1$ | — | S | O | 1 | H | H | $CH_3$ | $CH_3$ | $OCH_3$ | O | |
| $J_1$ | — | S | S | 0 | H | H | H | H | $OCH_2CH_3$ | $CH_2$ | |
| $J_1$ | — | S | S | 0 | H | H | H | $CH_3$ | $OCF_2H$ | O | |
| $J_1$ | — | S | S | 0 | H | H | $CH_3$ | $CH_3$ | $CH_3$ | O | |
| $J_1$ | — | S | S | 1 | H | H | H | H | $OCH_3$ | $CH_2$ | |
| $J_1$ | — | S | S | 1 | H | H | H | $CH_3$ | $OCH_2CH_3$ | O | |
| $J_1$ | — | S | S | 1 | H | H | $CH_3$ | $CH_3$ | $OCF_2H$ | $CH_2$ | |
| $J_1$ | — | S | $SO_2$ | 0 | H | H | H | H | $CH_3$ | $CH_2$ | |
| $J_1$ | — | O | $SO_2$ | 0 | H | H | H | $CH_3$ | $OCH_3$ | O | |
| $J_1$ | — | NH | $SO_2$ | 0 | H | H | $CH_3$ | $CH_3$ | $OCH_2CH_3$ | $CH_2$ | |
| $J_1$ | — | S | $SO_2$ | 1 | H | H | H | H | $OCF_2H$ | O | |
| $J_1$ | — | S | $SO_2$ | 1 | H | H | H | $CH_3$ | $CH_3$ | O | |
| $J_1$ | — | S | $SO_2$ | 1 | H | H | $CH_3$ | $CH_3$ | $OCH_3$ | $CH_2$ | |
| $J_2$ | — | S | O | 0 | H | H | H | H | $OCH_2CH_3$ | O | |
| $J_2$ | — | S | O | 0 | H | H | H | $CH_3$ | $OCF_2H$ | $CH_2$ | |
| $J_2$ | — | S | O | 0 | H | H | $CH_3$ | $CH_3$ | $CH_3$ | $CH_2$ | |
| $J_2$ | — | S | O | 1 | H | H | H | H | $OCH_3$ | O | |
| $J_2$ | — | S | O | 1 | H | H | H | $CH_3$ | $OCH_2CH_3$ | $CH_2$ | |
| $J_2$ | — | S | O | 1 | H | H | $CH_3$ | $CH_3$ | $OCF_2H$ | O | |
| $J_2$ | — | S | S | 0 | H | H | H | H | $CH_3$ | O | |
| $J_2$ | — | S | S | 0 | H | H | H | $CH_3$ | $OCH_3$ | $CH_2$ | |
| $J_2$ | — | S | S | 0 | H | H | $CH_3$ | $CH_3$ | $OCH_2CH_3$ | O | |
| $J_2$ | — | S | S | 1 | H | H | H | H | $OCF_2H$ | $CH_2$ | |
| $J_2$ | — | S | S | 1 | H | H | H | $CH_3$ | $CH_3$ | $CH_2$ | |
| $J_2$ | — | S | S | 1 | H | H | $CH_3$ | $CH_3$ | $OCH_3$ | O | |
| $J_2$ | — | S | $SO_2$ | 0 | H | H | H | H | $OCH_2CH_3$ | $CH_2$ | |
| $J_2$ | — | S | $SO_2$ | 0 | H | H | H | $CH_3$ | $OCF_2H$ | O | |
| $J_2$ | — | S | $SO_2$ | 0 | H | H | $CH_3$ | $CH_3$ | $CH_3$ | O | |
| $J_2$ | — | S | $SO_2$ | 1 | H | H | H | H | $OCH_3$ | $CH_2$ | |
| $J_2$ | — | S | $SO_2$ | 1 | H | H | H | $CH_3$ | $OCH_2CH_3$ | O | |
| $J_2$ | — | S | $SO_2$ | 1 | H | H | $CH_3$ | $CH_3$ | $OCF_2H$ | $CH_2$ | |
| $J_3$ | O | S | — | 0 | H | H | H | H | $CH_3$ | $CH_2$ | |
| $J_3$ | O | S | — | 0 | H | H | H | $CH_3$ | $OCH_3$ | O | |
| $J_3$ | O | S | — | 0 | H | H | $CH_3$ | $CH_3$ | $OCH_2CH_3$ | $CH_2$ | |
| $J_3$ | O | S | — | 1 | H | H | H | H | $OCF_2H$ | O | |
| $J_3$ | O | S | — | 1 | H | H | H | $CH_3$ | $CH_3$ | O | |
| $J_3$ | O | S | — | 1 | H | H | $CH_3$ | $CH_3$ | $OCH_3$ | $CH_2$ | |
| $J_4$ | O | S | — | 0 | H | H | H | H | $OCH_2CH_3$ | O | |
| $J_4$ | O | S | — | 0 | H | H | H | $CH_3$ | $OCF_2H$ | $CH_2$ | |
| $J_4$ | O | S | — | 0 | H | H | $CH_3$ | $CH_3$ | $CH_3$ | $CH_2$ | |
| $J_4$ | O | S | — | 1 | H | H | H | H | $OCH_3$ | O | |
| $J_4$ | O | S | — | 1 | H | H | H | $CH_3$ | $OCH_2CH_3$ | $CH_2$ | |
| $J_4$ | O | S | — | 1 | H | H | $CH_3$ | $CH_3$ | $OCF_2H$ | O | |
| $J_1$ | — | S | $CH_2$ | 0 | H | H | H | H | $CH_3$ | O | |
| $J_1$ | — | S | $CH_2$ | 0 | H | H | H | $CH_3$ | $OCH_3$ | $CH_2$ | |
| $J_1$ | — | S | $CHCH_3$ | 0 | H | H | H | H | $OCH_2CH_3$ | O | |
| $J_1$ | — | S | $CH_2$ | 1 | H | H | H | H | $OCF_2H$ | O | |
| $J_1$ | — | S | $CH_2$ | 1 | H | H | H | $CH_3$ | $CH_3$ | $CH_2$ | |
| $J_1$ | — | S | $CHCH_3$ | 1 | H | H | H | H | $OCH_3$ | O | |
| $J_{13}$ | — | S | — | — | H | H | H | — | $OCH_2CH_3$ | $CH_2$ | |
| $J_{13}$ | — | S | — | — | H | H | Cl | — | $OCH_2CH_3$ | $CH_2$ | |
| $J_{14}$ | — | S | — | — | H | H | H | — | $OCF_2H$ | O | |
| $J_{14}$ | — | S | — | — | H | H | Cl | — | $OCF_2H$ | O | |

TABLE IIb

Structure IIb

| J | $W_2$ | G | n | R | $R_1(R_1')$ | $R_4$ | $R_5$ | $R_6$ | $X_1$ | $Y_1$ | m.p. (°C.) |
|---|---|---|---|---|---|---|---|---|---|---|---|
| $J_5$ | O | S | 0 | H | H | H | H | — | $CH_3$ | $CH_2$ | |
| $J_5$ | O | S | 0 | H | H | H | $CH_3$ | — | $OCH_3$ | O | |
| $J_5$ | O | S | 0 | H | H | H | $CH_3$ | — | $OCH_2CH_3$ | $CH_2$ | |
| $J_5$ | O | S | 1 | H | H | H | H | — | $OCF_2H$ | O | |
| $J_5$ | O | S | 1 | H | H | $CH_3$ | H | — | $CH_3$ | O | |
| $J_5$ | O | S | 1 | H | H | $CH_3$ | $CH_3$ | — | $OCH_3$ | $CH_2$ | |
| $J_6$ | O | S | 0 | H | H | H | H | — | $OCH_2CH_3$ | O | |
| $J_6$ | O | S | 0 | H | H | H | $CH_3$ | — | $OCF_2H$ | $CH_2$ | |
| $J_6$ | O | S | 0 | H | H | H | $CH_3$ | — | $CH_3$ | $CH_2$ | |
| $J_6$ | O | S | 1 | H | H | H | H | — | $OCH_3$ | O | |
| $J_6$ | O | S | 1 | H | H | $CH_3$ | H | — | $OCH_2CH_3$ | $CH_2$ | |
| $J_6$ | O | S | 1 | H | H | $CH_3$ | $CH_3$ | — | $OCF_2H$ | O | |
| $J_7$ | — | S | 0 | H | H | — | H | $CH_3$ | $CH_3$ | O | |
| $J_7$ | — | S | 0 | H | H | — | $CH_3$ | $CH_3$ | $OCH_3$ | $CH_2$ | |

TABLE IIb-continued

Structure IIb

| J | $W_2$ | G | n | R | $R_1(R_1')$ | $R_4$ | $R_5$ | $R_6$ | $X_1$ | $Y_1$ | m.p. (°C.) |
|---|---|---|---|---|---|---|---|---|---|---|---|
| $J_7$ | — | S | 1 | H | H | — | H | $CH_3$ | $OCH_2CH_3$ | O | |
| $J_7$ | — | S | 1 | H | H | — | $CH_3$ | $CH_3$ | $OCF_2H$ | $CH_2$ | |
| $J_8$ | — | S | 0 | H | H | — | H | $CH_3$ | $CH_3$ | $CH_2$ | |
| $J_8$ | — | S | 0 | H | H | — | $CH_3$ | $CH_3$ | $OCH_3$ | O | |
| $J_8$ | — | S | 1 | H | H | — | H | $CH_3$ | $OCH_2CH_3$ | $CH_2$ | |
| $J_8$ | — | S | 1 | H | H | — | $CH_3$ | $CH_3$ | $OCF_2H$ | O | |
| $J_9$ | O | S | — | H | H | H | — | — | $CH_3$ | O | |
| $J_9$ | O | S | — | H | H | $CH_3$ | — | — | $OCH_3$ | $CH_2$ | |
| $J_{10}$ | O | S | — | H | H | H | — | — | $OCH_2CH_3$ | O | |
| $J_{10}$ | O | S | — | H | H | $CH_3$ | — | — | $OCF_2H$ | $CH_2$ | |
| $J_{11}$ | — | S | — | H | H | — | H | $CH_3$ | $CH_3$ | $CH_2$ | |
| $J_{11}$ | — | S | — | H | H | — | $CH_3$ | $CH_3$ | $OCH_3$ | O | |
| $J_{12}$ | — | S | — | H | H | — | H | $CH_3$ | $OCH_2CH_3$ | $CH_2$ | |
| $J_{12}$ | — | S | — | H | H | — | $CH_3$ | $CH_3$ | $OCF_2H$ | O | |
| $J_{15}$ | O | S | 1 | H | H | $CH_3$ | H | — | $OCH_3$ | O | |
| $J_{16}$ | O | S | 1 | H | H | $CH_3$ | H | — | $OCH_3$ | O | |
| $J_{17}$ | — | S | — | H | H | — | H | — | $OCH_3$ | O | |
| $J_{18}$ | — | S | — | H | H | — | H | — | $OCH_3$ | O | |
| $J_{19}$ | O | S | — | H | H | $CH_3$ | H | — | $OCH_3$ | O | |
| $J_{20}$ | O | S | — | H | H | $CH_3$ | H | — | $OCH_3$ | O | |
| $J_{21}$ | — | S | — | H | H | — | H | — | $OCH_3$ | O | |
| $J_{22}$ | — | S | — | H | H | — | H | — | $OCH_3$ | O | |

TABLE IIIa

Structure IIIa

| J | $W_2$ | G | Q | n | R | $R_1(R_1')$ | $R_2$ | $R_3$ | $X_1$ | m.p. (°C.) |
|---|---|---|---|---|---|---|---|---|---|---|
| $J_1$ | — | S | O | 0 | H | H | H | H | $CH_3$ | |
| $J_1$ | — | S | O | 0 | H | H | H | $CH_3$ | $OCH_3$ | |
| $J_1$ | — | S | O | 0 | H | H | $CH_3$ | $CH_3$ | $OCH_2CH_3$ | |
| $J_1$ | — | S | O | 1 | H | H | H | $CH_3$ | $OCF_2H$ | |
| $J_1$ | — | S | O | 1 | H | H | H | $CH_3$ | $CH_3$ | |
| $J_1$ | — | S | O | 1 | H | H | $CH_3$ | $CH_3$ | $OCH_3$ | |
| $J_1$ | — | S | S | 0 | H | H | H | H | $OCH_2CH_3$ | |
| $J_1$ | — | S | S | 0 | H | H | H | $CH_3$ | $OCF_2H$ | |
| $J_1$ | — | S | S | 0 | H | H | $CH_3$ | $CH_3$ | $CH_3$ | |
| $J_1$ | — | S | S | 1 | H | H | H | H | $OCH_3$ | |
| $J_1$ | — | S | S | 1 | H | H | H | $CH_3$ | $OCH_2CH_3$ | |
| $J_1$ | — | S | S | 1 | H | H | $CH_3$ | $CH_3$ | $OCF_2H$ | |
| $J_1$ | — | S | $SO_2$ | 0 | H | H | H | H | $CH_3$ | |
| $J_1$ | — | S | $SO_2$ | 0 | H | H | H | $CH_3$ | $OCH_3$ | |
| $J_1$ | — | S | $SO_2$ | 0 | H | H | $CH_3$ | $CH_3$ | $OCH_2CH_3$ | |
| $J_1$ | — | S | $SO_2$ | 1 | H | H | H | H | $OCF_2H$ | |
| $J_1$ | — | S | $SO_2$ | 1 | H | H | H | $CH_3$ | $CH_3$ | |
| $J_1$ | — | S | $SO_2$ | 1 | H | H | $CH_3$ | $CH_3$ | $OCH_3$ | |
| $J_2$ | — | S | O | 0 | H | H | H | H | $OCH_2CH_3$ | |
| $J_2$ | — | S | O | 0 | H | H | H | $CH_3$ | $OCF_2H$ | |
| $J_2$ | — | S | O | 0 | H | H | $CH_3$ | $CH_3$ | $CH_3$ | |
| $J_2$ | — | S | O | 1 | H | H | H | H | $OCH_3$ | |
| $J_2$ | — | S | O | 1 | H | H | H | $CH_3$ | $OCH_2CH_3$ | |
| $J_2$ | — | S | O | 1 | H | H | $CH_3$ | $CH_3$ | $OCF_2H$ | |
| $J_2$ | — | S | S | 0 | H | H | H | H | $CH_3$ | |
| $J_2$ | — | S | S | 0 | H | H | H | $CH_3$ | $OCH_3$ | |
| $J_2$ | — | S | S | 0 | H | H | $CH_3$ | $CH_3$ | $OCH_2CH_3$ | |
| $J_2$ | — | S | S | 1 | H | H | H | H | $OCF_2H$ | |
| $J_2$ | — | S | S | 1 | H | H | H | $CH_3$ | $CH_3$ | |
| $J_2$ | — | S | S | 1 | H | H | $CH_3$ | $CH_3$ | $OCH_3$ | |
| $J_2$ | — | S | $SO_2$ | 0 | H | H | H | H | $OCH_2CH_3$ | |
| $J_2$ | — | S | $SO_2$ | 0 | H | H | H | $CH_3$ | $OCF_2H$ | |
| $J_2$ | — | S | $SO_2$ | 0 | H | H | $CH_3$ | $CH_3$ | $CH_3$ | |
| $J_2$ | — | S | $SO_2$ | 1 | H | H | H | H | $OCH_3$ | |
| $J_2$ | — | S | $SO_2$ | 1 | H | H | H | $CH_3$ | $OCH_2CH_3$ | |
| $J_2$ | — | S | $SO_2$ | 1 | H | H | $CH_3$ | $CH_3$ | $OCF_2H$ | |
| $J_3$ | O | S | — | 0 | H | H | H | H | $CH_3$ | |
| $J_3$ | O | S | — | 0 | H | H | H | $CH_3$ | $OCH_3$ | |
| $J_3$ | O | S | — | 0 | H | H | $CH_3$ | $CH_3$ | $OCH_2CH_3$ | |
| $J_3$ | O | S | — | 1 | H | H | H | H | $OCF_2H$ | |
| $J_3$ | O | S | — | 1 | H | H | H | $CH_3$ | $CH_3$ | |
| $J_3$ | O | S | — | 1 | H | H | $CH_3$ | $CH_3$ | $OCH_3$ | |
| $J_4$ | O | S | — | 0 | H | H | H | H | $OCH_2CH_3$ | |
| $J_4$ | O | S | — | 0 | H | H | H | $CH_3$ | $OCF_2H$ | |
| $J_4$ | O | S | — | 0 | H | H | $CH_3$ | $CH_3$ | $CH_3$ | |
| $J_4$ | O | S | — | 1 | H | H | H | H | $OCH_3$ | |
| $J_4$ | O | S | — | 1 | H | H | H | $CH_3$ | $OCH_2CH_3$ | |
| $J_4$ | O | S | — | 1 | H | H | $CH_3$ | $CH_3$ | $OCF_2H$ | |
| $J_1$ | — | S | $CH_2$ | 0 | H | H | H | H | $CH_3$ | |

TABLE IIIa-continued

Structure IIIa

| J | W$_2$ | G | Q | n | R | R$_1$(R$_1'$) | R$_2$ | R$_3$ | X$_1$ | m.p. (°C.) |
|---|---|---|---|---|---|---|---|---|---|---|
| J$_1$ | — | S | CH$_2$ | 0 | H | H | H | CH$_3$ | OCH$_3$ | |
| J$_1$ | — | S | CHCH$_3$ | 0 | H | H | H | H | OCH$_2$CH$_3$ | |
| J$_1$ | — | S | CH$_2$ | 1 | H | H | H | H | OCF$_2$H | |
| J$_1$ | — | S | CH$_2$ | 1 | H | H | H | CH$_3$ | CH$_3$ | |
| J$_1$ | — | S | CHCH$_3$ | 1 | H | H | H | H | OCH$_3$ | |
| J$_{13}$ | — | S | — | — | H | H | H | — | OCH$_2$CH$_3$ | |
| J$_{13}$ | — | S | — | — | H | H | Cl | — | OCH$_2$CH$_3$ | |
| J$_{14}$ | — | S | — | — | H | H | H | — | OCF$_2$H | |
| J$_{14}$ | — | S | — | — | H | H | Cl | — | OCF$_2$H | |

Table IIIb

Structure IIIb

| J | W$_2$ | G | n | R | R$_1$ (R$_1'$) | R$_4$ | R$_5$ | R$_6$ | X$_1$ | m.p. (°C.) |
|---|---|---|---|---|---|---|---|---|---|---|
| J$_5$ | O | S | 0 | H | H | H | H | — | CH$_3$ | |
| J$_5$ | O | S | 0 | H | H | H | CH$_3$ | — | OCH$_3$ | |
| J$_5$ | O | S | 0 | H | H | H | CH$_3$ | — | OCH$_2$CH$_3$ | |
| J$_5$ | O | S | 1 | H | H | H | H | — | OCF$_2$H | |
| J$_5$ | O | S | 1 | H | H | CH$_3$ | H | — | CH$_3$ | |
| J$_5$ | O | S | 1 | H | H | CH$_3$ | CH$_3$ | — | OCH$_3$ | |
| J$_6$ | O | S | 0 | H | H | H | H | — | OCH$_2$CH$_3$ | |
| J$_6$ | O | S | 0 | H | H | H | CH$_3$ | — | OCF$_2$H | |
| J$_6$ | O | S | 0 | H | H | H | CH$_3$ | — | CH$_3$ | |
| J$_6$ | O | S | 1 | H | H | H | H | — | OCH$_3$ | |
| J$_6$ | O | S | 1 | H | H | CH$_3$ | H | — | OCH$_2$CH$_3$ | |
| J$_6$ | O | S | 1 | H | H | CH$_3$ | CH$_3$ | — | OCF$_2$H | |
| J$_7$ | — | S | 0 | H | H | — | H | CH$_3$ | CH$_3$ | |
| J$_7$ | — | S | 0 | H | H | — | CH$_3$ | CH$_3$ | OCH$_3$ | |
| J$_7$ | — | S | 1 | H | H | — | H | CH$_3$ | OCH$_2$CH$_3$ | |
| J$_7$ | — | S | 1 | H | H | — | CH$_3$ | CH$_3$ | OCF$_2$H | |
| J$_8$ | — | S | 0 | H | H | — | H | CH$_3$ | CH$_3$ | |
| J$_8$ | — | S | 0 | H | H | — | CH$_3$ | CH$_3$ | OCH$_3$ | |
| J$_8$ | — | S | 1 | H | H | — | H | CH$_3$ | OCH$_2$CH$_3$ | |
| J$_8$ | — | S | 1 | H | H | — | CH$_3$ | CH$_3$ | OCF$_2$H | |
| J$_9$ | O | S | — | H | H | H | — | — | CH$_3$ | |
| J$_9$ | O | S | — | H | H | CH$_3$ | — | — | OCH$_3$ | |
| J$_{10}$ | O | S | — | H | H | H | — | — | OCH$_2$CH$_3$ | |
| J$_{10}$ | O | S | — | H | H | CH$_3$ | — | — | OCF$_2$H | |
| J$_{11}$ | — | S | — | H | H | — | H | CH$_3$ | CH$_3$ | |
| J$_{11}$ | — | S | — | H | H | — | CH$_3$ | CH$_3$ | OCH$_3$ | |
| J$_{12}$ | — | S | — | H | H | — | H | CH$_3$ | OCH$_2$CH$_3$ | |
| J$_{12}$ | — | S | — | H | H | — | CH$_3$ | CH$_3$ | OCF$_2$H | |
| J$_{15}$ | O | S | 1 | H | H | CH$_3$ | H | — | OCH$_3$ | |
| J$_{16}$ | O | S | 1 | H | H | CH$_3$ | H | — | OCH$_3$ | |
| J$_{17}$ | — | S | — | H | H | — | H | — | OCH$_3$ | |
| J$_{18}$ | — | S | — | H | H | — | H | — | OCH$_3$ | |
| J$_{19}$ | O | S | — | H | H | — | CH$_3$ | — | OCH$_3$ | |
| J$_{20}$ | O | S | — | H | H | — | CH$_3$ | — | OCH$_3$ | |
| J$_{21}$ | — | S | — | H | H | — | H | — | OCH$_3$ | |
| J$_{22}$ | — | S | — | H | H | — | H | — | OCH$_3$ | |

TABLE IVa

Structure IVa

| J | W$_2$ | G | Q | n | R | R$_1$(R$_1'$) | R$_4$ | R$_5$ | R$_6$ | X$_1$ | m.p. (°C.) |
|---|---|---|---|---|---|---|---|---|---|---|---|
| J$_1$ | — | S | O | 0 | H | H | H | H | H | CH$_3$ | |
| J$_1$ | — | S | O | 0 | H | H | H | H | CH$_3$ | OCH$_3$ | |
| J$_1$ | — | S | O | 0 | H | H | H | CH$_3$ | CH$_3$ | OCH$_2$CH$_3$ | |
| J$_1$ | — | S | O | 1 | H | H | H | H | H | OCF$_2$H | |
| J$_1$ | — | S | O | 1 | H | H | H | H | CH$_3$ | CH$_3$ | |
| J$_1$ | — | S | O | 1 | H | H | H | CH$_3$ | CH$_3$ | OCH$_3$ | |
| J$_1$ | — | S | S | 0 | H | H | H | H | H | OCH$_2$CH$_3$ | |
| J$_1$ | — | S | S | 0 | H | H | H | H | CH$_3$ | OCF$_2$H | |
| J$_1$ | — | S | S | 0 | H | H | H | CH$_3$ | CH$_3$ | CH$_3$ | |
| J$_1$ | — | S | S | 1 | H | H | H | H | H | OCH$_3$ | |
| J$_1$ | — | S | S | 1 | H | H | H | H | CH$_3$ | OCH$_2$CH$_3$ | |
| J$_1$ | — | S | S | 1 | H | H | H | CH$_3$ | CH$_3$ | OCF$_2$H | |
| J$_1$ | — | S | SO$_2$ | 0 | H | H | H | H | H | CH$_3$ | |
| J$_1$ | — | S | SO$_2$ | 0 | H | H | H | H | CH$_3$ | OCH$_3$ | |
| J$_1$ | — | S | SO$_2$ | 0 | H | H | H | CH$_3$ | CH$_3$ | OCH$_2$CH$_3$ | |
| J$_1$ | — | S | SO$_2$ | 1 | H | H | H | H | H | OCF$_2$H | |
| J$_1$ | — | S | SO$_2$ | 1 | H | H | H | H | CH$_3$ | CH$_3$ | |
| J$_1$ | — | S | SO$_2$ | 1 | H | H | H | CH$_3$ | CH$_3$ | OCH$_3$ | |
| J$_2$ | — | S | O | 0 | H | H | H | H | H | OCH$_2$CH$_3$ | |
| J$_2$ | — | S | O | 0 | H | H | H | H | CH$_3$ | OCF$_2$H | |
| J$_2$ | — | S | O | 0 | H | H | H | CH$_3$ | CH$_3$ | CH$_3$ | |
| J$_2$ | — | S | O | 1 | H | H | H | H | H | OCH$_3$ | |
| J$_2$ | — | S | O | 1 | H | H | H | H | CH$_3$ | OCH$_2$CH$_3$ | |
| J$_2$ | — | S | O | 1 | H | H | H | CH$_3$ | CH$_3$ | OCF$_2$H | |
| J$_2$ | — | S | S | 0 | H | H | H | H | H | CH$_3$ | |
| J$_2$ | — | S | S | 0 | H | H | H | H | CH$_3$ | OCH$_3$ | |
| J$_2$ | — | S | S | 0 | H | H | H | CH$_3$ | CH$_3$ | OCH$_2$CH$_3$ | |
| J$_2$ | — | S | S | 1 | H | H | H | H | H | OCF$_2$H | |
| J$_2$ | — | S | S | 1 | H | H | H | H | CH$_3$ | CH$_3$ | |
| J$_2$ | — | S | S | 1 | H | H | H | CH$_3$ | CH$_3$ | OCH$_3$ | |
| J$_2$ | — | S | SO$_2$ | 0 | H | H | H | H | H | OCH$_2$CH$_3$ | |
| J$_2$ | — | S | SO$_2$ | 0 | H | H | H | H | CH$_3$ | OCF$_2$H | |
| J$_2$ | — | S | SO$_2$ | 0 | H | H | H | CH$_3$ | CH$_3$ | CH$_3$ | |
| J$_2$ | — | S | SO$_2$ | 1 | H | H | H | H | H | OCH$_3$ | |
| J$_2$ | — | S | SO$_2$ | 1 | H | H | H | H | CH$_3$ | OCH$_2$CH$_3$ | |
| J$_2$ | — | S | SO$_2$ | 1 | H | H | H | CH$_3$ | CH$_3$ | OCF$_2$H | |

TABLE IVa-continued

Structure IVa

| J | W₂ | G | Q | n | R | R₁(R₁') | R₄ | R₅ | R₆ | X₁ | m.p. (°C.) |
|---|---|---|---|---|---|---|---|---|---|---|---|
| J₃ | O | S | — | 0 | H | H | H | H | H | CH₃ | |
| J₃ | O | S | — | 0 | H | H | H | H | CH₃ | OCH₃ | |
| J₃ | O | S | — | 0 | H | H | H | CH₃ | CH₃ | OCH₂CH₃ | |
| J₃ | O | S | — | 1 | H | H | H | H | H | OCF₂H | |
| J₃ | O | S | — | 1 | H | H | H | H | CH₃ | CH₃ | |
| J₃ | O | S | — | 1 | H | H | H | CH₃ | CH₃ | OCH₃ | |
| J₄ | O | S | — | 0 | H | H | H | H | H | OCH₂CH₃ | |
| J₄ | O | S | — | 0 | H | H | H | H | CH₃ | OCF₂H | |
| J₄ | O | S | — | 0 | H | H | H | CH₃ | CH₃ | CH₃ | |
| J₄ | O | S | — | 1 | H | H | H | H | H | OCH₃ | |
| J₄ | O | S | — | 1 | H | H | H | H | CH₃ | OCH₂CH₃ | |
| J₄ | O | S | — | 1 | H | H | H | CH₃ | CH₃ | OCF₂H | |
| J₁ | — | S | CH₂ | 0 | H | H | H | H | H | CH₃ | |
| J₁ | — | S | CH₂ | 0 | H | H | H | H | CH₃ | OCH₃ | |
| J₁ | — | S | CHCH₃ | 0 | H | H | H | H | H | OCH₂CH₃ | |
| J₁ | — | S | CH₂ | 1 | H | H | H | H | H | OCF₂H | |
| J₁ | — | S | CH₂ | 1 | H | H | H | H | CH₃ | CH₃ | |
| J₁ | — | S | CHCH₃ | 1 | H | H | H | H | H | OCH₃ | |
| J₁₃ | — | S | — | — | H | H | H | H | — | OCH₂CH₃ | |
| J₁₃ | — | S | — | — | H | H | H | Cl | — | OCH₂CH₃ | |
| J₁₄ | — | S | — | — | H | H | H | H | — | OCF₂H | |
| J₁₄ | — | S | — | — | H | H | H | Cl | — | OCF₂H | |

TABLE IVb

Structure IVb

| J | W₂ | G | n | R | R₁(R₁') | R₄ | R₅ | R₆ | X₁ | m.p. (°C.) |
|---|---|---|---|---|---|---|---|---|---|---|---|
| J₅ | O | S | 0 | H | H | H | H | — | CH₃ | |
| J₅ | O | S | 0 | H | H | H | CH₃ | — | OCH₃ | |
| J₅ | O | S | 0 | H | H | H | CH₃ | — | OCH₂CH₃ | |
| J₅ | O | S | 1 | H | H | H | H | — | OCF₂H | |
| J₅ | O | S | 1 | H | H | CH₃ | H | — | CH₃ | |
| J₅ | O | S | 1 | H | H | CH₃ | CH₃ | — | OCH₃ | |
| J₆ | O | S | 0 | H | H | H | H | — | OCH₂CH₃ | |
| J₆ | O | S | 0 | H | H | H | CH₃ | — | OCF₂H | |
| J₆ | O | S | 0 | H | H | H | CH₃ | — | CH₃ | |
| J₆ | O | S | 1 | H | H | H | H | — | OCH₃ | |
| J₆ | O | S | 1 | H | H | CH₃ | H | — | OCH₂CH₃ | |
| J₆ | O | S | 1 | H | H | CH₃ | CH₃ | — | OCF₂H | |
| J₇ | — | S | 0 | H | H | — | H | CH₃ | CH₃ | |
| J₇ | — | S | 0 | H | H | — | CH₃ | CH₃ | OCH₃ | |
| J₇ | — | S | 1 | H | H | — | H | CH₃ | OCH₂CH₃ | |
| J₇ | — | S | 1 | H | H | — | CH₃ | CH₃ | OCF₂H | |
| J₈ | — | S | 0 | H | H | — | H | CH₃ | CH₃ | |
| J₈ | — | S | 0 | H | H | — | CH₃ | CH₃ | OCH₃ | |
| J₈ | — | S | 1 | H | H | — | H | CH₃ | OCH₂CH₃ | |
| J₈ | — | S | 1 | H | H | — | CH₃ | CH₃ | OCF₂H | |
| J₉ | O | S | — | H | H | H | — | — | CH₃ | |
| J₉ | O | S | — | H | H | CH₃ | — | — | OCH₃ | |
| J₁₀ | O | S | — | H | H | H | — | — | OCH₂CH₃ | |
| J₁₀ | O | S | — | H | H | CH₃ | — | — | OCF₂H | |
| J₁₁ | — | S | — | H | H | — | H | CH₃ | CH₃ | |
| J₁₁ | — | S | — | H | H | — | CH₃ | CH₃ | OCH₃ | |
| J₁₂ | — | S | — | H | H | — | H | CH₃ | OCH₂CH₃ | |
| J₁₂ | — | S | — | H | H | — | CH₃ | CH₃ | OCF₂H | |
| J₁₅ | O | S | 1 | H | H | CH₃ | H | — | OCH₃ | |
| J₁₆ | O | S | 1 | H | H | CH₃ | H | — | OCH₃ | |
| J₁₇ | — | S | — | H | H | — | H | — | OCH₃ | |
| J₁₈ | — | S | — | H | H | — | H | — | OCH₃ | |
| J₁₉ | O | S | — | H | H | CH₃ | — | — | OCH₃ | |
| J₂₀ | O | S | — | H | H | CH₃ | — | — | OCH₃ | |
| J₂₁ | — | S | — | H | H | — | H | — | OCH₃ | |
| J₂₂ | — | S | — | H | H | — | H | — | OCH₃ | |

TABLE Va

Structure Va

| J | W₂ | G | Q | n | R | R₁(R₁') | R₂ | R₃ | X₂ | Y₂ | m.p (°C.) |
|---|---|---|---|---|---|---|---|---|---|---|---|
| J₁ | — | S | O | 0 | H | H | H | H₃ | CH₃ | OCH | |
| J₁ | — | S | O | 0 | H | H | H₃ | CH₂ | CH₂CH₃ | OCH CH | |
| J₁ | — | S | O | 0 | H | H | CH₃ | CH₃ | CH₂CF₃ | SCH₃ | |
| J₁ | — | S | O | 1 | H | H | H | H | CH₃ | SCH₂CH₃ | |
| J₁ | — | S | O | 1 | H | H | H | CH₃ | CH₂CH₃ | CH₃ | |
| J₁ | — | S | O | 1 | H | H | CH₃ | CH₃ | CH₂CF₃ | CH₂CH₃ | |
| J₁ | — | S | S | 0 | H | H | H | H | CH₃ | CH₂CH₃ | |
| J₁ | — | S | S | 0 | H | H | H | CH₃ | CH₂CH₃ | CH₃ | |
| J₁ | — | S | S | 0 | H | H | CH₃ | CH₃ | CH₂CF₃ | SCH₂CH₃ | |
| J₁ | — | S | S | 1 | H | H | H | H₃ | CH₃ | SCH | |
| J₁ | — | S | S | 1 | H | H | H | CH₃ | CH₂CH₃ | OCH₂CH₃ | |
| J₁ | — | S | S | 1 | H | H | CH₃ | CH₃ | CH₂CF₃ | OCH₃ | |
| J₁ | — | S | SO₂ | 0 | H | H | H | H | CH₃ | OCH₃ | |
| J₁ | — | S | SO₂ | 0 | H | H | H | CH₃ | CH₂CH₃ | OCH₂CH₃ | |
| J₁ | — | S | SO₂ | 0 | H | H | CH₃ | CH₃ | CH₂CF₃ | SCH₃ | |
| J₁ | — | S | SO₂ | 1 | H | H | H | H | CH₃ | SCH₂CH₃ | |
| J₁ | — | S | SO₂ | 1 | H | H | H | CH₃ | CH₂CH₃ | CH₃ | |
| J₁ | — | S | SO₂ | 1 | H | H | CH₃ | CH₃ | CH₂CF₃ | CH₂CH₃ | |
| J₂ | — | S | O | 0 | H | H | H | H | CH₃ | CH₂CH₃ | |
| J₂ | — | S | O | 0 | H | H | H | CH₃ | CH₂CH₃ | CH₃ | |
| J₂ | — | S | O | 0 | H | H | CH₃ | CH₃ | CH₂CF₃ | SCH₃ | |
| J₂ | — | S | O | 1 | H | H | H | H | CH₃ | SCH₂CH₃ | |
| J₂ | — | S | O | 1 | H | H | H | CH₃ | CH₂CH₃ | OCH₃ | |

TABLE Va-continued

Structure Va

| J | $W_2$ | G | Q | n | R | $R_1(R_1')$ | $R_2$ | $R_3$ | $X_2$ | $Y_2$ | m.p (°C.) |
|---|---|---|---|---|---|---|---|---|---|---|---|
| $J_2$ | — | S | O | 1 | H | H | $CH_3$ | $CH_3$ | $CH_2CH_3$ | $OCH_2CH_3$ | |
| $J_2$ | — | S | S | 0 | H | H | H | H | $CH_3$ | $OCH_3$ | |
| $J_2$ | — | S | S | 0 | H | H | H | $CH_3$ | $CH_2CH_3$ | $OCH_2CH_3$ | |
| $J_2$ | — | S | S | 0 | H | H | $CH_3$ | $CH_3$ | $CH_2CF_3$ | $SCH_3$ | |
| $J_2$ | — | S | S | 1 | H | H | H | H | $CH_3$ | $SCH_2CH_3$ | |
| $J_2$ | — | S | S | 1 | H | H | H | $CH_3$ | $CH_3$ | $OCH_3$ | |
| $J_2$ | — | S | S | 1 | H | H | $CH_3$ | $CH_3$ | $CH_2CH_3$ | $OCH_2CH_3$ | |
| $J_2$ | — | S | $SO_2$ | 0 | H | H | H | H | $CH_2CF_3$ | $SCH_3$ | |
| $J_2$ | — | S | $SO_2$ | 0 | H | H | H | $CH_3$ | $CH_3$ | $SCH_2CH_3$ | |
| $J_2$ | — | S | $SO_2$ | 0 | H | H | $CH_3$ | $CH_3$ | $CH_2CH_3$ | $CH_3$ | |
| $J_2$ | — | S | $SO_2$ | 1 | H | H | H | H | $CH_2CF_3$ | $CH_2CH_3$ | |
| $J_2$ | — | S | $SO_2$ | 1 | H | H | H | $CH_3$ | $CH_3$ | $CH_2CH_3$ | |
| $J_2$ | — | S | $SO_2$ | 1 | H | H | $CH_3$ | $CH_3$ | $CH_2CH_3$ | $CH_3$ | |
| $J_3$ | O | S | — | 0 | H | H | H | H | $CH_2CF_3$ | $SCH_2CH_3$ | |
| $J_3$ | O | S | — | 0 | H | H | H | $CH_3$ | $CH_3$ | $SCH_3$ | |
| $J_3$ | O | S | — | 0 | H | H | $CH_3$ | $CH_3$ | $CH_2CH_3$ | $OCH_2CH_3$ | |
| $J_3$ | O | S | — | 1 | H | H | H | H | $CH_2CF_3$ | $OCH_3$ | |
| $J_3$ | O | S | — | 1 | H | H | H | $CH_3$ | $CH_3$ | $OCH_3$ | |
| $J_3$ | O | S | — | 1 | H | H | $CH_3$ | $CH_3$ | $CH_2CH_3$ | $OCH_2CH_3$ | |
| $J_4$ | O | S | — | 0 | H | H | H | H | $CH_2CF_3$ | $SCH_3$ | |
| $J_4$ | O | S | — | 0 | H | H | H | $CH_3$ | $CH_3$ | $SCH_2CH_3$ | |
| $J_4$ | O | S | — | 0 | H | H | $CH_3$ | $CH_3$ | $CH_2CH_3$ | $CH_3$ | |
| $J_4$ | O | S | — | 1 | H | H | H | H | $CH_2CF_3$ | $CH_2CH_3$ | |
| $J_4$ | O | S | — | 1 | H | H | H | $CH_3$ | $CH_3$ | $CH_2CH_3$ | |
| $J_4$ | O | S | — | 1 | H | H | $CH_3$ | $CH_3$ | $CH_2CH_3$ | $CH_3$ | |
| $J_1$ | — | S | $CH_2$ | 0 | H | H | H | H | $CH_2CF_3$ | $SCH_3$ | |
| $J_1$ | — | S | $CH_2$ | 0 | H | H | H | $CH_3$ | $CH_3$ | $SCH_2CH_3$ | |
| $J_1$ | — | S | $CHCH_3$ | 0 | H | H | H | H | $CH_2CH_3$ | $OCH_3$ | |
| $J_1$ | — | S | $CH_2$ | 1 | H | H | H | H | $CH_2CF_3$ | $OCH_2CH_3$ | |
| $J_1$ | — | S | $CH_2$ | 1 | H | H | H | $CH_3$ | $CH_3$ | $OCH_3$ | |
| $J_1$ | — | S | $CHCH_3$ | 1 | H | H | H | H | $CH_2CH_3$ | $OCH_2CH_3$ | |
| $J_{13}$ | — | S | — | — | H | H | H | — | $CH_2CF_3$ | $SCH_3$ | |
| $J_{13}$ | — | S | — | — | H | H | Cl | — | $CH_2CF_3$ | $SCH_3$ | |
| $J_{14}$ | — | S | — | — | H | H | H | — | $CH_3$ | $SCH_2CH_3$ | |
| $J_{14}$ | — | S | — | — | H | H | Cl | — | $CH_3$ | $SCH_2CH_3$ | |

TABLE Vb

Structure Vb

| J | $W_2$ | G | n | R | $R_1(R_1')$ | $R_4$ | $R_5$ | $R_6$ | $X_2$ | $Y_2$ | m.p. (°C.) |
|---|---|---|---|---|---|---|---|---|---|---|---|
| $J_5$ | O | S | 0 | H | H | H | H | — | $CH_3$ | $OCH_3$ | |
| $J_5$ | O | S | 0 | H | H | H | $CH_3$ | — | $CH_2OCH_3$ | $OCH_2CH_3$ | |
| $J_5$ | O | S | 0 | H | H | H | $CH_3$ | — | $CH_2CF_3$ | $SCH_3$ | |
| $J_5$ | O | S | 1 | H | H | H | H | — | $CH_3$ | $SCH_2CH_3$ | |
| $J_5$ | O | S | 1 | H | H | $CH_3$ | H | — | $CH_2CH_3$ | $OCH_3$ | |
| $J_5$ | O | S | 1 | H | H | $CH_3$ | $CH_3$ | — | $OCH_2CF_3$ | $CH_2CH_3$ | |
| $J_6$ | O | S | 0 | H | H | H | H | — | $CH_3$ | $OCH_2CH_3$ | |
| $J_6$ | O | S | 0 | H | H | H | $CH_3$ | — | $CH_2CH_3$ | $CH_3$ | |
| $J_6$ | O | S | 0 | H | H | H | $CH_3$ | — | $CH_2CF_3$ | $SCH_2CH_3$ | |
| $J_6$ | O | S | 1 | H | H | H | H | — | $CH_3$ | $SCH_3$ | |
| $J_6$ | O | S | 1 | H | H | $CH_3$ | H | — | $CH_2CH_3$ | $OCH_2CH_3$ | |
| $J_6$ | O | S | 1 | H | H | $CH_3$ | $CH_3$ | — | $CH_2CF_3$ | $OCH_3$ | |
| $J_7$ | — | S | 0 | H | H | — | H | $CH_3$ | $CH_3$ | $OCH_3$ | |
| $J_7$ | — | S | 0 | H | H | — | $CH_3$ | $CH_3$ | $CH_2CH_3$ | $OCH_2CH_3$ | |
| $J_7$ | — | S | 1 | H | H | — | H | $CH_3$ | $CH_2CF_3$ | $SCH_3$ | |
| $J_7$ | — | S | 1 | H | H | — | $CH_3$ | $CH_3$ | $CH_3$ | $SCH_2CH_3$ | |
| $J_8$ | — | S | 0 | H | H | — | H | $CH_3$ | $CH_2CH_3$ | $CH_3$ | |
| $J_8$ | — | S | 0 | H | H | — | $CH_3$ | $CH_3$ | $CH_2CF_3$ | $CH_2CH_3$ | |
| $J_8$ | — | S | 1 | H | H | — | H | $CH_3$ | $CH_3$ | $CH_2CH_3$ | |
| $J_8$ | — | S | 1 | H | H | — | $CH_3$ | $CH_3$ | $CH_2CH_3$ | $CH_3$ | |
| $J_9$ | O | S | — | H | H | H | — | — | $CH_2CF_3$ | $SCH_3$ | |
| $J_9$ | O | S | — | H | H | $CH_3$ | — | — | $CH_3$ | $SCH_2CH_3$ | |
| $J_{10}$ | O | S | — | H | H | H | — | — | $CH_2CH_3$ | $OCH_3$ | |
| $J_{10}$ | O | S | — | H | H | $CH_3$ | — | — | $CH_2CF_3$ | $OCH_3$ | |
| $J_{11}$ | — | S | — | H | H | — | H | $CH_3$ | $CH_3$ | $OCH_3$ | |
| $J_{11}$ | — | S | — | H | H | — | $CH_3$ | $CH_3$ | $CH_2CH_3$ | $OCH_2CH_3$ | |
| $J_{12}$ | — | S | — | H | H | — | H | $CH_3$ | $CH_2CF_3$ | $SCH_3$ | |
| $J_{12}$ | — | S | — | H | H | — | $CH_3$ | $CH_3$ | $CH_3$ | $SCH_2CH_3$ | |
| $J_{15}$ | O | S | 1 | H | H | $CH_3$ | H | — | $CH_3$ | $OCH_3$ | |
| $J_{16}$ | O | S | 1 | H | H | $CH_3$ | H | — | $CH_3$ | $OCH_3$ | |
| $J_{17}$ | — | S | — | H | H | — | H | — | $CH_3$ | $OCH_3$ | |
| $J_{18}$ | — | S | — | H | H | — | H | — | $CH_3$ | $OCH_3$ | |
| $J_{19}$ | O | S | — | H | H | $CH_3$ | H | — | $CH_3$ | $OCH_3$ | |
| $J_{20}$ | O | S | — | H | H | $CH_3$ | H | — | $CH_3$ | $OCH_3$ | |
| $J_{21}$ | — | S | — | H | H | — | H | — | $CH_3$ | $OCH_3$ | |

TABLE Vb-continued

Structure Vb

| J | W$_2$ | G | n | R | R$_1$(R$_1$') | R$_4$ | R$_5$ | R$_6$ | X$_2$ | Y$_2$ | m.p. (°C.) |
|---|---|---|---|---|---|---|---|---|---|---|---|
| J$_{22}$ | — | S | — | H | H | — | H | — | CH$_3$ | OCH$_3$ | |

TABLE VIa

Structure VIa

| J | W$_2$ | G | Q | n | R | R$_1$(R$_1$') | R$_2$ | R$_3$ | X$_3$ | m.p. (°C.) |
|---|---|---|---|---|---|---|---|---|---|---|
| J$_1$ | — | S | O | 0 | H | H | H | H | CH$_3$ | |
| J$_1$ | — | S | O | 0 | H | H | H | CH$_3$ | OCH$_3$ | |
| J$_1$ | — | S | O | 0 | H | H | CH$_3$ | CH$_3$ | CH$_3$ | |
| J$_1$ | — | S | O | 1 | H | H | H | H | OCH$_3$ | |
| J$_1$ | — | S | O | 1 | H | H | H | CH$_3$ | CH$_3$ | |
| J$_1$ | — | S | O | 1 | H | H | CH$_3$ | CH$_3$ | OCH$_3$ | |
| J$_1$ | — | S | S | 0 | H | H | H | H | CH$_3$ | |
| J$_1$ | — | S | S | 0 | H | H | H | CH$_3$ | OCH$_3$ | |
| J$_1$ | — | S | S | 0 | H | H | CH$_3$ | CH$_3$ | CH$_3$ | |
| J$_1$ | — | S | S | 1 | H | H | H | H | OCH$_3$ | |
| J$_1$ | — | S | S | 1 | H | H | H | CH$_3$ | CH$_3$ | |
| J$_1$ | — | S | S | 1 | H | H | CH$_3$ | CH$_3$ | OCH$_3$ | |
| J$_1$ | — | S | SO$_2$ | 0 | H | H | H | H | CH$_3$ | |
| J$_1$ | — | S | SO$_2$ | 0 | H | H | H | CH$_3$ | OCH$_3$ | |
| J$_1$ | — | S | SO$_2$ | 0 | H | H | CH$_3$ | CH$_3$ | CH$_3$ | |
| J$_1$ | — | S | SO$_2$ | 1 | H | H | H | H | OCH$_3$ | |
| J$_1$ | — | S | SO$_2$ | 1 | H | H | H | CH$_3$ | CH$_3$ | |
| J$_1$ | — | S | SO$_2$ | 1 | H | H | CH$_3$ | CH$_3$ | OCH$_3$ | |
| J$_2$ | — | S | O | 0 | H | H | H | H | CH$_3$ | |
| J$_2$ | — | S | O | 0 | H | H | H | CH$_3$ | OCH$_3$ | |
| J$_2$ | — | S | O | 0 | H | H | CH$_3$ | CH$_3$ | CH$_3$ | |
| J$_2$ | — | S | O | 1 | H | H | H | H | OCH$_3$ | |
| J$_2$ | — | S | O | 1 | H | H | H | CH$_3$ | CH$_3$ | |
| J$_2$ | — | S | O | 1 | H | H | CH$_3$ | CH$_3$ | OCH$_3$ | |
| J$_2$ | — | S | S | 0 | H | H | H | H | CH$_3$ | |
| J$_2$ | — | S | S | 0 | H | H | H | CH$_3$ | OCH$_3$ | |
| J$_2$ | — | S | S | 0 | H | H | CH$_3$ | CH$_3$ | CH$_3$ | |
| J$_2$ | — | S | S | 1 | H | H | H | H | OCH$_3$ | |
| J$_2$ | — | S | S | 1 | H | H | H | CH$_3$ | CH$_3$ | |
| J$_2$ | — | S | S | 1 | H | H | CH$_3$ | CH$_3$ | OCH$_3$ | |
| J$_2$ | — | S | SO$_2$ | 0 | H | H | H | H | CH$_3$ | |
| J$_2$ | — | S | SO$_2$ | 0 | H | H | H | CH$_3$ | OCH$_3$ | |
| J$_2$ | — | S | SO$_2$ | 0 | H | H | CH$_3$ | CH$_3$ | CH$_3$ | |
| J$_2$ | — | S | SO$_2$ | 1 | H | H | H | H | OCH$_3$ | |
| J$_2$ | — | S | SO$_2$ | 1 | H | H | H | CH$_3$ | CH$_3$ | |
| J$_2$ | — | S | SO$_2$ | 1 | H | H | CH$_3$ | CH$_3$ | OCH$_3$ | |
| J$_3$ | O | S | — | 0 | H | H | H | H | CH$_3$ | |
| J$_3$ | O | S | — | 0 | H | H | H | CH$_3$ | OCH$_3$ | |
| J$_3$ | O | S | — | 0 | H | H | CH$_3$ | CH$_3$ | CH$_3$ | |
| J$_3$ | O | S | — | 1 | H | H | H | H | OCH$_3$ | |
| J$_3$ | O | S | — | 1 | H | H | CH$_3$ | CH$_3$ | OCH$_3$ | |
| J$_4$ | O | S | — | 0 | H | H | H | H | CH$_3$ | |
| J$_4$ | O | S | — | 0 | H | H | H | CH$_3$ | OCH$_3$ | |
| J$_4$ | O | S | — | 0 | H | H | CH$_3$ | CH$_3$ | CH$_3$ | |
| J$_4$ | O | S | — | 1 | H | H | H | H | OCH$_3$ | |
| J$_4$ | O | S | — | 1 | H | H | H | CH$_3$ | CH$_3$ | |
| J$_4$ | O | S | — | 1 | H | H | CH$_3$ | CH$_3$ | OCH$_3$ | |
| J$_1$ | — | S | CH$_2$ | 0 | H | H | H | H | CH$_3$ | |
| J$_1$ | — | S | CH$_2$ | 0 | H | H | H | CH$_3$ | OCH$_3$ | |
| J$_1$ | — | S | CHCH$_3$ | 0 | H | H | H | H | CH$_3$ | |
| J$_1$ | — | S | CH$_2$ | 1 | H | H | H | H | OCH$_3$ | |
| J$_1$ | — | S | CH$_2$ | 1 | H | H | H | CH$_3$ | CH$_3$ | |
| J$_1$ | — | S | CHCH$_3$ | 1 | H | H | H | H | OCH$_3$ | |
| J$_{13}$ | — | S | — | — | H | H | H | — | CH$_3$ | |
| J$_{13}$ | — | S | — | — | H | H | Cl | — | OCH$_3$ | |
| J$_{14}$ | — | S | — | — | H | H | H | — | CH$_3$ | |
| J$_{14}$ | — | S | — | — | H | H | Cl | — | OCH$_3$ | |

TABLE VIb

Structure VIb

| J | W$_2$ | G | n | R | R$_1$(R$_1$') | R$_4$ | R$_5$ | R$_6$ | X$_3$ | m.p. (°C.) |
|---|---|---|---|---|---|---|---|---|---|---|
| J$_5$ | O | S | 0 | H | H | H | H | — | CH$_3$ | |
| J$_5$ | O | S | 0 | H | H | H | CH$_3$ | — | OCH$_3$ | |
| J$_5$ | O | S | 0 | H | H | H | CH$_3$ | — | CH$_3$ | |
| J$_5$ | O | S | 1 | H | H | H | H | — | OCH$_3$ | |
| J$_5$ | O | S | 1 | H | H | CH$_3$ | H | — | CH$_3$ | |
| J$_5$ | O | S | 1 | H | H | CH$_3$ | CH$_3$ | — | OCH$_3$ | |
| J$_6$ | O | S | 0 | H | H | H | H | — | CH$_3$ | |
| J$_6$ | O | S | 0 | H | H | H | CH$_3$ | — | OCH$_3$ | |
| J$_6$ | O | S | 0 | H | H | H | CH$_3$ | — | CH$_3$ | |
| J$_6$ | O | S | 1 | H | H | H | H | — | OCH$_3$ | |
| J$_6$ | O | S | 1 | H | H | CH$_3$ | H | — | CH$_3$ | |
| J$_6$ | O | S | 1 | H | H | CH$_3$ | CH$_3$ | — | OCH$_3$ | |
| J$_7$ | — | S | 0 | H | H | — | H | CH$_3$ | CH$_3$ | |
| J$_7$ | — | S | 0 | H | H | — | CH$_3$ | CH$_3$ | OCH$_3$ | |
| J$_7$ | — | S | 1 | H | H | — | H | CH$_3$ | CH$_3$ | |
| J$_7$ | — | S | 1 | H | H | — | CH$_3$ | CH$_3$ | OCH$_3$ | |
| J$_8$ | — | S | 0 | H | H | — | H | CH$_3$ | CH$_3$ | |
| J$_8$ | — | S | 0 | H | H | — | CH$_3$ | CH$_3$ | OCH$_3$ | |
| J$_8$ | — | S | 1 | H | H | — | H | CH$_3$ | CH$_3$ | |
| J$_8$ | — | S | 1 | H | H | — | CH$_3$ | CH$_3$ | OCH$_3$ | |
| J$_9$ | O | S | — | H | H | H | — | — | CH$_3$ | |
| J$_9$ | O | S | — | H | H | CH$_3$ | — | — | OCH$_3$ | |
| J$_{10}$ | O | S | — | H | H | H | — | — | CH$_3$ | |
| J$_{10}$ | O | S | — | H | H | CH$_3$ | — | — | OCH$_3$ | |
| J$_{11}$ | — | S | — | H | H | H | — | CH$_3$ | CH$_3$ | |
| J$_{11}$ | — | S | — | H | H | H | — | CH$_3$ | CH$_3$ OCH$_3$ | |
| J$_{12}$ | — | S | — | H | — | — | H | CH$_3$ | CH$_3$ | |
| J$_{12}$ | — | S | — | H | — | — | CH$_3$ | CH$_3$ | OCH$_3$ | |
| J$_{15}$ | O | S | 1 | H | H | CH$_3$ | H | — | OCH$_3$ | |
| J$_{16}$ | O | S | 1 | H | H | CH$_3$ | H | — | OCH$_3$ | |
| J$_{17}$ | — | S | — | H | — | H | — | — | OCH$_3$ | |
| J$_{18}$ | — | S | — | H | — | H | — | — | OCH$_3$ | |
| J$_{19}$ | O | S | — | H | H | CH$_3$ | H | — | OCH$_3$ | |
| J$_{20}$ | O | S | — | H | H | CH$_3$ | — | — | OCH$_3$ | |
| J$_{21}$ | — | S | — | H | — | H | — | — | OCH$_3$ | |
| J$_{22}$ | — | S | — | H | H | H | — | — | OCH$_3$ | |

TABLE VIIa

Structure VIIa

| J | W$_2$ | G | Q | n | R | R$_1$(R$_1$') | R$_2$ | R$_3$ | X$_4$ | Y$_4$ | Z$_1$ | m.p. (°C.) |
|---|---|---|---|---|---|---|---|---|---|---|---|---|
| J-1 | — | S | SO$_2$ | 0 | H | H | CH$_3$ | H | CH$_3$ | CH$_3$ | N | |
| J-2 | — | S | SO$_2$ | 1 | H | H | H | CH$_3$ | CH$_3$ | CH$_3$ | N | |
| J-3 | O | S | — | 1 | H | H | H | H | CH$_3$ | CH$_3$ | N | |
| J-4 | O | S | — | 1 | H | H | H | H | CH$_3$ | CH$_3$ | N | |
| J-13 | — | S | — | — | H | H | — | CH$_3$ | CH$_3$ | CH$_3$ | N | |
| J-14 | — | S | — | — | H | H | H | — | CH$_3$ | CH$_3$ | N | |
| J-1 | — | S | SO$_2$ | 0 | H | H | CH$_3$ | H | CH$_3$ | CH$_3$ | CH | |
| J-1 | — | S | SO$_2$ | 0 | H | H | CH$_3$ | H | CH$_3$ | OCH$_3$ | N | |
| J-1 | — | S | SO$_2$ | 0 | H | H | CH$_3$ | H | CH$_3$ | OCH$_2$CH$_3$ | N | |
| J-1 | — | S | SO$_2$ | 0 | H | H | CH$_3$ | H | Cl | OCH$_3$ | CH | |
| J-1 | — | S | SO$_2$ | 0 | H | H | CH$_3$ | H | CH$_2$OCH$_3$ | CH$_3$ | N | |

TABLE VIIa-continued

Structure VIIa

| J | W$_2$ | G | Q | n | R | R$_1$(R$_1'$) | R$_2$ | R$_3$ | X$_4$ | Y$_4$ | Z$_1$ | m.p. (°C.) |
|---|---|---|---|---|---|---|---|---|---|---|---|---|
| J-1 | — | S | SO$_2$ | 0 | H | H | CH$_3$ | H | OCH$_2$CH$_3$ | CH$_3$ | N | |

TABLE VIIb

Structure VIIb

| J | W$_2$ | G | n | R | R$_1$(R$_1'$) | R$_4$ | R$_5$ | R$_6$ | X$_4$ | Y$_4$ | Z$_1$ | m.p. (°C.) |
|---|---|---|---|---|---|---|---|---|---|---|---|---|
| J-5 | O | S | 1 | H | H | H | H | — | CH$_3$ | CH$_3$ | N | |
| J-6 | O | S | 1 | H | H | H | H | — | CH$_3$ | CH$_3$ | N | |
| J-7 | — | S | 0 | H | H | — | H | CH$_3$ | CH$_3$ | CH$_3$ | N | |
| J-8 | — | S | 0 | H | H | — | H | CH$_3$ | CH$_3$ | CH$_3$ | N | |
| J-9 | O | S | — | H | H | H | H | — | CH$_3$ | CH$_3$ | N | |
| J-10 | O | S | — | H | H | H | — | — | CH$_3$ | CH$_3$ | N | |
| J-11 | — | S | — | H | H | — | H | CH$_3$ | CH$_3$ | CH$_3$ | N | |
| J-12 | — | S | — | H | H | — | H | CH$_3$ | CH$_3$ | CH$_3$ | N | |
| J-15 | O | S | 1 | H | H | CH$_3$ | H | — | CH$_3$ | CH$_3$ | N | |
| J-16 | O | S | 1 | H | H | CH$_3$ | H | — | CH$_3$ | CH$_3$ | N | |
| J-18 | — | S | — | H | H | — | H | — | CH$_3$ | CH$_3$ | N | |
| J-19 | O | S | — | H | H | CH$_3$ | H | — | CH$_3$ | CH$_3$ | N | |
| J-20 | O | S | — | H | H | CH$_3$ | H | — | CH$_3$ | CH$_3$ | N | |
| J-21 | — | S | — | H | H | — | H | — | CH$_3$ | CH$_3$ | N | |
| J-22 | — | S | — | H | H | — | H | — | CH$_3$ | CH$_3$ | N | |

TABLE VIII

Structures A, B, C, D, E, and F

| J | G | n | R$_1$(R$_1'$) | R$_4$ | R$_5$ | R$_{17}$ | R$_{18}$ | R$_{33}$ |
|---|---|---|---|---|---|---|---|---|
| 23 | S | 0 | H | — | — | H | OH | — |
| 23 | S | 1 | H | — | — | H | OH | — |
| 23 | S | 0 | H | — | — | CO$_2$CH$_3$ | H | — |
| 23 | S | 1 | H | — | — | OCH$_3$ | OCH$_3$ | — |
| 23 | S | 1 | H | — | — | —OCH$_2$CH$_2$O— | | — |
| 23 | S | 1 | H | — | — | —OCH$_2$CH$_2$CH$_2$O— | | — |
| 24 | S | 1 | H | — | — | H | OH | — |
| 45 | S | 0 | H | — | — | H | H | — |
| 45 | S | 1 | H | — | — | H | H | — |
| 46 | S | 0 | H | — | — | H | H | — |
| 47 | S | 0 | H | — | — | H | H | — |
| 48 | S | 0 | H | H | — | H | H | — |
| 49 | S | 1 | H | CH$_3$ | — | H | H | — |
| 50 | S | 1 | H | — | — | H | H | — |
| 63 | S | — | H | — | — | H | H | — |
| 64 | S | — | H | — | — | H | H | — |
| 65 | S | — | H | — | — | H | H | — |
| 66 | S | — | H | — | — | H | H | — |
| 67 | S | — | H | — | H | H | H | — |
| 68 | S | — | H | — | H | H | H | — |
| 75 | S | — | H | — | — | H | H | — |
| 76 | S | — | H | — | — | H | H | — |
| 161 | S | — | H | — | — | H | — | H |
| 162 | S | — | H | — | — | CH$_3$ | — | CH$_3$ |
| 163 | S | — | H | — | — | CH$_3$ | CH$_3$ | H |
| 164 | S | — | H | — | — | H | H | CH$_3$ |
| 23 | O | 1 | H | — | — | H | OH | — |
| 23 | NH | 1 | H | — | — | H | OH | — |
| 23 | NCH$_3$ | 1 | H | — | — | H | OH | — |

TABLE IX

Structures A, B, C, D, E, and F

| J | G | n | R$_1$(R$_1'$) | R$_4$ | R$_9$ | R$_{19}$ | R$_{20}$ |
|---|---|---|---|---|---|---|---|
| 25 | S | 0 | H | H | H | H | — |
| 25 | S | 1 | H | H | H | H | — |
| 26 | S | 1 | H | H | H | H | — |
| 77 | S | — | H | — | H | H | — |
| 77 | O | — | H | — | H | H | — |
| 77 | NH | — | H | — | H | H | — |
| 77 | NCH$_3$ | — | H | — | H | H | — |
| 78 | S | — | H | — | — | H | — |
| 79 | S | — | H | — | — | — | CH$_3$ |
| 79 | O | — | H | — | — | — | CH$_3$ |
| 79 | NH | — | H | — | — | — | CH$_3$ |
| 79 | NCH$_3$ | — | H | — | — | — | CH$_3$ |
| 80 | S | — | H | — | — | — | CH$_3$ |

TABLE X

Structures A, B, C, D, E, and F

| J | G | n | R$_1$(R$_1'$) | R$_4$ | R$_{21}$ | R$_{22}$ | R$_{24}$ | R$_{25}$ | g |
|---|---|---|---|---|---|---|---|---|---|
| 35 | S | 0 | H | — | H | H | — | — | — |
| 36 | S | 0 | H | — | H | H | — | — | — |
| 37 | S | 0 | H | — | H | H | — | — | — |
| 38 | S | 0 | H | — | H | H | — | — | — |
| 39 | S | 0 | H | CH$_3$ | H | H | — | — | — |
| 40 | S | 0 | H | CH$_3$ | H | H | — | — | — |
| 105 | S | — | H | — | — | — | H | — | 0 |
| 105 | S | — | H | — | — | — | H | — | 1 |
| 106 | S | — | H | — | — | — | CH$_3$ | — | 0 |
| 107 | S | — | H | — | — | — | H | — | 0 |
| 108 | S | — | H | — | — | — | H | — | 0 |
| 109 | S | — | H | — | — | — | H | H | — |
| 110 | S | — | H | — | — | — | H | H | — |
| 111 | S | — | H | — | — | — | H | H | — |
| 112 | S | — | H | — | — | — | H | H | — |
| 113 | S | — | H | — | — | — | — | — | — |
| 114 | S | — | H | — | — | — | — | — | — |
| 115 | S | — | H | — | — | — | CH$_3$ | — | — |
| 116 | S | — | H | — | — | — | CH$_3$ | — | — |
| 117 | S | — | H | — | — | — | H | — | — |
| 118 | S | — | H | — | — | — | H | — | — |
| 119 | S | — | H | — | — | — | H | — | — |
| 120 | S | — | H | — | — | — | H | — | — |
| 121 | S | — | H | — | — | — | H | H | — |
| 122 | S | — | H | — | — | — | H | H | — |

TABLE XI

Structures A, B, C, D, E, and F

| J | G | n | R$_1$(R$_1'$) | R$_2$ | R$_3$ | R$_4$ | R$_5$ |
|---|---|---|---|---|---|---|---|
| 51 | S | 0 | CH$_3$ | H | H | — | — |
| 51 | S | 1 | CH$_3$ | H | H | — | — |
| 52 | S | 1 | H | H | H | — | — |
| 53 | S | 0 | CH$_3$ | H | H | — | — |
| 53 | S | 1 | CH$_3$ | H | H | — | — |
| 54 | S | 1 | H | H | H | — | — |
| 55 | S | 0 | CH$_3$ | H | H | CH$_3$ | — |

TABLE XI-continued

Structures A, B, C, D, E, and F

| J | G | n | $R_1(R_1')$ | $R_2$ | $R_3$ | $R_4$ | $R_5$ |
|---|---|---|---|---|---|---|---|
| 56 | S | 0 | H | H | H | $CH_3$ | — |
| 57 | S | 1 | $CH_3$ | H | H | — | — |
| 58 | S | 1 | H | H | H | — | — |
| 59 | S | 1 | $CH_3$ | H | H | — | — |
| 60 | S | 1 | H | H | H | — | — |
| 61 | S | 1 | $CH_3$ | H | H | $CH_3$ | — |
| 62 | S | 1 | H | H | H | $CH_3$ | — |
| 69 | S | — | $CH_3$ | H | H | — | — |
| 69 | O | — | $CH_3$ | H | H | — | — |
| 69 | NH | — | $CH_3$ | H | H | — | — |
| 69 | $NCH_3$ | — | $CH_3$ | H | H | — | — |
| 70 | S | — | H | H | H | — | — |
| 71 | S | — | $CH_3$ | H | H | — | — |
| 72 | S | — | H | H | H | — | — |
| 73 | S | — | $CH_3$ | H | H | — | H |
| 74 | S | — | H | H | H | — | H |
| 99 | S | — | $CH_3$ | H | H | — | — |
| 100 | S | — | H | H | H | — | — |
| 101 | S | — | $CH_3$ | H | H | — | — |
| 102 | S | — | H | H | H | — | — |
| 103 | S | — | $CH_3$ | H | H | — | H |
| 104 | S | — | H | H | H | — | H |
| 51 | O | 1 | $CH_3$ | H | H | — | — |
| 51 | $NCH_3$ | 1 | $CH_3$ | H | H | — | — |

TABLE XII

Structures A, B, C, D, E, and F

| J | G | n | $R_1(R_1')$ | $R_4$ | $R_5$ | $R_9$ | $W_2$ | p |
|---|---|---|---|---|---|---|---|---|
| 27 | S | 1 | H | H | — | — | — | — |
| 28 | S | 1 | H | H | — | — | — | — |
| 29 | S | 1 | H | H | — | — | — | — |
| 30 | S | 1 | H | H | — | — | — | — |
| 31 | S | 1 | H | H | — | $CH_3$ | — | — |
| 32 | S | 1 | H | H | — | $CH_3$ | — | — |
| 33 | S | 1 | H | — | H | $CH_3$ | — | — |
| 34 | S | 1 | H | — | H | $CH_3$ | — | — |
| 41 | S | 1 | H | H | H | — | O | — |
| 41 | S | 1 | H | H | H | — | S | — |
| 42 | S | 1 | H | H | H | — | O | — |
| 43 | S | 1 | H | H | H | — | — | — |
| 44 | S | 1 | H | H | H | — | — | — |
| 81 | S | — | H | $CH_3$ | $CH_3$ | — | — | — |
| 82 | S | — | H | $CH_3$ | $CH_3$ | — | — | — |
| 83 | S | — | H | $CH_3$ | $CH_3$ | — | — | 0 |
| 83 | S | — | H | H | H | — | — | 2 |
| 84 | S | — | H | $CH_3$ | $CH_3$ | — | — | 2 |
| 85 | S | — | H | $CH_3$ | $CH_3$ | H | — | — |
| 86 | S | — | H | $CH_3$ | $CH_3$ | H | — | — |
| 87 | S | — | H | H | — | — | — | — |
| 88 | S | — | H | H | — | — | — | — |
| 89 | S | — | H | H | — | — | — | — |
| 90 | S | — | H | H | — | — | — | — |
| 91 | S | — | H | H | — | $CH_3$ | — | — |
| 92 | S | — | H | H | — | $CH_3$ | — | — |
| 93 | S | — | H | — | H | $CH_3$ | — | — |
| 94 | S | — | H | — | H | $CH_3$ | — | — |
| 95 | S | — | H | H | — | — | — | — |
| 96 | S | — | H | H | — | — | — | — |
| 97 | S | — | H | H | — | — | — | — |
| 98 | S | — | H | H | — | — | — | — |

TABLE XIII

Structures A, B, C, D, E, and F

| J | G | n | $R_1(R_1')$ | $R_{26}$ | $R_{27}$ | $Q_1$ |
|---|---|---|---|---|---|---|
| 123 | S | — | H | H | H | O |
| 123 | S | — | H | H | H | S |
| 123 | S | — | H | H | H | $CH_3$ |
| 123 | S | — | H | H | H | $NCH_3$ |
| 124 | S | — | H | H | H | $CH_2$ |
| 125 | S | — | H | $CH_3$ | — | — |
| 126 | S | — | H | $CH_3$ | — | — |
| 127 | S | — | H | $CH_3$ | — | — |
| 165 | S | — | H | H | H | O |
| 165 | S | — | H | H | H | S |
| 165 | S | — | H | H | H | $CH_2$ |
| 165 | S | — | H | H | H | $NCH_3$ |
| 166 | S | — | H | H | H | $CH_2$ |

TABLE XIV

Structures A, B, C, D, E, and F

| J | G | $R_1(R_1')$ | $R_4$ | $R_5$ | $R_{28}$ | $R_{29}$ | $R_{30}$ | $R_{31}$ |
|---|---|---|---|---|---|---|---|---|
| 127 | S | $CH_3$ | — | — | $CH_3$ | $CH_3$ | — | — |
| 127 | O | H | — | — | H | H | — | — |
| 128 | S | H | — | — | H | H | — | — |
| 129 | S | H | H | — | $CH_3$ | $CH_3$ | — | — |
| 129 | NH | H | H | — | H | H | — | — |
| 129 | $NCH_3$ | H | $CH_3$ | — | H | H | — | — |
| 130 | S | H | $CH_3$ | — | H | H | — | — |
| 131 | O | $CH_3$ | — | — | — | H | $CH_3$ | — |
| 132 | S | H | — | — | — | $CH_3$ | $CH_3$ | — |
| 133 | S | $CH_3$ | — | — | — | H | $CH_3$ | — |
| 134 | S | H | — | — | — | $CH_3$ | $CH_3$ | — |
| 135 | NH | H | — | H | — | H | H | — |
| 135 | $NCH_3$ | H | — | $CH_3$ | — | H | H | — |
| 136 | S | H | — | H | — | $CH_3$ | $CH_3$ | — |
| 137 | S | $CH_3$ | — | — | — | — | — | H |
| 138 | S | H | — | — | — | — | — | H |
| 139 | S | $CH_3$ | — | — | — | — | — | H |
| 140 | S | H | — | — | — | — | — | H |
| 141 | S | $CH_3$ | $CH_3$ | — | — | — | — | H |
| 142 | S | H | $CH_3$ | — | — | — | — | H |

TABLE XV

Structures A, B, C, D, E, and F

| J | G | $R_1(R_1')$ | $R_4$ | $R_5$ | $R_{32}$ | $R_{33}$ |
|---|---|---|---|---|---|---|
| 143 | S | $CH_3$ | — | — | $CH_3$ | — |
| 144 | S | H | — | — | $CH_3$ | — |
| 145 | S | $CH_3$ | — | — | $CH_3$ | — |
| 146 | S | H | — | — | $CH_3$ | — |
| 147 | S | $CH_3$ | $CH_3$ | — | — | $CH_3$ |
| 148 | S | H | $CH_3$ | — | — | $CH_3$ |
| 149 | S | $CH_3$ | — | — | — | $CH_3$ |
| 150 | S | H | — | — | — | $CH_3$ |
| 151 | S | $CH_3$ | — | — | — | $CH_3$ |
| 152 | S | H | — | — | — | $CH_3$ |
| 153 | S | $CH_3$ | — | H | $CH_3$ | — |
| 154 | S | H | — | H | $CH_3$ | — |
| 155 | S | $CH_3$ | — | — | — | $CH_3$ |
| 156 | S | H | — | — | — | $CH_3$ |
| 157 | S | $CH_3$ | — | — | — | $CH_3$ |
| 158 | S | H | — | — | — | $CH_3$ |
| 159 | S | $CH_3$ | — | H | — | $CH_3$ |
| 160 | S | H | — | H | — | $CH_3$ |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE XVI

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N. J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8–57ff.

In the following examples, all parts are by weight unless otherwise indicated.

EXAMPLE 12

| Wettable Powder | |
|---|---|
| N—[(4-methoxy-6-methylpyrimidin-2-yl)aminocarbonyl]-6,7-dihydro-5H—thieno[3,2-B]thiopyran-3-sulfonamide, 4,4-dioxide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 13

| Wettable Powder | |
|---|---|
| N—[(4,6-dimethoxypyrimidin-2-yl)aminocarbonyl]-6,7-dihydro-5H—thieno[3,2-B]thiopyran-3-sulfonamide, 4,4-dioxide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 14

| Granule | |
|---|---|
| Wettable Powder of Example 13 | 5% |
| attapulgite granules (U.S.S. 20–40 mesh; 0.84–0.42 mm) | 95% |

A slurry of wettable powder containing 25% solids is sprayed on the surface of attapulgite granules while tumbling in a double-cone blender. The granules are dried and packaged.

EXAMPLE 15

| Extruded Pellet | |
|---|---|
| N—[(4,6-dimethoxypyrimidin-2-yl)aminocarbonyl]-5,6-dihydro-5-methylthieno[3,2-B]thiophene-3-sulfonamide, 4,4-dioxide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 16

| Oil Suspension | |
|---|---|
| N—[(4-methoxy-6-methyltriazin-2-yl)aminocarbonyl-5,6-dihydro-5-methylthieno[3,2-B]-thiophene sulfonamide, 4,4-dioxide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 17

| Wettable Powder | |
|---|---|
| N—[(4-chloro-6-methoxypyrimidin-2-yl)aminocarbonyl]-5,6-dihydro-5-methylthieno[3,2-B]thiophene-3-sulfonamide, 4,4-dioxide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 18

| Low Strength Granule | |
|---|---|
| N—[(4-chloro-6-methoxypyrimidin-2-yl)aminocarbonyl]-5,6-dihydro-5-methylthieno[3,2-B]thiophene-3-sulfonamide, 4,4-dioxide | 1% |
| N,N—dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 19

| Aqueous Suspension | |
|---|---|
| N—[(4-methoxy-6-methylpyrimidin-2-yl)aminocarbonyl]-6,7-dihydro-5H—thieno[3,2-B]thiopyran-3-sulfonamide, 4,4-dioxide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 20

| Solution | |
|---|---|
| N—[(4,6-dimethoxypyrimidin-2-yl)aminocarbonyl]-5,6-dihydro-5methylthieno[3,2-B]thiophene-3-sulfonamide, 4,4-dioxide, sodium salt | 5% |
| water | 95% |

The salt is added directly to the water with stirring to produce the solution, which may then be packaged for use.

EXAMPLE 21

| Low Strength Granule | |
|---|---|
| N—[(4,6-dimethoxypyrimidin-2-yl)aminocarbonyl]-6,7-dihydro-5H—thieno[3,2-B]thiopyran-3-sulfonamide, 4,4-dioxide | 0.1% |
| attapulgite granules (U.S.S. 20-40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 22

| Granule | |
|---|---|
| N—[(4-methoxy-6-methyltriazin-2-yl)aminocarbonyl]-5,6-dihydro-5-methylthieno[3,2-B]-thiophene-3-sulfonamide-4,4-dioxide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 23

| High Strength Concentrate | |
|---|---|
| N—[(4-chloro-6-methoxypyrimidin-2-yl)aminocarbonyl]-5,6-dihydro-5-methylthieno[3,2-B]thiophene-3-sulfonamide, 4,4-dioxide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 24

| Wettable Powder | |
|---|---|
| N—[(4-methoxy-6-methylpyrimidin-2-yl)aminocarbonyl]-6,7-dihydro-5H—thieno[3,2-B]thiopyran-3-sulfonamide, 4,4-dioxide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 25

| Wettable Powder | |
| --- | --- |
| N—[(4,6-dimethoxypyrimidin-2-yl)aminocarbonyl]-6,7-dihydro-5H—thieno[3,2-B]thiopyran-3-sulfonamide, 4,4-dioxide | 40% |
| sodium ligninsulfonate | 20% |
| montmorillonite clay | 40% |

The ingredients are thorougly blended, coarsely hammer-milled and then air-milled to produce particles essentially all below 10 microns in size. The material is reblended and then packaged.

EXAMPLE 26

| Oil Suspension | |
| --- | --- |
| N—[(4,6-dimethoxypyrimidin-2-yl)aminocarbonyl]-5,6-dihydro-5-methylthieno[3,2-B]thiophene-3-sulfonamide, 4,4-dioxide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 27

| Dust | |
| --- | --- |
| N—[(4-methoxy-6-methyltriazin-2-yl)aminocarbonyl]-5,6-dihydro-5-methylthieno[3,2-B]thiophene-3-sulfonamide, 4,4-dioxide | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

UTILITY

Test results indicate that the compounds of the present invention are active herbicides. Many of the compounds have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, many of the subject compounds should be useful for plant growth modification, such as growth retardation. Some of the compounds when used at lower rates of application are selective on certain crops, e.g., cotton.

The rates of application for the compounds of the invention are determined by a number of factors, including their use as selective or general herbicides, the crop species involved, the types of weeds to be controlled, weather and climate, formulations selected, mode of application, amount of foilage present, etc. In general terms, the subject compounds should be applied at levels of around 50 to 1000 g/ha, the lower rates being suggested for use on lighter soils and/or those having a low organic matter content, for plant growth modification or for situations where only short-term persistence is required.

The compounds of the invention may be used in combination with any other commercial herbicide examples of which are those of the triazine, triazole, uracil, urea, amide, diphenylether, carbamate and bipyridylium types. Combinations with mefluidide are useful as well.

The herbicidal and plant growth modifying properties of the subject compounds were discovered in the greenhouse. The test procedures and results follow.

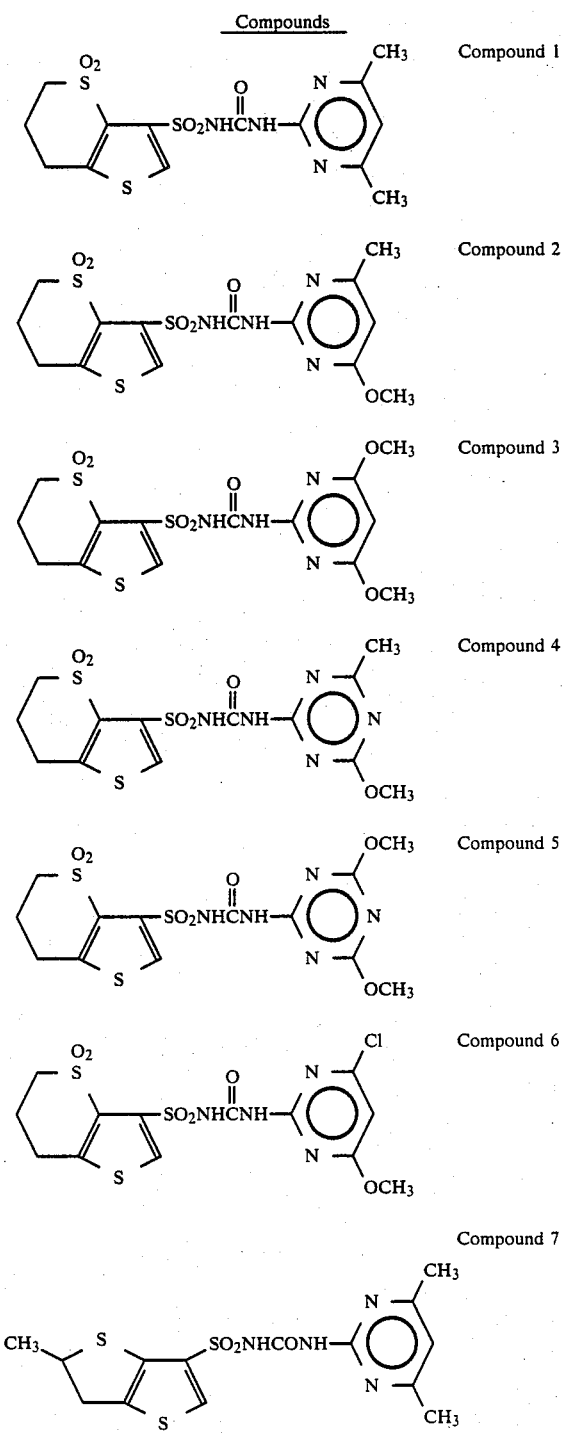

Compounds

-continued
Compounds
Compound 8
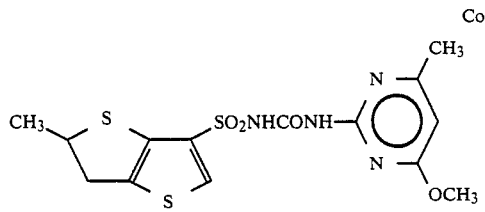
Compound 9
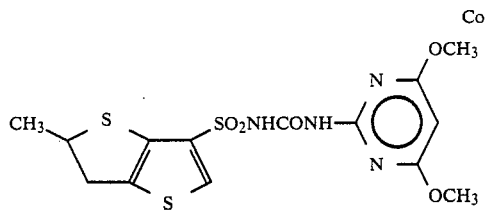
Compound 10
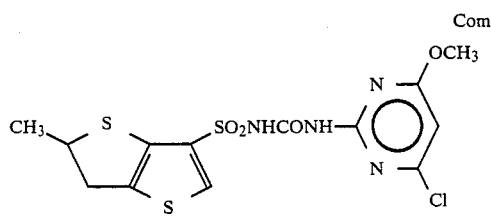
Compound 11
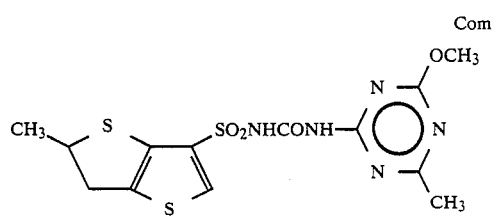
Compound 12
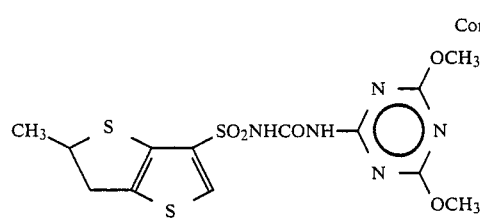
Compound 13
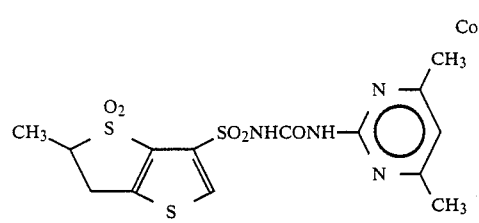
Compound 14
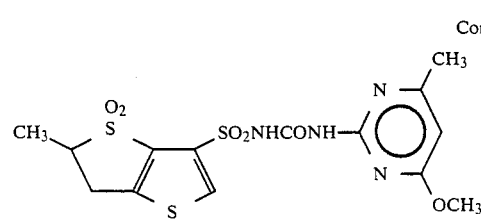
-continued
Compounds
Compound 15
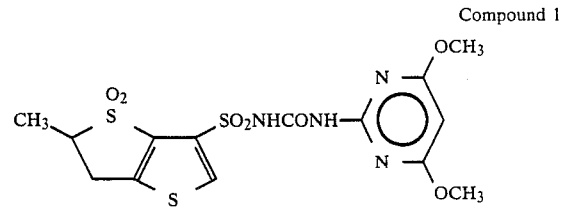
Compound 16
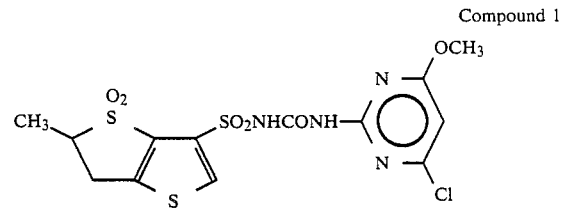
Compound 17
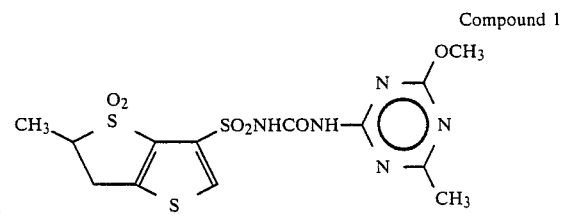
Compound 18
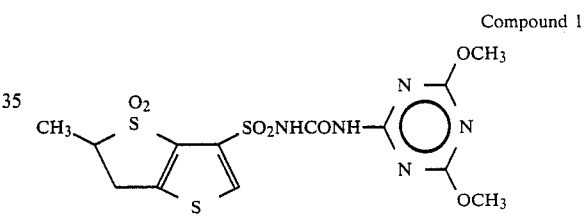
Compound 19
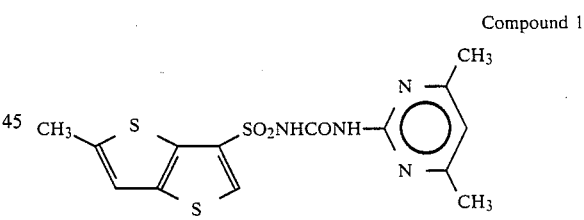
Compound 20
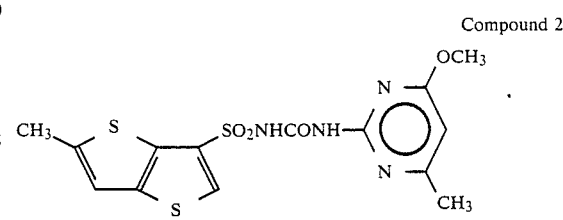
Compound 21
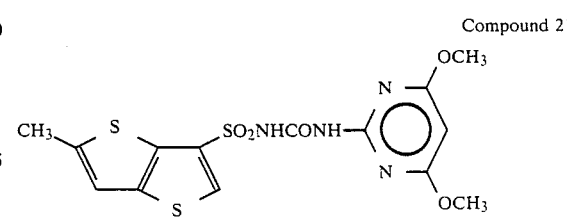

-continued
Compounds

Compound 22

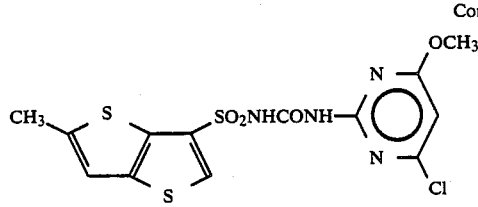

Compound 23

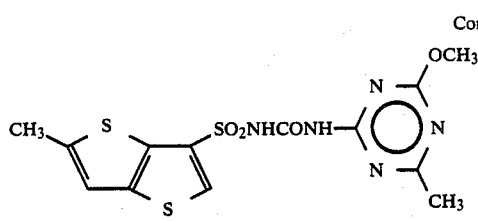

Compound 24

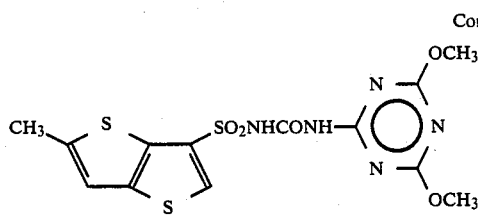

-continued
Compounds

Test A

Seeds of crabgrass (Digitaria sp.), barnyardgrass (*Echinochloa crusgalli*), wild oats (*Avena fatua*), sicklepod (*Cassia obtusifolia*), morningglory (Ipomoea sp.), cocklebur (*Xanthium pensylvanicum*), sorghum, corn, soybean, cotton, sugar beet, rice, wheat and purple nutsedge (*Cyperus rotundus*) tubers were planted in a growth medium and treated pre-emergence with the chemicals dissolved in a non-phytotoxic solvent. It will be noted in the data that in some instances velvetleaf (*Abutilon theophrasti*) has been substituted for sicklepod (*Cassia obtusifolia*). At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:
C=chlorosis or necrosis;
E=emergence inhibition;
G=growth retardation;
H=formative effect; and
U=unusual pigmentation.

TABLE A

| | Compound 1 | | Cmpd. 2 | Cmpd. 3 | Cmpd. 4 | | Cmpd. 5 | Cmpd. 6 | Cmpd. 7 | Cmpd. 8 | Cmpd. 9 | Cmpd. 10 | Cmpd. 11 | Cmpd. 12 |
|---|---|---|---|---|---|---|---|---|---|---|---|---|---|---|
| Rate (kg/ha) | 0.05 | 2.0 | 0.05 | 0.05 | 0.05 | 2.0 | 2.0 | 0.05 | 0.05 | 0.05 | 0.05 | 0.05 | 0.05 | 0.05 |
| POST-EMERGENCE | | | | | | | | | | | | | | |
| Morningglory | 0 | 1C | 4C,8H | 4C,8H | 0 | 0 | 2G | 3G | 4C,8H | 5C,9G | 10C | 4C,9G | 2C,6G | 3G |
| Cocklebur | 0 | 1C,2G | 4C,8H | 3C,8G | 0 | 0 | 3G | 5G | 4C,8H | 9C | 10C | 10C | 2C,9H | 0 |
| Velvetleaf | 0 | 0 | 4C,6H | 4C,8H | 0 | 0 | | | 4C,9G | 9C | 9C | 4C,8G | 4C,9G | 4C,9G |
| Sicklepod | 0 | 0 | 0 | 2C,5G | 0 | 0 | 1C | 0 | 2C,8G | 4C,8G | 9C | 0 | 0 | 0 |
| Nutsedge | 0 | 0 | 2C,4H | 2C,7G | 0 | 1C,3G | 0 | 0 | 3C,7G | 9C | 9C | 2C,5G | 0 | 0 |
| Crabgrass | 0 | 1H | 5C,9H | 5C,9H | 3C,8H | 4C,9H | 1C,3G | 2G | 3C,5H | 9C | 9C | 0 | 0 | 0 |
| Barnyardgrass | 0 | 1C,5G | 4C,9G | 4C,9G | 4C,9G | 3C,9G | 4C,9H | 9H | 2C,6G | 4C,8G | 9C | 1C | 0 | 0 |
| Wild Oats | 0 | 2C,8G | 4C,9G | 5C,9G | 4C,9G | 3C,9G | 5C,9G | 0 | 3C,9H | 4C,8G | 10C | 0 | 2C,5G | 0 |
| Wheat | 0 | 0 | 3U,9G | 4U,9G | 2C,6H | 4C,9G | 4C,9G | 2C,8H | 2C,6G | 10C | 9C | 5C,9G | 3C,9G | 2C,6H |
| Corn | 0 | 0 | 4C,8G | 4H,9G | 2C,4H | 4C,9G | 2U,9H | 2G | 3C,9H | 5C,9G | 9C | 4C,9G | 4C,9G | 4C,9G |
| Soybean | 0 | 0 | 5C,9G | 9C | 4C,9G | 4C,9G | 2H,5G | 5C,9G | 4C,8H | 9C | 9C | 4C,9G | 4C,9G | 4C,9G |
| Rice | 0 | 5G | 9C | 9C | 3C,9G | 4C,9G | 3C,9H | 5C,9G | 5C,9G | 9C | 9C | 9C | 3C,7H | 2C,8G |
| Sorghum | 0 | 1C | 4C,9H | 4C,9H | 3C,7H | 5C,9G | 3C,9H | 2C,9H | 3C,7G | 10C | 10C | 9C | 1C | 2C,4G |
| Cheatgrass | 0 | 2H | 4C,8H | 9C | 0 | 0 | 1C,3H | 5G | 4C,9G | 9C | 9C | 5C,9G | 9C | 3C,7H |
| Sugar beet | 0 | 2C,9G | 4C,8H | 2C,9H | 2C,7H | 2C | 1C,2G | 5G | 4C,9G | 10C | 10C | 5C,9G | 5C,9G | 10C |
| Cotton | | | | | | | | 3C,5G | 9C | 10C | 9C | | 1C | |
| PRE-EMERGENCE | | | | | | | | | | | | | | |
| Morningglory | 0 | 2C | 1H | 7H | 0 | 0 | 1C | 3C,5G | 7H | 9G | 9C | 9H | 2C,6G | 5G |
| Cocklebur | 0 | 9G | 3H | 8H | 0 | 2H | 2H | 0 | — | 8H | 8H | 9H | 6H | 0 |
| Velvetleaf | 0 | 2H | 0 | 7G | 0 | 0 | 3G | 7G | 7G | 10E | 5C,9G | 2C,8G | 6G | 2G |
| Sicklepod | 0 | 2C,5G | 0 | 0 | 0 | 0 | 0 | 2C,5G | 5G | 8G | 10E | 3C,5G | 0 | 0 |
| Nutsedge | 0 | 0 | 3G | 3G | 0 | 0 | 0 | 0 | 2C,5G | 4C,8G | 4C,9G | 3C,7G | 0 | 0 |
| Crabgrass | 0 | 2C | 2C | 2C | 0 | 2C,5G | 8G | 0 | 0 | 2C,6H | 4C,9H | 3C,9H | 0 | 0 |
| Barnyardgrass | 0 | 2C,7G | 0 | 4C,9G | 0 | 7G | 1C,7G | 0 | 3C,8H | 4C,8G | 1C | 1C | 0 | 2C,2G |
| Wild Oats | 0 | 8G | 0 | 9C | 0 | 2C,8G | 3C,8H | 2G | 2C,5H | 0 | 1C | 2C,9H | 7G | 0 |
| Wheat | 0 | 2C,9H | 2C,6G | 3C,9H | 0 | 0 | 1H | 0 | 3C,8H | 10H | 2C,9H | 3C,7G | 2C,4H | 2C |
| Corn | 0 | 2C | 2C | 8H | 0 | 2C,8G | 2C,5G | 2G | 2C,5G | 2G | 3C,7G | 10E | 3G | 2C 5G |
| Soybean | 0 | 3C,7H | 2G | 10E | 0 | 0 | 0 | 5G | 3C,7G | 10E | 10E | 0 | 0 | 0 |
| Rice | 0 | 3C,8G | 3C,4G | 4C,9H | 0 | 2C,9G | 2C,5G | 2C,9H | 3C,8H | 4C,9H | 4C,9H | 5C,9H | 0 | 0 |
| Sorghum | | | | | | | | | 2C,7G | 5C,9H | 5C,9H | | | |
| Cheatgrass | 0 | 4C,8H | 2C | 2C,9G | 0 | 0 | 0 | 0 | 8G | 4C,9G | 9C | 8H | 6G | 6G |
| Sugar beet | 0 | 6G | 2C | 9G | 0 | 2C,7H | 2G | 1C | 8G | 9G | 9G | 9G | 9G | 9G |
| Cotton | | | | | | | | | | | | | | |

| | Cmpd. 13 | Cmpd. 14 | Cmpd. 15 | Cmpd. 16 | Cmpd. 17 | Cmpd. 18 | Cmpd. 19 | Cmpd. 20 | Cmpd. 21 | Cmpd. 22 | Cmpd. 23 | Cmpd. 24 |
|---|---|---|---|---|---|---|---|---|---|---|---|---|
| Rate (kg/ha) | 0.05 | 0.05 | 0.05 | 0.05 | 0.05 | 0.05 | 0.05 | 0.05 | 0.05 | 0.05 | 0.05 | 0.05 |
| POST-EMERGENCE | | | | | | | | | | | | |
| Morningglory | 9C | 10C | 9C | 9C | 5G | 2G | 4G | 5C,9G | 5C,9G | 2C,8G | 9C | 10C |
| Cocklebur | 10C | 10C | 10C | 10C | 2H,7G | 4G | 2C,8G | 9C | 2C,6G | 4G | 9C | 2G |
| Velvetleaf | 9C | 9C | 5C,9G | 5C,9G | 4G | 5G | 4G | 2C,8G | 10C | | 5G | 4G |
| Sicklepod | 9C | 10C | 9C | 9C | 2G | 3C,8G | 2G | 2G | 5G | 2C,6G | 2C,6H | 0 |
| Nutsedge | 6C,9G | 9C | 2C,5G | 2C,5G | 3C,9H | 5C,9G | 2H | 3C,8H | 2H | 0 | 0 | 0 |
| Crabgrass | 9C | 9C | 2C,5G | 2C,5G | 3C,9G | 5C,9G | 0 | 1C | 0 | 0 | 0 | 0 |
| Barnyardgrass | 10C | 10C | 10C | 10C | 5C,9G | 9C | 0 | 5C,9G | 5C,9G | 5H | 2C,9H | 2C,3H |
| Wild Oats | 6C,9G | 5C,9G | 4C,9H | 4C,9H | 2H,3G | 3H,5G | 2C,6H | 5C,9G | 3C,8G | 4G | 5C,9G | 5C,9G |
| Wheat | 6C,9G | 6C,9G | 9C | 9C | 5C,9G | 5C,9G | 7G | 4C,9G | 2H | 0 | 4C,9G | 5C,9G |
| Corn | 9C | 10C | 10C | 10C | 5C,9H | 4C,9H | 2G | 2C,8H | 9G | | 3C,8H | 2C,5H |

TABLE A-continued

| | | | | | | | | | | | | |
|---|---|---|---|---|---|---|---|---|---|---|---|---|
| Cheatgrass | 6C,9G | 5C,9G | 9C | 5C,9G | 3C,8G | 2C,7G | 0 | 4G | 4G | 2C,7G | 4G | 0 |
| Sugar beet | 9C | 9C | 9C | 9C | 3C,6H | 3C,7G | 4C,9H | 9C | 10C | 9C | 9C | 5C,9G |
| Cotton | 9C | 9C | 9C | 9C | 3C,5G | 1C | 7G | 9C | 9C | 4C,9G | 9C | 5C,9G |
| PRE-EMERGENCE | | | | | | | | | | | | |
| Morningglory | 9G | 9G | 9C | 9H | 5G | 7G | 2C,5G | 9G | 9G | 8G | 9G | 9G |
| Cocklebur | 9H | 9H | 9H | 9H | — | 5G | 5H | 3C,8G | 7G | 5H | 9H | 6G |
| Velvetleaf | 5C,9G | 5C,9G | 10C | 5C,9G | 0 | 2C | 5G | 9C | 9G | 6G | 9C | 2C,9G |
| Sicklepod | 10E | 10E | 10E | 10E | 0 | 0 | 0 | 9G | 10E | 0 | 5G | 5G |
| Nutsedge | 5C,9G | 9C | 9C | 4C,8G | 0 | 0 | 0 | 5G | 2C,4G | 0 | 0 | 0 |
| Crabgrass | 3H | 2C,9H | 3C,9H | 5C,9H | 0 | 0 | 0 | 3C,8H | 3C,7H | 0 | 2G | 3H |
| Barnardgrass | 2C,8G | 4C,9H | 4C,9H | 7G | 2C,8G | 2C,8G | 0 | 2C,5G | 0 | 0 | 0 | 2G |
| Wild Oats | 9G | 7C,9H | 7C,9H | 6G | 8G | 5G | 0 | 5G | 2G | 0 | 0 | 0 |
| Wheat | 3C,9G | 10H | 5C,9H | 5C,9H | 4C,9H | 4C,9H | 4G | 2C,8G | 9G | 5G | 2C,8G | 2C,7G |
| Corn | 3C,7H | 9H | 3C,8H | 4C,7H | 0 | 0 | 2C,2H | 3C,7H | 7H | 3G | 3C,7H | 3C,5H |
| Soybean | 10E | 10E | 10E | 10E | 9H | 9H | 2C,7G | 4C,9H | 9H | 5G | 10E | 9H |
| Rice | 5C,9H | 9H | 7C,9H | 10H | 2C,8H | 3C,7H | 2C | 4C,8H | 4C,9H | 5G | 3C,8H | 2C,6H |
| Sorghum | 10E | 6C,9H | 10E | 9G | 3G | 3G | 5G | 5G | 6G | 2G | 3G | 0 |
| Cheatgrass | 9C | 10E | 10E | 9C | 6G | 3C,7G | 9G | 10C | 10E | 8G | 9C | 9C |
| Sugar beet | 9G | 5C,9G | 5C,9G | 9C | 0 | 3C,7G | 8G | 9G | 9G | 7G | 9C | 9G |
| Cotton | 9G | 9G | 9C | 9G | 0 | 5G | 8G | 9G | 9G | 9G | 9G | |

Test B

Post-emergence

Two round pans (25 cm diameter by 12.5 cm deep) were filled with Woodstown sandy loam soil. One pan was planted with blackgrass (*Alopecurus myosuroides*), sugar beets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xanthium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed post-emergence with the chemicals dissolved in a non-phytotoxic solvent.

Pre-emergence

Two round pans (25 cm diameter by 12.5 cm deep) were filled with Woodstown sandy loam soil. One pan was planted with blackgrass (*Alopecurus myosuroides*), sugar beets, nutsedge, crabgrass, sicklepod, teaweed, jimsonweed, velvetleaf, and giant foxtail. The other pan was planted with wheat, cotton, rice, corn, soybean, wild oats, cocklebur, morningglory, johnsongrass and barnyardgrass. The two pans were sprayed preemergence with the chemicals dissolved in a non-phytotoxic solvent.

Treated plants and controls were maintained in the greenhouse for 28 days, then all treated plants were compared to controls and visually rated for plant response.

Response ratings are based on a scale of 0 to 10: where 0 = no effect, and 10 = complete control. The type of response is indicated by letters where G = growth retardation and C = chlorosis and/or necrosis.

Response ratings are contained in Table B.

TABLE B

| | Compound Number 2 | | | | | |
|---|---|---|---|---|---|---|
| | Pre- Emergence | | Post-Emergence | | | |
| Rate g/ha | 16 | 62 | 1 | 4 | 16 | 62 |
| Corn | 0 | 0 | 2G | 3G | 5G | 9G |
| Wheat | 0 | 0 | 0 | 0 | 0 | 6G |
| Rice | 0 | 0 | 0 | 0 | 3G | 10G |
| Soybean | 0 | 0 | 0 | 0 | 3G | 5G |
| Cotton | 0 | 0 | 0 | 0 | 0 | 4G |
| Sugar beet | 0 | 0 | 0 | 0 | 2G | 5G |
| Crabgrass | 0 | 0 | 0 | 2G | 4G | 5G |
| Johnsongrass | 0 | 0 | 0 | 0 | 0 | 3G |
| Blackgrass | 0 | 0 | 0 | 0 | 0 | 3G |
| Barnyardgrass | 0 | 0 | 0 | 0 | 0 | 0 |
| Nutsedge | 0 | 0 | 0 | 0 | 0 | 0 |
| Giant Foxtail | 0 | 0 | 0 | 0 | 0 | 4G |
| Wild Oats | 0 | 0 | 0 | 0 | 3G | 8G |
| Cocklebur | 0 | 0 | 0 | 0 | 0 | 0 |
| Morningglory | 0 | 0 | 0 | 0 | 0 | 3G |
| Teaweed | 0 | 2G | 0 | 0 | 3G | 7G |
| Sicklepod | 0 | 0 | 0 | 2G | 5G | 9G |
| Jimsonweed | 0 | 0 | 0 | 0 | 2G | 4G |
| Velvetleaf | 0 | 0 | 0 | 0 | 2G | 6G |

| | Compound Number 3 | | | | | |
|---|---|---|---|---|---|---|
| | Pre-Emergence | | Post-Emergence | | | |
| Rate g/ha | 16 | 62 | 1 | 4 | 16 | 62 |
| Corn | 0 | 0 | 2G | 7G | 10C | 10C |
| Wheat | 0 | 0 | 0 | 3G | 8C | 10C |
| Rice | 3G | 9G | 2G | 8G | 10G | 10C |
| Soybean | 0 | 2G | 0 | 2G | 8G | 10G |

TABLE B-continued

| Cotton | 0 | 0 | 0 | 0 | 2G | 8G |
|---|---|---|---|---|---|---|
| Sugar beet | 0 | 5G | 0 | 5G | 9G | 10G |
| Crabgrass | 0 | 5G | 0 | 0 | 6G | 9G |
| Johnsongrass | 3G | 9G | 0 | 3G | 9G | 10C |
| Blackgrass | 4G | 8G | 0 | 3G | 9C | 10C |
| Barnyardgrass | 0 | 0 | 0 | 0 | 3G | 10C |
| Nutsedge | 4G | 9G | 0 | 0 | 0 | 0 |
| Giant foxtail | 5G | 8G | 0 | 0 | 3G | 10G |
| Wild Oats | 0 | 3G | 0 | 3G | 8G | 10C |
| Cocklebur | 0 | 0 | 0 | 0 | 3G | 9G |
| Morningglory | 0 | 0 | 0 | 0 | 2G | 8G |
| Teaweed | 0 | 0 | 0 | 2G | 7G | 8G |
| Sicklepod | 0 | 0 | 0 | 5G | 9G | 10G |
| Jimsonweed | 0 | 0 | 0 | 3G | 6G | 7G |
| Velvetleaf | 0 | 0 | 0 | 3G | 8G | 9G |

What is claimed is:

1. A compound of the formula:

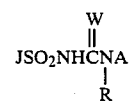

wherein
J is

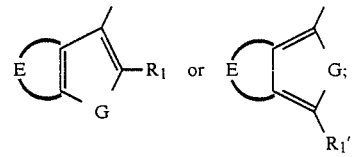

E is a bridge of 3 or 4 atoms, which may be substituted or unsubstituted, containing 0-2 heteroatoms selected from the group consisting of oxygen, sulfur and nitrogen and also containing 1-4 atoms of carbon, said bridge together with two carbon attachment sites forming a partially saturated 5 to 6 membered carbocyclic or heterocyclic ring; or E is a bridge of 3 or 4 atoms which may be substituted or unsubstituted containing at least 1 heteroatom selected from 0-1 oxygen or sulfur or 0-2 nitrogen and 1-3 atoms of carbon, said bridge together with two carbon attachment sites forming an unsaturated 5 to 6 membered heterocyclic ring, with the proviso that when E contains two atoms of oxygen or sulfur, then they must be separated by at least one atom of carbon and that oxygen and sulfur are only linked to each other if the sulfur is in the form of SO or $SO_2$; in the bridging group E nitrogen may take the form of N or N—O, sulfur may take the form of S, SO or $SO_2$, and one of the atoms of carbon may be a carbonyl, thiocarbonyl or the cyclic 5 and 6 membered ketals thereof; when one of the bridging atoms is a substituted carbon, the substituent on said carbon is selected from H, halogen, $C_1$-$C_4$ alkyl, $C_1$-$C_4$ haloalkyl, $C_3$-$C_4$ alkenyl, $C_3$-$C_4$ haloalkenyl, $C_3$-$C_4$ alkynyl, $C_3$-$C_4$ haloalkynyl, $C_1$-$C_3$ alkoxycarbonyl, CN, $NO_2$, OH, $C_1$-$C_3$ alkoxy, $C_1$-$C_3$ haloalkoxy, $C_1$-$C_3$ alkylthio, $C_1$-$C_3$ alkylsulfinyl, $C_1$-$C_3$ alkylsulfonyl, $C_1$-$C_3$ alkylcarbonyl, $C_1$-$C_3$ alkylsulfamoyl, di($C_1$-$C_3$ alkyl)sulfamoyl and $C_1$-$C_2$ alkyl substituted with $C_1$-$C_2$ alkoxy, $C_1$-$C_2$ alkylthio or CN; when at least one of the bridging atoms is a nitrogen (other than nitrogen in the form of $R_6NSO_2$ in $J_7$, $J_8$, $J_{11}$ and $J_{12}$) substituents on said nitrogen are selected from H, $C_1$-$C_4$ alkyl, $C_1$-$C_4$ haloalkyl, $C_3$-$C_4$ alkenyl, $C_3$-$C_4$ haloalkenyl, $C_3$-$C_4$ alkynyl, $C_3$-$C_4$ haloalkynyl, $C_1$-$C_3$ alkoxy, $C_1$-$C_4$ alkylcarbonyl, $C_1$-$C_3$ alkoxycarbonyl, $C_1$-$C_3$ alkylaminocarbonyl or $C_1$-$C_4$ alkylsulfonyl; when at least one of the bridging atoms is a nitrogen, in the form of $R_6NSO_2$ as in $J_7$, $J_8$, $J_{11}$ and $J_{12}$, the nitrogen substituents are as defined for $R_6$;

G is O, S, NH or $NCH_3$;

W is O or S;

R is H or $CH_3$;

$R_1$ is H, F, Cl, Br, $NO_2$, $C_1$-$C_3$ alkyl, $C_1$-$C_3$ haloalkyl, $C_1$-$C_3$ alkoxy, $C_1$-$C_3$ haloalkoxy, $S(O)_pC_1$-$C_3$ alkyl, $S(O)_pC_1$-$C_3$ haloalkyl, $CO_2(C_1$-$C_3$ alkyl), $CO_2(C_1$-$C_3$ haloalkyl), $OCH_2C=CHR_a$, $OCH_2C\equiv CR_a$, $CO_2(CH_2C=CHR_a)$, $CO_2(CH_2C\equiv CR_a)$ or $SO_2NR_bR_c$;

$R_1'$ is H, $CH_3$, F or Cl;

p is 0, 1 or 2;

$R_a$ is H or $CH_3$;

$R_b$ is H, $C_1$-$C_3$ alkyl or $C_1$-$C_3$ haloalkyl;

$R_c$ is H, $C_1$-$C_3$ alkyl or $C_1$-$C_3$ haloalkyl;

A is 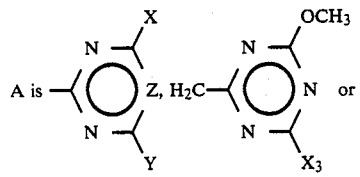

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkoxy, amino, $C_1$-$C_3$ alkylamino, di($C_1$-$C_3$-alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_3$-$C_5$ cycloalkyl, $C_2$-$C_4$ alkynyl,

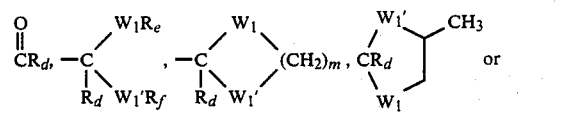

N(OCH$_3$)CH$_3$;

$W_1$ and $W'_1$ are independently O or S;

m is 2 or 3;

$R_d$ is H or $CH_3$;

$R_e$ is $C_1$-$C_2$ alkyl;

$R_f$ is $C_1$-$C_2$ alkyl;

Z is N;

$X_3$ is $CH_3$ or $OCH_3$;

$R_6$ is H, $R_8$, $SR_8$, $SO_2R_8$, $OR_8$, $C(O)R_8$, $C(O)L$, $(CO)_2OR_8$, $(CO)_2R_8$, $C(O)NR_9R_{10}$, $C(O)NRA$, $C(S)SR_8$, $NH_2$, $NR_9R_{10}$, OH, CN, $P(O)R_{11}R_{12}$, $P(S)R_{11}R_{12}$ or $Si(CH_3)_2R_{13}$;

$R_7$ is H, $C_1$-$C_6$ alkyl, Cl, Br, CN, $NO_2$, $SR_{13}$, $SO_2R_{13}$, $CO_2R_{13}$ or $C(O)R_{13}$;

$R_8$ is $C_1$-$C_{10}$ alkyl, $C_1$-$C_{10}$ alkoxyalkoxyalkyl, $C_2$-$C_{10}$ alkenyl, $C_2$-$C_{10}$ epoxyalkyl, $C_2$-$C_{10}$ alkynyl, $C_3$-$C_6$ cycloalkyl, $C_4$-$C_7$ cycloalkylalkyl or phenyl optionally substituted with $R_{14}$; when $R_8$ is $C_3$-$C_6$ cycloalkyl or $C_4$-$C_7$ cycloalkylalkyl, it may optionally be substituted by $C_1$-$C_4$ alkyl, 1 to 3 atoms of Cl or F or 1 Br; when $R_8$ is $C_1$-$C_{10}$ alkyl, $C_2$-$C_{10}$ alkenyl or $C_2$-$C_{10}$ alkynyl, it may optionally be substituted by one or more halogens and/or by $(R_{15})_r$ provided that when r is 2, the values of $R_{15}$ may be identical or different;

$R_9$ is H or $C_1$-$C_4$ alkyl;

$R_{10}$ is H, $C_1$-$C_{10}$ alkyl, $C_1$-$C_{10}$ haloalkyl, $C_2$-$C_{10}$ alkenyl, $C_2$-$C_{10}$ alkynyl, $C_3$-$C_6$ cycloalkyl or phenyl subsituted with $R_{14}$;

$R_{11}$ and $R_{12}$ are independently $C_1$-$C_4$ alkyl, $C_1$-$C_4$ alkoxy or $C_1$-$C_4$ alkylthio;

$R_{13}$ is $C_1$-$C_{10}$ alkyl, benzyl or phenyl optionally substituted with $R_{14}$;

$R_{14}$ is H, F, Cl, Br, $CH_3$, $OCH_3$, $NO_2$, CN, $SCH_3$, $SO_2CH_3$ or $CF_3$;

r is 1 or 2;

$R_{15}$ is $OR_{10}$, $OC(O)R_{10}$, $OC(O)NR_9R_{10}$, $OSO_2R_{10}$, $OP(O)R_{11}R_{12}$, $OSi(CH_3)_2R_{13}$, $SR_{10}$, $SOR_{10}$, $SO_2R_{10}$, SCN, CN, $SP(O)R_{11}R_{12}$, $SP(S)R_{11}R_{12}$, $P(O)R_{11}R_{12}$, $P(S)R_{11}R_{12}$, $NR_9R_{10}$, $N^+R_9R_{10}R_{13}$, $NR_9C(O)R_{10}$, $NR_9C(O)OR_{10}$, $NR_9C(O)NR_9R_{10}$, $NR_9SO_2R_{10}$, $NR_9P(O)R_{11}R_{12}$, $NR_9P(S)R_{11}R_{12}$, $NO_2$, $C(O)R_{10}$, $C(O)OR_{10}$, $C(O)NR_9R_{10}$, $C(R_{10})=NOR_{10}$, naphthyl, L, phenyl optionally substituted with $R_{14}$ and/or $R_{16}$,

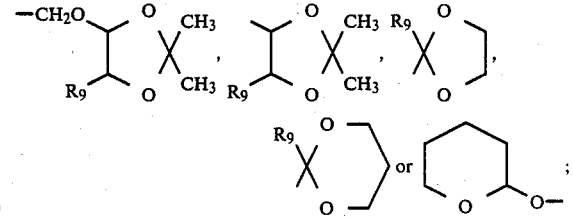

$R_{16}$ is H, F, Cl, Br, phenoxy optionally substituted with $R_{14}$, or phenyl optionally substituted with $R_{14}$;

L is selected from pyridine, thiophene, furan, cyclopentanone, α-butyrolactone, triazole and oxazole;

provided that (a) when W is S, then R is H, A is A-1, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

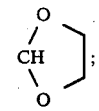

(b) the total number of carbon atoms in $R_6$ is less than or equal to 13;

(c) when the total number of carbon atoms of X and Y is greater than four, then the number of carbon atoms of $R_1$ is less than or equal to two, and the number of carbon atoms of $R_6$ is less than or equal to four;

and their agriculturally suitable salts.

2. A compound of claim 1 wherein J is

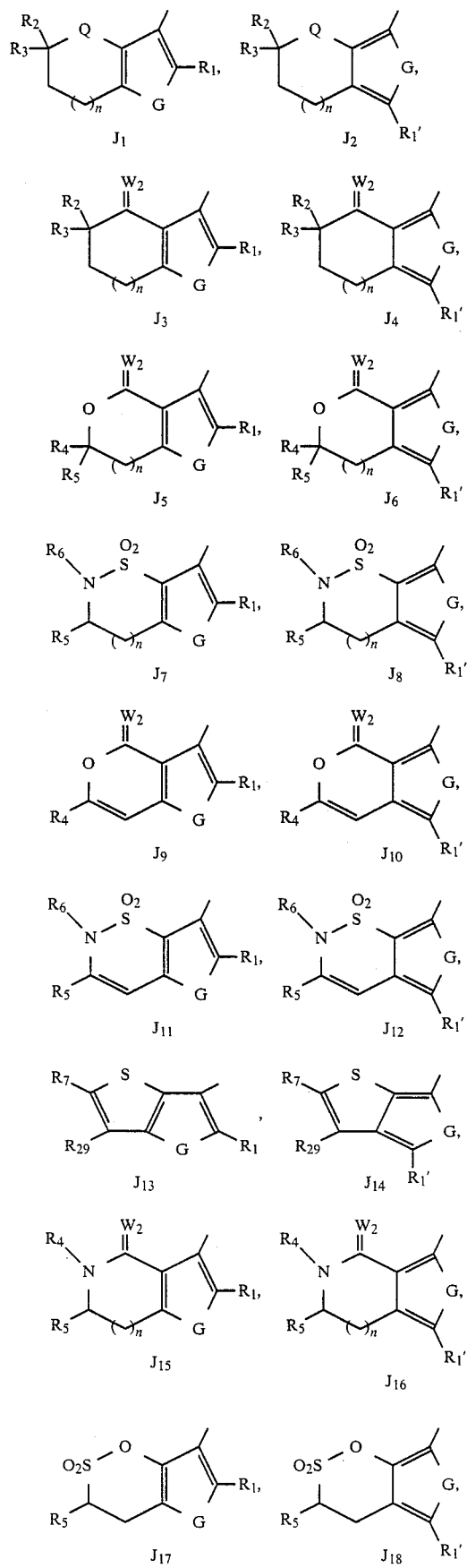
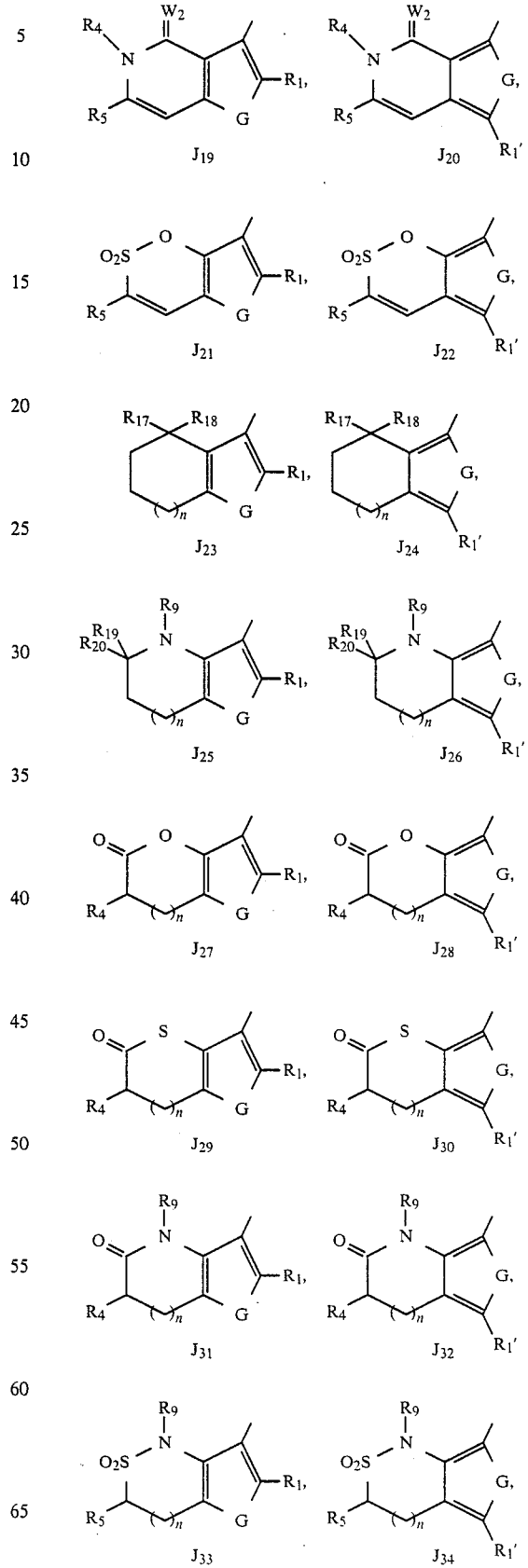

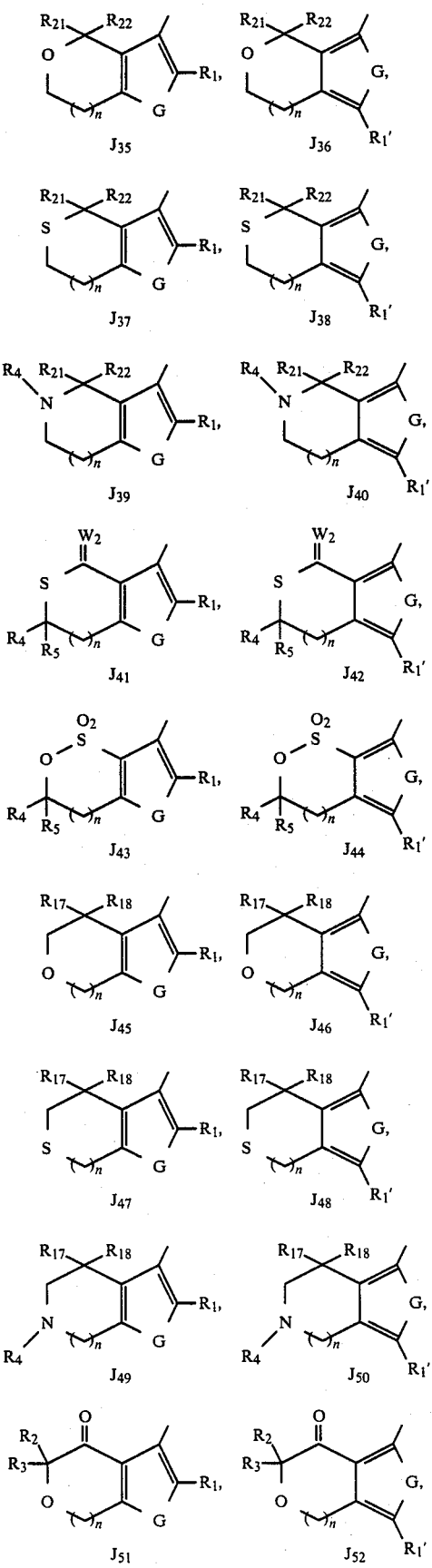
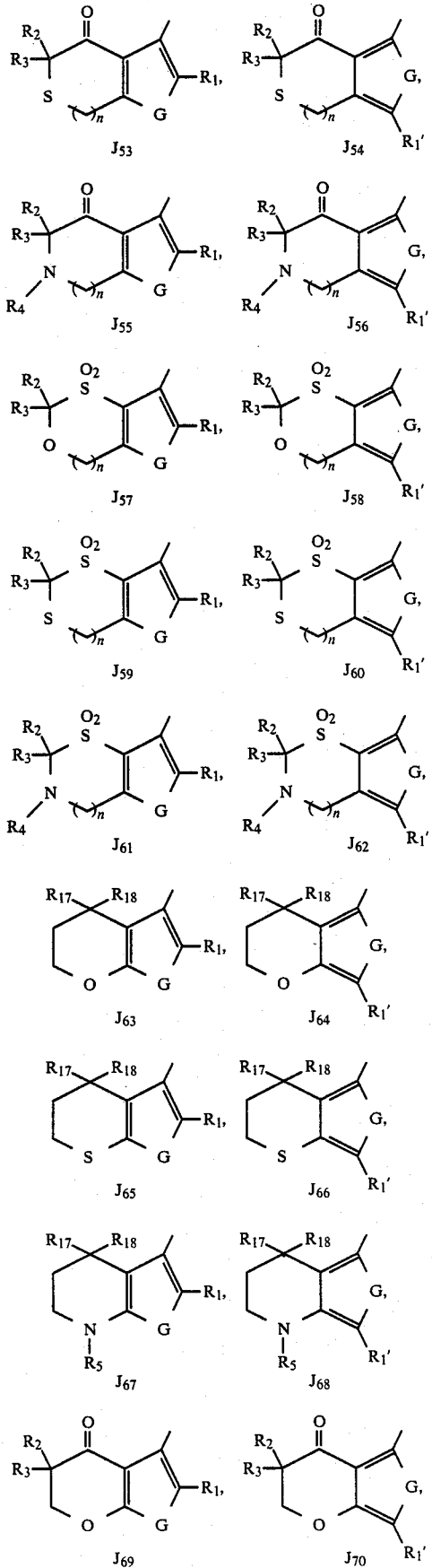

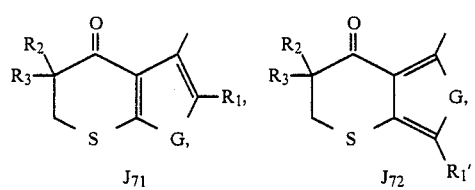
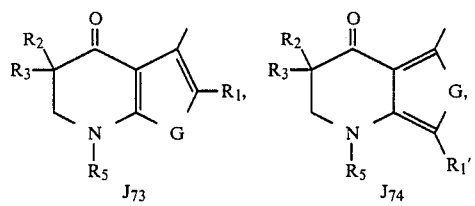
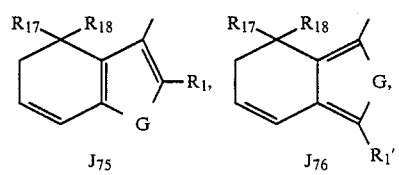
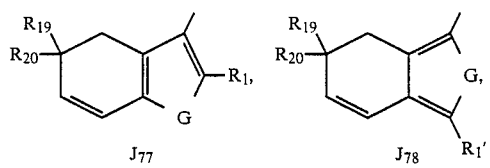
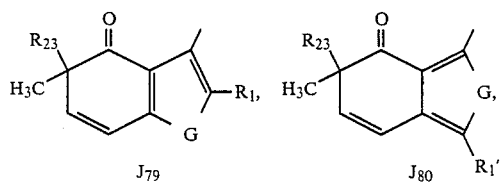
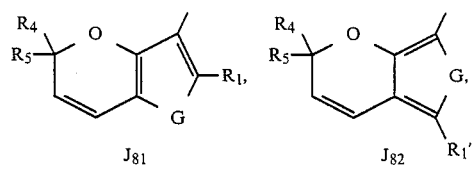
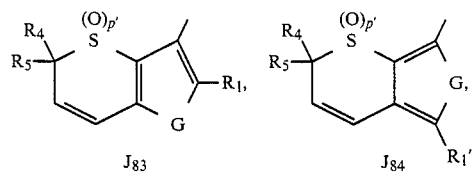
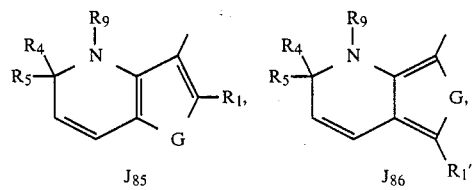
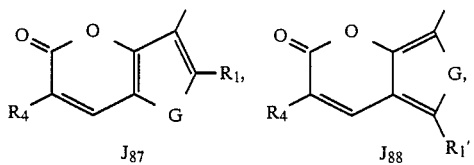
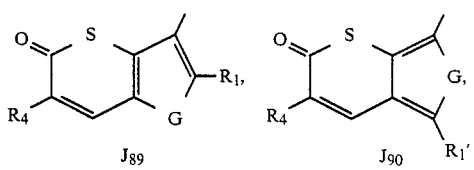
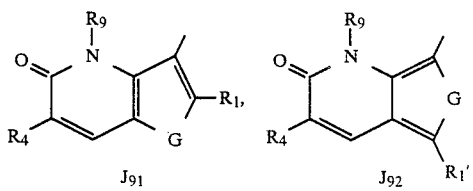
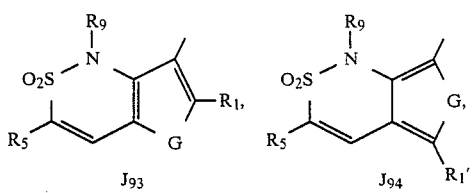
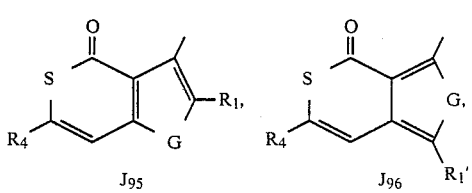
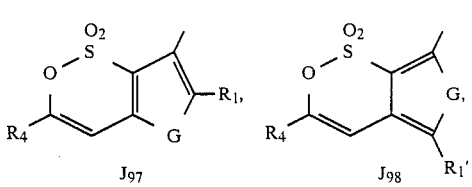
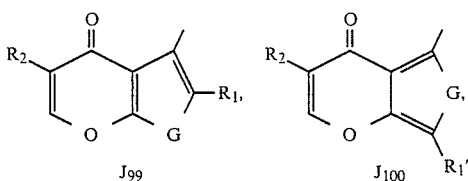
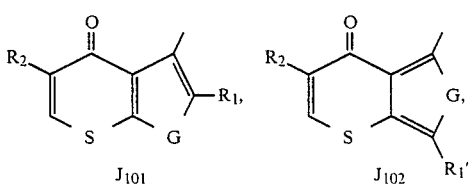

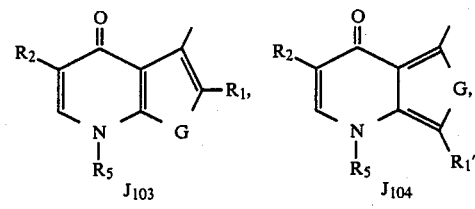
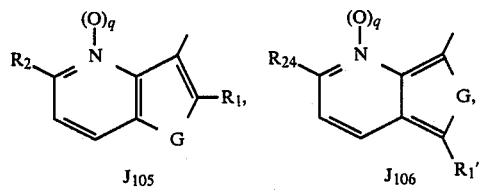
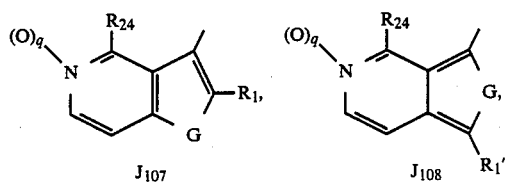
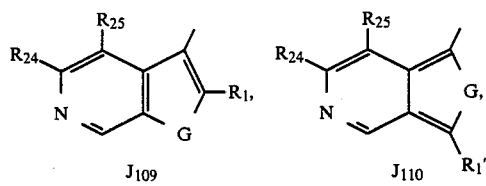
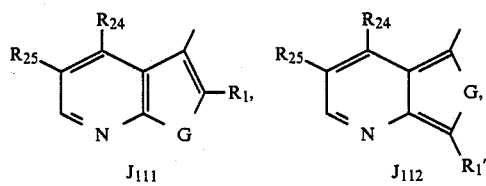
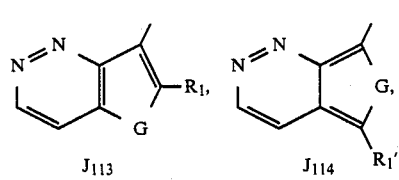
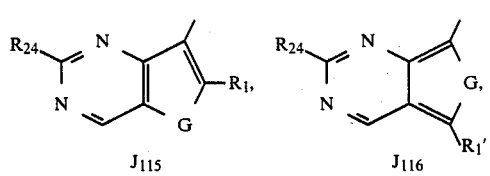
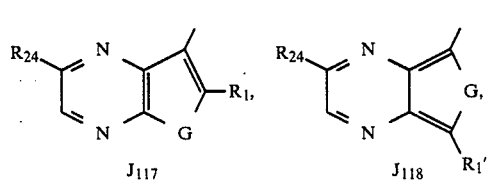
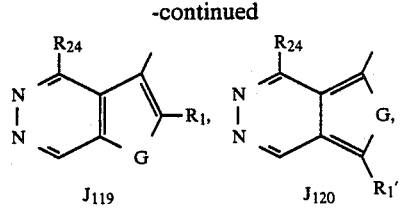
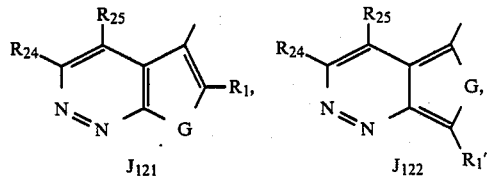
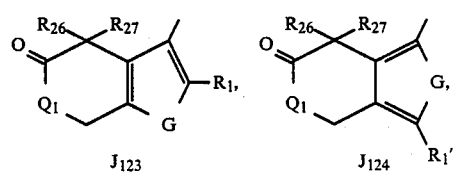
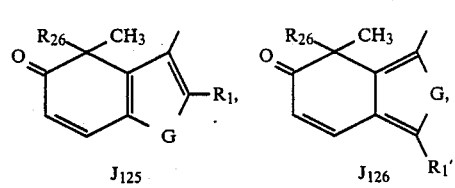
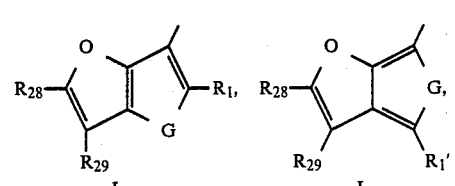
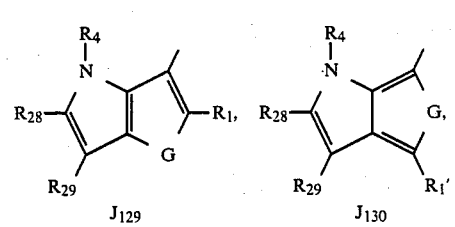
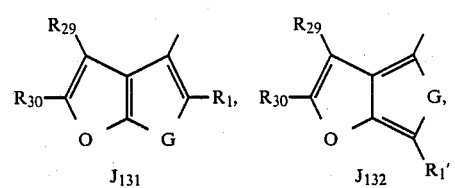
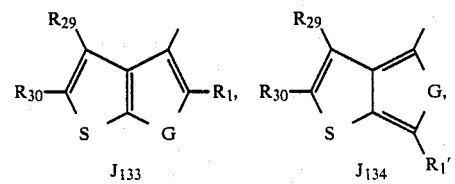

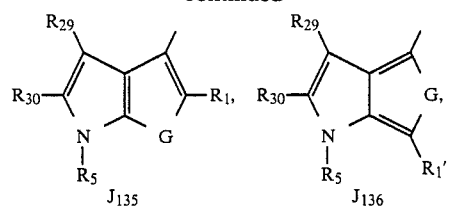
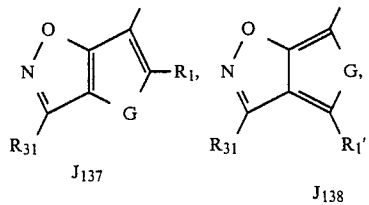
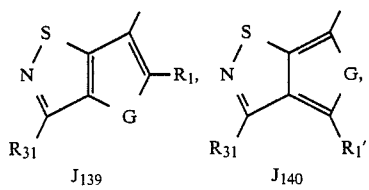
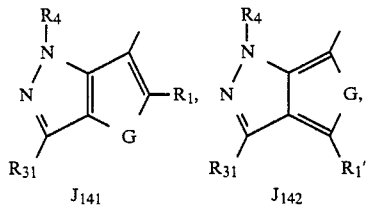
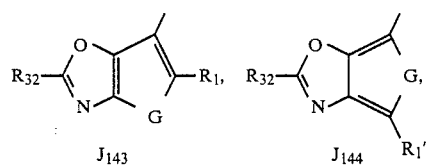
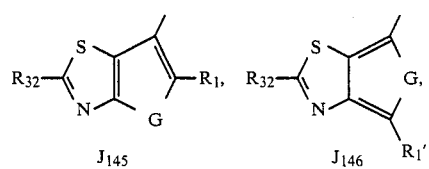
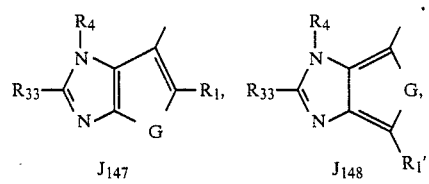
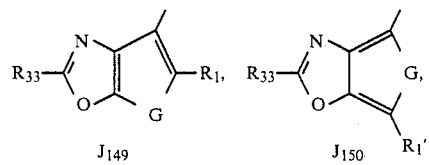
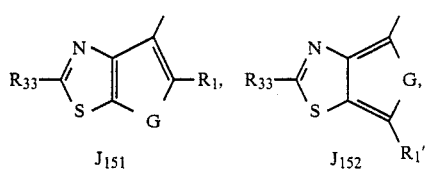
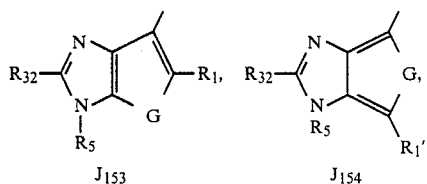
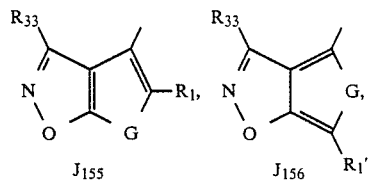
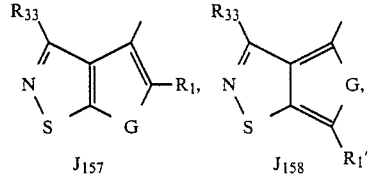
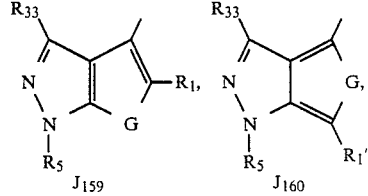
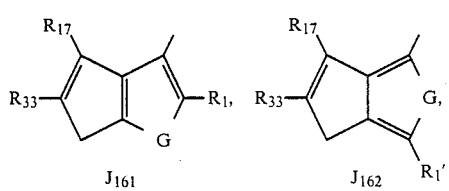
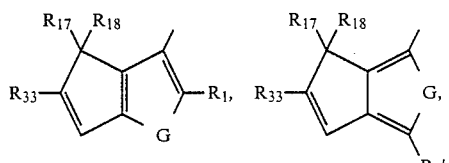
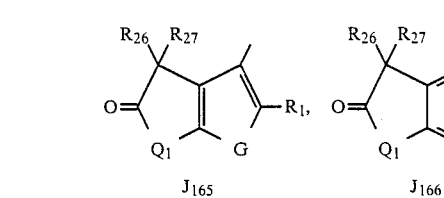
Q is O, S, SO, $SO_2$, $CH_2$ or $CHCH_3$;
$Q_1$ is O, S, $CH_2$ or $NR_4$;
$W_2$ is O or S;
$R_2$ is H, F, Cl or $C_1-C_4$ alkyl;
$R_3$ is H, F, Cl or $CH_3$;

131

$R_4$ is H or $C_1$-$C_4$ alkyl;
$R_5$ is H is $CH_3$;
$R_6$ is H, $R_8$, $SR_8$, $SO_2R_8$, $OR_8$, $C(O)R_8$, $C(O)L$, $(CO)_2OR_8$, $(CO)_2R_8$, $C(O)NR_9R_{10}$, $C(O)NRA$, $C(S)SR_8$, $NH_2$, $NR_9R_{10}$, OH, CN, $P(O)R_{11}R_{12}$, $P(S)R_{11}R_{12}$ or $Si(CH_3)_2R_{13}$;
$R_7$ is H, $C_1$-$C_6$ alkyl, Cl, Br, CN, $NO_2$, $SR_{13}$, $SO_2R_{13}$, $CO_2R_{13}$ or $C(O)R_{13}$;
$R_8$ is $C_1$-$C_{10}$ alkyl, $C_1$-$C_{10}$ alkoxyalkoxyalkyl, $C_2$-$C_{10}$ alkenyl, $C_2$-$C_{10}$ epoxyalkyl, $C_2$-$C_{10}$ alkynyl, $C_3$-$C_6$ cycloalkyl, $C_4$-$C_7$ cycloalkylalkyl or phenyl optionally substituted with $R_{14}$; when $R_8$ is $C_3$-$C_6$ cycloalkyl or $C_4$-$C_7$ cycloalkylalkyl, it may optionally be substituted by $C_1$-$C_4$ alkyl, 1 to 3 atoms of Cl or F or 1 Br; when $R_8$ is $C_1$-$C_{10}$ alkyl, $C_2$-$C_{10}$ alkenyl or $C_2$-$C_{10}$ alkynyl, it may optionally be substituted by one or more halogens and/or by $(R_{15})_r$ provided that when r is 2, the values of $R_{15}$ may be identical or different;
$R_9$ is H or $C_1$-$C_4$ alkyl;
$R_{10}$ is H, $C_1$-$C_{10}$ alkyl, $C_1$-$C_{10}$ haloalkyl, $C_2$-$C_{10}$ alkenyl, $C_2$-$C_{10}$ alkynyl, $C_3$-$C_6$ cycloalkyl or phenyl substituted with $R_{14}$;
$R_{11}$ and $R_{12}$ are independently $C_1$-$C_4$ alkyl, $C_1$-$C_4$ alkoxy or $C_1$-$C_4$ alkylthio;
$R_{13}$ is $C_1$-$C_{10}$ alkyl, benzyl or phenyl optionally substituted with $R_{14}$;
$R_{14}$ is H, F, Cl, Br, $CH_3$, $OCH_3$, $NO_2$, CN, $SCH_3$, $SO_2CH_3$ or $CF_3$;
$R_{15}$ is $OR_{10}$, $OC(O)R_{10}$, $OC(O)NR_9R_{10}$, $OSO_2R_{10}$, $OP(O)R_{11}R_{12}$, $OSi(CH_3)_2R_{13}$, $SR_{10}$, $SOR_{10}$, $SO_2R_{10}$, SCN, CN, $SP(O)R_{11}R_{12}$, $SP(S)R_{11}R_{12}$, $P(O)R_{11}R_{12}$, $P(S)R_{11}R_{12}$, $NR_9R_{10}$, $N^+R_9R_{10}R_{13}$, $NR_9C(O)R_{10}$, $NR_9C(O)OR_{10}$, $NR_9C(O)NR_9R_{10}$, $NR_9SO_2R_{10}$, $NR_9P(O)R_{11}R_{12}$, $NR_9P(S)R_{11}R_{12}$, $NO_2$, $C(O)R_{10}$, $C(O)OR_{10}$, $C(O)NR_9R_{10}$, $C(R_{10})=NOR_{10}$, naphthyl, L, phenyl optionally substituted with $R_{14}$ and/or $R_{16}$,

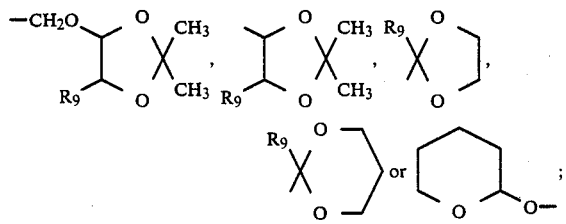

$R_{16}$ is H, F, Cl, Br, phenoxy optionally substituted with $R_{14}$, or phenyl optionally substituted with $R_{14}$;
r is 1 or 2;
$R_{17}$ is H, $C_1$-$C_3$ alkyl, $C_1$-$C_3$ alkoxy, $C_1$-$C_3$ alkoxycarbonyl, F, Cl or CN;
$R_{18}$ is H, $CH_3$, $C_1$-$C_3$ alkoxy, F, Cl or OH; or
$R_{17}$ and $R_{18}$ may be taken together to form —$OCH_2CH_2O$— or —$OCH_2CH_2CH_2O$—;
$R_{19}$ is H or $C_1$-$C_4$ alkyl;
$R_{20}$ is H or $CH_3$;
$R_{21}$ and $R_{22}$ are independently H or $CH_3$;
$R_{23}$ is $C_1$-$C_4$ alkyl;
$R_{24}$ is H, F, Cl, $C_1$-$C_3$ alkyl or $C_1$-$C_3$ alkoxy;
$R_{25}$ is H, F, Cl or $C_1$-$C_3$ alkyl;
$R_{26}$ is H, F, Cl or $C_1$-$C_2$ alkyl;
$R_{27}$ is H, F, Cl or $CH_3$;

132

$R_{28}$ is H, $C_1$-$C_4$ alkyl, Cl, Br, CN, $NO_2$, $C_1$-$C_3$ alkylthio, $C_1$-$C_3$ alkylsulfonyl, $C_1$-$C_3$ alkoxycarbonyl or $C_1$-$C_3$ alkylcarbonyl;
$R_{29}$ is H, $CH_3$, Cl or Br;
$R_{30}$ is H, $CH_3$, Cl or Br;
$R_{31}$ is H or $CH_3$;
$R_{32}$ is H or $C_1$-$C_4$ alkyl;
$R_{33}$ is H, $C_1$-$C_4$ alkyl, $C_1$-$C_4$ alkoxy, $C_1$-$C_4$ alkylthio, F or Cl;
L is selected from pyridine, thiophene, furan, cyclopentanone, α-butyrolactone, triazole and oxazole;
n is 0 or 1;
p' is 0, 1 or 2; and
q is 0 or 1;
provided that
(a) the total number of carbon atoms in $R_2$ and $R_3$ is less than or equal to 4;
(b) when J is $J_1$ or $J_2$, then $R_2$ and $R_3$ are other than F or Cl;
(c) the total number of carbon atoms in $R_4$ and $R_5$ is less than or equal to 4;
(d) J is $J_5$, $J_6$, $J_{27}$, $J_{28}$, $J_{29}$, $J_{30}$, $J_{31}$, $J_{32}$, $J_{33}$, $J_{34}$, $J_{41}$, $J_{42}$, $J_{43}$ or $J_{44}$ and n is O, then $R_4$ and/or $R_5$ is H;
(e) when J is $J_{61}$ or $J_{62}$ and n is O, then $R_4$ is H or $CH_3$;
(f) when $R_{17}$ is $C_1$-$C_3$ alkoxy, then $R_{18}$ is H, $CH_3$ or $C_1$-$C_3$ alkoxy; and when $R_{18}$ is $C_1$-$C_3$ alkoxy, then $R_{17}$ is not F, or Cl; and
(g) when $R_{18}$ is OH, then $R_{17}$ is H or $C_1$-$C_3$ alkyl.

3. A compound of claim 2 wherein R is H: W is O, and G is O or S.

4. A compound of claim 3 wherein Y is $CH_3$, $OCH_3$, $OCH_2CH_3$, $OCF_2H$, $CH_2F$, $CF_3$, $OCH_2CH_2F$, $OCH_2CHF_2$, $OCH_2CF_3$, $CH_2Cl$ or $CH_2Br$; and Y is H, $CH_3$, $OCH_3$, $OC_2H_5$, $CH_2OCH_3$, $NHCH_3$, $N(OCH_3)CH_3$, $N(CH_3)_2$, $CH_2CH_3$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $CH_2SCH_2CH_3$,

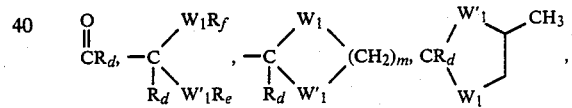

$OCF_2H$, $SCF_2H$, $C\equiv CH$ or $C\equiv CCH_3$.

5. A compound of claim 4 wherein G is S; $R_1$ is H, Cl, Br or $CH_3$; $R_2$ and $R_4$ are H or $C_1$-$C_3$ alkyl; $R_3$ is H or $CH_3$; $R_6$ is H, $R_8$, $C(O)R_8$ or $CO_2R_8$; $R_7$ is H, $C_1$-$C_2$ alkyl, Cl, Br, $SC_1$-$C_2$ alkyl, $SO_2C_1$-$C_2$ alkyl, $CO_2C_1$-$C_2$ alkyl or $C(O)C_1$-$C_2$ alkyl; $R_8$ is $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ epoxyalkyl or $C_1$-$C_4$ alkyl substituted with $C_1$-$C_2$ alkoxy, $C_1$-$C_2$ alkylthio, $C_1$-$C_2$ alkylsulfinyl, $C_1$-$C_2$ alkylsulfonyl, $CO_2(C_1$-$C_2$ alkyl), $C(O)C_1$-$C_2$ alkyl, CN or OH. $R_{17}$ is H, $C_1$-$C_3$ alkyl, $C_1$-$C_2$ alkoxy or $C_1$-$C_2$ alkoxycarbonyl; $R_{18}$ is H, $CH_3$, $C_1$-$C_2$ alkoxy or OH; or $R_{17}$ and $R_{18}$ may be taken together to form —$OCH_2CH_2O$— or —$OCH_2CH_2CH_2O$—; $R_{28}$ is H, $C_1$-$C_3$ alkyl, Cl, Br or $NO_2$; and $R_{33}$ is H or $CH_3$.

6. A compound of claim 5 wherein $R_8$ is $C_1$-$C_6$ alkyl, $C_1$-$C_4$ haloalkyl, $C_3$-$C_4$ alkenyl, $C_3$-$C_4$ haloalkenyl, $C_3$-$C_4$ alkynyl, or $C_1$-$C_3$ alkyl substituted with $C_1$-$C_2$ alkoxy, $C_1$-$C_2$ alkylthio, $C_1$-$C_2$ alkylsulfonyl, CN, $CO_2(C_1$-$C_2$ alkyl) or $C(O)C_1$-$C_2$ alkyl.

7. A compound of claim 6 wherein A is A-1; X is $CH_3$, $OCH_3$, $OCH_2CH_3$, $OCF_2H$ or $OCH_2CF_3$; and Y is $CH_3$, $OCH_3$, $C_2H_5$, $CH_2OCH_3$, $NHCH_3$ or $CH(OCH_3)_2$.

8. A compound of claim 7 wherein J is $J_1$ or $J_2$.
9. A compound of claim 7 wherein J is $J_3$ or $J_4$.
10. A compound of claim 7 wherein J is $J_5$ or $J_6$.
11. A compound of claim 7 wherein J is $J_7$ or $J_8$.
12. A compound of claim 7 wherein J is $J_9$ or $J_{10}$.
13. A compound of claim 7 wherein J is $J_{11}$ or $J_{12}$.
14. A compound of claim 7 wherein J is $J_{13}$ or $J_{14}$.
15. A compound of claim 7 wherein J is $J_{15}$.
16. A compound of claim 7 wherein J is $J_{23}$.
17. A compound of claim 7 wherein J is $J_{25}$.
18. A compound of claim 7 where J is $J_{27}$.
19. A compound of claim 7 wherein J is $J_{35}$, $J_{37}$ or $J_{39}$.
20. A compound of claim 7 where J is $J_{41}$.
21. A compound of claim 7 wherein J is $J_{69}$ or $J_{71}$.
22. A compound of claim 7 wherein J is $J_{79}$.
23. A compound of claim 7 wherein J is $J_{87}$.
24. A compound of claim 7 where J is $J_{95}$.
25. A compound of claim 7 wherein J is $J_{105}$ or $J_{106}$.
26. A compound of claim 7 where J is $J_{127}$ or $J_{129}$.
27. A compounds of claim 7 wherein J is $J_{131}$ or $J_{133}$.
28. A composition suitable for controlling the growth of undesired vegetation which comprises an effective amount of a compound of claim 1 and at least one of the following: surfactant, solid or liquid diluent.
29. A composition suitable for controlling the growth of undesired vegetation which comprises an effective amount of a compound of claim 2 and at least one of the following: surfactant, solid or liquid diluent.
30. A composition suitable for controlling the growth of undesired vegetation which comprises an effective amount of a compound of claim 3 and at least one of the following: surfactant, solid or liquid diluent.
31. A composition suitable for controlling the growth of undesired vegetation which comprises an effective amount of a compound of claim 4 and at least one of the following: surfactant, solid or liquid diluent.
32. A composition suitable for controlling the growth of undesired vegetation which comprises an effective amount of a compound of claim 5 and at least one of the following: surfactant, solid or liquid diluent.
33. A composition suitable for controlling the growth of undesired vegetation which comprises an effective amount of a compound of claim 6 and at least one of the following: surfactant, solid or liquid diluent.
34. A composition suitable for controlling the growth of undesired vegetation which comprises an effective amount of a compound of claim 7 and at least one of the following: surfactant, solid or liquid diluent.
35. A composition suitable for controlling the growth of undesired vegetation which comprises an effective amount of the compound of claim 8 and at least one of the following: surfactant, solid or liquid diluent.
36. A composition suitable for controlling the growth of undesired vegetation which comprises an effective amount of a compound of claim 9 and at least one of the following: surfactant, solid or liquid diluent.
37. A composition suitable for controlling the growth of undesired vegetation which comprises an effective amount of a compound of claim 10 and at least one of the following: surfactant, solid or liquid diluent.
38. A composition suitable for controlling the growth of undesired vegetation which comprises an effective amount of a compound of claim 11 and at least one of the following: surfactant, solid or liquid diluent.
39. A composition suitable for controlling the growth of undesired vegetation which comprises an effective amount of a compound of claim 12 and at least one of the following: surfactant, solid or liquid diluent.
40. A composition suitable for controlling the growth of undesired vegetation which comprises an effective amount of a compound of claim 13 and at least one of the following: surfactant, solid or liquid diluent.
41. A composition suitable for controlling the growth of undesired vegetation which comprises an effective amount of a compound of claim 14 and at least one of the following: surfactant, solid or liquid diluent.
42. A composition suitable for controlling the growth of undesired vegetation which comprises an effective amount of a compound of claim 15 and at least one of the following: surfactant, solid or liquid diluent.
43. A composition suitable for controlling the growth of undesired vegetation which comprises an effective amount of the compound of claim 16 and at least one of the following: surfactant, solid or liquid diluent.
44. A composition suitable for controlling the growth of undesired vegetation which comprises an effective amount of a compound of claim 17 and at least one of the following: surfactant, solid or liquid diluent.
45. A composition suitable for controlling the growth of undesired vegetation which comprises an effective amount of a compound of claim 18 and at least one of the following: surfactant, solid or liquid diluent.
46. A composition suitable for controlling the growth of undesired vegetation which comprises an effective amount of a compound of claim 19 and at least one of the following: surfactant, solid or liquid diluent.
47. A composition suitable for controlling the growth of undesired vegetation which comprises an effective amount of a compound of claim 20 and at least one of the following: surfactant, solid or liquid diluent.
48. A composition suitable for controlling the growth of undesired vegetation which comprises an effective amount of a compound of claim 21 and at least one of the following: surfactant, solid or liquid diluent.
49. A composition suitable for controlling the growth of undesired vegetation which comprises an effective amount of a compound of claim 22 and at least one of the following: surfactant, solid or liquid diluent.
50. A composition suitable for controlling the growth of undesired vegetation which comprises an effective amount of a compound of claim 23 and at least one of the following: surfactant, solid or liquid diluent.
51. A composition suitable for controlling the growth of undesired vegetation which comprises an effective amount of the compound of claim 24 and at least one of the following: surfactant, solid or liquid diluent.
52. A composition suitable for controlling the growth of undesired vegetation which comprises an effective amount of a compound of claim 25 and at least one of the following: surfactant, solid or liquid diluent.
53. A composition suitable for controlling the growth of undesired vegetation which comprises an effective amount of a compound of claim 26 and at least one of the following: surfactant, solid or liquid diluent.
54. A composition suitable for controlling the growth of undesired vegetation which comprises an effective amount of a compound of claim 27 and at least one of the following: surfactant, solid or liquid diluent.
55. A method for controlling the growth of undesired vegetation which comprises applying to the locus to be protected an effective amount of a compound of claim 1.
56. A method for controlling the growth of undesired vegetation which comprises applying to the locus to be protected an effective amount of a compound of claim 2.

57. A method for controlling the growth of undesired vegetation which comprises applying to the locus to be protected an effective amount of a compound of claim 3.

58. A method for controlling the growth of undesired vegetation which comprises applying to the locus to be protected an effective amount of a compound of claim 4.

59. A method for controlling the growth of undesired vegetation which comprises applying to the locus to be protected an effective amount of a compound of claim 5.

60. A method for controlling the growth of undesired vegetation which comprises applying to the locus to be protected an effective amount of a compound of claim 6.

61. A method for controlling the growth of undesired vegetation which comprises applying to the locus to be protected an effective amount of a compound of claim 7.

62. A method for controlling the growth of undesired vegetation which comprises applying to the locus to be protected an effective amount of the compound of claim 8.

63. A method for controlling the growth of undesired vegetation which comprises applying to the locus to be protected an effective amount of a compound of claim 9.

64. A method for controlling the growth of undesired vegetation which comprises applying to the locus to be protected an effective amount of a compound of claim 10.

65. A method for controlling the growth of undesired vegetation which comprises applying to the locus to be protected an effective amount of a compound of claim 11.

66. A method for controlling the growth of undesired vegetation which comprises applying to the locus to be protected an effective amount of a compound of claim 12.

67. A method for controlling the growth of undesired vegetation which comprises applying to the locus to be protected an effective amount of a compound of claim 13.

68. A method for controlling the growth of undesired vegetation which comprises applying to the locus to be protected an effective amount of a compound of claim 14.

69. A method for controlling the growth of undesired vegetation which comprises applying to the locus to be protected an effective amount of a compound of claim 15.

70. A method for controlling the growth of undesired vegetation which comprises applying to the locus to be protected an effective amount of the compound of claim 16.

71. A method for controlling the growth of undesired vegetation which comprises applying to the locus to be protected an effective amount of a compound of claim 17.

72. A method for controlling the growth of undesired vegetation which comprises applying to the locus to be protected an effective amount of a compound of claim 18.

73. A method for controlling the growth of undesired vegetation which comprises applying to the locus to be protected an effective amount of a compound of claim 19.

74. A method for controlling the growth of undesired vegetation which comprises applying to the locus to be protected an effective amount of a compound of claim 20.

75. A method for controlling the growth of undesired vegetation which comprises applying to the locus to be protected an effective amount of a compound of claim 21.

76. A method for controlling the growth of undesired vegetation which comprises applying to the locus to be protected a effective amount of a compound of claim 22.

77. A method for controlling the growth of undesired vegetation which comprises applying to the locus to be protected an effective amount of a compound of claim 23.

78. A method for controlling the growth of undesired vegetation which comprises applying to the locus to be protected an effective amount of the compound of claim 24.

79. A method for controlling the growth of undesired vegetation which comprises applying to the locus to be protected an effective amount of a compound of claim 25.

80. A method for controlling the growth of undesired vegetation which comprises applying to the locus to be protected an effective amount of a compound of claim 26.

81. A method for controlling the growth of undesired vegetation which comprises applying to the locus to be protected an effective amount of a compound of claim 27.

* * * * *